US010385476B2

(12) United States Patent
Nelson et al.

(10) Patent No.: US 10,385,476 B2
(45) Date of Patent: Aug. 20, 2019

(54) METHODS AND COMPOSITIONS FOR THE SELECTION AND OPTIMIZATION OF OLIGONUCLEOTIDE TAG SEQUENCES

(71) Applicant: GEN-PROBE INCORPORATED, San Diego, CA (US)

(72) Inventors: Norman C. Nelson, San Diego, CA (US); Jijumon Chelliserry, San Diego, CA (US)

(73) Assignee: GEN-PROBE INCORPORATED, San Diego, CA (US)

(*) Notice: Subject to any disclaimer, the term of this patent is extended or adjusted under 35 U.S.C. 154(b) by 320 days.

(21) Appl. No.: 15/362,692

(22) Filed: Nov. 28, 2016

(65) Prior Publication Data
US 2017/0218435 A1   Aug. 3, 2017

Related U.S. Application Data

(62) Division of application No. 14/004,107, filed as application No. PCT/US2012/028797 on Mar. 12, 2012, now Pat. No. 9,512,467.
(Continued)

(51) Int. Cl.
| | |
|---|---|
| *C12Q 1/6811* | (2018.01) |
| *C40B 30/00* | (2006.01) |
| *C12N 15/10* | (2006.01) |
| *C07H 21/00* | (2006.01) |
| *G16B 25/00* | (2019.01) |
| *G16B 30/00* | (2019.01) |

(52) U.S. Cl.
CPC ............. *C40B 30/00* (2013.01); *C07H 21/00* (2013.01); *C12N 15/1065* (2013.01); *C12Q 1/6811* (2013.01); *G16B 25/00* (2019.02); *G16B 30/00* (2019.02)

(58) Field of Classification Search
CPC .. C07H 21/00; C12N 15/1065; C12Q 1/6811; C40B 30/00; G16B 25/00; G16B 30/00
See application file for complete search history.

(56) References Cited

U.S. PATENT DOCUMENTS

| 6,403,312 B1 | 6/2002 | Dahiyat et al. |
| 9,512,467 B2 | 12/2016 | Nelson et al. |
| (Continued) | | |

FOREIGN PATENT DOCUMENTS

| EP | 0721016 A2 | 10/1996 |
| EP | 1690947 A2 | 8/2006 |
| (Continued) | | |

OTHER PUBLICATIONS

Ben-Dor et al., "Universal DNA Tag Systems: A Combinatorial Design Scheme", Journal of Computational Biology, 7(3-4):503-519, dol: 10.1089/106652700750050916, (2000).
(Continued)

*Primary Examiner* — Jeremy C Flinders
(74) *Attorney, Agent, or Firm* — Jeff Landes; Alston & Bird LLP

(57) ABSTRACT

Methods for selecting tag-oligonucleotide sequences for use in an in vitro nucleic acid assay. The selected tag sequences are useful for nucleic acid assay wherein interference between the nucleic acid sequences is the assay is to be controlled. Selected tag sequences are incorporated into nucleic acid assay to improve the performance of and/or minimize any interference between nucleic acids in the assay compared to untagged assays.

4 Claims, 46 Drawing Sheets

Specification includes a Sequence Listing.

Related U.S. Application Data

(60) Provisional application No. 61/451,285, filed on Mar. 10, 2011.

(56) References Cited

U.S. PATENT DOCUMENTS

| | | |
|---|---|---|
| 2003/0129659 A1 | 7/2003 | Whelihan et al. |
| 2004/0180327 A1 | 9/2004 | Ladner et al. |
| 2006/0088821 A1 | 4/2006 | Short |
| 2006/0269940 A1 | 11/2006 | Li et al. |
| 2007/0059743 A1 | 3/2007 | Alejandro et al. |
| 2008/0064610 A1 | 3/2008 | Lipovsek et al. |
| 2009/0215119 A1 | 8/2009 | Ladner |
| 2009/0280994 A1 | 11/2009 | Furste et al. |

FOREIGN PATENT DOCUMENTS

| | | |
|---|---|---|
| WO | WO 10/099378 A2 | 9/2010 |
| WO | WO 12/122571 A1 | 9/2012 |

OTHER PUBLICATIONS

Gerry et al., "Universal DNA microarray method for multiplex detection of low abundance point mutations," Journal of Molecular Biology, 292(2):251-262, (1999).
Kaderali et al., "Primer-design for multiplexed genotyping," Nucleic Acids Research, 31(6):1796-1802, (2003).
Pancoska et al., "Rational design of DNA sequences for nanotechnology, microarrays and molecular computers using Eulerian graphs," Nucleic Acids Research, 32(15):4630-4645, (2004).
Shoemaker et al., "Quantitative Phenotypic Analysis of Yeast Deletion Mutants Using a Highly Parallel Molecular Bar-Coding Strategy," Nature Genetics, 14(4):450-456, (1996).
U.S. Appl. No. 14/004,107, Final Office Action dated Aug. 3, 2016.
U.S. Appl. No. 14/004,107, Requirement for Restriction/Election dated Nov. 19, 2015.
WIPO Application No. PCT/US2012/028797, PCT International Preliminary Report on Patentability dated Sep. 10, 2013.
WIPO Application No. PCT/US2012/028797, PCT International Search Report dated Jul. 27, 2012.
WIPO Application No. PCT/US2012/028797, PCT Written Opinion of the International Searching Authority dated Jul. 27, 2012.
U.S. Appl. No. 61/451,285, filed Mar. 10, 2011.
PCT/US2012/028797, Mar. 12, 2012, WO 12/122571.
U.S. Appl. No. 14/004,107, filed Oct. 21, 2013, U.S. Pat. No. 9,512,467.

SELECTED

AGGAGGAACCGGAAGATCTAATCTG

| Seq # | Sequence (5'- 3') | Length | GC content | Tm (C) | Hairpin stabilization energy, max (dG, KCal/mol) | Self dimer stabilization energy, max (KCal/mol) |
|---|---|---|---|---|---|---|
| 25 | GTCGGAACGCCAGGTACAGTTAGCGCATCC | 30 | 60.0 | 66.7 | -2.08 | -9.89 |
| 26 | AAGTCACTGGCCAGCATAATGCGTGAAGGG | 30 | 53.3 | 65.4 | -0.76 | -16.38 |
| 27 | GTGATGCTTTATGAGATTCCGGTCTCCGAC | 30 | 50.0 | 61.7 | -2.15 | -9.75 |
| 28 | GACGGTGCATCACCCGCATTTGCTGTAGCG | 30 | 60.0 | 67.6 | -2.79 | -7.05 |
| 34 | AGAATTCTTGCAGGTAGAGGTCCCCTCATT | 30 | 46.7 | 62.2 | -2.22 | -11.71 |
| 35 | AAGCCAAAATTACAATCGATCCCTACCAAC | 30 | 40.0 | 59.1 | 1.41 | -9.71 |
| 37 | ATCTTGCACCTTCCCAGATGTAAACCCCT | 30 | 50.0 | 64.3 | 0.40 | -7.05 |
| 42 | GAAGCGGCAGCTCAGCCGGTTCTCGGAGAG | 30 | 66.7 | 69.6 | -6.97 | -9.82 |
| 43 | GCACGCGGGCTCCTTGGGACACTATGATTG | 30 | 60.0 | 67.1 | -0.10 | -10.36 |
| 61 | CCCATCAGGACAGTCAGCTGCCCACGAATT | 30 | 56.7 | 66.5 | -1.35 | -10.24 |
| 78 | CTTTAGTGCGGTAGGACCGAGACTACCGTG | 30 | 56.7 | 64.0 | -5.07 | -10.58 |
| 79 | TTATGTGCCAGCTGGGCCTAAGGCTCCGGG | 30 | 63.3 | 69.6 | -2.60 | -16.38 |
| 80 | GACTCTCCTAGGGCGTTCGTCTGGGACTGC | 30 | 63.3 | 67.3 | -0.43 | -10.30 |
| 82 | CGGAGAATACCCTCGACTGTATCATATCGT | 30 | 46.7 | 60.1 | -0.83 | -6.76 |
| 84 | TTCATCGAGGTACATTGGTGCTATTCCATT | 30 | 40.0 | 59.6 | -0.18 | -6.76 |

Not selected

FIGURE 3

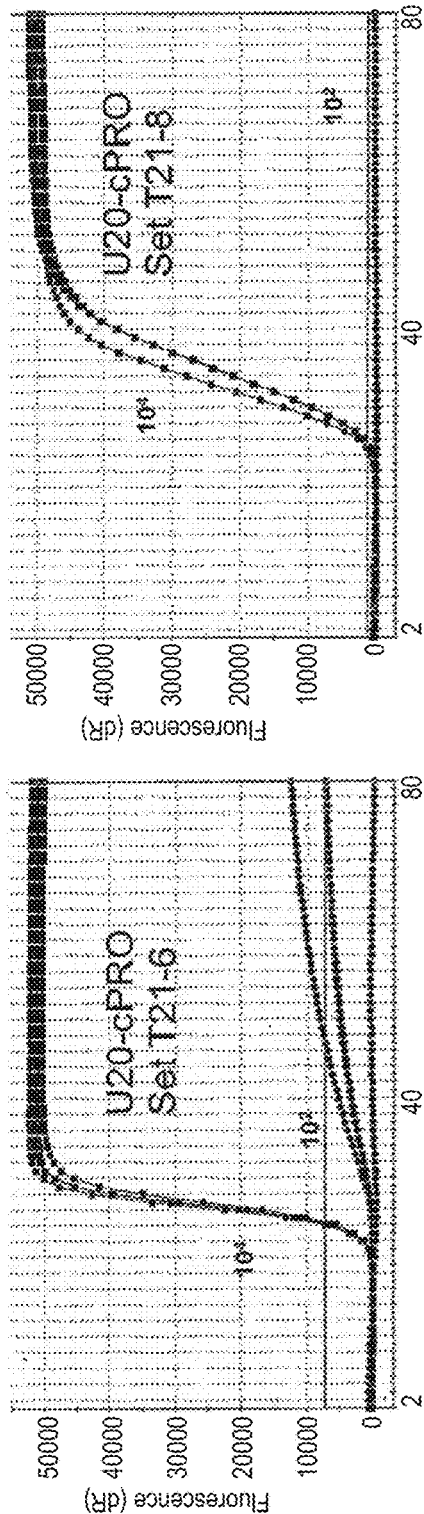
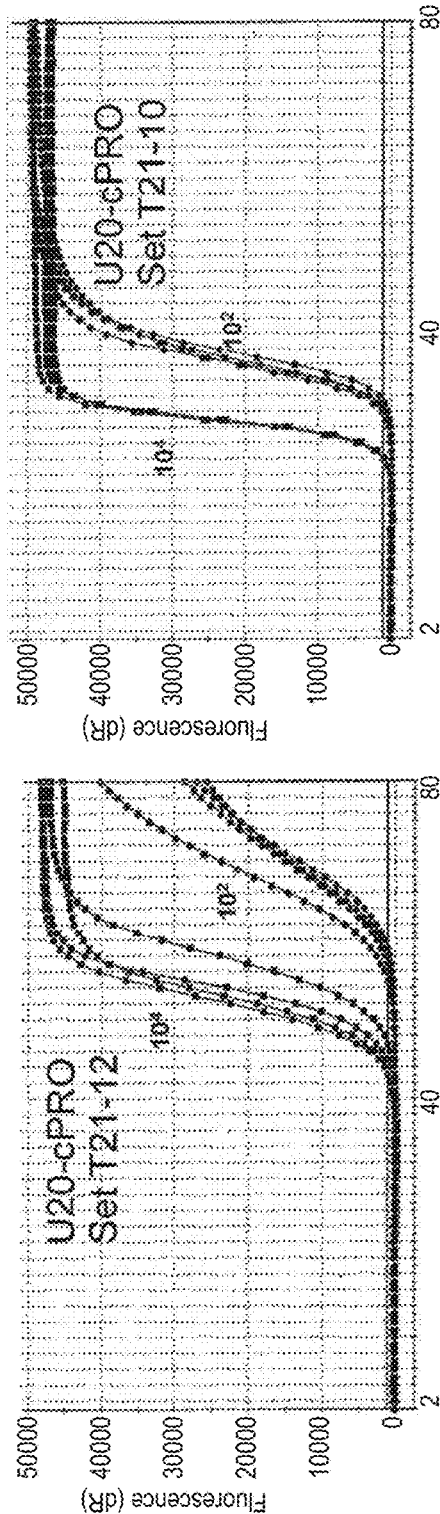
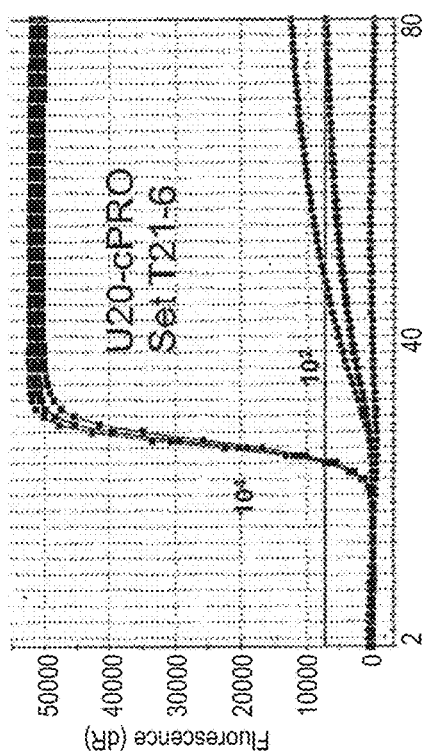
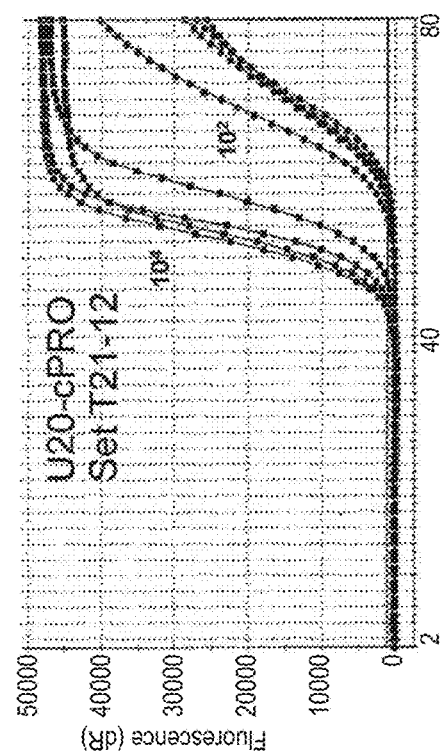
FIG. 18C
FIG. 19A
FIG. 19B
FIG. 19C

| Tag | | Uniplex | | Duplex Oligos | | Duplex Oligos and Analytes | | Analyte Interference (I-Value) | | |
|---|---|---|---|---|---|---|---|---|---|---|
| PCA3 | PSA | PCA3 | PSA | PCA3 | PSA | PCA3 | PSA | I-Value (PCA3) | I-Value (PSA) | Total I-Value |
| U20 | N216 | GOOD | GOOD | GOOD | GOOD | GOOD | GOOD | 8.45 | 9.26 | 17.71 |
| N54 | N226 | GOOD | GOOD | GOOD | GOOD | GOOD | GOOD | 10.63 | 7.1 | 17.73 |
| N54 | N216 | GOOD | GOOD | GOOD | GOOD | GOOD | GOOD | 10.31 | 9.08 | 19.39 |
| N54 | U20 | GOOD | GOOD | GOOD | GOOD | GOOD | GOOD | 12.11 | 7.86 | 19.97 |
| N54 | N209 | GOOD | GOOD | GOOD | GOOD | GOOD | GOOD | 15.57 | 4.43 | 20 |
| N54 | N207 | GOOD | GOOD | GOOD | GOOD | GOOD | GOOD | 13.66 | 6.73 | 20.39 |
| N34 | N201 | GOOD | GOOD | GOOD | GOOD | GOOD | GOOD | 8.96 | 12.24 | 21.2 |
| N14 | U20 | GOOD | GOOD | GOOD | GOOD | GOOD | GOOD | 8.25 | 13.15 | 21.4 |
| N42 | N201 | GOOD | GOOD | GOOD | GOOD | GOOD | GOOD | 16.9 | 6.78 | 23.68 |
| N14 | N216 | GOOD | GOOD | GOOD | GOOD | GOOD | GOOD | 11.77 | 12.28 | 24.05 |
| N42 | N347 | GOOD | GOOD | GOOD | WEAK | GOOD | WEAK | 2.83 | 10.33 | 13.16 |
| N34 | N347 | GOOD | GOOD | GOOD | WEAK | GOOD | WEAK | 2.99 | 12.56 | 15.55 |
| N34 | N12 | GOOD | GOOD | GOOD | WEAK | GOOD | BAD | 1.16 | 18.23 | 19.39 |
| N54 | N347 | GOOD | GOOD | GOOD | WEAK | GOOD | WEAK | 4.6 | 15.57 | 20.17 |
| N42 | N207 | GOOD | GOOD | GOOD | WEAK | GOOD | GOOD | 12.26 | 8.4 | 20.66 |
| N54 | N201 | GOOD | GOOD | GOOD | GOOD | GOOD | GOOD | 15.45 | 6.06 | 21.51 |
| N14 | N347 | GOOD | GOOD | GOOD | WEAK | GOOD | BAD | 3.99 | 17.67 | 21.66 |
| N42 | N216 | GOOD | GOOD | GOOD | WEAK | GOOD | GOOD | 13.39 | 8.63 | 22.02 |
| N34 | N201 | GOOD | GOOD | GOOD | WEAK | GOOD | WEAK | 6.1 | 16.75 | 22.85 |
| N24 | N347 | GOOD | GOOD | GOOD | BAD | GOOD | BAD | 2.17 | 21.07 | 23.24 |
| N15 | N209 | GOOD | GOOD | BAD | GOOD | WEAK | GOOD | 17.68 | 6.22 | 23.9 |
| N15 | N216 | GOOD | GOOD | WEAK | WEAK | BAD | GOOD | 19.16 | 5.51 | 24.67 |
| N42 | N209 | GOOD | GOOD | GOOD | WEAK | GOOD | GOOD | 17.47 | 7.67 | 25.14 |
| N34 | N216 | GOOD | GOOD | GOOD | WEAK | GOOD | WEAK | 5.62 | 19.59 | 25.21 |

*FIG. 27A*

| Tag | | Uniplex | | Duplex Oligos | | Duplex Oligos and Analytes | | Analyte Interference (I-Value) | | |
|---|---|---|---|---|---|---|---|---|---|---|
| PCA3 | PSA | PCA3 | PSA | PCA3 | PSA | PCA3 | PSA | I-Value (PCA3) | I-Value (PSA) | Total I-Value |
| N42 | N226 | GOOD | GOOD | GOOD | WEAK | GOOD | WEAK | 12.68 | 12.73 | 25.41 |
| N14 | N207 | GOOD | GOOD | GOOD | GOOD | GOOD | WEAK | 5.93 | 22.28 | 28.21 |
| N15 | N207 | GOOD | GOOD | GOOD | WEAK | GOOD | GOOD | 20.45 | 7.83 | 28.28 |
| N34 | N209 | GOOD | GOOD | GOOD | WEAK | GOOD | WEAK | 7.09 | 21.77 | 28.86 |
| N24 | N207 | GOOD | GOOD | BAD | GOOD | BAD | GOOD | 25.69 | 4.08 | 29.77 |
| N54 | N54 | GOOD | BAD | GOOD | BAD | GOOD | BAD | 2.12 | 30.18 | 32.3 |
| N39 | N216 | GOOD | GOOD | WEAK | GOOD | BAD | GOOD | 31.92 | 0.39 | 32.31 |
| N24 | N226 | GOOD | GOOD | BAD | WEAK | BAD | BAD | 27.76 | 4.89 | 32.65 |
| N14 | N209 | GOOD | GOOD | GOOD | GOOD | GOOD | WEAK | 15.88 | 17.17 | 33.05 |
| N14 | N201 | GOOD | GOOD | GOOD | WEAK | GOOD | BAD | 9.33 | 23.76 | 33.09 |
| N34 | N226 | GOOD | GOOD | GOOD | WEAK | GOOD | BAD | 4.77 | 30.32 | 35.09 |
| N15 | N226 | GOOD | GOOD | WEAK | BAD | WEAK | WEAK | 28.78 | 6.96 | 35.74 |
| N39 | N209 | GOOD | GOOD | WEAK | GOOD | BAD | GOOD | 36.57 | 2.92 | 39.49 |
| N14 | N226 | GOOD | GOOD | GOOD | WEAK | WEAK | BAD | 8.99 | 30.51 | 39.5 |
| N39 | N201 | GOOD | GOOD | WEAK | GOOD | BAD | GOOD | 39.22 | 1.77 | 40.99 |
| N24 | N216 | GOOD | GOOD | BAD | WEAK | BAD | WEAK | 37.99 | 3.57 | 41.56 |
| N34 | N207 | GOOD | GOOD | GOOD | WEAK | GOOD | BAD | 5.36 | 36.22 | 41.58 |
| N15 | N201 | GOOD | GOOD | WEAK | WEAK | BAD | WEAK | 41.73 | 2.35 | 44.08 |
| N39 | N226 | GOOD | GOOD | WEAK | WEAK | BAD | WEAK | 45.01 | 1.05 | 46.06 |
| N34 | N304 | GOOD | GOOD | GOOD | BAD | GOOD | BAD | 1.75 | 44.5 | 46.25 |
| N24 | N201 | GOOD | GOOD | BAD | GOOD | BAD | GOOD | 44.03 | 2.37 | 46.4 |
| N24 | N209 | GOOD | GOOD | BAD | WEAK | BAD | WEAK | 47.11 | 1.24 | 48.35 |
| N39 | N207 | GOOD | GOOD | WEAK | GOOD | BAD | GOOD | 47.07 | 2.33 | 49.4 |
| N34 | N325 | GOOD | GOOD | GOOD | WEAK | GOOD | WEAK | 1.16 | 49.16 | 50.32 |
| N34 | N15 | GOOD | GOOD | GOOD | GOOD | GOOD | BAD | 2.2 | 51.65 | 53.85 |
| U20 | U20 | GOOD | GOOD | GOOD | GOOD | BAD | BAD | 12.03 | 54.62 | 66.65 |
| U20 | N54 | GOOD | BAD | GOOD | BAD | GOOD | BAD | 0.94 | 80 | 80.94 |
| N34 | N6 | GOOD | GOOD | GOOD | BAD | GOOD | BAD | 1.26 | 80 | 81.26 |

Analyte copy levels used

| | 1 | 2 | 3 | 4 | 5 | 6 |
|---|---|---|---|---|---|---|
| PCA3 Copy | 102 | 102 | 102 | 102 | 102 | 102 |
| PSA Copy | 2914 | 8,800 | 25,483 | 78,224 | 710,238 | 6,114,911 |
| Reps | 4 | 4 | 4 | 4 | 4 | 4 |

| | 7 | 8 | 9 | 10 | 11 | 12 | 13 |
|---|---|---|---|---|---|---|---|
| PCA3 Copy | 102 | 305 | 914 | 24,691 | 74,074 | 222,222 | 666,667 |
| PSA Copy | 2914 | 2914 | 2914 | 2914 | 2914 | 2914 | 2914 |
| Reps | 4 | 4 | 2 | 2 | 4 | 4 | 4 |

*FIG. 28B*

Analyte copy levels used

| | 1 | 2 | 3 | 4 | 5 | 6 |
|---|---|---|---|---|---|---|
| PCA3 Copy | 51 | 51 | 51 | 51 | 51 | 51 |
| PSA Copy | 2914 | 8,800 | 19,556 | 710,238 | 2,116,029 | 4,615,873 |
| Reps | 4 | 4 | 4 | 4 | 4 | 4 |

| | 7 | 8 | 9 | 10 | 11 | 12 |
|---|---|---|---|---|---|---|
| PCA3 Copy | 102 | 305 | 914 | 2,743 | 222,222 | 666,667 |
| PSA Copy | 1956 | 1956 | 1956 | 1956 | 1956 | 1956 |
| Reps | 4 | 4 | 4 | 4 | 4 | 4 |

*FIG. 30*

| | T2 ERGa Amt | PSA Amt | AvgTTime | SDLogCopy | AvgCp/rxn | % Recovery |
|---|---|---|---|---|---|---|
| Cal 1 | 28 | 1,342 | 41.97 | 0.10 | 42 | 153.3% |
| Cal 2 | 107 | 2,684 | 38.18 | 0.13 | 146 | 135.9% |
| Cal 3 | 269 | 7,159 | 36.62 | 0.11 | 268 | 99.5% |
| Cal 4 | 724 | 22,672 | 34.77 | 0.14 | 633 | 87.4% |
| Cal 5 | 1,995 | 65,812 | 32.72 | 0.09 | 1,889 | 94.7% |
| Cal 6 | 6,457 | 175,240 | 30.86 | 0.08 | 6,261 | 97.0% |
| Cal 7 | 22,387 | 569,759 | 29.27 | 0.01 | 20,589 | 92.0% |
| Cal 8 | 57,544 | 2,838,579 | 27.82 | 0.09 | 74,371 | 129.2% |
| CON A | 107 | 569,759 | 41.21 | 0.06 | 52 | 48.5% |
| CON B | 107 | 65,812 | 39.13 | 0.10 | 101 | 94.5% |
| CON C | 107 | 22,672 | 39.98 | 0.09 | 76 | 71.2% |
| CON D | 107 | 7,159 | 37.92 | 0.06 | 156 | 145.3% |
| CON H | 724 | 2,684 | 33.82 | 0.09 | 1,123 | 155.0% |
| CON I | 1,995 | 569,759 | 33.85 | 0.13 | 1,015 | 50.9% |
| CON G | 1,995 | 2,684 | 32.05 | 0.05 | 2,803 | 140.5% |
| CON J | 6,457 | 569,759 | 31.24 | 0.06 | 4,771 | 73.9% |
| CON F | 6,457 | 2,684 | 30.27 | 0.05 | 9,466 | 146.6% |
| CON E | 22,387 | 2,684 | 29.00 | 0.07 | 25,854 | 115.5% |

Quantitation of PSA

| | PSA Amt | T2 ERGa Amt | AvgTTime | SDLogCopy | AvgCp/rxn | % Recovery |
|---|---|---|---|---|---|---|
| Cal 1 | 1,349 | 27 | 39.16 | 0.11 | 1,592 | 118.0% |
| Cal 2 | 2,692 | 105 | 37.86 | 0.10 | 2,854 | 106.0% |
| Cal 3 | 7,244 | 268 | 35.55 | 0.06 | 8,557 | 118.1% |
| Cal 4 | 22,909 | 721 | 33.81 | 0.12 | 21,882 | 95.5% |
| Cal 5 | 66,069 | 1,976 | 31.91 | 0.10 | 63,788 | 96.5% |
| Cal 6 | 177,828 | 6,431 | 30.23 | 0.07 | 179,493 | 100.9% |
| Cal 7 | 575,440 | 22,005 | 28.59 | 0.05 | 534,398 | 92.9% |
| Cal 8 | 2,884,032 | 57,459 | 26.18 | 0.11 | 3,239,235 | 112.3% |
| CON E | 2,692 | 22,005 | 39.83 | 0.11 | 1,200 | 44.6% |
| CON F | 2,692 | 6,431 | 38.59 | 0.10 | 2,041 | 75.8% |
| CON G | 2,692 | 1,976 | 38.20 | 0.11 | 2,453 | 91.1% |
| CON H | 2,692 | 721 | 37.62 | 0.04 | 3,132 | 116.4% |
| CON D | 7,244 | 105 | 35.38 | 0.02 | 9,284 | 128.2% |
| CON C | 22,909 | 105 | 33.88 | 0.12 | 20,952 | 91.5% |
| CON B | 66,069 | 105 | 32.16 | 0.01 | 54,049 | 81.8% |
| CON J | 575,440 | 6,431 | 28.24 | 0.04 | 681,960 | 118.5% |
| CON I | 575,440 | 1,976 | 28.23 | 0.05 | 685,148 | 119.1% |
| CON A | 575,440 | 105 | 28.60 | 0.03 | 527,394 | 91.7% |

Quantitation of T2 ERG

| | T2 ERGa Amt | PSA Amt | AvgTTime | SDLogCopy | AvgCp/rxn | % Recovery |
|---|---|---|---|---|---|---|
| Cal 1 | 28 | 1,342 | 42.91 | 0.09 | 21 | 76.0% |
| Cal 2 | 107 | 2,684 | 38.28 | 0.15 | 134 | 124.6% |
| Cal 3 | 269 | 7,159 | 36.66 | 0.14 | 283 | 105.2% |
| Cal 4 | 724 | 22,672 | 34.31 | 0.03 | 911 | 125.7% |
| Cal 5 | 1,995 | 65,812 | 32.48 | 0.12 | 2,665 | 133.6% |
| Cal 6 | 6,457 | 175,240 | 30.60 | 0.07 | 8,575 | 132.8% |
| Cal 7 | 22,387 | 569,759 | 29.40 | 0.04 | 19,439 | 86.8% |
| Cal 8 | 57,544 | 2,838,579 | 27.84 | 0.12 | 62,752 | 109.1% |
| CON A | 107 | 569,759 | 44.11 | 0.11 | 14 | 13.0% |
| CON B | 107 | 65,812 | 40.23 | 0.19 | 61 | 56.7% |
| CON C | 107 | 22,672 | 38.64 | 0.15 | 114 | 106.8% |
| CON F | 724 | 2,684 | 34.16 | 0.04 | 991 | 136.8% |
| CON E | 1,995 | 2,684 | 32.60 | 0.09 | 2,460 | 123.3% |
| CON G | 1,995 | 569,759 | 34.07 | 0.10 | 1,060 | 53.1% |
| CON H | 6,457 | 569,759 | 31.42 | 0.06 | 5,053 | 78.3% |
| CON D | 6,607 | 2,684 | 30.75 | 0.06 | 7,745 | 117.2% |
| CON I | 22,387 | 569,759 | 29.36 | 0.01 | 19,883 | 88.8% |

*FIG. 36A*

Quantitation of PSA

| | PSA Amt | T2 ERGa Amt | AvgTTime | SDLogCopy | AvgCp/rxn | % Recovery |
|---|---|---|---|---|---|---|
| Cal 1 | 1,349 | 27 | 44.99 | 0.07 | 1,065 | 78.9% |
| Cal 2 | 2,692 | 105 | 41.40 | 0.10 | 4,652 | 172.8% |
| Cal 3 | 7,244 | 268 | 40.85 | 0.04 | 5,816 | 80.3% |
| Cal 4 | 22,909 | 721 | 37.41 | 0.07 | 27,771 | 121.2% |
| Cal 5 | 66,069 | 1,976 | 35.59 | 0.02 | 66,251 | 100.3% |
| Cal 6 | 177,828 | 6,431 | 33.12 | 0.06 | 234,046 | 131.6% |
| Cal 7 | 575,440 | 22,005 | 31.70 | 0.02 | 495,718 | 86.1% |
| Cal 8 | 2,884,032 | 57,459 | 28.40 | 0.04 | 3,191,365 | 110.7% |
| CON D | 2,692 | 6,457 | 45.43 | 0.08 | 899 | 33.4% |
| CON E | 2,692 | 1,976 | 42.82 | 0.04 | 2,523 | 93.7% |
| CON F | 2,692 | 721 | 41.58 | 0.08 | 4,296 | 159.6% |
| CON C | 22,909 | 105 | 37.11 | 0.08 | 32,176 | 140.5% |
| CON B | 66,069 | 105 | 34.84 | 0.06 | 97,000 | 146.8% |
| CON A | 575,440 | 105 | 31.13 | 0.06 | 682,025 | 118.5% |
| CON G | 575,440 | 1,976 | 30.75 | 0.04 | 838,023 | 145.6% |
| CON H | 575,440 | 6,431 | 30.84 | 0.04 | 890,572 | 154.8% |

FIG. 36B

Quantitation of T2 ERG (N347/N15/N42)

| | T2 ERGa Amt | PSA Amt | # Reps | AvgTTime | SDTTime | SDLogCopy | AvgCp/rxn (T2) | % Recovery |
|---|---|---|---|---|---|---|---|---|
| Cal 1 | 32 | 2,303 | 4 | 36.69 | 0.75 | 0.18 | 74 | 234.4% |
| Cal 2 | 123 | 4,606 | 4 | 36.80 | 0.79 | 0.20 | 70 | 56.6% |
| Cal 3 | 331 | 12,866 | 4 | 33.18 | 1.12 | 0.29 | 589 | 177.8% |
| Cal 4 | 1,090 | 39,084 | 4 | 32.77 | 0.49 | 0.13 | 653 | 65.3% |
| Cal 5 | 2,818 | 140,739 | 4 | 31.04 | 0.46 | 0.15 | 2,050 | 72.7% |
| Cal 6 | 9,120 | 341,221 | 4 | 29.63 | 0.35 | 0.13 | 6,234 | 68.4% |
| Cal 7 | 26,815 | 921,031 | 4 | 28.35 | 0.16 | 0.08 | 22,354 | 83.1% |
| Cal 8 | 69,183 | 4,857,228 | 4 | 27.27 | 0.03 | 0.02 | 96,632 | 139.7% |
| HDQ 1258 | 1,660 | 1,620,281 | 2 | 33.58 | 0.03 | 0.01 | 393 | 23.7% |
| HDQ 1431 | 153 | 1,434,570 | 2 | 38.04 | 3.02 | 1.00 | 56 | 36.7% |
| HDQ 1434 | 673 | 889,305 | 2 | 35.41 | 0.08 | 0.02 | 143 | 21.2% |
| HDQ 1438 | 1,503 | 1,130,997 | 2 | 30.43 | 0.61 | 0.21 | 3,305 | 219.9% |
| HDQ 1440 | 201 | 730,072 | 2 | 35.75 | 1.30 | 0.31 | 133 | 66.1% |
| HDQ 1441 | 224 | 735,541 | 2 | 37.93 | 0.21 | 0.06 | 34 | 15.0% |
| HDQ 1507 | 366 | 891,081 | 2 | 31.93 | 0.71 | 0.20 | 1,130 | 308.6% |
| HDQ 1517 | 219 | 799,189 | 2 | 34.50 | 1.70 | 0.41 | 291 | 132.8% |
| HDQ 1525 | 4,379 | 1,223,868 | 2 | 31.76 | 0.23 | 0.06 | 1,202 | 27.4% |
| HDQ 1551 | 106 | 980,947 | 2 | 42.29 | 1.00 | #DIV/0! | #DIV/0! | #DIV/0! |
| HDQ 1577 | 93 | 1,150,851 | 2 | 37.10 | 1.99 | 0.51 | 72 | 77.4% |
| HDQ 1598 | 693 | 1,006,485 | 2 | 35.93 | 0.65 | 0.16 | 110 | 15.9% |
| HDQ 1605 | 438 | 653,872 | 2 | 36.12 | 0.94 | 0.23 | 103 | 23.4% |
| HDQ 1637 | 77 | 320,222 | 2 | 38.84 | 1.72 | 0.64 | 23 | 29.7% |
| HDQ 1653 | 67 | 611,260 | 1 | 39.67 | 1.99 | #DIV/0! | 27 | 40.2% |

*FIG. 38A*

Quantitation of PSA

| | T2 ERGa Amt | PSA Amt | # Reps | AvgTTime | SDTTime | SDLogCopy | AvgCp/rxn (PSA) | % Recovery |
|---|---|---|---|---|---|---|---|---|
| Cal 1 | 31 | 2,344 | 4 | 36.5 | 0.65 | 0.12 | 2,030 | 66.6% |
| Cal 2 | 121 | 4,677 | 4 | 34.4 | 0.19 | 0.04 | 5,218 | 111.6% |
| Cal 3 | 324 | 12,882 | 4 | 32.1 | 0.49 | 0.12 | 18,976 | 147.3% |
| Cal 4 | 984 | 39,811 | 3 | 31.3 | 0.31 | 0.08 | 28,357 | 71.2% |
| Cal 5 | 2,761 | 141,254 | 3 | 28.9 | 0.57 | 0.17 | 144,778 | 102.5% |
| Cal 6 | 9,029 | 346,737 | 4 | 27.9 | 0.26 | 0.08 | 287,942 | 83.0% |
| Cal 7 | 26,548 | 933,254 | 4 | 26.5 | 0.23 | 0.08 | 810,770 | 86.9% |
| Cal 8 | 68,199 | 4,887,789 | 4 | 24.0 | 0.02 | 0.01 | 6,863,434 | 140.1% |
| HDQ 1258 | 1,660 | 1,620,281 | 2 | 25.7 | 0.20 | 0.07 | 1,583,367 | 97.7% |
| HDQ 1431 | 153 | 1,434,570 | 2 | 24.4 | 0.44 | 0.17 | 4,914,130 | 342.6% |
| HDQ 1434 | 673 | 889,305 | 2 | 24.9 | 0.42 | 0.16 | 3,331,257 | 374.6% |
| HDQ 1438 | 1,503 | 1,130,997 | 2 | 22.4 | 0.45 | 0.20 | 34,793,856 | 3076.4% |
| HDQ 1440 | 201 | 730,072 | 2 | 25.3 | 0.02 | 0.01 | 2,183,193 | 299.0% |
| HDQ 1441 | 224 | 735,541 | 2 | 25.2 | 0.32 | 0.12 | 2,349,614 | 319.4% |
| HDQ 1507 | 366 | 891,081 | 2 | 24.2 | 0.01 | 0.00 | 5,683,148 | 637.8% |
| HDQ 1517 | 219 | 799,169 | 2 | 24.9 | 0.02 | 0.01 | 3,050,949 | 381.8% |
| HDQ 1525 | 4,379 | 1,223,868 | 2 | 24.8 | 0.39 | 0.15 | 3,510,249 | 286.8% |
| HDQ 1551 | 106 | 980,947 | 2 | 26.0 | 0.75 | 0.27 | 1,335,302 | 136.1% |
| HDQ 1577 | 93 | 1,150,951 | 2 | 25.3 | 0.03 | 0.01 | 2,179,347 | 188.6% |
| HDQ 1598 | 693 | 1,006,485 | 2 | 26.9 | 0.06 | 0.02 | 566,413 | 56.3% |
| HDQ 1605 | 438 | 653,872 | 2 | 27.0 | 0.03 | 0.01 | 547,809 | 83.8% |
| HDQ 1637 | 77 | 320,222 | 2 | 27.6 | 0.52 | 0.17 | 357,053 | 111.5% |
| HDQ 1653 | 67 | 611,250 | 2 | 27.7 | 0.71 | 0.23 | 342,169 | 56.0% |

*FIG. 38B*

SEQUENCE LISTING

<160> NUMBER OF SEQ ID NOS: 409

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide Sequence

<400> SEQUENCE: 1
gtcatatgcg acgatctcag                                              20

<210> SEQ ID NO 2
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 2
ccccgtcaaa caaaaacggg agcgtgtacc                                   30

<210> SEQ ID NO 3
<211> LENGTH: 30

<212> TYPE: DNA
<213> ORGANISM: Artificial Sequence
<220> FEATURE:
<223> OTHER INFORMATION: Synthetic Oligonucleotide Sequence

<400> SEQUENCE: 3
ccataggcct tctgcactgc tccatatacc         30

<210> SEQ ID NO 4
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 4
gtccccatcg gagggcatct tatcgtgcct         30

<210> SEQ ID NO 5
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 5
ccgccctcct tcgcccccccg gtgaaataac         30

<210> SEQ ID NO 6
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 6
aatgctcacc tctattcggg acttgagtac         30

<210> SEQ ID NO 7
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 7
cccgcgcacc acctccatca cgcagaagag         30

<210> SEQ ID NO 8
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 8
gtcggaacgc caggtacagt tagcgcatcc         30

<210> SEQ ID NO 9
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 9
aagtcactgg ccagcataat gcgtgaaggg    30

<210> SEQ ID NO 10
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 10
gtgatgcttt atgagattcc ggtctccgac    30

<210> SEQ ID NO 11
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 11
gacggtgcat cacccgcatt tgctgtagcg    30

<210> SEQ ID NO 12
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 12
agaattcttg caggtagagg tcccctcatt    30

<210> SEQ ID NO 13
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 13
aagccaaaat tacaatcgat ccctaccaac    30

<210> SEQ ID NO 14
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 14
atcttgcacc ttcccagatg taaaccccct    30

<210> SEQ ID NO 15
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 15
gaagcggcag ctcagccggt tctcggagag    30

<210> SEQ ID NO 16
<211> LENGTH: 30
<212> TYPE: DNA
<213> ORGANISM: Artificial Sequence

```
<220> FEATURE:
<223> OTHER INFORMATION: Synthetic Oligonucleotide Sequence

<400> SEQUENCE: 16
gcacgcgggc tccttgggac actatgattg                                  30

<210> SEQ ID NO 17
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 17
cccatcagga cagtcagctg cccacgaatt                                  30

<210> SEQ ID NO 18
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 18
ctttagtgcg gtaggaccga gactaccgtg                                  30

<210> SEQ ID NO 19
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 19
ttatgtgcca gctgggccta aggctccggg                                  30

<210> SEQ ID NO 20
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 20
gactctccta gggcgttcgt ctgggactgc                                  30

<210> SEQ ID NO 21
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 21
cggagaatac cctcgactgt atcatatcgt                                  30

<210> SEQ ID NO 22
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 22
ttcatcgagg tacattggtg ctattccatt                                  30
```

<210> SEQ ID NO 23
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 23
taccacctgg ttcaaggtgt gccgtacgcg                                30

<210> SEQ ID NO 24
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 24
aggagaacca gcctggagcg tttaagcatc                                30

<210> SEQ ID NO 25
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 25
gatgtcctaa aatgaggcgt ggcaatagag                                30

<210> SEQ ID NO 26
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 26
cagagtcatg tatcccact gtcggtcgaa                                 30

<210> SEQ ID NO 27
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 27
gtcaggctag ggggttatcc cagcaacggc                                30

<210> SEQ ID NO 28
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 28
tgggttctgc taaccggtgc cgttcttaac                                30

<210> SEQ ID NO 29
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 29
tttttgacag tgatgaagag ggaggtacga                                       30

<210> SEQ ID NO 30
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 30
gagaactcgc gctccctcac tccgtttaga                                       30

<210> SEQ ID NO 31
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 31
ctatggttcg ttactgaatc gaaaagccgc                                       30

<210> SEQ ID NO 32
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 32
tagctatcaa aacaggcgtc atcggttaag                                       30

<210> SEQ ID NO 33
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 33
aggacgctga caccgttggg gtaaagcgtg                                       30

<210> SEQ ID NO 34
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 34
cctgcttagg gtcacttaaa ctactggcgc                                       30

<210> SEQ ID NO 35
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 35
ggtgatggcc cataccgatc acgcccgcag                                       30

<210> SEQ ID NO 36

```
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 36
cggcaggagg gactgcgatt tccatagagc                                     30

<210> SEQ ID NO 37
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 37
tggccggaga gaggatagga agcgggacta                                     30

<210> SEQ ID NO 38
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 38
tagcaggtgt ctcggtcctc aactgcaaac                                     30

<210> SEQ ID NO 39
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 39
acacatccca ggactgccgt ggcctacgta                                     30

<210> SEQ ID NO 40
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 40
gtgctagccc gggcccttct taactcggga                                     30

<210> SEQ ID NO 41
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 41
cggaatctga acatctatca gagccgcgct                                     30

<210> SEQ ID NO 42
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 42
```
gacgagcttg ttccaattcc tcgagccgag                                          30

<210> SEQ ID NO 43
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 43
gttggggagg ggcactacga cttagggcta                                          30

<210> SEQ ID NO 44
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 44
aatgtggacg gccgctccgt acttctgaca                                          30

<210> SEQ ID NO 45
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 45
agggccagca gctggttcct tcgccagtta                                          30

<210> SEQ ID NO 46
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 46
ggccgtcaat gtgttttgca cccaaccgga                                          30

<210> SEQ ID NO 47
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 47
cagtgactgg gctagtgaag tgagtcacag                                          30

<210> SEQ ID NO 48
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 48
tcccacgtcc ttcgacgcac actgtaactt                                          30

<210> SEQ ID NO 49
<211> LENGTH: 25
<212> TYPE: DNA

<213> ORGANISM: Artificial Sequence
<220> FEATURE:
<223> OTHER INFORMATION: Synthetic Oligonucleotide Sequence

<400> SEQUENCE: 49
tcatgtatcg cccgtgggta agctc  25

<210> SEQ ID NO 50
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 50
atgttatgga gagtgggtta ggcaa  25

<210> SEQ ID NO 51
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 51
atgagggagt aaggagatta ggttc  25

<210> SEQ ID NO 52
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 52
catgctgccc gcatacactt gcggg  25

<210> SEQ ID NO 53
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 53
gcccagcagt tatacaattc gtggc  25

<210> SEQ ID NO 54
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 54
ttgggctctc cagtagccga acaaa  25

<210> SEQ ID NO 55
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 55
tgacgttaaa cgcaatccgc gtaaa  25

<210> SEQ ID NO 56
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 56
gtcgccattc aggacacgcg aaact                                    25

<210> SEQ ID NO 57
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 57
gtggttgcta cagcctagcc tagat                                    25

<210> SEQ ID NO 58
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 58 ccactttca ttccgagtcc acgcg                                     25

<210> SEQ ID NO 59
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 59
aggaggaacc ggaagatcta atctg                                    25

<210> SEQ ID NO 60
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 60
ccaatgcttt caaataaccc gttct                                    25

<210> SEQ ID NO 61
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 61
gcgactgtgg caaccccatt tcgca                                    25

<210> SEQ ID NO 62
<211> LENGTH: 25
<212> TYPE: DNA
<213> ORGANISM: Artificial Sequence
<220> FEATURE:

<223> OTHER INFORMATION: Synthetic Oligonucleotide Sequence

<400> SEQUENCE: 62
aaaaaacgga ggagtcgaac cttgg                                          25

<210> SEQ ID NO 63
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 63
agttggatgg atatctcgct cgtga                                          25

<210> SEQ ID NO 64
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 64
cgctgtcctc tctgacacta aaggt                                          25

<210> SEQ ID NO 65
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 65
atttcaatag tcaacccggt atcca                                          25

<210> SEQ ID NO 66
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 66
ttcgcgccag cgaccccact tatga                                          25

<210> SEQ ID NO 67
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 67
ggttgggggg ctcggctcat gtatc                                          25

<210> SEQ ID NO 68
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 68
atgatgctga atcgcgatgg ggggg                                          25

```
<210> SEQ ID NO 69
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 69
taaggagact aggttccaat agctg                                           25

<210> SEQ ID NO 70
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 70
ttacacaaat cgtgggttgg cctct                                           25

<210> SEQ ID NO 71
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 71
cgaaagcgtt ccgcaggacc ccctt                                           25

<210> SEQ ID NO 72
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 72
cacccttgga cacgtggaag tgggc                                           25

<210> SEQ ID NO 73
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 73
aaagtctgag aatgagtgat accat                                           25

<210> SEQ ID NO 74
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 74
atattggtag ttttgtccgc tgtag                                           25

<210> SEQ ID NO 75
<211> LENGTH: 25
<212> TYPE: DNA
<213> ORGANISM: Artificial Sequence
<220> FEATURE:
<223> OTHER INFORMATION: Synthetic Oligonucleotide Sequence
```

```
<400> SEQUENCE: 75
cggaagatct aatctgcacg caatt                                              25

<210> SEQ ID NO 76
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 76
gcgcctcgtt gggcagaagt ttgtggaaat                                         30

<210> SEQ ID NO 77
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 77
atcttcacct accgagttct acgggcctac                                         30

<210> SEQ ID NO 78
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 78
cccacaactt gcacccgcta tgcgaccctg                                         30

<210> SEQ ID NO 79
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 79
gcccaggagc tctcctgggt aacagtagcg                                         30

<210> SEQ ID NO 80
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 80
cacggccccc aggcggcgta tcagggatga                                         30

<210> SEQ ID NO 81
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 81
tccccggcac ggaccgcaag ggaccaaagc                                         30

<210> SEQ ID NO 82
<211> LENGTH: 30
```

```
<212> TYPE: DNA
<213> ORGANISM: Artificial Sequence
<220> FEATURE:
<223> OTHER INFORMATION: Synthetic Oligonucleotide Sequence

<400> SEQUENCE: 82
gattagtggc ccaacgggaa caaacttcct                                      30

<210> SEQ ID NO 83
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 83
cgcccgtccc agacccttac tcactatgga                                      30

<210> SEQ ID NO 84
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 84
gctacacgcc agaggcgccg ctacagcgat                                      30

<210> SEQ ID NO 85
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 85
gagattgtac cctacagtcc gattaccgat                                      30

<210> SEQ ID NO 86
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 86
cgcagtaaaa gggcacaggt aattacctta                                      30

<210> SEQ ID NO 87
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 87
agggtgtctt gaactactgg cgcagcccat                                      30

<210> SEQ ID NO 88
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 88
```
ccgcaatccg gtgacggccg gaccggcagg                                        30

<210> SEQ ID NO 89
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 89
tcggcggcgg gtagtcagtt cgctacctgg                                        30

<210> SEQ ID NO 90
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 90
ccaggactgc cgtggcccac gcactcacga                                        30

<210> SEQ ID NO 91
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 91
ttgacgcagg cccccggggc gacttcatac                                        30

<210> SEQ ID NO 92
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 92
cgaaaggagt tcgagtgtat ccggaaggcg                                        30

<210> SEQ ID NO 93
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 93
aggcgcactg cgacttaggg ctagccccccc                                       30

<210> SEQ ID NO 94
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 94
gatgtgatct ggaccctacg ggaggggaca                                        30

<210> SEQ ID NO 95
<211> LENGTH: 30
<212> TYPE: DNA
<213> ORGANISM: Artificial Sequence

```
<220> FEATURE:
<223> OTHER INFORMATION: Synthetic Oligonucleotide Sequence

<400> SEQUENCE: 95
tgggctgggg gagtgagtcg ctcccgcagc                                    30

<210> SEQ ID NO 96
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 96
agtcccagat atgagagaag cgaagcataa                                    30

<210> SEQ ID NO 97
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 97
cgtttcagca tcgatgtcct aaaat                                         25

<210> SEQ ID NO 98
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 98
actattacac cacgtaccgt aggtc                                         25

<210> SEQ ID NO 99
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 99
gggcaacacc gcgagctaat tatcc                                         25

<210> SEQ ID NO 100
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 100
gcgcgcggcc gagaatcgtt ggagg                                         25

<210> SEQ ID NO 101
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 101
cgcgtcgggc tttcgtctac cctgg                                         25
```

```
<210> SEQ ID NO 102
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 102
gggcggccac cgggggaccc tgccc                                    25

<210> SEQ ID NO 103
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 103
tggctaatcc cg                                                  12

<210> SEQ ID NO 104
<211> LENGTH: 16
<212> TYPE: DNA
<213> ORGANISM: Artificial Sequence
<220> FEATURE:
<223> OTHER INFORMATION: Synthetic Oligonucleotide Sequence

<400> SEQUENCE: 104
gcgttggcta atcccg                                              16

<210> SEQ ID NO 105
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 105
ctgtgctaga gg                                                  12

<210> SEQ ID NO 106
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 106
catgtaccaa cg                                                  12

<210> SEQ ID NO 107
<211> LENGTH: 16
<212> TYPE: DNA
<213> ORGANISM: Artificial Sequence
<220> FEATURE:
<223> OTHER INFORMATION: Synthetic Oligonucleotide Sequence

<400> SEQUENCE: 107
tcaccatgta ccaacg                                              16

<210> SEQ ID NO 108
<211> LENGTH: 12
<212> TYPE: DNA
<213> ORGANISM: Artificial Sequence
<220> FEATURE:
<223> OTHER INFORMATION: Synthetic Oligonucleotide Sequence
```

<400> SEQUENCE: 108
tcggtcggac ta          12

<210> SEQ ID NO 109
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 109
cctcccccaa gc          12

<210> SEQ ID NO 110
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 110
gggtttgcta cg          12

<210> SEQ ID NO 111
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 111
atgtgcgcac aa          12

<210> SEQ ID NO 112
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 112
cgggactaga ga          12

<210> SEQ ID NO 113
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 113
aatctccgag cg          12

<210> SEQ ID NO 114
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 114
aagtgcaggt tc          12

<210> SEQ ID NO 115

```
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 115
tccagtttaa cc                                                         12

<210> SEQ ID NO 116
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 116
tagccgcaca gg                                                         12

<210> SEQ ID NO 117
<211> LENGTH: 18
<212> TYPE: DNA
<213> ORGANISM: Artificial Sequence
<220> FEATURE:
<223> OTHER INFORMATION: Synthetic Oligonucleotide Sequence

<400> SEQUENCE: 117
tatgaatgcg acccggaa                                                   18

<210> SEQ ID NO 118
<211> LENGTH: 18
<212> TYPE: DNA
<213> ORGANISM: Artificial Sequence
<220> FEATURE:
<223> OTHER INFORMATION: Synthetic Oligonucleotide Sequence

<400> SEQUENCE: 118
aacaatggtc actgcatc                                                   18

<210> SEQ ID NO 119
<211> LENGTH: 20
<212> TYPE: DNA
<213> ORGANISM: Artificial Sequence
<220> FEATURE:
<223> OTHER INFORMATION: Synthetic Oligonucleotide Sequence

<400> SEQUENCE: 119
gggccgtttc ccggacataa                                                 20

<210> SEQ ID NO 120
<211> LENGTH: 20
<212> TYPE: DNA
<213> ORGANISM: Artificial Sequence
<220> FEATURE:
<223> OTHER INFORMATION: Synthetic Oligonucleotide Sequence

<400> SEQUENCE: 120
aggttgagtc cgcatctgaa                                                 20

<210> SEQ ID NO 121
<211> LENGTH: 22
<212> TYPE: DNA
<213> ORGANISM: Artificial Sequence
<220> FEATURE:
<223> OTHER INFORMATION: Synthetic Oligonucleotide Sequence

<400> SEQUENCE: 121
```
tcgaccaaga gccgctagat gc                                              22

<210> SEQ ID NO 122
<211> LENGTH: 22
<212> TYPE: DNA
<213> ORGANISM: Artificial Sequence
<220> FEATURE:
<223> OTHER INFORMATION: Synthetic Oligonucleotide Sequence

<400> SEQUENCE: 122
agctcgtgtc aagccgtcgc ct                                              22

<210> SEQ ID NO 123
<211> LENGTH: 24
<212> TYPE: DNA
<213> ORGANISM: Artificial Sequence
<220> FEATURE:
<223> OTHER INFORMATION: Synthetic Oligonucleotide Sequence

<400> SEQUENCE: 123
tgaaagagtt gtcagtttgc tggt                                            24

<210> SEQ ID NO 124
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 124
tcaggtaaag gttcctcacg ctacc                                           25

<210> SEQ ID NO 125
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 125
cccataactt ggtgcgaata cgggt                                           25

<210> SEQ ID NO 126
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 126
cgtagcaatg ttcgtctgac tatga                                           25

<210> SEQ ID NO 127
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 127
caactacggg gattcttgga gagcc                                           25

<210> SEQ ID NO 128
<211> LENGTH: 25
<212> TYPE: DNA

-continued

<213> ORGANISM: Artificial Sequence
<220> FEATURE:
<223> OTHER INFORMATION: Synthetic Oligonucleotide Sequence

<400> SEQUENCE: 128
gtgtagtatt agcaaacgat aagtc                                    25

<210> SEQ ID NO 129
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 129
cgggggctgg gaatctgtga catga                                    25

<210> SEQ ID NO 130
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 130
tgcctgtcga tccataggac tcgtg                                    25

<210> SEQ ID NO 131
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 131
gaaatgtccg gggccaaaga caacc                                    25

<210> SEQ ID NO 132
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 132
ctgacatagt atagcataga tattg                                    25

<210> SEQ ID NO 133
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 133
gaatttatag atactgccaa tctag                                    25

<210> SEQ ID NO 134
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 134
atcagttgga cagagggctg tgtta                                    25

<210> SEQ ID NO 135
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 135
cttctagaga agaagagtac tgact                                   25

<210> SEQ ID NO 136
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 136
ggttcagttg taaccatata cttac                                   25

<210> SEQ ID NO 137
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 137
aatgacgtag ctatgtattt tgcac                                   25

<210> SEQ ID NO 138
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 138
aggtagccaa cgggtttcac atttc                                   25

<210> SEQ ID NO 139
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 139
gcgtaaacta cgatggcacc tactc                                   25

<210> SEQ ID NO 140
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 140
ctcataactt ggtgcgaata cgggt                                   25

<210> SEQ ID NO 141
<211> LENGTH: 25
<212> TYPE: DNA
<213> ORGANISM: Artificial Sequence
<220> FEATURE:

<223> OTHER INFORMATION: Synthetic Oligonucleotide Sequence

<400> SEQUENCE: 141
tgtagcaatg ttcgtctgac tatga        25

<210> SEQ ID NO 142
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 142
taaaatagta cagctactgg tgatc        25

<210> SEQ ID NO 143
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 143
caactacgag gatttttaga gagcc        25

<210> SEQ ID NO 144
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 144
atgtagtatt agcaaacaat aagtc        25

<210> SEQ ID NO 145
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 145
aattgaatgg agtctgatca atctt        25

<210> SEQ ID NO 146
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 146
gaagttggag gattaacgtg ggaat        25

<210> SEQ ID NO 147
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 147
ggtttactat tgtctctaat gggag        25

```
<210> SEQ ID NO 148
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 148
ttgacatagt atagcataga tattg                                              25

<210> SEQ ID NO 149
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 149
cagataactt acctacattg aaagt                                              25

<210> SEQ ID NO 150
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 150
tatagacgac tattccgact agcaa                                              25

<210> SEQ ID NO 151
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 151
gaatttatag atactaccaa tctag                                              25

<210> SEQ ID NO 152
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 152
attaattgga cagagggctg tgtta                                              25

<210> SEQ ID NO 153
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 153
ctgttgccac tctttagaaa gatta                                              25

<210> SEQ ID NO 154
<211> LENGTH: 25
<212> TYPE: DNA
<213> ORGANISM: Artificial Sequence
<220> FEATURE:
<223> OTHER INFORMATION: Synthetic Oligonucleotide Sequence
```

<400> SEQUENCE: 154
actacaataa taccaactat ttgcc                                              25

<210> SEQ ID NO 155
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 155
gatactaaat aacaacttag ttttt                                              25

<210> SEQ ID NO 156
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 156
tagatttcat tccgagtcca catgt                                              25

<210> SEQ ID NO 157
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 157
aactctaata taagatatca agtta                                              25

<210> SEQ ID NO 158
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 158
attgttaaag tagactaatt atcta                                              25

<210> SEQ ID NO 159
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 159
gaaggaactg gaagatttaa tttgc                                              25

<210> SEQ ID NO 160
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 160
acgcaattaa tatacatatt tatac                                              25

<210> SEQ ID NO 161
<211> LENGTH: 25

```
<212> TYPE: DNA
<213> ORGANISM: Artificial Sequence
<220> FEATURE:
<223> OTHER INFORMATION: Synthetic Oligonucleotide Sequence

<400> SEQUENCE: 161
caattatgcg aattccattt cacat                                              25

<210> SEQ ID NO 162
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 162
cttatgagat gttagatata gtatt                                              25

<210> SEQ ID NO 163
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 163
cttttacaat atcagacttt agcaa                                              25

<210> SEQ ID NO 164
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 164
gatgtagacg gattccatag aattt                                              25

<210> SEQ ID NO 165
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 165
aatgattgtg tggagtacaa accaa                                              25

<210> SEQ ID NO 166
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 166 ttttttggc gtaaagtcta gagtt                                               25

<210> SEQ ID NO 167
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 167
```

```
atcacgtaag accactgtta gtata                                           25

<210> SEQ ID NO 168
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 168
ctttaatagt caaaccgata tccat                                           25

<210> SEQ ID NO 169
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 169
cagtcaagtg atggactcta acaca                                           25

<210> SEQ ID NO 170
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 170
tcattagcgg aaaaaactga ccttc                                           25

<210> SEQ ID NO 171
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 171
ctcctatcct tcgccacaac tttag                                           25

<210> SEQ ID NO 172
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 172
ttgctttgag attgaaatat aaaag                                           25

<210> SEQ ID NO 173
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 173
atcatataca gtgccaggga acaac                                           25

<210> SEQ ID NO 174
<211> LENGTH: 25
<212> TYPE: DNA
<213> ORGANISM: Artificial Sequence
```

```
<220> FEATURE:
<223> OTHER INFORMATION: Synthetic Oligonucleotide Sequence

<400> SEQUENCE: 174
acttgtagaa ataccttata aagtt                                              25

<210> SEQ ID NO 175
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 175
attcttgatg tatgtagagt cctaa                                              25

<210> SEQ ID NO 176
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 176
tgatatcgaa tacataagta ctcga                                              25

<210> SEQ ID NO 177
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 177
atgactgaat tgcttacaca tttaa                                              25

<210> SEQ ID NO 178
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 178
aaaaacaatt agtatataac tatta                                              25

<210> SEQ ID NO 179
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 179
taatagtgtc atcggctcca cttat                                              25

<210> SEQ ID NO 180
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 180
tacaatcaaa acgtgaagtt attga                                              25
```

<210> SEQ ID NO 181
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 181
gtttagttat tgacttgtag atagt                                    25

<210> SEQ ID NO 182
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 182
ctcgacaccg agtgctagat caacg                                    25

<210> SEQ ID NO 183
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 183
acccggacat attggctatt caaac                                    25

<210> SEQ ID NO 184
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 184
aatatttaaa agcctggttt atgta                                    25

<210> SEQ ID NO 185
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 185
ctttagtgcc gatttacggc cttgg                                    25

<210> SEQ ID NO 186
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 186
ggtaagataa cgaagtttta atagc                                    25

<210> SEQ ID NO 187
<211> LENGTH: 25
<212> TYPE: DNA
<213> ORGANISM: Artificial Sequence
<220> FEATURE:
<223> OTHER INFORMATION: Synthetic Oligonucleotide Sequence

```
<400> SEQUENCE: 187
tgctttgaca ctgttcatta taccg                                         25

<210> SEQ ID NO 188
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 188
ttttctttta cccactggtg aaata                                         25

<210> SEQ ID NO 189
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 189
tcaagattgt ccttgattgt tgaat                                         25

<210> SEQ ID NO 190
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 190
aaagatctga ttaacttata acaga                                         25

<210> SEQ ID NO 191
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 191
atgaataaat cttgtaaagt gtggc                                         25

<210> SEQ ID NO 192
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 192
agctacacta aacctagaat gatct                                         25

<210> SEQ ID NO 193
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 193
cttcaatttg agacttgaaa tctaa                                         25

<210> SEQ ID NO 194
```

<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 194
gtttcactca gtgtagacat catcc                                    25

<210> SEQ ID NO 195
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 195
tggtatctga attactgctt tgtca                                    25

<210> SEQ ID NO 196
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 196
aagtgtctat tatccttaaa cgcat                                    25

<210> SEQ ID NO 197
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 197
atctcgcata ataactcctc aatat                                    25

<210> SEQ ID NO 198
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 198
gagttagtct tgtgctcacg gaatt                                    25

<210> SEQ ID NO 199
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 199
aaatgttagt tagctcgttc aagta                                    25

<210> SEQ ID NO 200
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 200
aaagttcttc acactacgtc aaaat					25

<210> SEQ ID NO 201
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 201
aaaaaaatgg ttgtaacaaa aaaaa					25

<210> SEQ ID NO 202
<211> LENGTH: 27
<212> TYPE: DNA
<213> ORGANISM: Artificial Sequence
<220> FEATURE:
<223> OTHER INFORMATION: Synthetic Oligonucleotide Sequence

<400> SEQUENCE: 202
ggctcatcga tgacccaaga tggcggc					27

<210> SEQ ID NO 203
<211> LENGTH: 27
<212> TYPE: DNA
<213> ORGANISM: Artificial Sequence
<220> FEATURE:
<223> OTHER INFORMATION: Synthetic Oligonucleotide Sequence

<400> SEQUENCE: 203
tctccctata gtgagtcgta ttaaatt					27

<210> SEQ ID NO 204
<211> LENGTH: 20
<212> TYPE: DNA
<213> ORGANISM: Artificial Sequence
<220> FEATURE:
<223> OTHER INFORMATION: Synthetic Oligonucleotide Sequence

<400> SEQUENCE: 204
gtctaagtag tgacatgttt					20

<210> SEQ ID NO 205
<211> LENGTH: 32
<212> TYPE: DNA
<213> ORGANISM: Artificial Sequence
<220> FEATURE:
<223> OTHER INFORMATION: Synthetic Oligonucleotide Sequence

<400> SEQUENCE: 205
tggctaatcc cggtctaagt agtgacatgt tt					32

<210> SEQ ID NO 206
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 206
ggctcatcga tgacccaaga tggcggctgg ctaatcccg					39

<210> SEQ ID NO 207
<211> LENGTH: 59
<212> TYPE: DNA

```
<213> ORGANISM: Artificial Sequence
<220> FEATURE:
<223> OTHER INFORMATION: Synthetic Oligonucleotide Sequence

<400> SEQUENCE: 207
ggctcatcga tgacccaaga tggcggctgg ctaatcccgg tctaagtagt gacatgttt        59

<210> SEQ ID NO 208
<211> LENGTH: 32
<212> TYPE: DNA
<213> ORGANISM: Artificial Sequence
<220> FEATURE:
<223> OTHER INFORMATION: Synthetic Oligonucleotide Sequence

<400> SEQUENCE: 208
ctgtgctaga gggtctaagt agtgacatgt tt                                     32

<210> SEQ ID NO 209
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 209
ggctcatcga tgacccaaga tggcggcctg tgctagagg                              39

<210> SEQ ID NO 210
<211> LENGTH: 59
<212> TYPE: DNA
<213> ORGANISM: Artificial Sequence
<220> FEATURE:
<223> OTHER INFORMATION: Synthetic Oligonucleotide Sequence

<400> SEQUENCE: 210
ggctcatcga tgacccaaga tggcggcctg tgctagaggg tctaagtagt gacatgttt        59

<210> SEQ ID NO 211
<211> LENGTH: 32
<212> TYPE: DNA
<213> ORGANISM: Artificial Sequence
<220> FEATURE:
<223> OTHER INFORMATION: Synthetic Oligonucleotide Sequence

<400> SEQUENCE: 211
catgtaccaa cggtctaagt agtgacatgt tt                                     32

<210> SEQ ID NO 212
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 212
ggctcatcga tgacccaaga tggcggccat gtaccaacg                              39

<210> SEQ ID NO 213
<211> LENGTH: 59
<212> TYPE: DNA
<213> ORGANISM: Artificial Sequence
<220> FEATURE:
<223> OTHER INFORMATION: Synthetic Oligonucleotide Sequence

<400> SEQUENCE: 213
ggctcatcga tgacccaaga tggcggccat gtaccaacgg tctaagtagt gacatgttt        59
```

<210> SEQ ID NO 214
<211> LENGTH: 32
<212> TYPE: DNA
<213> ORGANISM: Artificial Sequence
<220> FEATURE:
<223> OTHER INFORMATION: Synthetic Oligonucleotide Sequence

<400> SEQUENCE: 214
tcggtcggac tagtctaagt agtgacatgt tt                          32

<210> SEQ ID NO 215
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 215
ggctcatcga tgacccaaga tggcggctcg gtcggacta                    39

<210> SEQ ID NO 216
<211> LENGTH: 59
<212> TYPE: DNA
<213> ORGANISM: Artificial Sequence
<220> FEATURE:
<223> OTHER INFORMATION: Synthetic Oligonucleotide Sequence

<400> SEQUENCE: 216
ggctcatcga tgacccaaga tggcggctcg gtcggactag tctaagtagt gacatgttt    59

<210> SEQ ID NO 217
<211> LENGTH: 32
<212> TYPE: DNA
<213> ORGANISM: Artificial Sequence
<220> FEATURE:
<223> OTHER INFORMATION: Synthetic Oligonucleotide Sequence

<400> SEQUENCE: 217
cctcccccaa gcgtctaagt agtgacatgt tt                          32

<210> SEQ ID NO 218
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 218
ggctcatcga tgacccaaga tggcggccct cccccaagc                   39

<210> SEQ ID NO 219
<211> LENGTH: 59
<212> TYPE: DNA
<213> ORGANISM: Artificial Sequence
<220> FEATURE:
<223> OTHER INFORMATION: Synthetic Oligonucleotide Sequence

<400> SEQUENCE: 219
ggctcatcga tgacccaaga tggcggccct cccccaagcg tctaagtagt gacatgttt    59

<210> SEQ ID NO 220
<211> LENGTH: 32
<212> TYPE: DNA
<213> ORGANISM: Artificial Sequence
<220> FEATURE:

<223> OTHER INFORMATION: Synthetic Oligonucleotide Sequence

<400> SEQUENCE: 220
gggtttgcta cggtctaagt agtgacatgt tt             32

<210> SEQ ID NO 221
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 221
ggctcatcga tgacccaaga tggcggcggg tttgctacg       39

<210> SEQ ID NO 222
<211> LENGTH: 59
<212> TYPE: DNA
<213> ORGANISM: Artificial Sequence
<220> FEATURE:
<223> OTHER INFORMATION: Synthetic Oligonucleotide Sequence

<400> SEQUENCE: 222
ggctcatcga tgacccaaga tggcggcggg tttgctacgg tctaagtagt gacatgttt    59

<210> SEQ ID NO 223
<211> LENGTH: 32
<212> TYPE: DNA
<213> ORGANISM: Artificial Sequence
<220> FEATURE:
<223> OTHER INFORMATION: Synthetic Oligonucleotide Sequence

<400> SEQUENCE: 223
atgtgcgcac aagtctaagt agtgacatgt tt              32

<210> SEQ ID NO 224
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 224
ggctcatcga tgacccaaga tggcggcatg tgcgcacaa      39

<210> SEQ ID NO 225
<211> LENGTH: 59
<212> TYPE: DNA
<213> ORGANISM: Artificial Sequence
<220> FEATURE:
<223> OTHER INFORMATION: Synthetic Oligonucleotide Sequence

<400> SEQUENCE: 225
ggctcatcga tgacccaaga tggcggcatg tgcgcacaag tctaagtagt gacatgttt    59

<210> SEQ ID NO 226
<211> LENGTH: 32
<212> TYPE: DNA
<213> ORGANISM: Artificial Sequence
<220> FEATURE:
<223> OTHER INFORMATION: Synthetic Oligonucleotide Sequence

<400> SEQUENCE: 226
cgggactaga gagtctaagt agtgacatgt tt              32

<210> SEQ ID NO 227
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 227
ggctcatcga tgacccaaga tggcggccgg gactagaga                                39

<210> SEQ ID NO 228
<211> LENGTH: 59
<212> TYPE: DNA
<213> ORGANISM: Artificial Sequence
<220> FEATURE:
<223> OTHER INFORMATION: Synthetic Oligonucleotide Sequence

<400> SEQUENCE: 228
ggctcatcga tgacccaaga tggcggccgg gactagagag tctaagtagt gacatgttt          59

<210> SEQ ID NO 229
<211> LENGTH: 32
<212> TYPE: DNA
<213> ORGANISM: Artificial Sequence
<220> FEATURE:
<223> OTHER INFORMATION: Synthetic Oligonucleotide Sequence

<400> SEQUENCE: 229
aatctccgag cggtctaagt agtgacatgt tt                                       32

<210> SEQ ID NO 230
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 230
ggctcatcga tgacccaaga tggcggcaat ctccgagcg                                39

<210> SEQ ID NO 231
<211> LENGTH: 59
<212> TYPE: DNA
<213> ORGANISM: Artificial Sequence
<220> FEATURE:
<223> OTHER INFORMATION: Synthetic Oligonucleotide Sequence

<400> SEQUENCE: 231
ggctcatcga tgacccaaga tggcggcaat ctccgagcgg tctaagtagt gacatgttt          59

<210> SEQ ID NO 232
<211> LENGTH: 32
<212> TYPE: DNA
<213> ORGANISM: Artificial Sequence
<220> FEATURE:
<223> OTHER INFORMATION: Synthetic Oligonucleotide Sequence

<400> SEQUENCE: 232
aagtgcaggt tcgtctaagt agtgacatgt tt                                       32

<210> SEQ ID NO 233
<211> LENGTH: 39
<212> TYPE: DNA
<213> ORGANISM: Artificial Sequence
<220> FEATURE:
<223> OTHER INFORMATION: Synthetic Oligonucleotide Sequence

```
<400> SEQUENCE: 233
ggctcatcga tgacccaaga tggcggcaag tgcaggttc                          39

<210> SEQ ID NO 234
<211> LENGTH: 59
<212> TYPE: DNA
<213> ORGANISM: Artificial Sequence
<220> FEATURE:
<223> OTHER INFORMATION: Synthetic Oligonucleotide Sequence

<400> SEQUENCE: 234
ggctcatcga tgacccaaga tggcggcaag tgcaggttcg tctaagtagt gacatgttt    59

<210> SEQ ID NO 235
<211> LENGTH: 32
<212> TYPE: DNA
<213> ORGANISM: Artificial Sequence
<220> FEATURE:
<223> OTHER INFORMATION: Synthetic Oligonucleotide Sequence

<400> SEQUENCE: 235
tccagtttaa ccgtctaagt agtgacatgt tt                                 32

<210> SEQ ID NO 236
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 236
ggctcatcga tgacccaaga tggcggctcc agtttaacc                          39

<210> SEQ ID NO 237
<211> LENGTH: 59
<212> TYPE: DNA
<213> ORGANISM: Artificial Sequence
<220> FEATURE:
<223> OTHER INFORMATION: Synthetic Oligonucleotide Sequence

<400> SEQUENCE: 237
ggctcatcga tgacccaaga tggcggctcc agtttaaccg tctaagtagt gacatgttt    59

<210> SEQ ID NO 238
<211> LENGTH: 32
<212> TYPE: DNA
<213> ORGANISM: Artificial Sequence
<220> FEATURE:
<223> OTHER INFORMATION: Synthetic Oligonucleotide Sequence

<400> SEQUENCE: 238
tagccgcaca gggtctaagt agtgacatgt tt                                 32

<210> SEQ ID NO 239
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 239
ggctcatcga tgacccaaga tggcggctag ccgcacagg                          39

<210> SEQ ID NO 240
<211> LENGTH: 59
```

```
<212> TYPE: DNA
<213> ORGANISM: Artificial Sequence
<220> FEATURE:
<223> OTHER INFORMATION: Synthetic Oligonucleotide Sequence

<400> SEQUENCE: 240
ggctcatcga tgacccaaga tggcggctag ccgcacaggg tctaagtagt gacatgtttt    59

<210> SEQ ID NO 241
<211> LENGTH: 36
<212> TYPE: DNA
<213> ORGANISM: Artificial Sequence
<220> FEATURE:
<223> OTHER INFORMATION: Synthetic Oligonucleotide Sequence

<400> SEQUENCE: 241
gcgttggcta atcccggtct aagtagtgac atgttt                              36

<210> SEQ ID NO 242
<211> LENGTH: 43
<212> TYPE: DNA
<213> ORGANISM: Artificial Sequence
<220> FEATURE:
<223> OTHER INFORMATION: Synthetic Oligonucleotide Sequence

<400> SEQUENCE: 242
ggctcatcga tgacccaaga tggcggcgcg ttggctaatc ccg                      43

<210> SEQ ID NO 243
<211> LENGTH: 63
<212> TYPE: DNA
<213> ORGANISM: Artificial Sequence
<220> FEATURE:
<223> OTHER INFORMATION: Synthetic Oligonucleotide Sequence

<400> SEQUENCE: 243
ggctcatcga tgacccaaga tggcggcgcg ttggctaatc ccggtctaag tagtgacatg    60
ttt                                                                  63

<210> SEQ ID NO 244
<211> LENGTH: 36
<212> TYPE: DNA
<213> ORGANISM: Artificial Sequence
<220> FEATURE:
<223> OTHER INFORMATION: Synthetic Oligonucleotide Sequence

<400> SEQUENCE: 244
tcaccatgta ccaacggtct aagtagtgac atgttt                              36

<210> SEQ ID NO 245
<211> LENGTH: 43
<212> TYPE: DNA
<213> ORGANISM: Artificial Sequence
<220> FEATURE:
<223> OTHER INFORMATION: Synthetic Oligonucleotide Sequence

<400> SEQUENCE: 245
ggctcatcga tgacccaaga tggcggctca ccatgtacca acg                      43

<210> SEQ ID NO 246
<211> LENGTH: 63
<212> TYPE: DNA
<213> ORGANISM: Artificial Sequence
<220> FEATURE:
<223> OTHER INFORMATION: Synthetic Oligonucleotide Sequence
```

<400> SEQUENCE: 246
ggctcatcga tgacccaaga tggcggctca ccatgtacca acggtctaag tagtgacatg    60
ttt                                                                  63

<210> SEQ ID NO 247
<211> LENGTH: 38
<212> TYPE: DNA
<213> ORGANISM: Artificial Sequence
<220> FEATURE:
<223> OTHER INFORMATION: Synthetic Oligonucleotide Sequence

<400> SEQUENCE: 247
tatgaatgcg acccggaagt ctaagtagtg acatgttt                            38

<210> SEQ ID NO 248
<211> LENGTH: 45
<212> TYPE: DNA
<213> ORGANISM: Artificial Sequence
<220> FEATURE:
<223> OTHER INFORMATION: Synthetic Oligonucleotide Sequence

<400> SEQUENCE: 248
ggctcatcga tgacccaaga tggcggctat gaatgcgacc cggaa                    45

<210> SEQ ID NO 249
<211> LENGTH: 65
<212> TYPE: DNA
<213> ORGANISM: Artificial Sequence
<220> FEATURE:
<223> OTHER INFORMATION: Synthetic Oligonucleotide Sequence

<400> SEQUENCE: 249
ggctcatcga tgacccaaga tggcggctat gaatgcgacc cggaagtcta agtagtgaca    60
tgttt                                                                65

<210> SEQ ID NO 250
<211> LENGTH: 38
<212> TYPE: DNA
<213> ORGANISM: Artificial Sequence
<220> FEATURE:
<223> OTHER INFORMATION: Synthetic Oligonucleotide Sequence

<400> SEQUENCE: 250
aacaatggtc actgcatcgt ctaagtagtg acatgttt                            38

<210> SEQ ID NO 251
<211> LENGTH: 45
<212> TYPE: DNA
<213> ORGANISM: Artificial Sequence
<220> FEATURE:
<223> OTHER INFORMATION: Synthetic Oligonucleotide Sequence

<400> SEQUENCE: 251
ggctcatcga tgacccaaga tggcggcaac aatggtcact gcatc                    45

<210> SEQ ID NO 252
<211> LENGTH: 65
<212> TYPE: DNA
<213> ORGANISM: Artificial Sequence
<220> FEATURE:
<223> OTHER INFORMATION: Synthetic Oligonucleotide Sequence

<400> SEQUENCE: 252
ggctcatcga tgacccaaga tggcggcaac aatggtcact gcatcgtcta agtagtgaca    60
tgttt 65

<210> SEQ ID NO 253
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 253
gggccgtttc ccggacataa gtctaagtag tgacatgttt                    40

<210> SEQ ID NO 254
<211> LENGTH: 47
<212> TYPE: DNA
<213> ORGANISM: Artificial Sequence
<220> FEATURE:
<223> OTHER INFORMATION: Synthetic Oligonucleotide Sequence

<400> SEQUENCE: 254
ggctcatcga tgacccaaga tggcggcggg ccgtttcccg gacataa            47

<210> SEQ ID NO 255
<211> LENGTH: 67
<212> TYPE: DNA
<213> ORGANISM: Artificial Sequence
<220> FEATURE:
<223> OTHER INFORMATION: Synthetic Oligonucleotide Sequence

<400> SEQUENCE: 255
ggctcatcga tgacccaaga tggcggcggg ccgtttcccg gacataagtc taagtagtga   60
catgttt                                                         67

<210> SEQ ID NO 256
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 256
aggttgagtc cgcatctgaa gtctaagtag tgacatgttt                    40

<210> SEQ ID NO 257
<211> LENGTH: 47
<212> TYPE: DNA
<213> ORGANISM: Artificial Sequence
<220> FEATURE:
<223> OTHER INFORMATION: Synthetic Oligonucleotide Sequence

<400> SEQUENCE: 257
ggctcatcga tgacccaaga tggcggcagg ttgagtccgc atctgaa            47

<210> SEQ ID NO 258
<211> LENGTH: 67
<212> TYPE: DNA
<213> ORGANISM: Artificial Sequence
<220> FEATURE:
<223> OTHER INFORMATION: Synthetic Oligonucleotide Sequence

<400> SEQUENCE: 258
ggctcatcga tgacccaaga tggcggcagg ttgagtccgc atctgaagtc taagtagtga   60
catgttt                                                         67

<210> SEQ ID NO 259
<211> LENGTH: 42
<212> TYPE: DNA
<213> ORGANISM: Artificial Sequence
<220> FEATURE:
<223> OTHER INFORMATION: Synthetic Oligonucleotide Sequence

<400> SEQUENCE: 259
tcgaccaaga gccgctagat gcgtctaagt agtgacatgt tt                42

<210> SEQ ID NO 260
<211> LENGTH: 49
<212> TYPE: DNA
<213> ORGANISM: Artificial Sequence
<220> FEATURE:
<223> OTHER INFORMATION: Synthetic Oligonucleotide Sequence

<400> SEQUENCE: 260
ggctcatcga tgacccaaga tggcggctcg accaagagcc gctagatgc         49

<210> SEQ ID NO 261
<211> LENGTH: 69
<212> TYPE: DNA
<213> ORGANISM: Artificial Sequence
<220> FEATURE:
<223> OTHER INFORMATION: Synthetic Oligonucleotide Sequence

<400> SEQUENCE: 261
ggctcatcga tgacccaaga tggcggctcg accaagagcc gctagatgcg tctaagtagt    60
gacatgttt                                                            69

<210> SEQ ID NO 262
<211> LENGTH: 42
<212> TYPE: DNA
<213> ORGANISM: Artificial Sequence
<220> FEATURE:
<223> OTHER INFORMATION: Synthetic Oligonucleotide Sequence

<400> SEQUENCE: 262
agctcgtgtc aagccgtcgc ctgtctaagt agtgacatgt tt                42

<210> SEQ ID NO 263
<211> LENGTH: 49
<212> TYPE: DNA
<213> ORGANISM: Artificial Sequence
<220> FEATURE:
<223> OTHER INFORMATION: Synthetic Oligonucleotide Sequence

<400> SEQUENCE: 263
ggctcatcga tgacccaaga tggcggcagc tcgtgtcaag ccgtcgcct         49

<210> SEQ ID NO 264
<211> LENGTH: 69
<212> TYPE: DNA
<213> ORGANISM: Artificial Sequence
<220> FEATURE:
<223> OTHER INFORMATION: Synthetic Oligonucleotide Sequence

<400> SEQUENCE: 264
ggctcatcga tgacccaaga tggcggcagc tcgtgtcaag ccgtcgcctg tctaagtagt    60
gacatgttt                                                            69

<210> SEQ ID NO 265
<211> LENGTH: 44

```
<212> TYPE: DNA
<213> ORGANISM: Artificial Sequence
<220> FEATURE:
<223> OTHER INFORMATION: Synthetic Oligonucleotide Sequence

<400> SEQUENCE: 265
tgaaagagtt gtcagtttgc tggtgtctaa gtagtgacat gttt            44

<210> SEQ ID NO 266
<211> LENGTH: 51
<212> TYPE: DNA
<213> ORGANISM: Artificial Sequence
<220> FEATURE:
<223> OTHER INFORMATION: Synthetic Oligonucleotide Sequence

<400> SEQUENCE: 266
ggctcatcga tgacccaaga tggcggctga aagagttgtc agtttgctgg t     51

<210> SEQ ID NO 267
<211> LENGTH: 71
<212> TYPE: DNA
<213> ORGANISM: Artificial Sequence
<220> FEATURE:
<223> OTHER INFORMATION: Synthetic Oligonucleotide Sequence

<400> SEQUENCE: 267
ggctcatcga tgacccaaga tggcggctga aagagttgtc agtttgctgg tgtctaagta    60
gtgacatgtt t                                                        71

<210> SEQ ID NO 268
<211> LENGTH: 45
<212> TYPE: DNA
<213> ORGANISM: Artificial Sequence
<220> FEATURE:
<223> OTHER INFORMATION: Synthetic Oligonucleotide Sequence

<400> SEQUENCE: 268
tcaggtaaag gttcctcacg ctaccgtcta agtagtgaca tgttt            45

<210> SEQ ID NO 269
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 269
ggctcatcga tgacccaaga tggcggctca ggtaaaggtt cctcacgcta cc    52

<210> SEQ ID NO 270
<211> LENGTH: 72
<212> TYPE: DNA
<213> ORGANISM: Artificial Sequence
<220> FEATURE:
<223> OTHER INFORMATION: Synthetic Oligonucleotide Sequence

<400> SEQUENCE: 270
ggctcatcga tgacccaaga tggcggctca ggtaaaggtt cctcacgcta ccgtctaagt    60
agtgacatgt tt                                                       72

<210> SEQ ID NO 271
<211> LENGTH: 27
<212> TYPE: DNA
<213> ORGANISM: Artificial Sequence
<220> FEATURE:
```

<223> OTHER INFORMATION: Synthetic Oligonucleotide Sequence

<400> SEQUENCE: 271
ggctcatcga tgacccaaga tggcggc                                27

<210> SEQ ID NO 272
<211> LENGTH: 47
<212> TYPE: DNA
<213> ORGANISM: Artificial Sequence
<220> FEATURE:
<223> OTHER INFORMATION: Synthetic Oligonucleotide Sequence

<400> SEQUENCE: 272
gtcatatgcg acgatctcag ggctcatcga tgacccaaga tggcggc           47

<210> SEQ ID NO 273
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 273
gtccccatcg agggcatct tatcgtgcct ggctcatcga tgacccaaga tggcggc  57

<210> SEQ ID NO 274
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 274
ccgccctcct tcgcccccg gtgaaataac ggctcatcga tgacccaaga tggcggc  57

<210> SEQ ID NO 275
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 275
aatgctcacc tctattcggg acttgagtac ggctcatcga tgacccaaga tggcggc  57

<210> SEQ ID NO 276
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 276
gtcggaacgc caggtacagt tagcgcatcc ggctcatcga tgacccaaga tggcggc  57

<210> SEQ ID NO 277
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 277
gtgatgcttt atgagattcc ggtctccgac ggctcatcga tgacccaaga tggcggc  57

```
<210> SEQ ID NO 278
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 278
gacggtgcat cacccgcatt tgctgtagcg ggctcatcga tgacccaaga tggcggc        57

<210> SEQ ID NO 279
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 279
aagccaaaat tacaatcgat ccctaccaac ggctcatcga tgacccaaga tggcggc        57

<210> SEQ ID NO 280
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 280
atcttgcacc ttcccagatg taaacccct ggctcatcga tgacccaaga tggcggc         57

<210> SEQ ID NO 281
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 281
cggagaatac cctcgactgt atcatatcgt ggctcatcga tgacccaaga tggcggc       57

<210> SEQ ID NO 282
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 282
ttcatcgagg tacattggtg ctattccatt ggctcatcga tgacccaaga tggcggc       57

<210> SEQ ID NO 283
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 283
aggagaacca gcctggagcg tttaagcatc ggctcatcga tgacccaaga tggcggc       57

<210> SEQ ID NO 284
<211> LENGTH: 57
<212> TYPE: DNA
<213> ORGANISM: Artificial Sequence
<220> FEATURE:
<223> OTHER INFORMATION: Synthetic Oligonucleotide Sequence
```

<400> SEQUENCE: 284
gatgtcctaa aatgaggcgt ggcaatagag ggctcatcga tgacccaaga tggcggc    57

<210> SEQ ID NO 285
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 285
cagagtcatg tatcccact gtcggtcgaa ggctcatcga tgacccaaga tggcggc    57

<210> SEQ ID NO 286
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 286
gtcaggctag ggggttatcc cagcaacggc ggctcatcga tgacccaaga tggcggc    57

<210> SEQ ID NO 287
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 287
tttttgacag tgatgaagag ggaggtacga ggctcatcga tgacccaaga tggcggc    57

<210> SEQ ID NO 288
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 288
ctatggttcg ttactgaatc gaaaagccgc ggctcatcga tgacccaaga tggcggc    57

<210> SEQ ID NO 289
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 289
tagctatcaa aacaggcgtc atcggttaag ggctcatcga tgacccaaga tggcggc    57

<210> SEQ ID NO 290
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 290
cctgcttagg gtcacttaaa ctactggcgc ggctcatcga tgacccaaga tggcggc    57

<210> SEQ ID NO 291
<211> LENGTH: 57

<212> TYPE: DNA
<213> ORGANISM: Artificial Sequence
<220> FEATURE:
<223> OTHER INFORMATION: Synthetic Oligonucleotide Sequence

<400> SEQUENCE: 291
ggtgatggcc cataccgatc acgcccgcag ggctcatcga tgacccaaga tggcggc    57

<210> SEQ ID NO 292
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 292
cggcaggagg gactgcgatt tccatagagc ggctcatcga tgacccaaga tggcggc    57

<210> SEQ ID NO 293
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 293
tggccggaga gaggatagga agcgggacta ggctcatcga tgacccaaga tggcggc    57

<210> SEQ ID NO 294
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 294
acacatccca ggactgccgt ggcctacgta ggctcatcga tgacccaaga tggcggc    57

<210> SEQ ID NO 295
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 295
gacgagcttg ttccaattcc tcgagccgag ggctcatcga tgacccaaga tggcggc    57

<210> SEQ ID NO 296
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 296
gttggggagg ggcactacga cttagggcta ggctcatcga tgacccaaga tggcggc    57

<210> SEQ ID NO 297
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 297
ggccgtcaat gtgttttgca cccaaccgga ggctcatcga tgacccaaga tggcggc    57

<210> SEQ ID NO 298
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 298
tcccacgtcc ttcgacgcac actgtaactt ggctcatcga tgacccaaga tggcggc    57

<210> SEQ ID NO 299
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 299
tcatgtatcg cccgtgggta agctcggctc atcgatgacc aagatggcg gc    52

<210> SEQ ID NO 300
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 300
atgttatgga gagtgggtta ggcaaggctc atcgatgacc aagatggcg gc    52

<210> SEQ ID NO 301
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 301
atgagggagt aaggagatta ggttcggctc atcgatgacc aagatggcg gc    52

<210> SEQ ID NO 302
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 302
gcccagcagt tatacaattc gtggcggctc atcgatgacc aagatggcg gc    52

<210> SEQ ID NO 303
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 303
ttgggctctc cagtagccga acaaaggctc atcgatgacc aagatggcg gc    52

<210> SEQ ID NO 304
<211> LENGTH: 52
<212> TYPE: DNA
<213> ORGANISM: Artificial Sequence

```
<220> FEATURE:
<223> OTHER INFORMATION: Synthetic Oligonucleotide Sequence

<400> SEQUENCE: 304
gtggttgcta cagcctagcc tagatggctc atcgatgacc caagatggcg gc        52

<210> SEQ ID NO 305
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 305
aggaggaacc ggaagatcta atctgggctc atcgatgacc caagatggcg gc        52

<210> SEQ ID NO 306
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 306
gcgactgtgg caacccatt tcgcaggctc atcgatgacc caagatggcg gc         52

<210> SEQ ID NO 307
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 307
agttggatgg atatctcgct cgtgaggctc atcgatgacc caagatggcg gc        52

<210> SEQ ID NO 308
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 308
cgctgtcctc tctgacacta aaggtggctc atcgatgacc caagatggcg gc        52

<210> SEQ ID NO 309
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 309
atttcaatag tcaacccggt atccaggctc atcgatgacc caagatggcg gc        52

<210> SEQ ID NO 310
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 310
ggttgggggg ctcggctcat gtatcggctc atcgatgacc caagatggcg gc        52
```

<210> SEQ ID NO 311
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 311
taaggagact aggttccaat agctgggctc atcgatgacc aagatggcg gc            52

<210> SEQ ID NO 312
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 312
ttacacaaat cgtgggttgg cctctggctc atcgatgacc aagatggcg gc            52

<210> SEQ ID NO 313
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 313
cgaaagcgtt ccgcaggacc cccttggctc atcgatgacc aagatggcg gc            52

<210> SEQ ID NO 314
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 314
aaagtctgag aatgagtgat accatggctc atcgatgacc aagatggcg gc            52

<210> SEQ ID NO 315
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 315
atattggtag ttttgtccgc tgtagggctc atcgatgacc aagatggcg gc            52

<210> SEQ ID NO 316
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 316
cggaagatct aatctgcacg caattggctc atcgatgacc aagatggcg gc            52

<210> SEQ ID NO 317
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 317
gcgcctcgtt gggcagaagt ttgtggaaat ggctcatcga tgacccaaga tggcggc       57

<210> SEQ ID NO 318
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 318
atcttcacct accgagttct acgggcctac ggctcatcga tgacccaaga tggcggc       57

<210> SEQ ID NO 319
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 319
cccacaactt gcacccgcta tgcgaccctg ggctcatcga tgacccaaga tggcggc       57

<210> SEQ ID NO 320
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 320
gattagtggc ccaacgggaa caaacttcct ggctcatcga tgacccaaga tggcggc       57

<210> SEQ ID NO 321
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 321
cgcccgtccc agacccttac tcactatgga ggctcatcga tgacccaaga tggcggc       57

<210> SEQ ID NO 322
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 322
gagattgtac cctacagtcc gattaccgat ggctcatcga tgacccaaga tggcggc       57

<210> SEQ ID NO 323
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 323
cgcagtaaaa gggcacaggt aattaccta ggctcatcga tgacccaaga tggcggc        57

<210> SEQ ID NO 324

```
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 324
agggtgtctt gaactactgg cgcagcccat ggctcatcga tgacccaaga tggcggc      57

<210> SEQ ID NO 325
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 325
tcggcggcgg gtagtcagtt cgctacctgg ggctcatcga tgacccaaga tggcggc      57

<210> SEQ ID NO 326
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 326
gatgtgatct ggaccctacg ggaggggaca ggctcatcga tgacccaaga tggcggc      57

<210> SEQ ID NO 327
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 327
agtcccagat atgagagaag cgaagcataa ggctcatcga tgacccaaga tggcggc      57

<210> SEQ ID NO 328
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 328
actattacac cacgtaccgt aggtcggctc atcgatgacc caagatggcg gc           52

<210> SEQ ID NO 329
<211> LENGTH: 47
<212> TYPE: DNA
<213> ORGANISM: Artificial Sequence
<220> FEATURE:
<223> OTHER INFORMATION: Synthetic Oligonucleotide Sequence

<400> SEQUENCE: 329
gtcatatgcg acgatctcag ggctcatcga tgacccaaga tggcggc                 47

<210> SEQ ID NO 330
<211> LENGTH: 47
<212> TYPE: DNA
<213> ORGANISM: Artificial Sequence
<220> FEATURE:
<223> OTHER INFORMATION: Synthetic Oligonucleotide Sequence

<400> SEQUENCE: 330
```

```
tctccctata gtgagtcgta ttaaattgtc atatgcgacg atctcag                          47
```

<210> SEQ ID NO 331
<211> LENGTH: 74
<212> TYPE: DNA
<213> ORGANISM: Artificial Sequence
<220> FEATURE:
<223> OTHER INFORMATION: Synthetic Oligonucleotide Sequence

<400> SEQUENCE: 331

```
tctccctata gtgagtcgta ttaaattgtc atatgcgacg atctcagggc tcatcgatga          60
cccaagatgg cggc                                                            74
```

<210> SEQ ID NO 332
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 332

```
gtgatgcttt atgagattcc ggtctccgac ggctcatcga tgacccaaga tggcggc             57
```

<210> SEQ ID NO 333
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 333

```
tctccctata gtgagtcgta ttaaattgtg atgctttatg agattccggt ctccgac             57
```

<210> SEQ ID NO 334
<211> LENGTH: 84
<212> TYPE: DNA
<213> ORGANISM: Artificial Sequence
<220> FEATURE:
<223> OTHER INFORMATION: Synthetic Oligonucleotide Sequence

<400> SEQUENCE: 334

```
tctccctata gtgagtcgta ttaaattgtg atgctttatg agattccggt ctccgacggc          60
tcatcgatga cccaagatgg cggc                                                 84
```

<210> SEQ ID NO 335
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 335

```
ttcatcgagg tacattggtg ctattccatt ggctcatcga tgacccaaga tggcggc             57
```

<210> SEQ ID NO 336
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 336

```
tctccctata gtgagtcgta ttaaattttc atcgaggtac attggtgcta ttccatt             57
```

<210> SEQ ID NO 337
<211> LENGTH: 84
<212> TYPE: DNA
<213> ORGANISM: Artificial Sequence
<220> FEATURE:
<223> OTHER INFORMATION: Synthetic Oligonucleotide Sequence

<400> SEQUENCE: 337
tctccctata gtgagtcgta ttaaattttc atcgaggtac attggtgcta ttccattggc    60
tcatcgatga cccaagatgg cggc    84

<210> SEQ ID NO 338
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 338
gatgtcctaa aatgaggcgt ggcaatagag ggctcatcga tgacccaaga tggcggc    57

<210> SEQ ID NO 339
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 339
tctccctata gtgagtcgta ttaaattgat gtcctaaaat gaggcgtggc aatagag    57

<210> SEQ ID NO 340
<211> LENGTH: 84
<212> TYPE: DNA
<213> ORGANISM: Artificial Sequence
<220> FEATURE:
<223> OTHER INFORMATION: Synthetic Oligonucleotide Sequence

<400> SEQUENCE: 340
tctccctata gtgagtcgta ttaaattgat gtcctaaaat gaggcgtggc aatagagggc    60
tcatcgatga cccaagatgg cggc    84

<210> SEQ ID NO 341
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 341
cagagtcatg tatcccact gtcggtcgaa ggctcatcga tgacccaaga tggcggc    57

<210> SEQ ID NO 342
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 342
tctccctata gtgagtcgta ttaaattcag agtcatgtat acccactgtc ggtcgaa    57

<210> SEQ ID NO 343
<211> LENGTH: 84

```
<212> TYPE: DNA
<213> ORGANISM: Artificial Sequence
<220> FEATURE:
<223> OTHER INFORMATION: Synthetic Oligonucleotide Sequence

<400> SEQUENCE: 343
tctccctata gtgagtcgta ttaaattcag agtcatgtat acccactgtc ggtcgaaggc    60
tcatcgatga cccaagatgg cggc                                          84

<210> SEQ ID NO 344
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 344
atgttatgga gagtgggtta ggcaaggctc atcgatgacc caagatggcg gc           52

<210> SEQ ID NO 345
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 345
tctccctata gtgagtcgta ttaaattatg ttatggagag tgggttaggc aa           52

<210> SEQ ID NO 346
<211> LENGTH: 79
<212> TYPE: DNA
<213> ORGANISM: Artificial Sequence
<220> FEATURE:
<223> OTHER INFORMATION: Synthetic Oligonucleotide Sequence

<400> SEQUENCE: 346
tctccctata gtgagtcgta ttaaattatg ttatggagag tgggttaggc aaggctcatc    60
gatgacccaa gatggcggc                                                79

<210> SEQ ID NO 347
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 347
aaagtctgag aatgagtgat accatggctc atcgatgacc caagatggcg gc           52

<210> SEQ ID NO 348
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 348
tctccctata gtgagtcgta ttaaattaaa gtctgagaat gagtgatacc at           52

<210> SEQ ID NO 349
<211> LENGTH: 79
<212> TYPE: DNA
<213> ORGANISM: Artificial Sequence
<220> FEATURE:
```

<223> OTHER INFORMATION: Synthetic Oligonucleotide Sequence

<400> SEQUENCE: 349
tctccctata gtgagtcgta ttaaattaaa gtctgagaat gagtgatacc atggctcatc    60
gatgacccaa gatggcggc                                                 79

<210> SEQ ID NO 350
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 350
cccacaactt gcacccgcta tgcgaccctg ggctcatcga tgacccaaga tggcggc      57

<210> SEQ ID NO 351
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 351
tctccctata gtgagtcgta ttaaattccc acaacttgca cccgctatgc gaccctg      57

<210> SEQ ID NO 352
<211> LENGTH: 84
<212> TYPE: DNA
<213> ORGANISM: Artificial Sequence
<220> FEATURE:
<223> OTHER INFORMATION: Synthetic Oligonucleotide Sequence

<400> SEQUENCE: 352
tctccctata gtgagtcgta ttaaattccc acaacttgca cccgctatgc gaccctgggc    60
tcatcgatga cccaagatgg cggc                                           84

<210> SEQ ID NO 353
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 353
gattagtggc ccaacgggaa caaacttcct ggctcatcga tgacccaaga tggcggc      57

<210> SEQ ID NO 354
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 354
tctccctata gtgagtcgta ttaaattgat tagtggccca acgggaacaa acttcct      57

<210> SEQ ID NO 355
<211> LENGTH: 84
<212> TYPE: DNA
<213> ORGANISM: Artificial Sequence
<220> FEATURE:
<223> OTHER INFORMATION: Synthetic Oligonucleotide Sequence

<400> SEQUENCE: 355

```
tctccctata gtgagtcgta ttaaattgat tagtggccca acgggaacaa acttcctggc    60
tcatcgatga cccaagatgg cggc                                           84
```

<210> SEQ ID NO 356
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 356

```
cgcccgtccc agaccttac tcactatgga ggctcatcga tgacccaaga tggcggc       57
```

<210> SEQ ID NO 357
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 357

```
tctccctata gtgagtcgta ttaaattcgc ccgtcccaga cccttactca ctatgga       57
```

<210> SEQ ID NO 358
<211> LENGTH: 84
<212> TYPE: DNA
<213> ORGANISM: Artificial Sequence
<220> FEATURE:
<223> OTHER INFORMATION: Synthetic Oligonucleotide Sequence

<400> SEQUENCE: 358

```
tctccctata gtgagtcgta ttaaattcgc ccgtcccaga cccttactca ctatggaggc    60
tcatcgatga cccaagatgg cggc                                           84
```

<210> SEQ ID NO 359
<211> LENGTH: 24
<212> TYPE: DNA
<213> ORGANISM: Artificial Sequence
<220> FEATURE:
<223> OTHER INFORMATION: Synthetic Oligonucleotide Sequence

<400> SEQUENCE: 359

```
gaugcagugg gcagcuguga ggac                                           24
```

<210> SEQ ID NO 360
<211> LENGTH: 24
<212> TYPE: DNA
<213> ORGANISM: Artificial Sequence
<220> FEATURE:
<223> OTHER INFORMATION: Synthetic Oligonucleotide Sequence

<400> SEQUENCE: 360

```
ugugucuuca ggaugaaaca caca                                           24
```

<210> SEQ ID NO 361
<211> LENGTH: 26
<212> TYPE: DNA
<213> ORGANISM: Artificial Sequence
<220> FEATURE:
<223> OTHER INFORMATION: Synthetic Oligonucleotide Sequence

<400> SEQUENCE: 361

```
aucuguuuuc cugcccaucc uuuaag                                         26
```

<210> SEQ ID NO 362
<211> LENGTH: 57
<212> TYPE: DNA
<213> ORGANISM: Artificial Sequence
<220> FEATURE:
<223> OTHER INFORMATION: Synthetic Oligonucleotide Sequence

<400> SEQUENCE: 362
aucuguuuuc cugcccaucc uuuaaguuua aaaaaaaaaa aaaaaaaaaa aaaaaaa    57

<210> SEQ ID NO 363
<211> LENGTH: 31
<212> TYPE: DNA
<213> ORGANISM: Artificial Sequence
<220> FEATURE:
<223> OTHER INFORMATION: Synthetic Oligonucleotide Sequence

<400> SEQUENCE: 363
ccactgcatc aggaacaaaa gcgtgatctt g    31

<210> SEQ ID NO 364
<211> LENGTH: 43
<212> TYPE: DNA
<213> ORGANISM: Artificial Sequence
<220> FEATURE:
<223> OTHER INFORMATION: Synthetic Oligonucleotide Sequence

<400> SEQUENCE: 364
tggctaatcc cgccactgca tcaggaacaa agcgtgatc ttg    43

<210> SEQ ID NO 365
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 365
ggctcatcga tgacccaaga tggcggctgg ctaatcccg    39

<210> SEQ ID NO 366
<211> LENGTH: 70
<212> TYPE: DNA
<213> ORGANISM: Artificial Sequence
<220> FEATURE:
<223> OTHER INFORMATION: Synthetic Oligonucleotide Sequence

<400> SEQUENCE: 366
ggctcatcga tgacccaaga tggcggctgg ctaatcccgc cactgcatca ggaacaaaag    60
cgtgatcttg    70

<210> SEQ ID NO 367
<211> LENGTH: 51
<212> TYPE: DNA
<213> ORGANISM: Artificial Sequence
<220> FEATURE:
<223> OTHER INFORMATION: Synthetic Oligonucleotide Sequence

<400> SEQUENCE: 367
aggttgagtc cgcatctgaa ccactgcatc aggaacaaaa gcgtgatctt g    51

<210> SEQ ID NO 368
<211> LENGTH: 47
<212> TYPE: DNA
<213> ORGANISM: Artificial Sequence

```
<220> FEATURE:
<223> OTHER INFORMATION: Synthetic Oligonucleotide Sequence

<400> SEQUENCE: 368
ggctcatcga tgacccaaga tggcggcagg ttgagtccgc atctgaa            47

<210> SEQ ID NO 369
<211> LENGTH: 78
<212> TYPE: DNA
<213> ORGANISM: Artificial Sequence
<220> FEATURE:
<223> OTHER INFORMATION: Synthetic Oligonucleotide Sequence

<400> SEQUENCE: 369
ggctcatcga tgacccaaga tggcggcagg ttgagtccgc atctgaacca ctgcatcagg    60
aacaaaagcg tgatcttg                                           78

<210> SEQ ID NO 370
<211> LENGTH: 43
<212> TYPE: DNA
<213> ORGANISM: Artificial Sequence
<220> FEATURE:
<223> OTHER INFORMATION: Synthetic Oligonucleotide Sequence

<400> SEQUENCE: 370
atgtgcgcac aaccactgca tcaggaacaa aagcgtgatc ttg               43

<210> SEQ ID NO 371
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 371
ggctcatcga tgacccaaga tggcggcatg tgcgcacaa                    39

<210> SEQ ID NO 372
<211> LENGTH: 70
<212> TYPE: DNA
<213> ORGANISM: Artificial Sequence
<220> FEATURE:
<223> OTHER INFORMATION: Synthetic Oligonucleotide Sequence

<400> SEQUENCE: 372
ggctcatcga tgacccaaga tggcggcatg tgcgcacaac cactgcatca ggaacaaaag    60
cgtgatcttg                                                    70

<210> SEQ ID NO 373
<211> LENGTH: 49
<212> TYPE: DNA
<213> ORGANISM: Artificial Sequence
<220> FEATURE:
<223> OTHER INFORMATION: Synthetic Oligonucleotide Sequence

<400> SEQUENCE: 373
tatgaatgcg acccggaacc actgcatcag gaacaaaagc gtgatcttg          49

<210> SEQ ID NO 374
<211> LENGTH: 45
<212> TYPE: DNA
<213> ORGANISM: Artificial Sequence
<220> FEATURE:
<223> OTHER INFORMATION: Synthetic Oligonucleotide Sequence
```

```
<400> SEQUENCE: 374
ggctcatcga tgacccaaga tggcggctat gaatgcgacc cggaa                45

<210> SEQ ID NO 375
<211> LENGTH: 76
<212> TYPE: DNA
<213> ORGANISM: Artificial Sequence
<220> FEATURE:
<223> OTHER INFORMATION: Synthetic Oligonucleotide Sequence

<400> SEQUENCE: 375
ggctcatcga tgacccaaga tggcggctat gaatgcgacc cggaaccact gcatcaggaa    60
caaaagcgtg atcttg                                                    76

<210> SEQ ID NO 376
<211> LENGTH: 43
<212> TYPE: DNA
<213> ORGANISM: Artificial Sequence
<220> FEATURE:
<223> OTHER INFORMATION: Synthetic Oligonucleotide Sequence

<400> SEQUENCE: 376
catgtaccaa cgccactgca tcaggaacaa aagcgtgatc ttg                   43

<210> SEQ ID NO 377
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 377
ggctcatcga tgacccaaga tggcggccat gtaccaacg                        39

<210> SEQ ID NO 378
<211> LENGTH: 70
<212> TYPE: DNA
<213> ORGANISM: Artificial Sequence
<220> FEATURE:
<223> OTHER INFORMATION: Synthetic Oligonucleotide Sequence

<400> SEQUENCE: 378
ggctcatcga tgacccaaga tggcggccat gtaccaacgc cactgcatca ggaacaaaag    60
cgtgatcttg                                                          70

<210> SEQ ID NO 379
<211> LENGTH: 43
<212> TYPE: DNA
<213> ORGANISM: Artificial Sequence
<220> FEATURE:
<223> OTHER INFORMATION: Synthetic Oligonucleotide Sequence

<400> SEQUENCE: 379
aatctccgag cgccactgca tcaggaacaa aagcgtgatc ttg                   43

<210> SEQ ID NO 380
<211> LENGTH: 39
<212> TYPE: DNA
<213> ORGANISM: Artificial Sequence
<220> FEATURE:
<223> OTHER INFORMATION: Synthetic Oligonucleotide Sequence

<400> SEQUENCE: 380
ggctcatcga tgacccaaga tggcggcaat ctccgagcg                        39
```

```
<210> SEQ ID NO 381
<211> LENGTH: 70
<212> TYPE: DNA
<213> ORGANISM: Artificial Sequence
<220> FEATURE:
<223> OTHER INFORMATION: Synthetic Oligonucleotide Sequence

<400> SEQUENCE: 381
ggctcatcga tgacccaaga tggcggcaat ctccgagcgc cactgcatca ggaacaaaag    60
cgtgatcttg                                                           70

<210> SEQ ID NO 382
<211> LENGTH: 47
<212> TYPE: DNA
<213> ORGANISM: Artificial Sequence
<220> FEATURE:
<223> OTHER INFORMATION: Synthetic Oligonucleotide Sequence

<400> SEQUENCE: 382
tcaccatgta ccaacgccac tgcatcagga acaaaagcgt gatcttg                  47

<210> SEQ ID NO 383
<211> LENGTH: 43
<212> TYPE: DNA
<213> ORGANISM: Artificial Sequence
<220> FEATURE:
<223> OTHER INFORMATION: Synthetic Oligonucleotide Sequence

<400> SEQUENCE: 383
ggctcatcga tgacccaaga tggcggctca ccatgtacca acg                      43

<210> SEQ ID NO 384
<211> LENGTH: 74
<212> TYPE: DNA
<213> ORGANISM: Artificial Sequence
<220> FEATURE:
<223> OTHER INFORMATION: Synthetic Oligonucleotide Sequence

<400> SEQUENCE: 384
ggctcatcga tgacccaaga tggcggctca ccatgtacca acgccactgc atcaggaaca    60
aaagcgtgat cttg                                                      74

<210> SEQ ID NO 385
<211> LENGTH: 49
<212> TYPE: DNA
<213> ORGANISM: Artificial Sequence
<220> FEATURE:
<223> OTHER INFORMATION: Synthetic Oligonucleotide Sequence

<400> SEQUENCE: 385
aacaatggtc actgcatccc actgcatcag gaacaaaagc gtgatcttg                49

<210> SEQ ID NO 386
<211> LENGTH: 45
<212> TYPE: DNA
<213> ORGANISM: Artificial Sequence
<220> FEATURE:
<223> OTHER INFORMATION: Synthetic Oligonucleotide Sequence

<400> SEQUENCE: 386
ggctcatcga tgacccaaga tggcggcaac aatggtcact gcatc                    45

<210> SEQ ID NO 387
```

```
<211> LENGTH: 76
<212> TYPE: DNA
<213> ORGANISM: Artificial Sequence
<220> FEATURE:
<223> OTHER INFORMATION: Synthetic Oligonucleotide Sequence

<400> SEQUENCE: 387
ggctcatcga tgacccaaga tggcggcaac aatggtcact gcatcccact gcatcaggaa      60
caaaagcgtg atcttg                                                     76

<210> SEQ ID NO 388
<211> LENGTH: 51
<212> TYPE: DNA
<213> ORGANISM: Artificial Sequence
<220> FEATURE:
<223> OTHER INFORMATION: Synthetic Oligonucleotide Sequence

<400> SEQUENCE: 388
gggccgtttc ccggacataa ccactgcatc aggaacaaaa gcgtgatctt g               51

<210> SEQ ID NO 389
<211> LENGTH: 47
<212> TYPE: DNA
<213> ORGANISM: Artificial Sequence
<220> FEATURE:
<223> OTHER INFORMATION: Synthetic Oligonucleotide Sequence

<400> SEQUENCE: 389
ggctcatcga tgacccaaga tggcggcggg ccgtttcccg gacataa                   47

<210> SEQ ID NO 390
<211> LENGTH: 78
<212> TYPE: DNA
<213> ORGANISM: Artificial Sequence
<220> FEATURE:
<223> OTHER INFORMATION: Synthetic Oligonucleotide Sequence

<400> SEQUENCE: 390
ggctcatcga tgacccaaga tggcggcggg ccgtttcccg gacataacca ctgcatcagg      60
aacaaaagcg tgatcttg                                                   78

<210> SEQ ID NO 391
<211> LENGTH: 55
<212> TYPE: DNA
<213> ORGANISM: Artificial Sequence
<220> FEATURE:
<223> OTHER INFORMATION: Synthetic Oligonucleotide Sequence

<400> SEQUENCE: 391
tgaaagagtt gtcagtttgc tggtccactg catcaggaac aaaagcgtga tcttg           55

<210> SEQ ID NO 392
<211> LENGTH: 51
<212> TYPE: DNA
<213> ORGANISM: Artificial Sequence
<220> FEATURE:
<223> OTHER INFORMATION: Synthetic Oligonucleotide Sequence

<400> SEQUENCE: 392
ggctcatcga tgacccaaga tggcggctga aagagttgtc agtttgctgg t               51

<210> SEQ ID NO 393
<211> LENGTH: 82
<212> TYPE: DNA
<213> ORGANISM: Artificial Sequence
```

<220> FEATURE:
<223> OTHER INFORMATION: Synthetic Oligonucleotide Sequence

<400> SEQUENCE: 393
ggctcatcga tgacccaaga tggcggctga aagagttgtc agtttgctgg tccactgcat    60
caggaacaaa agcgtgatct tg    82

<210> SEQ ID NO 394
<211> LENGTH: 56
<212> TYPE: DNA
<213> ORGANISM: Artificial Sequence
<220> FEATURE:
<223> OTHER INFORMATION: Synthetic Oligonucleotide Sequence

<400> SEQUENCE: 394
tcaggtaaag gttcctcacg ctaccccact gcatcaggaa caaaagcgtg atcttg    56

<210> SEQ ID NO 395
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 395
ggctcatcga tgacccaaga tggcggctca ggtaaaggtt cctcacgcta cc    52

<210> SEQ ID NO 396
<211> LENGTH: 83
<212> TYPE: DNA
<213> ORGANISM: Artificial Sequence
<220> FEATURE:
<223> OTHER INFORMATION: Synthetic Oligonucleotide Sequence

<400> SEQUENCE: 396
ggctcatcga tgacccaaga tggcggctca ggtaaaggtt cctcacgcta ccccactgca    60
tcaggaacaa aagcgtgatc ttg    83

<210> SEQ ID NO 397
<211> LENGTH: 22
<212> TYPE: DNA
<213> ORGANISM: Artificial Sequence
<220> FEATURE:
<223> OTHER INFORMATION: Synthetic Oligonucleotide Sequence

<400> SEQUENCE: 397
gctgtggctg acctgaaata cc    22

<210> SEQ ID NO 398
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 398
gtgatgcttt atgagattcc ggtctccgac gctgtggctg acctgaaata cc    52

<210> SEQ ID NO 399
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 399
gatgtcctaa aatgaggcgt ggcaatagag gctgtggctg acctgaaata cc             52

<210> SEQ ID NO 400
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 400
cagagtcatg tatcccact gtcggtcgaa gctgtggctg acctgaaata cc              52

<210> SEQ ID NO 401
<211> LENGTH: 47
<212> TYPE: DNA
<213> ORGANISM: Artificial Sequence
<220> FEATURE:
<223> OTHER INFORMATION: Synthetic Oligonucleotide Sequence

<400> SEQUENCE: 401
atgttatgga gagtgggtta ggcaagctgt ggctgacctg aaatacc                   47

<210> SEQ ID NO 402
<211> LENGTH: 47
<212> TYPE: DNA
<213> ORGANISM: Artificial Sequence
<220> FEATURE:
<223> OTHER INFORMATION: Synthetic Oligonucleotide Sequence

<400> SEQUENCE: 402
aaagtctgag aatgagtgat accatgctgt ggctgacctg aaatacc                   47

<210> SEQ ID NO 403
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 403
cccacaactt gcacccgcta tgcgaccctg gctgtggctg acctgaaata cc             52

<210> SEQ ID NO 404
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 404
gattagtggc ccaacgggaa caaacttcct gctgtggctg acctgaaata cc             52

<210> SEQ ID NO 405
<211> LENGTH: 52
<212> TYPE: DNA
<213> ORGANISM: Artificial Sequence
<220> FEATURE:
<223> OTHER INFORMATION: Synthetic Oligonucleotide Sequence

<400> SEQUENCE: 405
cgcccgtccc agacccttac tcactatgga gctgtggctg acctgaaata cc             52

<210> SEQ ID NO 406
<211> LENGTH: 24

```
<212> TYPE: DNA
<213> ORGANISM: Artificial Sequence
<220> FEATURE:
<223> OTHER INFORMATION: Synthetic Oligonucleotide Sequence

<400> SEQUENCE: 406
gaugcagugg gcagcuguga ggac                                         24

<210> SEQ ID NO 407
<211> LENGTH: 24
<212> TYPE: DNA
<213> ORGANISM: Artificial Sequence
<220> FEATURE:
<223> OTHER INFORMATION: Synthetic Oligonucleotide Sequence

<400> SEQUENCE: 407
ugugucuuca ggaugaaaca caca                                         24

<210> SEQ ID NO 408
<211> LENGTH: 26
<212> TYPE: DNA
<213> ORGANISM: Artificial Sequence
<220> FEATURE:
<223> OTHER INFORMATION: Synthetic Oligonucleotide Sequence

<400> SEQUENCE: 408
cgaacuugcg cacacacguc auugga                                       26

<210> SEQ ID NO 409
<211> LENGTH: 59
<212> TYPE: DNA
<213> ORGANISM: Artificial Sequence
<220> FEATURE:
<223> OTHER INFORMATION: Synthetic Oligonucleotide Sequence

<400> SEQUENCE: 409
cgaacuugcg cacacacguc auuggattta aaaaaaaaaa aaaaaaaaaa aaaaaaaa    59
```

METHODS AND COMPOSITIONS FOR THE SELECTION AND OPTIMIZATION OF OLIGONUCLEOTIDE TAG SEQUENCES

CROSS REFERENCE TO RELATED APPLICATIONS

This application is a divisional application of U.S. application Ser. No. 14/004,107, now allowed and which was filed under 35 USC § 371(c) on Oct. 21, 2013 as a U.S. national phase application of international Application No. PCT/US2012/028797, filed on Mar. 12, 2012, which claims priority from U.S. provisional application Ser. No. 61/451,285 filed Mar. 10, 2011, the contents of each of which are incorporated herein by reference in their entirety.

This application includes an electronic sequence listing in a file named 488843 SEQLST.TXT, created on Feb. 13, 2017, and containing 88,164 bytes, which is hereby incorporated by reference.

FIELD OF THE INVENTION

This present disclosure is directed to the field of nucleic acid-based assays incorporating one or more tag sequences into nucleic acid(s) of the assay. More specifically, methods and compositions are described related to the selection and optimization of oligonucleotide sequences referred to as "tags" for minimizing undesired nucleic acid interactions within the assay.

BACKGROUND

The use of short, user-selected (i.e., not defined by the target nucleic acid(s)) nucleic acid sequences (also known as "tags") is a very powerful technique for the design and development of novel nucleic acid assay formats. These nucleic acid formats include nucleic acid amplification, sequencing or other assay formats.

Nucleic acid amplification provides a means for making more copies of a nucleic acid sequence that is relatively rare or unknown, for identifying the source of nucleic acids, or for making sufficient nucleic acid to provide a readily detectable amount. Amplification is useful in many applications, for example, in research, diagnostics, drug development, forensic investigations, environmental analysis, and food testing.

Typically, nucleic acid amplification uses one or more nucleic acid polymerase and/or transcriptase enzymes to produce at least one copy, and preferably multiple copies of a target nucleic acid sequence and, optionally, a tag sequence.

Many methods for amplifying nucleic acid sequences in vitro are known, including polymerase chain reaction (PCR), ligase chain reaction (LCR), replicase-mediated amplification, strand-displacement amplification (SDA), "rolling circle" types of amplification, and various Transcription Mediated Amplification (TMA) and reverse TMA (rTMA) methods. These known methods use different techniques to make amplified sequences, which usually are detected by using a variety of methods. See, for example, Schweitzer and Kingsmore, combining nucleic acid amplification and detection, current opinion in Biotechnology, 2001, 12, 21-27. These methods can be exemplified by the following publications (each of which is hereby expressly incorporated by reference): PCR—U.S. Pat. Nos. 4,683,195, 4,683,202, and 4,800,159; LCR—U.S. Pat. No. 5,516,663 and EP 0320308 B1; Replicase-mediated amplification—U.S. Pat. No. 4,786,600; SDA—U.S. Pat. Nos. 5,422,252A and 5,547,861; Rolling circle types of amplification—U.S. Pat. Nos. 5,714,320 and 5,834,252; TMA—U.S. Pat. Nos. 4,868,105, 5,124,246, 5,130,238, 5,399,491, 5,554,516 and 5,437,990, 5,824,518, US 2006-0046265 A1 and WO 1988010315 A1; rTMA—US 2006-0046265.

Amplification methods may introduce nucleic acid sequences into the sequence being amplified. Some methods use modified primers to introduce non-target nucleic acid sequences to the sequence being amplified. One example of a modified primer is a "tag" primer. A tag primer contains two parts: (1) a "tag sequence" that is a nucleic acid sequence that does not hybridize to the target nucleic acid sequence and (2) a primer sequence that is a nucleic acid sequence that does hybridize to the target nucleic acid sequence. The tag sequence is located 5' to the primer sequence. The first round of amplification incorporates the tag sequence into the sequence being amplified. The second round of amplification uses primers that are complementary to the tag sequence.

Anchored PCR is a modified PCR method that uses an "adaptor" primer to amplify a sequence which is only partially known. See, for example, Loh et al., 1989, Science 243(4888):217-20; Lin et al., 1990, Mol. Cell. Biol. 10(4):1818-21).

Nested PCR may use primer(s) that contain a tag sequence unrelated to the target nucleic acid's target sequence to amplify nucleic acid from unknown target sequences in a reaction. See, for example, Sullivan et al, 1991, Electrophoresis 12(1):17-21; Sugimoto et al., 1991, Agric. Biol. Chem. 55(11):2687-92.

Other forms of amplification use a probe or probe set to introduce non-target priming sites located upstream and downstream of a target-specific sequence and adapter sequence(s). See, for example, U.S. Pat. Nos. 6,812,005 and 6,890,741, Fan et al. The two probes that bind in close proximity on a target sequence may be ligated together before being amplified by using the upstream and downstream universal priming sites.

Alternative assay methods may use probe hybridization and linear signal amplification by using a common sequence that is included in a variety of target nucleic acid-specific probes (e.g., US 20070111200, Hudson et al.). This method uses a labeled cassette that contains a sequence complementary to the common sequence to detect multiple target nucleic acids.

One problem that has heretofore existed with the use of tags is the lack of a rigorous selection method to identify the best tag for a given application. This has resulted in the use of less than optimal tags for particular applications.

Another problem is that tags may engage in undesired cross-reactions with other tags, primers, promoter providers, probes, amplicons, other target and non-target sequences and other such sequences in a given assay.

Another problem is that tags may engage in undesired cross-reaction with sequences in test samples from known or unknown sources, such as pathogenic or non-pathogenic organisms, mammalian nucleic acids, contaminating nucleic acids from enzymes, side-products of nucleic acid amplification reactions, etc.

One of the unsolved problems with multiplexed detection or amplification is the interference observed during multiplexing experiments, which limits the dynamic range, precision, and quantification characteristics for the target nucleic acids when present together in a sample.

In multiplex amplification reactions, a variety of undesired "side reactions" can occur that ultimately degrade assay performance. For instance, in the Transcription-Mediated Amplification (TMA) context, primers and/or promoter based amplification oligomers directed towards one target nucleic acid (or group of target nucleic acids) can interact with primers and/or promoter based amplification oligomers directed towards another target nucleic acid (or group of target nucleic acids), causing degraded performance of one, or the other or both amplification systems. This problem typically gets worse as the number of amplification systems present in a multiplex reaction increases. Other interactions that reduce assay performance include amplification oligomers interacting with one another or with other oligonucleotides in the amplification reaction, such as probes, blockers and target capture oligomers (TCOs), and amplicons. This problem of negative interaction between nucleic acids in a system can be reduced or solved by either converting all of the target specific primers/promoter providers in the assay or a portion of the target specific primers and/or promoter providers in the assay into primers and/or promoter based amplification oligomers containing tag sequences. Early rounds of amplification take place using these tagged amplification oligomers, thereby incorporating the tag sequences and their complements into the early amplification products. Subsequent rounds of amplification can take place using primers and/or promoter-based amplification oligomers having target hybridizing sequences directed to the incorporated tag sequence. In this way, the make-up of the subsequent round amplification oligomers is controlled by the user and undesired side reactions are reduced or eliminated. It is notable that the tag sequences used in two or more separate amplification oligomers can be the same sequence or different sequences.

Another related problem is the lack of a convenient procedure to quantitatively or qualitatively measure the relative levels of interferences in a multiplexed reaction.

Additionally, competition for amplification reaction resources may occur in multiplex amplification reactions when the same tag sequence is used for multiple tagged amplification oligomers. For example, in multiplex amplification reactions, target nucleic acid present at high levels will consume the amplification oligomers complementary to the tag sequence much faster than target nucleic acid present at low levels. The inability to uniformly amplify the target nucleic acids due to amplification resource competition may lead to false negatives because the target nucleic acids present at low levels are not amplified to a detectable amount.

One possible solution to these problems is to create unique tag sequences for incorporation into one or more oligomers in an assay. The unique tags are designed such that they do not interact with each other, or with any other sequences in the assay. In this way, an assay incorporating one or more tag sequences can proceed without reduced performance caused by the undesired interaction of various nucleic acids, including tag sequences, present in the assay reaction.

Clearly, there are numerous problems in the art of using nucleic acid tag sequences in a nucleic acid assay. It would be desirable to have tag sequences and methods for identifying tag sequences that are useful in a nucleic acid assay and that avoid the problems. It would be desirable to have methods for rapidly identifying tag sequences for use in a nucleic acid assay.

SUMMARY OF THE INVENTION

It is, therefore, our object of the present invention to provide an identification and selection method that can be used to generate unique tag sequence sets. Thus, the invention encompasses methods to identify and select nucleic acid tags for use in nucleic acid assays, sequencing, amplification, manipulation, interaction and other processing (sometimes referred to herein genetically as "nucleic acid assays"). The invention also encompasses a method of minimizing interference between nucleic acid sequences present in an assay, including amplification assays, multiplex amplification assays, sequencing assays and the like. In addition, the invention also encompasses compositions which have been selected by these methods.

The present invention encompasses a method for identifying a nucleic acid tag sequence for use in a nucleic acid assay, comprising: a) generating a pool of nucleic acid sequences, wherein the pool is at least three nucleic acid sequences; b) screening the pool of nucleic acid sequences to identify two or more nucleic acid sequences have two or more performance characteristics the; and c) selecting one or more nucleic acid sequences, each for use as tag sequence in a nucleic acid assay.

The invention further includes a method as described above, further comprising: d) comparing a nucleic acid sequences from the pool of nucleic acid sequences against a database having one or more nucleic acid sequences to determine complementarity of the nucleic acid sequences from the pool of nucleic acid sequences to the database having one or more sequences; e) generating a sub-pool of nucleic acid sequences, wherein the sub-pool is a collection of nucleic acid sequences with complementarity that is less than 95% to the nucleic acid sequence(s) in the database, that is less than 90% to the nucleic acid sequence(s) in the database; that is less than 80% to the nucleic acid sequence(s) in the database, that is less than 70% to the nucleic acid sequence(s) in the database, or that is less than 50% to the nucleic acid sequence(s) in the database; f) screening the sub-pool of nucleic acid sequences for one or more performance characteristics selected from melting temperature, activity in an enzyme reaction, G-C content, hybridization energy, multimer formation, internal structure formation, G-quartet formation, and hairpin-stability; and g) selecting one or more nucleic acid sequences from the sub-pool for use as tag sequences in a nucleic acid assay.

The invention further includes a method as described above, further comprising: h) synthesizing at least two different oligonucleotides for use in a nucleic acid assay, wherein each of the synthesized oligonucleotides has a tag sequence selected according to step g); and i) measuring for each of the different oligonucleotides synthesized in step h) one or more of the following performance characteristics: speed of reaction, limit of detection, interference, precision of replicates, performance against a specific target nucleic acid sequence, or performance against multiple target nucleic acid sequences in a nucleic acid assay, and optionally comparing the measurements to the measurements obtained for an untagged oligonucleotide; and j) selecting one or more of the nucleic acid tag sequences used in step i) for use in a nucleic acid assay.

The invention further includes a method as described above, further comprising the steps of: k) modifying the sequence of the tag sequence incorporated into an oligonucleotide from step h) to obtain a modified tag sequence for incorporation into an oligonucleotide; l) measuring for the oligonucleotide containing a modified tag sequence from step k) one or more of the following performance characteristics: speed of reaction, limit of detection, interference, precision of replicates, performance against a specific target nucleic acid sequence, or performance against multiple target nucleic acid sequences in a nucleic acid assay; and m) selecting one or more of the modified nucleic acid tag sequences used in step i) for use in a nucleic acid assay.

The invention further includes a method as described above, wherein the modification in step k) comprises systematically deleting nucleotides from the tag sequence.

The invention further includes a method as described above, further comprising at step g), the steps of: (i) modifying the sequence of the tag sequence from step g); (ii) synthesizing an oligonucleotide to contain the modified tag sequence; (iii) measuring for the oligonucleotide containing a modified tag sequence one or more of the following performance characteristics: speed of reaction, limit of detection, interference, precision of replicates, performance against a specific target nucleic acid sequence, or performance against multiple target nucleic acid sequences in a nucleic acid assay; and (iv) selecting one or more of the modified nucleic acid tag sequences used in step (iii) for use in a nucleic acid assay.

The invention further includes a method as described above, wherein the modification in step g) sub-step (i) comprises systematically deleting nucleotides from the tag sequence.

The invention further includes a method as described above, wherein the performance characteristic(s) is selected from the group consisting of one or more amplification performance characteristic(s); interference with nucleic acids in the nucleic acid assay; interference with one or more oligonucleotides in the nucleic acid assay; interference with one or more target nucleic acids in the nucleic acid assay; interference with one or more amplicons in the nucleic acid assay; assay reproducibility; or quantification.

The invention further includes a method as described above, wherein the performance characteristic is quantification.

The invention further includes a method as described above, wherein the quantification is real-time quantification.

The invention further includes a method as described above, wherein the quantification is end-point quantification.

The invention further includes a method as described above, wherein the performance characteristic is a dynamic range for detecting target nucleic acid; limit of detection; precision of replicates; or reaction kinetics.

The invention further includes a method as described above, wherein the performance characteristics comprise reaction kinetics.

The invention further includes a method as described above, wherein a nucleic acid sequence in the pool is used as a tag in a nucleic acid assay and reduces interference with a nucleic acid in the nucleic acid assay to about 95% or less compared to the amount of interference present in an untagged assay.

The invention further includes a method as described above, wherein a nucleic acid sequence in the pool is used as a tag in an in vitro nucleic acid assay and accelerates reaction kinetics to about 105% or more compared to the reaction kinetics in an untagged assay; slows reaction kinetics to about 95% or less compared to the reaction kinetics in an untagged assay; increases sensitivity for a target nucleic acid so that the amount of target nucleic acid needed to obtain a detectable signal is about 95% or less of the amount of target nucleic acid required in an untagged assay; decreases sensitivity for a target nucleic acid so that the amount of target nucleic acid needed to obtain a detectable signal is about 105% or more of the amount of target nucleic acid required in an untagged assay and/or increases replication precision by about 105% or more compared to an untagged assay.

The invention further includes a method as described above, wherein the nucleic acid assay is an in vitro isothermal amplification assay.

The invention further includes a method as described above, wherein the nucleic acid assay is an in vitro PCR amplification assay.

The invention further includes a method as described above, wherein the tag is part of an amplification oligomer.

The invention further includes a method wherein the tag is a barcode tag sequence for a sequencing reaction.

The invention further includes a method wherein the tag is a barcode tag sequence for a single molecule sequencing reaction.

The invention further includes a method as described above, wherein the tagged assay decreases the performance parameter by from 25% to 94%, from 50% to 94%, or from 75% to 94% compared to the untagged assay, wherein each range is inclusive of all whole and partial numbers therein.

The invention further includes a method as described above, wherein the tagged assay increases the performance parameter by from 105% to 150%, from 105% to 200%, or from 105% to 500% compared to the untagged assay, wherein each range is inclusive of all whole and partial numbers therein.

The invention further includes a method as described above, wherein the tag sequence has a Tm that is less than or equal to 72° C.

The invention further includes a method as described above, wherein the tag sequence has a primer dimer energy formation that is less than or equal to −10.0 kcal/mol; the tag sequence has a hairpin stability energy that is less than or equal to −4 kcal/mol; the 3' region of the tag sequence is less than 80% complementary to the one or more oligonucleotides in the searched database and/or the nucleic acid assay comprises two or more target nucleic acids.

The invention further includes a method as described above, wherein the database having one or more nucleic acid sequences is a collection of various nucleic acid sequences corresponding to a nucleic acid assay, a public collection of nucleic acid sequences, an aligned collection of nucleic acid sequences, the pool of nucleic acid sequences, or a combination thereof.

The invention further includes a method as described above, wherein the database having one or more nucleic acid sequences is a database containing sequence(s) that are derived from: collections of various nucleic acid sequences corresponding to a nucleic acid assay; a public collection of nucleic acid sequences; a collection of aligned sequences, the pool, or a combination thereof.

The present invention also encompasses a nucleic acid tag sequence obtained by any one of the methods as discussed above.

The present invention also encompasses an amplification oligomer having a nucleic acid sequence that includes a tag sequence obtained by any one of the methods discussed above.

The present invention further encompasses a method for identifying nucleic acid tag sequences for use in an in vitro nucleic acid amplification assay, comprising the steps of: a) generating a pool of nucleic acid sequences, wherein the pool is at least three nucleic acid sequences from Table 1; b) screening the pool of nucleic acid sequences against a database containing one or more nucleic acid sequences to identify percent complementarity between nucleic acid sequences in the pool and nucleic acid sequences in the database; c) screening the pool of nucleic acid sequences to determine a performance characteristic selected from the group consisting of: G-C content, multimer formation, primer-dimer formation, Tm, hairpin stabilization energy, self dimer stabilization energy, internal structure formation, G-quartet formation, hybridization energy, activity in an enzyme reaction, and combinations thereof; d) generating a sub-pool of nucleic acid sequences from the results obtained in step b), step c) or steps b) and c); and e) selecting one or more nucleic acid sequences from the sub-pool for use as tag sequences in a nucleic acid assay.

The invention further includes a method as described above, further comprising: f) synthesizing an amplification oligomer containing a tag sequence selected at step e); and g) performing an in vitro nucleic acid amplification reaction using the amplification oligomer.

The invention further includes a method as described above, wherein the sub-pool at step d) contains nucleic acid sequences with Tm values that are within ±2 degrees C. from a mean Tm of nucleic acids in the sub-pool; wherein the sub-pool at step d) contains nucleic acid sequences with Tm values that are within ±5 degrees C. from a mean Tm of nucleic acids in the sub-pool; nucleic acid sequences with Tm values that are within ±10 degrees C. from a mean Tm of nucleic acids in the sub-pool; nucleic acid sequences with G-C contents that are within ±5% from the mean G-C content of the nucleic acids in the sub-pool; nucleic acid sequences with G-C contents that are within ±10% from the mean G-C content of the nucleic acids in the sub-pool; and/or nucleic acid sequences with G-C contents that are within ±30% from the mean G-C content of the nucleic acids in the sub-pool.

The invention further includes a method as described above, wherein the sub-pool at step d) contains nucleic acid sequences with G-C contents from 30% to 80%, from 40% to 70%, or from 30% to 50%.

The invention further includes a method as described above, wherein the sub-pool at step d) consists of the nucleic acid sequences in Table 2.

The invention further includes a method as described above, wherein the sub-pool at step d) contains nucleic acid sequences with lengths from 5 nucleobases to 100 nucleobases.

The invention further includes a method as described above, wherein the in vitro amplification reaction performed at step g) has reduced interference between nucleic acids in the reaction when performed with the tagged amplification oligomer from step f) compared to when performed using an untagged amplification oligomer; the method has reaction kinetics that are accelerated by about 105% or more when performed with the tagged amplification oligomer from step f) compared to when performed using an untagged amplification oligomer; the method has reaction kinetics that are reduced to about 95% or less when performed with the tagged amplification oligomer from step f) compared to when performed using an untagged amplification oligomer; the method has increased sensitivity when performed with the tagged amplification oligomer from step f) compared to when performed using an untagged amplification oligomer, wherein the in vitro amplification reaction using the tagged amplification oligomer requires an amount of starting material that is about 95% or less than the minimum amount of starting material required in an untagged assay in order to obtain a detectable signal; the method has decreased sensitivity when performed with the tagged amplification oligomer from step f) compared to when performed using an untagged amplification oligomer, wherein the in vitro amplification reaction using the tagged amplification oligomer requires an amount of starting material that is about 105% or more than the amount of starting material required in an untagged assay in order to obtain a detectable signal; and/or the method has a replication precision that is about 105% or better when performed with the tagged amplification oligomer from step f) compared to when performed using an untagged amplification oligomer.

The invention further includes a method as described above, wherein the tagged assay decreases the performance parameter by from 25% to 94%, from 50% to 94%, or from 75% to 94% compared to the untagged assay, wherein each range is inclusive of all whole and partial numbers therein.

The invention further includes a method as described above, wherein the tagged assay increases the performance parameter by from 105% to 150%, from 105% to 200%, or from 105% to 500% compared to the untagged assay, wherein each range is inclusive of all whole and partial numbers therein.

The invention further includes a method as described above, wherein the one or more nucleic acid sequences in a database is a collection of various nucleic acid sequences corresponding to a nucleic acid assay, a public collection of nucleic acid sequences, an aligned collection of nucleic acid sequences, the pool of nucleic acid sequences, or a combination thereof.

The invention further includes a method as described above, wherein the one or more nucleic acid sequences in a database contains sequence(s) that are derived from: collections of various nucleic acid sequences corresponding to a nucleic acid assay; a public collection of nucleic acid sequences; a collection of aligned sequences, the pool, or a combination thereof.

The invention further includes a method as described above, wherein the in vitro amplification assay is an isothermal amplification assay; a multiplex amplification assay or a PCR amplification reaction.

The invention further encompasses a tagged amplification oligomer containing a tag sequence obtained by any one of the methods discussed above.

The invention further encompasses a multiplex in vitro amplification reaction mixture containing a tagged amplification oligomer with a tag sequence obtained by any one of the methods discussed above.

The invention also encompasses a multiplex in vitro amplification reaction mixture containing two tagged amplification oligomers, each with a tag obtained by any one of the methods discussed above.

The invention also encompasses a multiplex in vitro amplification reaction mixture, wherein the two tagged amplification oligomers each have a tag with the same nucleotide sequence.

The invention also encompasses a multiplex in vitro amplification reaction mixture containing three or more tagged amplification oligomers, each with a tag obtained by any one of the methods discussed above.

The invention also encompasses a kit for amplification of a target nucleic acid, wherein the kit contains a tagged amplification oligomer containing a tag sequence obtained by any one of the methods discussed above.

The invention also encompasses a kit for amplification of a target nucleic acid, wherein the kit contains at least two tagged amplification oligomers containing, each containing tag sequences obtained by any one of the methods discussed above.

The invention also encompasses a kit according as discussed above, wherein the tag sequences are the same nucleic acid sequence in each tagged amplification oligomer.

The invention also encompasses a collection of nucleic acid sequences useful as tag sequences for use in a nucleic acid assay, wherein the collection contains at least two of the sequences in Table 1, Table 2, or Table 3.

In another embodiment, the method can be applied to sequences intended to be used in uniplex or multiplex assays.

However, in multiplex assays, interference between the multiple target nucleic acids, from which at least a part of each is intended to be amplified or detected, can cause reduced and inaccurate measurement of the amount of the target nucleic acid in the reaction mixture.

To address this issue, the present disclosure provides a semi-quantitative method that allows for effective discrimination between the levels of interference among multiplex systems with different (or same) tag sequences. The method compares the performance of each of the sequences in a uniplex format, against their performance in a duplex format to arrive at a qualitative determination of the utility of a particular set of sequences together in a particular duplex or multiplex reaction. In a further aspect, the tags are ranked semi-quantitatively in order of their observed interference in the multiplex reaction. This information can be used for the studies which will enable a new user to quickly identify and test tag combinations for a new multiplexed amplification system, and ultimately determine an improved reaction mixture for nucleic acid assays.

BRIEF DESCRIPTION OF THE DRAWINGS

FIG. 1B illustrates that the random oligonucleotide sequences from FIG. 1B are preferably screened in uniplex format and then in duplex format. However, this is non-limiting. The random oligonucleotide sequences can be screened serially in uniplex then duplex formats, or concurrently in uniplex and duplex formats, or in duplex format without a uniplex screen, or in any arrangement of uniplex and/or multiplex formats.

FIG. 3. In silico screen: this figure illustrates a series of randomly generated oligomer sequences coupled with certain select characteristics. The illustrated characteristics are not limiting. Selections are made based upon the characteristics.

FIG. 10 illustrates PCA3 and PSA analytes for comparison. The in vitro nucleic acid assay format used to generate the results shown in FIGS. 4-6 was a RUt TMA nucleic acid assay. The in vitro nucleic acid assay format used to generate the results shown in FIGS. 7-10 was a RUf TMA, which used an amplification oligomer complex in the direct hybridization configuration. In FIG. 7 (continued) bottom panel, a line is drawn from the number 500 to each of the curves representing 500 copies of analyte in the reaction. In FIG. 9 Set T9 panel there the number $10^4$ is shown twice, indicating that a couple of the $10^4$ reactions were above a set threshold fluorescence amount and a couple $10^4$ reactions and all of the 500 copy reactions were under that threshold amount.

In FIG. 14 for the panel showing N28 & T18 tag sequences there are lines drawn from the $10^4$ copy number to the tracings representing $10^4$ reactions, and from the 500 copy number to the tracings representing 500 copy reactions. IN FIG. 15 for the panel showing the N47 &T9 tag sequences, there is a line drawn from the 500 copy number to the tracings representing the 500 copy reactions.

FIGS. 18-19 show emergence times from a RUf TMA amplification assay using the T21 and U20 tags incorporated into amplification oligomers in a direct-hybridization amplification oligomer complex. The T21 tag and modified versions of the T21 tag were used, wherein the modified tags are shortened by the number of nucleotides in the tag name (e.g. T21-# is shortened by # nucleotide residues). Residues were removed from the 3'end of the tag sequence. The target nucleic acid is PCA3 and is provided in the assay reactions in $10^4$ or $10^2$ copy number.

FIG. 22 bottom right panel=PCA3(N23); FIG. 23 bottom left panel=PSA(U20); FIG. 23 bottom right panel=PCA3(N23)). "NTC" means non-template control and represents a control nucleic acid that is not targeted by uniplex amplification oligomers or the potentially interfering amplification oligomer.

In FIG. 25, the tagged nucleic acids are the non-T7 amplification oligomers and are both U20 tags. In FIG. 26, the tagged nucleic acids are the non-T7 amplification oligomers, with the PCA3 non-T7 being tagged with N54 and PSA being tagged with U20.

FIG. 27 illustrates a number of values obtained for tagged amplification oligomers used in a series of TMA assay as described in FIGS. 22-26.

FIGS. 28 and 30 illustrate the target capture oligomers, blocker oligomers, amplification oligomers and torch detection probes used an a series of triplex amplification reaction containing varied amounts of analytes as indicated in the figures. The top set of oligomer in FIG. 28 targets PCA3, the middle set target PSA and the bottom set target an internal control sequence. In a first set of reactions, the oligomers in FIG. 28 were used against analytes in amounts also as indicated in FIG. 28, and the amplification oligomers all used U20 tag sequences. In a second set of reactions, a set of oligomers substantially identical to those shown in FIG. 28, except that the U20 tag sequence in the non-T7 targeting PCA3, was substituted with an N54 tag sequence. Exemplary results for the full U20 tagged reactions and for the U20/N54 tagged reactions are illustrated in FIGS. 29 and 31.

FIG. 36 illustrates quantitation data from the T2 ERGa/PSA/IC triplex RUh TMA reaction using the N42/N6/N42 tagged non-T7 amplification oligomers from FIG. 35. "Cal" means calibrator and "CON" means control sample.

FIG. 38. T2 ERGa/PSA/IC (N42/N6/N42) Quantitation

DETAILED DESCRIPTION

Figure 1A:
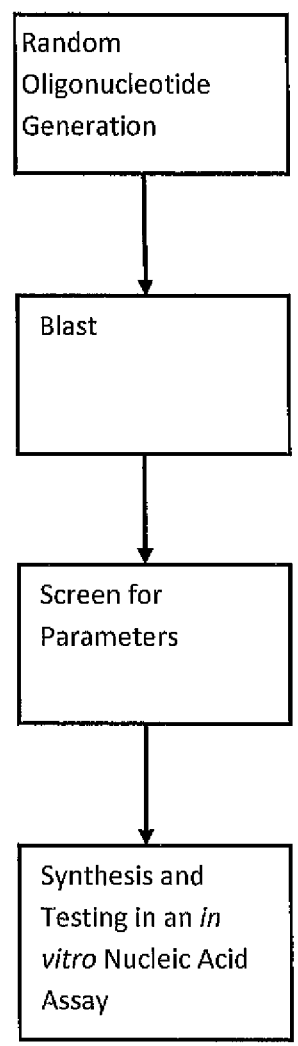
FIGS. 1A and 1B. Schematic flow charts illustrating a screen for universal Tags.

In nucleic acid assays which use tags, the selection of the right tag or combination of tags is important. The presently disclosed methods can be applied to various nucleic acid assays, but are particularly referenced in regard to nucleic acid amplification and sequencing. However, such reference is not intended to limit the scope of the application of the disclosed methods and sequences in any way.

DEFINITIONS

Unless otherwise described, scientific and technical terms used herein have the same meaning as commonly understood by those skilled in the art of molecular biology based on technical literature, e.g., Dictionary of Microbiology and Molecular Biology, 2nd ed. (Singleton et al., 1994, John Wiley & Sons, New York, N.Y.), or other well known technical publications related to molecular biology. Unless otherwise described, techniques employed or contemplated herein are standard methods well known in the art of molecular biology. To aid in understanding aspects of the disclosed methods and compositions, some terms are described in more detail or illustrated by embodiments described herein.

"Activity in an Enzyme Reaction" is used herein to refer to a number of enzyme driven functions. The term includes binding, extension, cleavage, recombination, repair, and transcription, when these functions are performed by an enzyme.

"Amplification" of a nucleic acid as used herein refers to the process of creating in vitro nucleic acid sequences that are substantially identical or substantially complementary to a complete or portion of a target nucleic acid sequence. The in vitro created nucleic acid sequences are referred to as "amplification product" or "amplicon" and may include one or more tag sequences or the complement of one or more tag sequences. The tag sequences are incorporated into amplification product using tagged amplification oligomers. Alternatively, the tags can be chemically incorporated into a nucleic acid sequence.

"Amplicon" or the term "Amplification Product" as used herein refers to the nucleic acid molecule generated during an amplification procedure that is complementary or homologous to a target sequence contained within a target nucleic acid. These terms can be used to refer to a single strand amplification product, a double strand amplification product or one of the strands of a double strand amplification product. Using an amplification oligomer comprising a target hybridizing sequence and at least one other region that incorporates into the extension product, results in an amplification product comprising the nucleic acid sequence that is homologous and/or complementary to the amplified portion of the target nucleic acid sequence and the incorporated regions of the amplification oligomer. Incorporated regions forming part of an amplification product include tag sequences.

"Amplification Oligomer" or "Amplification Oligonucleotide" as used herein refers to a nucleic acid oligomer that is used for generating complementary strands from a target sequence of a target nucleic acid. The complementary strand can be made by elongation of 3'-end of an amplification oligomer, as is common when using primers, or can serve as a recognition site for an enzyme to initiate complementary strand synthesis, as is common when using promoter sequences. Amplification oligomers include primers, promoter-based amplification oligomers, promoter primers (which allow for elongation for their 3'-ends and transcription from their promoter sequences), and promoter-providers (which are modified to prevent elongation of their 3'-ends but allow for promoter-driven transcription). Amplification oligomers as described herein may further comprise tag sequences.

Amplification oligomers may be directly or indirectly joined one to another to form an "Amplification Oligomer Complex." Typically joined together are first and second amplification oligomers targeting opposite binding sites of a target sequence. In this configuration, the first amplification oligomer of the complex hybridizes to a binding site on a target sequence, while the second amplification oligomer does not hybridize to the target sequence. The amplification oligomers may be joined one to the other using a connecting compound such as a C9 linker, an oligonucleotide that hybridizes to portions of each amplification oligomer or other such manners. Alternatively, the amplification oligomers may be joined one to the other by hybridizing together complementary portions of the amplification oligomers. Amplification oligomer complexes can comprise any combination of primer or promoter based amplification oligomer. See US Pat. Pub. No. 2008-0305482 A1 and U.S. patent application Ser. No. 12/828,676 disclosing exemplary Amplification Oligomer Complexes.

The term "barcode" is used herein to refer to a tag sequence incorporated into a nucleic acid allowing for identification of some feature of the nucleic acid. A feature of the nucleic acid includes SNPs. For example, the amplicon species in a SNP analysis are substantially identical except for the SNP. Two separate species of primers can be configured to have a 3' end that is complementary to one SNP sequence or the other, and to have a unique barcode tag sequence to identify to which SNP species the amplicon corresponds. Detection of the SNP species can then be made by identifying the corresponding barcode. A feature of a nucleic acid includes the sample from which the nucleic acid originated. For example, a plurality of samples can be analyzed for the presence of a target nucleic acid. Each sample can be independently barcoded by performing an amplification reaction to integrate a barcode tag into the sample target nucleic acid. The samples are then combined and subjected to subsequent analysis, which can be an additional amplification or a detection reaction. The various combined amplicons in the reaction will be substantially identical except for the barcode tag sequences indicating from which sample the amplicon originated. Other features of a nucleic acid can be identified by a barcode, as is understood by ordinarily skilled artisans.

"Complementarity" is the percentage or amount of a sequence that is complementary to a target sequence or other sequence. The present methods implicate different situations where both high and low levels of complementarity are useful and desirable. "Minimal complementarity" as used in this application refers to the desire to achieve the lowest possible amount of complementarity between a sequence (a tag sequence, for example) and other nucleic acid sequences that may be present in a reaction mixture so as to minimize binding/reaction there between. One example is that a tag sequence selected for use in an amplification reaction is selected to minimize its complementarity to other nucleic acids that may be present in the reaction that are not intended to bind to the tag sequence. In nucleic acid assays wherein a tag sequence is selected so that it is not used to generate amplification products, then it may be sufficient for only the 3'-portion of the tag sequence to possess minimal complementarity to other nucleic acid sequence and still function as desired. This could be particularly true in the case of primers, where the 3'-portion of the sequence is important for enzymatic extension. The 3'-portion of a sequence may refer to the 3'half, the 3' third or the 3' quarter of the sequence, or even less as long as the proper function of the tagged oligonucleotide is not prevented or impeded. In nucleic acid assays wherein it is desired that a tag sequence not randomly hybridize to a nucleic acid in the reaction, then the entire tag sequence is screened for complementarity to a nucleic acid in the system.

"Consisting essentially of" is used to mean that additional component(s), composition(s) or method step(s) that do not materially change the basic and novel characteristics of the methods and compositions described herein may be included in those methods and compositions. Such characteristics include the method of identifying and selecting nucleic acid tags for use in an assay wherein the tags are selected to reduce or eliminate undesired nucleic acid interactions within an assay.

"Database of Nucleic Acid Sequences" is used to refer to an in silico collection of nucleic acid sequences. The database of nucleic acid sequences can be the pool or sub-pool of tag sequences, or can be a collection of nucleic acid sequences that may be present in a nucleic acid assay. For example, the various nucleic acids corresponding to an amplification reaction to determine whether a blood sample contains HIV can include the amplification oligomers, the target capture oligomers, probe oligomers, positive control oligomers, HIV nucleic acids and blood cell nucleic acids. A database of nucleic acids, then, can be any one or combination of these nucleic acids in the assay system. The database of nucleic acid sequences can be a public collection of nucleic acid sequences, such as the collection kept by the National Institute of Health (GenBank, National Center for Biotechnology Information, U.S. National Library of Medicine, Maryland, USA).

"Dynamic Range" of an assay generally refers to how much a target concentration (e.g. in a sample) can vary and still be deleted and quantified. The smaller the range, the less robust is the assay, sometimes measured by the cycle number vs. log of the measured signal. These layer the dynamic range, the greater is the ability of the assay to detect samples/targets with high and low copy number in the same run.

"Hybridization Energy" is used to refer to a measurement of free energy released during hybridization of two nucleic acid sequences. Primer dimer hybridization, G-quartet hybridization, primer binding, hairpin structure formation, internal structure formation, and nucleic acid probe binding are all examples of hybridizations. Candidate nucleic acid tag sequences are screened for hybridization to determine the suitability of the tag sequence fro a given application in a nucleic acid assay. In some instances, hybridization energy favoring hybridization is preferred, in other instances; hybridization energy disfavoring hybridization is preferred. For example, in a nucleic acid amplification assay wherein the tag sequences are screened for use as part of an amplification oligomer, then the hybridization energy for useful tag sequences includes those that do not hybridize to nucleic acid sequences in the amplification system.

"Interference" during nucleic acid assays is a common recognized problem and can be seen in various aspects of an assay, including target sequence interference, amplicon interference and primer interference. For example, multiplex PCR assays are known to suffer from primer interference and dimer formation that can cause a reduction in PCR amplification efficiency and multiplexity capacity. Such interference issues can be measured by techniques known in the art.

"Isolated" as used herein means that a target nucleic acid is taken from its natural milieu, but the term does not connote any degree of purification.

"Label" refers to a molecular moiety or compound that can be detected or lead to a detectable response, which may be joined directly or indirectly to a nucleic acid probe. Methods of synthesizing labels, attaching labels to nucleic acids, and detecting labels are well known (e.g., Sambrook et al, Molecular Cloning, A Laboratory Manual, 2nd ed. (Cold Spring Harbor Laboratory Press, Cold Spring Harbor, N.Y., 1989), Chapt. 10; U.S. Pat. Nos. 5,658,737, 5,656,207, 5,547,842, 5,283,174, and 4,581,333). More than one label, and more than one type of label, may be present on a particular probe, or detection may use a mixture of probes in which each probe is labeled with a compound that produces a detectable signal (e.g., U.S. Pat. Nos. 6,180,340 and 6,350,579).

"Limit of Detection" or "Detection Sensitivity" generally refer to the ability of an assay to detect, measure or otherwise test or react with one particular target or objective as distinctive from others, e.g. in a sample. "Limit of Detection" as used herein is a measure of sensitivity of an assay. The detection limit for an analytical procedure can be defined as "the minimum single result which, with a stated probability, can be distinguished from a suitable blank value" and "the point where, with a stated probability, one can be confident that the signal due to the measurement can be distinguished from the instrumental background signal". For a specific analytical procedure, the LOD can also be defined as "the lowest amount of an analyte in a sample which can be detected but not necessarily quantified as an exact value." The LOD is generally expressed as the amount of analyte at which the analytical method detects the presence of the analyte at least 95% of the time. The LOD is often used in terms of the level at which detection starts to become problematic. There are a number of potential reasons for this, inclusive of the presence of noise or an unstable baseline, the contribution of interferences to the signal, the affect of analytical blanks, and losses during the extraction, isolation or cleanup process. One of the most important reasons for defining a LOD is to identify where the method performance becomes insufficient for acceptable detection of the target analyte, in order that subsequent analytical measurements can stay away from this problematic area. The evaluation of the LOD of an assay is thus critical for trace detection methods, especially where the result will be used for regulatory or public health applications.

"Melting Temperature" as used herein refers to the temperature at which half of the DNA strands are in the double helical state and half of the strands are in a random coil state. The desired melting temperature of a candidate tag sequence varies depending upon the intended use of the tag and the assay format it will be used in. (See e.g., Donald Voet and Judith G. Voet, Biochemistry (1990); Owczarzy et al., Predicting sequence-dependent melting stability of short duplex DNA oligomers, Biopolymers (1997) 44 (3):217-239; and Breslauer, et al., Predicting DNA Duplex Stability from the Base Sequence. Proc. Natl. Acad. Sci. USA. (1986) 83 (11): 3746-3750.)

"Nucleic acid" as used herein refers to a polynucleotide compound, which includes oligonucleotides, comprising nucleosides or nucleoside analogs that have nitrogenous heterocyclic bases or base analogs, covalently linked by standard phosphodiester bonds or other linkages. Nucleic acids include RNA, DNA, chimeric DNA-RNA polymers or analogs thereof. In a nucleic acid, the backbone may be made up of a variety of linkages, including one or more of sugar-phosphodiester linkages, peptide-nucleic acid (PNA) linkages (PCT No. WO 95/32305), phosphorothioate linkages, methylphosphonate linkages, or combinations thereof. Sugar moieties in a nucleic acid may be ribose, deoxyribose, or similar compounds with substitutions, e.g., 2' methoxy and 2' halide (e.g., 2'-F) substitutions. Nitrogenous bases may be conventional bases (A, G, C, T, U), analogs thereof (e.g., inosine; The Biochemistry of the Nucleic Acids 5-36, Adams et al., ed., 11$^{th}$ ed., 1992), derivatives of purine or pyrimidine bases (e.g., N$^4$-methyl deoxygaunosine, deaza- or aza-purines, deaza- or aza-pyrimidines, pyrimidines or purines with altered or replacement substituent groups at any of a variety of chemical positions, e.g., 2-amino-6-methyl-aminopurine, O$^6$-methylguanine, 4-thio-pyrimidines, 4-amino-pyrimidines, 4-dimethylhydrazine-pyrimidines, and O$^4$-alkyl-pyrimidines, or pyrazolo-compounds, such as unsubstituted or 3-substituted pyrazolo[3,4-d]pyrimidine (e.g. U.S. Pat. Nos. 5,378,825, 6,949,367 and PCT No. WO 93/13121). Nucleic acids may include "abasic" positions in which the backbone does not have a nitrogenous base at one or more locations (U.S. Pat. No. 5,585,481, Arnold et al.), e.g., one or more abasic positions may form a linker region that joins separate oligonucleotide sequences together. A nucleic acid may comprise only conventional sugars, bases, and linkages as found in conventional RNA and DNA, or may include conventional components and substitutions (e.g., conventional bases linked by a 2' methoxy backbone, or a polymer containing a mixture of conventional bases and one or more analogs). The term includes "locked nucleic acids" (LNA), which contain one or more LNA nucleotide monomers with a bicyclic furanose unit locked in an RNA mimicking sugar conformation, which enhances hybridization affinity for complementary sequences in ssRNA, ssDNA, or dsDNA (Vester et al., 2004, Biochemistry 43(42): 13233-41).

"Oligonucleotide" and "Oligomer" are interchangeable terms and used herein refer to nucleic acid polymers generally made of less than 1,000 nucleotides (nt), including those in a size range from about 5-200 nucleotides in length those having lower limit of about 2 to 5 nt and an upper limit of about 500 to 900 nt, or a lower limit of 5 to 15 nt and an upper limit of 50 to 500 nt, or a 10 to 20 nt lower limit and a 25 to 150 nt upper limit. Preferred oligonucleotides are made synthetically by using any well known in vitro chemical or enzymatic method, and may be purified after synthesis by using standard methods, e.g., high-performance liquid chromatography (HPLC).

"Performance Characteristic" means a characteristic of a nucleic acid tag sequence. A performance characteristic of a nucleic acid tag sequence includes a characteristic that is unique to the tag sequence by itself. This includes, but is not limited to, the length of a tag sequence, the G-C content of the tag sequence, the nucleobase composition of the tag sequence, the melt temperature of the tag sequence, etc. A performance characteristic of a nucleic acid tag sequence also includes a characteristic of an oligonucleotide sequence containing that tag. A performance characteristic can be independent of a nucleic acid assay, or a performance characteristic can be determined with regard to a nucleic acid assay. For example, a performance characteristic that is a hybridization event can be determined for a nucleic acid assay, wherein the hybridization is the formation of a primer dimer. Determination of performance characteristics can be in silico or it can be through wet chemistry.

"Pool of Nucleic Acid Sequences" or "Pool of Nucleic Acids" is used to refer to a collection of nucleic acid tag sequences that will be subjected to an analysis to determine at least one performance characteristic. The pool will have at least three nucleic acids. The pool can be an in silico collection of tag sequences, such as a database of nucleic acid tag sequences. The pool can also be a collection of the chemical compounds, such as a freezer box containing a plurality of vials each with a different tag sequence within. The pool can optionally include other information associated with the individual tag sequences, such as a reference name or a property of the chemical compound.

"Precision" in relation to assays, like PCR, generally refers to the variability (i.e. the lack of) among repeated measurements or observations. Precision can be affected by many different factors.

"Precision of Replicates" refers generally to the ability of the assay to produce the same replicates in the same quantities, often statistically measured by means of standard deviations, such as a t test.

"Primer" or "Non-Promoter Primer" is an amplification oligomer that does not comprise a promoter sequence. Thus, primers comprise at least a target hybridizing sequence that is configured to be substantially complementary to part of a target sequence. The target hybridizing sequence need not have 100% complementarity to its intended binding site, but instead may contain 1 or more of a mismatch, insertion, deletion or modification relative to its binding site, so long as the primer's target hybridizing sequence hybridizes to its binding site under stringent conditions. Primers may further comprise tag sequences, capture sequences, self-complementary sequences for forming hairpin loops, and other sequences in addition to the target hybridizing sequences.

"Probe," "Detection Probe" or "Detection Oligonucleotide" as used herein refers to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., biotin/streptavidin reporter). Probes may be DNA, RNA, analogs thereof or combinations thereof and they may be labeled or unlabeled. A probe may comprise target-specific sequences and other sequences that contribute to the three-dimensional conformation of the probe (e.g., U.S. Pat. Nos. 5,118,801; 5,312,728; 6,849,412; 6,835,542; 6,534,274; and 6,361,945; and US Pub. No. 20060068417).

"Promoter Primer" is an amplification oligomer that is similar to a primer except that the oligomer further comprises a promoter sequence. Promoter primers are capable of 3' extension by a polymerase and supply a promoter sequence for transcription by a polymerase. Preferred promoter sequences include promoter sequences recognized by RNA Polymerases, such as sp6 promoters, T3 promoters, T7 promoters and others. For example, the T7 promoter sequence is 5'-aatttaatacgactcactagggaga. Promoter-primers, therefore, comprise a target hybridizing sequence joined at its 5'-end to a promoter sequence. Promoter primers may further comprise tag sequences, capture sequences, self-complementary sequences for forming hairpin loops and other sequences. These additional sequences may be joined to the 5'-end of the promoter sequence, or they may be joined to the 3'-end of the promoter sequence, thereby being flanked on each end by the promoter sequence and the target hybridizing sequence.

"Promoter Provider" is an amplification oligomer that is similar to a promoter primer except that the 3'-end of the oligomer is modified to prevent elongation by a polymerase. Promoter providers supply a promoter sequence for transcription by a polymerase. Promoter providers may further comprise tag sequences, capture sequences, self-complementary sequences for forming hairpin loops and other sequences. These additional sequences may be joined to the 5'-end of the promoter sequence, or they may be joined to the 3'-end of the promoter sequence, thereby being flanked on each end by the promoter sequence and the target hybridizing sequence.

"Quantization" or "Quantification" is used when referring to accuracy in quantification, precision in quantification, and limit of quantification. Quantification can be end point quantification.

"Speed of Reaction" as used herein can encompass a variety of reaction characteristics by a variety of factors, including the reporter dye, nucleotide and primer concentration, enzymatic activity, and the like (see e.g. Lui and Saint, Analytical Biochemistry 302, 52-59 (2002)). Various mathematical models exist that can describe the reaction kinetics. (see e.g. King et. al., Bio Techniques 47:941-949 (November 2009)).

"Region" as used herein refers to a portion of a nucleic acid wherein said portion is smaller than the entire nucleic acid. For example, when the nucleic acid in reference is an oligonucleotide promoter provider, the term "region" may be used refer to the smaller promoter portion of the entire oligonucleotide. Similarly, and as example only, when the nucleic acid is a target nucleic acid, the term "region" may be used to refer to a smaller area of the nucleic acid, such as the target sequence, an oligomer binding sequence within the target sequence, or the like.

"Relative fluorescence unit" ("RFU") is an arbitrary unit of measurement of fluorescence intensity. RFU varies with the characteristics of the detection means used for the measurement.

"Sequencing" as used herein refers to methods for determining the precise nucleotide sequence of a target nucleic acid. Various sequencing methods are known including chain termination sequencing, dye terminator sequencing, sequencing by ligation, sequencing by synthesis, sequencing by hybridization, circular consensus sequencing, and single molecule sequencing. So-called next generation and third generation sequencing methods are designed to sequence numerous target templates in parallel. Such methods are particularly useful when the target nucleic acid is a heterogeneous mixture of variants, such as is often the case in a sample from a patient infected with a virus, such as HIV or HCV wherein the patient's viral load typically is a mixed population of a majority species and numerous minority species. Amongst the many advantages, sequencing variants in parallel provides a profile of drug resistant mutations in the sample, even drug mutations present in relatively minor proportions within the sample.

Some next generation sequence methods amplify by emulsion PCR. A target nucleic acid immobilized to beads via a capture probe provides a suitable starting material for emulsion PCR. The beads are mixed with PCR reagents and emulsion oil to create individual micro reactors containing single beads (Margulies et al., Nature. 15 Sep. 2005; 437 (7057):376-80). The emulsion is then broken and the individual beads with amplified DNA are sequenced. The sequencing can be pyrosequencing performed for example using a Roche 454 GS FLX sequencer (454 Life Sciences, Branford, Conn. 06405). Alternatively, sequencing can be ligation/detection performed for example using an ABI SOLiD Sequencing System (Life Technologies, Carlsbad, Calif. 92008). In another variation, target nucleic acids are eluted from the capture probe and immobilized in different locations on an array (e.g., the HiScanSQ (Illumina, San Diego, Calif. 92121)). The target nucleic acids are amplified by bridge amplification and sequenced by template-directed incorporation of labeled nucleotides in an array format (Illumina). In another approach, target nucleic acids are eluted from the capture probe and single molecules are analyzed by detecting in real-time the incorporation nucleotides by a polymerase. The nucleotides can labeled nucleotides that release a signal when incorporated (e.g., Pacific Biosciences, Eid et al., Sciences 323 pp. 133-138 (2009)) or unlabeled nucleotides, wherein the system measures a chemical change upon incorporation (e.g., Ion Torrent Personal Genome Machine (Life Technologies, Carlsbad, Calif. 92008)).

As a non-limiting example of identifying and selecting tags for use in a sequencing reaction, the following describes identifying and selecting barcode tag sequences for amplification and detection of majority and minority HIV sequences in a single sample. Human Immunodeficiency Virus (HIV) typically exists in a sample as both majority and minority species. Minority species are often undetected in a sample because of their low prevalence (e.g., 0.5% of total HIV population in the sample). Even with assays that are sensitive enough to detect the minority species, the generic nature of many assays hinders resolution of the various species (e.g., a PCR assay may detect but not differentiate between the species). Minority species are often drug resistant species. A failure to detect the minority species is then a failure to identify an important component of the tested sample. Retroviral therapy is then selected and administered without knowledge of the drug resistant species, thereby selecting for a drug resistant HIV population in the patient.

Sequencing assays, including single molecule sequencing assays, are useful analysis techniques for identifying both the majority and the minority species in a sample because the sequence analysis will provide a population of sequence results representing the majority species and a population of sequence results representing the minority species. Often in sequencing assays, though, the minority species are masked by sequencing errors, which are common with these types of assays.

In order to overcome the error rate problem encountered in sequencing assays and accurately identify minority HIV species in a sample, one can design a barcoded amplification oligomer that is configured to amplify the majority species and a separate barcoded amplification oligomer that is configured to amplify the minority species. The majority HIV species barcoded amplification oligomer can include a 3' nucleic acid residue that is complementary to and hybridizes with the SNP nucleobase that is associated with the majority species. The minority HIV species barcoded amplification oligomer can include a 3' nucleic acid residue that is complementary to and hybridizes with the SNP nucleobase that is associated with the minority species. The barcode sequence of the majority species amplification oligomer is unique when compared to the barcode sequence of the minority species amplification oligomer. Furthermore, these barcode sequences are selected using a performance characteristic profile that includes providing a unique identifier despite the error rate associated with single molecule sequencing. Typically, but not necessarily or exclusively, this performance characteristic is length and/or nucleobase composition. The length and/or nucleobase composition of the barcodes are preferably configured with the error rate of the sequencing platform in mind, thereby being able to buffer any errors from masking the presence and uniqueness of the barcode sequences. The majority amplification oligomer and the minority amplification oligomer are then used with a common reverse amplification oligomer, and an amplification reaction can be performed. The amplicons generated from the reaction will include one of the two barcode tag sequences, depending on from which HIV species the amplicon was derived. The amplicons can then be sequenced and the data analyzed. Sequencing errors will likely be present and mask the SNP site; however, the unique barcode sequences that were incorporated into the amplicons based upon the HIV species from which they derived will provide an identification of the SNP feature for species. Thus, either or both of the barcode tag sequences and SNP residue are good endpoints for detection of the HIV species in the tested sample.

In the tag identification method for this example, barcode tags would be selected for use in amplification oligomers that are configured to generate an amplification product from one or another SNP corresponding to different species of HIV. A pool of nucleic acid sequences would be generated and that pool screened for two or more performance characteristics useful for the HIV sequencing reaction. Preferably, but not necessarily or exclusively, the performance characteristics include length and/or nucleobase composition. At least one barcode tag sequence would then be selected for each of the amplification oligomers (i.e., the majority species amplification oligomer and the minority species amplification oligomer) and the barcode tagged amplification oligomers would be synthesized. One or more performance characteristics can then be measured for the various combinations of barcode tagged amplification oligomers. Two or more barcode tagged amplification oligomers can be used in a sequencing assay. Sequencing data can then be analyzed and the presence or absence of various HIV species in a sample can be determined by the sequence data including the unique barcode sequences. Further, the relative abundance of one species to another can be determined by the sequence data including using the relative abundance of unique barcode sequences, one to the other.

As a non-limiting example of identifying and selecting tags for use in sequencing assays, the following describes identifying and selecting barcode tag sequences for amplification and detection of nucleic acid sequences from two or more samples to be combined and sequenced in a single sequencing reaction. It is often desirable to determine via a sequencing reaction the presence, absence or composition of a target nucleic acid in a number of samples. In one such example, the presence or absence of a T2:ERG fusion can be determined for two or more different patients in a single sequencing reaction using barcoded amplification oligomers. In such an example, a sample from a first patient can be amplified to incorporate a barcode sequence. Separately, a sample from a second patient can be amplified to incorporate a barcode sequence that is unique from the barcode used in the first patient's sample. Following amplification and preparation of the amplicons for a sequencing reaction, the samples can be combined and analyzed by sequencing. Resultant sequencing data can then be identified via the barcode tag sequences as having come from amplicons of the first sample or of the second sample.

In the tag identification method for this example, barcode tags would be selected for use in amplification oligomers that are configured to generate an amplification product of the same target nucleic acid, but from separate samples, and then combined for analysis using a sequencing assay. A pool of nucleic acid sequences would be generated and that pool screened for two or more performance characteristics useful for the combined sequencing reaction. Preferably, but not necessarily or exclusively, the performance characteristics include length and/or nucleobase composition. At least one barcode tag sequence will be selected for the amplification oligomers used in a sample and at least one barcode tag sequence that is/are unique from those in the first sample will be selected for the amplification oligomers used in the second sample. The barcode tagged amplification oligomers would be synthesized, and one or more performance characteristics can then be measured for the various combinations of barcode tagged amplification oligomers. Two or more barcode tagged amplification oligomers can be used in a sequencing assay. Sequencing data can then be analyzed for the presence, absence or composition of the T2:ERG target nucleic acid sequence from each sample by using the sequence data including the unique barcode sequences.

"Sub-Pool of Nucleic Acid Sequences" is used to refer to a collection of nucleic acid tag sequences that have been subjected to an analysis to determine at least one performance characteristic, and that are selected for incorporation into at least one oligonucleotide sequence for use in a nucleic acid assay. The sub-pool can be an in silico collection of tag sequences, such as a database of nucleic acid sequences. It is not necessary that the sub-pool is a separate database from the pool database, but instead the sub-pool can be a sub-collection within the larger pool database that is somehow differentiated. For example, the sub-pool can be a smaller collection of tag sequences within the pool, wherein the smaller collection of tag sequences share a common melt temp range. The sub-pool can also be a collection of the chemical compounds, such as a freezer box containing a plurality of vials each with a different tag sequence within. Again, it is not necessary that the sub-pool is physically separate from the pool.

"Tag" as used herein is a user-selected nucleic acid sequence that does not hybridize to the target nucleic acid. A tag sequence can be tailored for a specific assay against a specific target sequence or can be designed to apply to a wide variety of assay formats and/or target sequences. One or more tags can be used in an assay. When two or more tags are used in an assay, the tag sequences can be different from one another or two or more tags in the assay can have substantially the same sequences. Tags can serve a number of functions in nucleic acid-related assays, including but not limited to, amplification oligomers, adapter sequences (e.g. SMRTbell), hairpin adapter sequences, sequencing primers, barcodes, detection sequences, displacer sequences, binding site sequences, sequencing primer binding sequence, stem-loop adapters to circularize a double stranded DNA, capture sequences and the like. Tag sequences may be selected to cause minimal undesired interference in the assay system using the disclosed methods. Tags are incorporated into a nucleic acid sequence enzymatically (e.g., using a polymerase to extend a tagged oligomer) or chemically (e.g., using an enzyme free reaction to attach a tag to a nucleic acid). The tags obtained by the presently disclosed methods may be applied for multiple purposes. For instance, in the TMA format, tags can be "joined" to (either directly or indirectly) or incorporated into a primer (or promoter primer, promoter provider, etc.) to form a tagged primer (or promoter primer, promoter provider, etc.). When used in an amplification reaction, these tagged amplification oligomers will introduce the tag sequence into an amplification product. Subsequent rounds of amplification can include amplification oligomers having target hybridizing sequences that hybridize to all or a portion of the incorporated tag. Incorporating tag sequences allows users to control certain aspects of amplification or multiplex amplification reactions (e.g., primer dimer formation, primer efficiency variations, and other aspects). Tagged amplification oligomers and amplification reactions are described more fully in United States Application Publication No. 2008-0305482, the subject matter of which is herein incorporated by reference in its entirety.

"Target Capture Oligomer", "Capture Oligonucleotide", or "Capture Probe" refers to a nucleic acid oligomer comprising at least two regions; a target hybridizing region and a support binding region. The target hybridizing region can be configured to specifically hybridize a target sequence of a target nucleic acid, or it can be configured to non-specifically hybridize to numerous nucleic acids in a sample. Specific and non-specific target capture oligomers are described in U.S. Pat. No. 6,116,078 and PCT Publication Number WO 2008/016988. The support binding region is configured to hybridize with a solid support. Preferably, the solid support comprises a complementary binding member that binds with the support binding region of the target capture oligomer. These complementary members can be nucleic acids, proteins or other complementary binding members. For example, the support binding region can be a nucleic acid and the complementary binding member of the solid support is a nucleic acid that is substantially complementary to the support binding region, thereby allowing for hybridization under a set of conditions. An exemplary nucleic acid support binding region is a substantially homopolymeric tail of about 10 to 40 nucleotides (e.g., $A_{10}$ to $A_{40}$ or, $T_3A_{14}$ to $T_3A_{30}$, or $T_{0-3}A_{14-40}$). The complementary member, then, is substantially complementary to all or a portion of the nucleic acid support binding region (e.g., $A_{0-3}T_{14-40}$. The complementary member is attached to a solid support, for example, using a covalent linker, ionic interaction, or chelation. Solid supports include nitrocellulose, nylon, glass, polyacrylate, mixed polymers, polystyrene, silane, polypropylene, metal, or other compositions, of which one is magnetically attractable particles.

"Target Nucleic Acid" as used herein is a nucleic acid on which an analytical assay is focused. In a diagnostic assay the target nucleic acid is the nucleic acid that, if present in a sample, indicates the presence of the corresponding nucleic acid of interest or organism. In an antisense RNA assay, the target nucleic acid is the mRNA that is targeted by the antisense oligomer. Target nucleic acids comprise one or more target sequences. Target nucleic acids may be DNA or RNA and may be either single-stranded or double-stranded. The target nucleic acid may include other sequences besides the target sequence. Typical target nucleic acids include virus genomes, bacterial genomes, fungal genomes, plant genomes, animal genomes, rRNA, miRNA, tRNA, or mRNA from viruses, bacteria or eukaryotic cells, mitochondrial DNA, or chromosomal DNA.

"Target Specific Sequence" or "Target Hybridizing Sequence" as used herein refers to an oligonucleotide sequence, which is configured to stably hybridize to a portion of the target sequence. In one embodiment, the target specific sequence is fully complementary with the target sequence, and contains no mismatches. In another embodiment, the target specific sequence is complementary to the target sequence and stably hybridizes to the target sequence under stringent conditions, but contains 1 or 2 or 3 or 4 or 5 mismatches. In one embodiment, the target specific sequence includes at least 10 to as many as 50 nucleotides which are complementary to the target sequence.

"Template Sequence" or "Target Sequence" as used herein is a sequence within a target nucleic acid on which an analytical assay is focused. For example, if the assay is focused on amplification of a target nucleic acid, then the target sequence is a part of the target nucleic acid wherein the amplification oligomers are configured to hybridize and generate an amplicon. Similarly, if the assay is a sequencing assay, then the target sequence is the portion of the target nucleic acid that is sequenced. A target sequence can be the entire target nucleic acid or the target sequence can be a portion of the target nucleic acid. Where the target nucleic acid is originally single-stranded, "target sequence" also refers to the sequence complementary to the target sequence as present in the target nucleic acid. Where the target nucleic acid is originally double-stranded, target sequence refers to both the sense (+) and antisense (−) strands. In choosing a target sequence, the skilled artisan will understand that a sequence should be chosen to distinguish between unrelated or closely related target nucleic acids.

Detection of target nucleic acids may be accomplished by using any known method. For example, amplified nucleic acids may be associated with a surface that results in a detectable physical change, e.g., an electrical change, or can be detected using mass spectrometry. Nucleic acids may be detected in solution phase or by concentrating them in or on a matrix and detecting labels associated with them (e.g., an intercalating agent such as ethidium bromide or cyber green). Nucleic acids may be detected using nucleic acid sequencing techniques. Other detection methods use probes complementary to a sequence in an amplified product and detect the presence of the probe:product complex, or use a complex of probes to amplify the signal detected from amplified products (e.g., U.S. Pat. Nos. 5,424,413 and 5,451,503, Hogan et al., U.S. Pat. No. 5,849,481, Urdea et al.). Other detection methods use a probe in which signal production is linked to the presence of the target sequence. In some instances, the probe is degraded by the amplification enzyme to release the fluorophore from the presence of the quencher (e.g., TaqMan, U.S. Pat. No. 5,210,015). In other instances a change in signal results only when the labeled probe binds to amplified product, such as in a molecular beacon, molecular torch, or hybridization switch probe (e.g., U.S. Pat. Nos. 5,118,801 and 5,312,728, Lizardi et al., U.S. Pat. Nos. 5,925,517 and 6,150,097, Tyagi et al., U.S. Pat. Nos. 6,849,412, 6,835,542, 6,534,274, and 6,361,945, Becker et al., US 2006-0068417 A1, Becker et al., and US 2006-0194240 A1, Arnold et al.). Such probes typically use a label (e.g., fluorophore) attached to one end of the probe and an interacting compound (e.g., quencher) attached to another location of the probe to inhibit signal production from the label when the probe is in one conformation ("closed") that indicates it is not hybridized to amplified product, but a detectable signal is produced when the probe is hybridized to the amplified product which changes its conformation (to "open"). Detection of a signal from directly or indirectly labeled probes that specifically associate with the amplified product indicates the presence of the target nucleic acid that is amplified.

"Transcription Mediated Amplification" refers to an isothermal amplification method wherein at least a portion of the amplification cycle include making RNA transcripts from a target sequence. depending on whether the primer or the promoter based amplification oligomer is designed to hybridize the initial target nucleic acid in a sample, then the TMA assay is referred to as reverse TMA (RTMA) or forward TMA (TMA). When using tag sequences in one or more of the amplification oligomer species in the reaction, the reactions are referred to herein as follows. (a) "Full," meaning that the amplification oligomer species used in the reaction include a first tagged-amplification oligomer in a 1:1 ratio with the captured target nucleic acids; a second tagged-amplification oligomer in a 1:1 ratio with the captured target nucleic acid; an excess of a first amplification oligomer that targets the complement of the tag sequence of the first tagged-amplification oligomer; and an excess of a second amplification oligomer that targets the complement of the tag sequence of the second tagged-amplification oligomer. A 1:1 ratio of the tagged-amplification oligomers is typically accomplished by including the first tagged-amplification oligomer and the second tagged amplification oligomer in a target capture reagent as an amplification oligomer complex. Amplification oligomer complexes are described in U.S. Published Application No.: 2011-0003305, and include, but are not limited to, direct-hybridization complexes, covalently linked complexes and others. Briefly, a target capture reaction is performed wherein a target capture oligomer and an amplification oligomer complex are both hybridized to a target nucleic acid. The hybridized nucleic acids are then removed from the remaining components of a sample, typically using a solid support like a magnetic bead, optionally followed by one or more wash steps. These removed components are then added to an amplification reaction mixture that contains reagents for performing the amplification reaction. It is understood that for the three-quarters and the half reactions described below, that the 1:1 ratios are typically achieved by including just the tagged amplification oligomer in the target capture reaction, though amplification oligomer complexes comprising a tagged amplification oligomer member and a non-tagged amplification oligomer member can be used. (b) "Three-quarters," meaning that the amplification oligomer species used in the reaction include a first tagged-amplification oligomer in a 1:1 ratio with the captured target nucleic acids; an excess of second tagged-amplification oligomer; an excess of a first amplification oligomer that targets the complement of the tag sequence of the first tagged-amplification oligomer; and an excess of a second amplification oligomer that targets the complement of the tag sequence of the second tagged-amplification oligomer. (c) "Half" meaning that the amplification oligomer species used in the reaction include a first tagged-amplification oligomer in a 1:1 ratio with the captured target nucleic acids; an excess of a second amplification oligomer; and an excess of an amplification oligomer that targets the complement of the tag sequence of the first tagged-amplification oligomer. As is used herein, RUf means Reverse TMA with the full tagged amplification oligomers format. RUh means Reverse TMA with the half tagged amplification oligomers format. RUt means Reverse TMA with the three-quarters tagged amplification oligomers format. (See e.g., WO 2011/003020, throughout and particularly in the Examples discussing half, full, three-quarter and other tag arrangements in TMA reactions; and see WO 2009/140374, throughout and particularly in the figures wherein the flow of a TMA reaction is illustrated. Both of these documents are incorporated herein by reference.)

A. Description of the Method for Identifying and Selecting Tags for Use in In Vitro Nucleic Acid Assays.

The overall method can be schematically represented as is generally shown in FIG. 1A. The Figures illustrate the general tag identification method by reciting an amplification assay as the in vitro assay for testing tagged nucleic acids. As is made clear in this disclosure, though, the tag identification methods are applicable to a variety of in vitro assays, not just amplification assays. Tags are identified as being useful in an in vitro assay that contains additional nucleic acid sequences. Identification is based upon a number of factors, as described herein. Once identified, the tags can be incorporated into one or more nucleic acids used in the in vitro assay. The steps for tag identification are as follows:

1. Random Oligo Generation:

To begin, a pool of oligonucleotide sequences is obtained or generated (as necessary), typically as a random pool of sequences. This can be performed in a variety of ways, including with the aid of a computer program. If desired, the user can set boundaries at this stage for desired characteristics or properties, such as sequence length and GC content. When a computer is used, this phase of the method can be described as an in silico screen. Sequence length as a parameter or boundary will be set depending upon the desired use of the tag. Lengths can be set, for example, to 25-30 nucleotides. G/C content is the amount of G residues and/or C residues in an oligonucleotide or polynucleotide sequence. G/C content in the Tag sequences is reflected as a percentage of the number of G and/or C residues as compared to the total number of residues in the oligonucleotide. Among other things, the G/C content alters the melting temperature of the sequence. Acceptable G/C content depends on the target nucleic acid under consideration. Typical G/C content can be in the range of 30 to 80%, 40 to 70%, or 30 to 50%.

2. Blast:

The pool is subjected to a search to identify sequences that have minimal sequence complementarity to all known sequences in one or more selected databases to obtain a sub-pool of sequences. An example of a useful tool for this purpose is the BLAST (Basic Local Alignment Search Tool) algorithm available from NCBI (National Center for Biotechnology Information). Sequences selected for the sub-pool are those having complementarity of less than 95%, less than 80%, less than 70% or less than 50% to the nucleic acid sequence in the database.

3. Screen for Oligonucleotide Parameters:

The sub-pool of sequences prepared from the step 2 Blast is then subjected to further screening, which may be in silico screening, for features that could negatively affect their performance in regards to the desired functionality, including melting temperatures, activity in an enzyme reaction, G-C content, hybridization energy, multimer formation, internal structure format, G-quartet formation and hairpin stability. A variety of features can be used for the in silico screening, depending upon the desired use of the tags. For example, if the intended use of candidate sequences is as primers/providers in an amplification reaction, the candidate sequences can be screened for one or more of primer/dimer formation, internal secondary structure, inappropriate melting temperature (Tm) values, cross-reaction or other unwanted interactions with other nucleic acid sequences to be used in an assay (including other tag sequences), and the like. Sequences identified to possess an undue amount of negative attributes are removed from the sub-pool. The following are exemplary parameters that can be screened for at this stage. Primer/dimer formation is a characteristic to be avoided in identifying useful tags for an in vitro amplification assay. Primer-dimer formation capability can be determined using software routinely available to one of ordinary skill in the art, e.g. *Oligo Primer Analysis Software from Molecular Biology Insight*, and references therein. Some internal structures are also understood to typically be undesirable in a nucleic acid assay system, such as the presence of hairpin loops, G-quartets and other unwanted structures. Such structures can be easily identified by methods known to those skilled in the art. Inappropriate melting temperature (Tm) value is another characteristic to be avoided in useful tags. Cross-reaction or other unwanted interactions with other nucleic acid sequences to be used in a reaction mixture (including other tag sequences) are also to be avoided for useful tags. Cross-reactions to be avoided can be from target nucleic acids or other nucleic acids suspected of being present in a sample and/or assay reaction, such as pathogenic or non-pathogenic organisms, mammalian nucleic acids, contaminating nucleic acids from enzymes, side-products of nucleic acid amplification reactions, etc. Cross-reactions can also occur with sequences intentionally included in the assay mixture. For instance cross reactions can occur between a tag sequence and the target sequence, the tag sequence and the target specific sequence of an oligomer, and the tag sequence and other templates, targets, primers, probes, detection sequences, displacer sequences, binding site sequences, capture sequences etc.

4. Synthesis and In Vitro Assays:

Based on the results from the screening steps described above, performance of candidate sequences can be optimized (if desired) by a cycle of systematic sequence design changes followed by a repeat of one or more of the in silico screen described above for the sub-pool and the in vitro screen discussed above.

The sequences that successfully pass the above two screens are then selected for use in the intended nucleic acid assay, or as a component in a reaction mixture, and subjected to rigorous experimentation to benchmark their activity against the desired performance characteristics. This additional experimentation is generally conducted in vitro, that is, the sequences are synthesized and run in an in vitro assay. Cross reactivity in a system inhibits or considerably degrades the amplification performance. The practitioner can then systematically eliminate tags from the candidate tag pool which cross-react with other tags, amplification oligomers, or particular templates, to obtain a non-biased assay.

In typical multiplex amplification reactions, a variety of undesired "side reactions" could occur that ultimately degrade assay performance. For example, various amplification oligomers can interact with one another or with other sequences within the assay. Commonly, primers and/or providers directed towards one target nucleic acid (or group of target nucleic acids) interact with primers and/or providers directed towards another target nucleic acid (or group of target nucleic acids), causing degraded performance of one, or the other or both amplification systems. This problem typically gets worse as the number of target sequences present in a multiplex reaction increases. This problem can be reduced or solved by incorporating a tag sequence into one or more amplification oligomers in the system. The tagged amplification oligomer(s) will then incorporate their tag sequences into the initial amplification product. Subsequent amplification can take place using amplification oligomer comprising sequences that are configured to hybridize to the incorporated tag regions However, even if specific primer and/or provider interactions are reduced or eliminated, other interactions that degrade assay performance can still be present. For example, the two tagged primers (or primer and provider) can interact with one another. In the half tagged amplification mode described above, the one tagged primer (for example) can interact with other remaining specific primers and/or providers. Furthermore, tagged primer(s) can interact with other oligos in the amplification reaction, such as probes, blockers and target capture oligomers (TCOs), and/or with target nucleic acid related sequences (such as amplicons). Additionally, in an amplification system using two or more tagged amplification oligomers, subsequent amplification reactions are driven by the same amplification oligomer(s) complementary to the tag sequence. Competition between the various amplification reactions for this limiting resource can be a problem. For example, amplification of a target sequence present in a multiplex reaction at high levels will consume the primers complementary to the tag sequence before amplification of a target sequence present in a multiplex reaction at low levels can "complete" its normal reaction.

One solution to this problem is to create unique tag sequences for some or all of the target sequences in a multiplex reaction, and to design them such that they do not interact with each other, or with any other tag set from different target sequences in the reaction, or with any other sequences in the reaction mixture. In this way, each amplification reaction can proceed independently and degradation of multiplex amplification performance is reduced or eliminated. The identification and selection method of this disclosure can be used to generate such unique tag sets.

B. Description of the Method for Identifying and Selecting Tags Having Minimized Interference in a Multiplex Assay.

The present invention further encompasses a method that draws on the power of combinatorial screen and selection to identify improved tag sequences that reduce or eliminate the problem of interference, which is generally observed in multiplexed amplification reactions. Another advantage of the method is that the criteria set for the screen can be varied to match a desired property that the user wants to screen for in a particular assay system. These criteria can be speed of an amplification reaction of a first target nucleic acid relative to the amplification speed on other target nucleic acids, performance of a tag sequence or tagged oligomer within a give system, lack of interference with or by other nucleic acids in the assay system, etc. The final solution in terms of tag sequence(s), number of tags to use in a system, which nucleic acids comprise tags, arrangement of tags and etc. is derived from a large repertoire of user-defined oligonucleotide tag sequences (as opposed to target-specific sequences). Thus, the method transcends the inherent limitation imposed by amplification systems that use target specific primers for amplification. Moreover, the tags are incorporated into the amplicon and can be utilized to enable downstream applications such as sequencing, signal amplification, microarray analysis, etc. One can envision the selected tags to be modified as signaling probes, adapters for ligation-based assays, as tags in sequencing applications and the like.

Figure 1B:
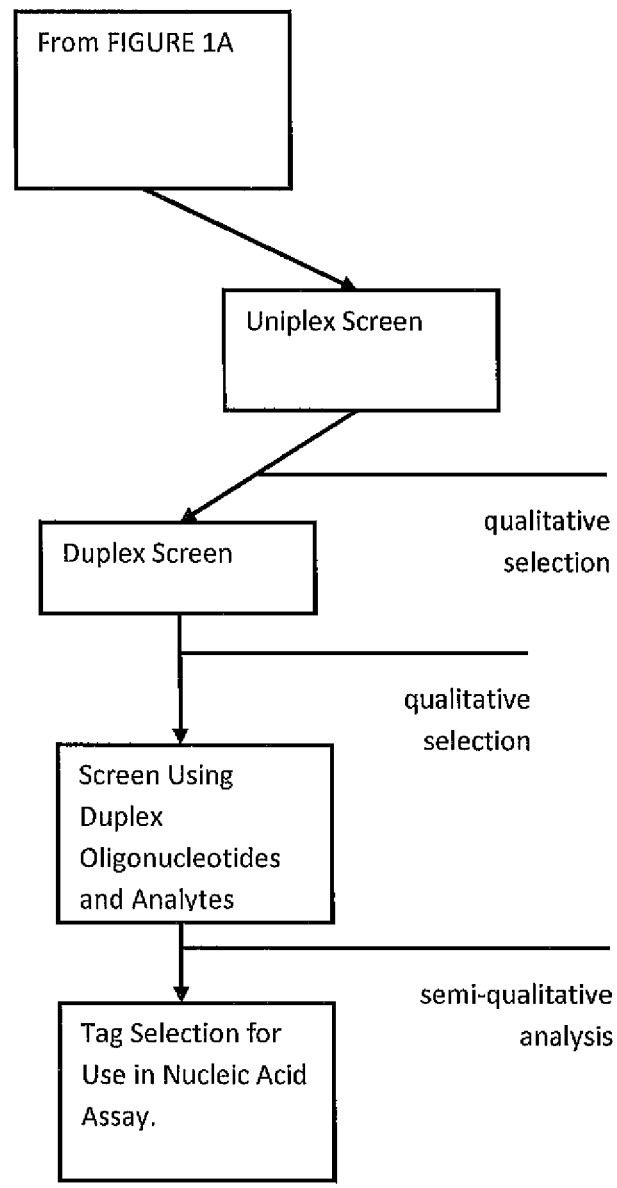

The overall method can be schematically represented as shown illustrated in FIG. 1B for using tag sequences in a given amplification format. In a multiplex amplification assay, one or more tags are selected by the following steps: 1-4. Preparation of Library of Tag Sequences: A library of tag sequences is prepared using the method described above for identifying useful tags, namely: 1. Random oligo generation; 2. Blast; 3. Screen for Oligonucleotide Parameters; 4. Synthesis and in vitro Assays After the completion of these steps, further identification of useful tags can be determined using the following steps:

5. Screening in Uniplex:

A library of tag sequences is screened for each target sequence individually in assays, for example in a uniplex nucleic acid amplification format, such as TMA. Each tag sequence is thus evaluated qualitatively or quantatively, based on, for example, the precision between replicates limit of detection, sensitivity, kinetics of reaction and emergence time relative to a standard reference tag, if available, or other appropriate parameters as desired.

6. Screening Using Duplex Oligos:

The tag sequences demonstrating optimal performance from the step 5 uniplex screen are subsequently screened in the presence of oligos of the competing target sequence (duplex oligo screen). This screen is done first without using a tag for the second target sequence, and then including the tag chosen from Step 5 for the second target sequence (this could be the same tag or another unique tag) in order to assess the level of oligo interference existing in a given multiplex amplification. The level of oligo interference for each target sequence is again determined qualitatively or quantitatively relative to their performance in uniplex assays.

Methods for such quantitative or qualitative determination are known to those skilled in the art and include, for example, by comparing Ct values between the uniplex and multiplex reactions, by determining the limit of detection of a particular target nucleic acid in a uniplex reaction and in a multiplex reaction, etc.

7. Screening Using Duplex Oligos and Target Nucleic Acids:

Each tag sequence pair showing minimal oligo interference and sufficient performance in the presence of duplex oligos from step 6 are then screened in the presence of duplex oligos and target sequences to ascertain the level of total interference. More specifically, relatively low copy levels of each target sequence are evaluated in the presence of high copies of the competing target sequence (in two separate conditions) with the tag of each target sequence chosen from the duplex oligos screens. The relative amounts of each target sequence to be used for these interference screens, where the target sequence interference can be observed from the amplification curves might be different for each system and therefore should be chosen on a case-by-case basis. The results of the reactions in steps 6 and 7 are then qualitatively and quantitatively evaluated to determine preferred combinations of tags to be used in an assay given the nucleic acids present in the multiplex reaction mixture.

Such qualitative evaluation methods are known to those skilled in the art and include determining whether or not one target nucleic acid can be detected (at a certain input copy level) in the presence of the other target nucleic acid(s).

8. Interference Analysis:

A novel method to quantitate the interference observed for each combination of tags screened as described above has been developed. With this method, an "interference value", or "I-value", is determined for each target sequence in a multiplex reaction, and these I-values are added together to yield the total I-value. For example, in a duplex system, [I-value (total)=I-value (target sequence1)+I-value (target sequence2)].

Figure 25:
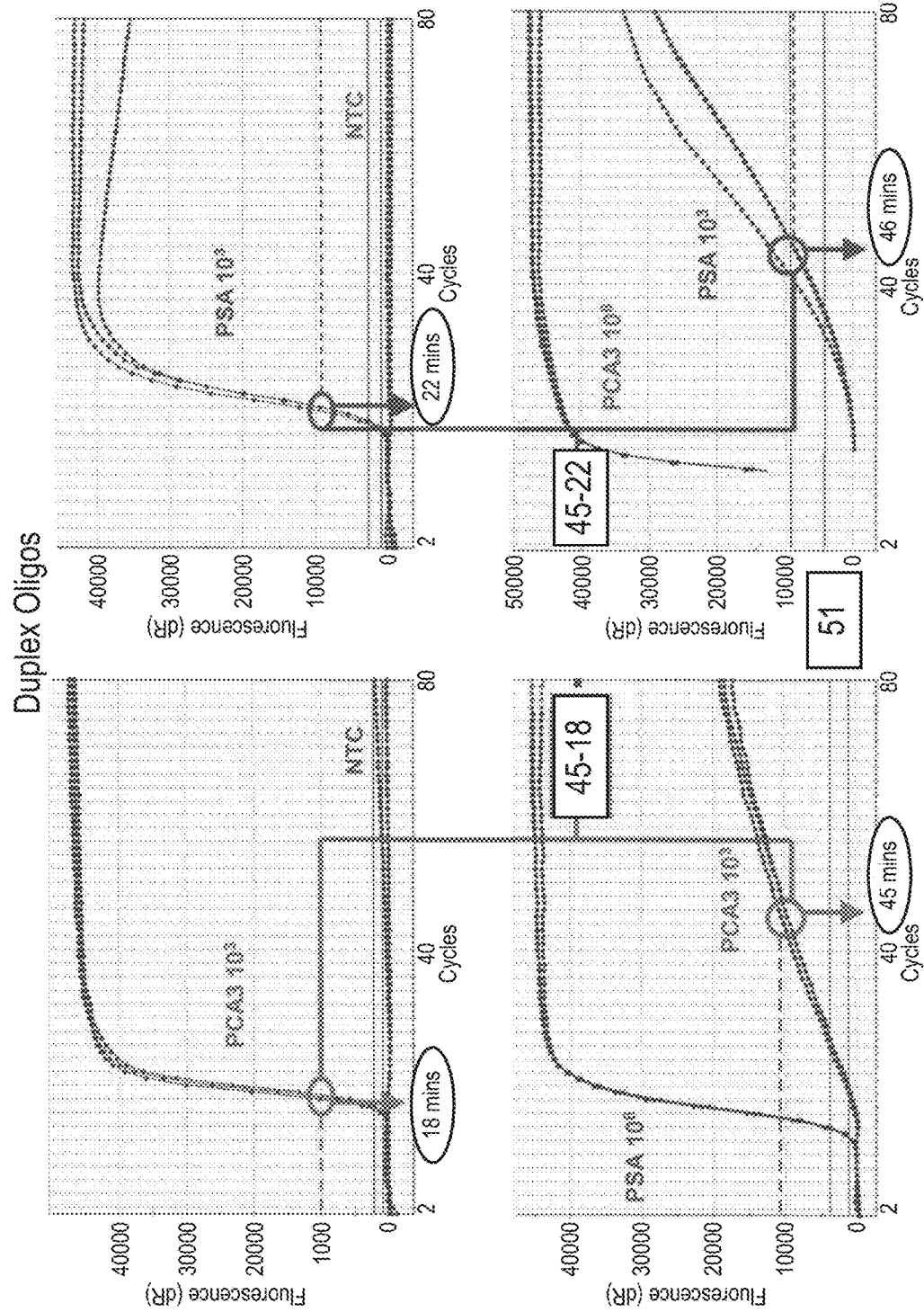
FIGS. 25-26 illustrate a semi-quantitative analysis for determining interference, which can be caused by any of a number of components in the amplification system. Lower interference values indicate that the tagged nucleic acid used in that system performed better in that system than did other tags. Top panels represent a duplex oligo reaction as described for FIG. 22-23 bottom panels. Bottom panels represent a multiplex amplification reaction as described for FIG. 24 bottom panel. The emergence time for each reaction condition to reach 10,000 fluorescent units is determined, and then an interference value (I-value) is calculated for each as the sum of the difference between the duplex oligo condition and the corresponding multiplex condition.
Figure 26:
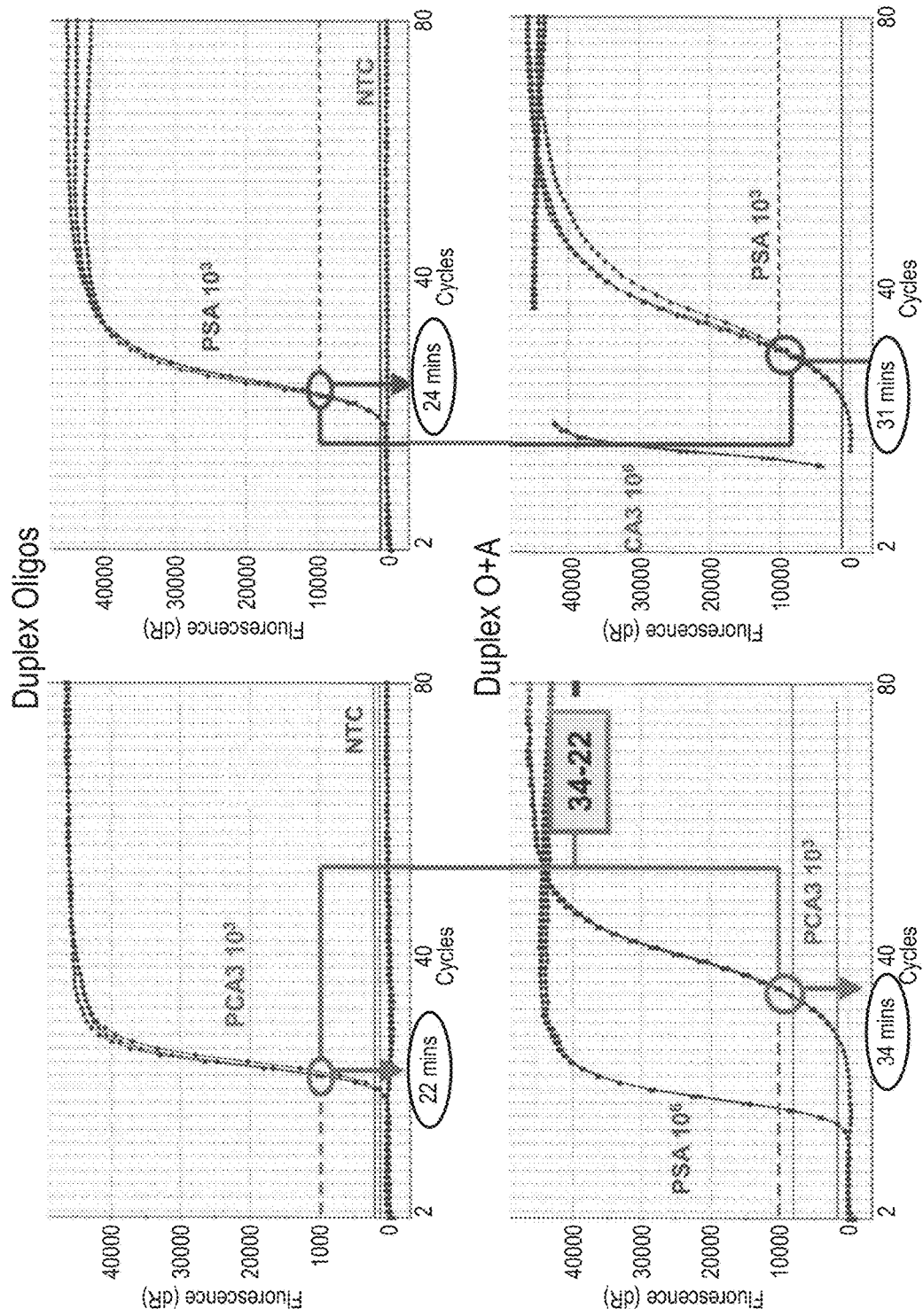

When using Real-Time TMA I-values can be calculated from emergence times. In a duplex system, for example, the I-value of target nucleic acid 1 is calculated by subtracting the emergence time of a relatively low copy level of target nucleic acid 1 in the absence of target nucleic acid 2 from the emergence time of the same (low) copy level of target nucleic acid 1 in the presence of a relatively high copy level of target nucleic acid 2. In an equivalent manner, the I-value of target nucleic acid 2 is calculated using a relatively low copy level of target nucleic acid 2 in the absence or presence of a relatively high copy level of target nucleic acid 1. The sum of these two I-values yields the total I-value for the given set of tags used. The lower the total I-value, the less interference there is between the tags. FIGS. 25 and 26 illustrate the calculation of I values for amplification assays using different tag in the primers. A wide variety of tags and combinations thereof can be screened and the relative interference levels can be rapidly quantitated using this method.

EXAMPLES

The following examples demonstrate the use of this method to select the best tag sequences for use in a TMA assay format. These examples are intended only to demonstrate the use of the selection method and are not intended to limit the scope of application to only TMA or to only amplification assays.

Example 1: Screen for NT7 Tag Sequences

Step 1—Random Oligo Generation:

A large pool of oligonucleotides 25-30 nucleotides in length are randomly generated. Random oligonucleotide sequences can be determined in a variety of manual or automated methods. One manual method for determining random oligonucleotide sequences of a desired length includes a blinded selection of a series of A, C, T, G and/or U residues. One automated method for determining random oligonucleotide sequences of a desired length includes using an algorithm for randomly selecting a series of A, C, T, G and/or U residues. Many algorithms are freely and commercially available to generate a random pool of nucleotide sequences. Suitable algorithms include those found at http://molbiol.ru/eng/scripts/01_16.html; http://www.faculty.ucr.edu/~mmaduro/random.htm; http://tandem.bu.edu/rsg.html; http://www2.uni-jena.de/biologie/mikrobio/tipps/rapd.html; and, described in Piva and Principato, In Silico Biology, 6, 0024 (2006). Many other algorithms can also be used. For this example, an initial population of ~1000 sequences was generated for screening (see step 2 below). These sequences were selected to vary in their GC content, length and Tm.

Step 2—Blast:

The oligonucleotides generated in step 1 above were then subjected to an in silico screen using the BLAST (Basic Local Alignment Search Tool) algorithm available from NCBI (National Center for Biotechnology Information) website. The basic workflow for each oligonucleotide was as follows:

Using the "BLAST Program Selection Guide" available on the website, "nucleotide blast" (blastn) was chosen to search the nucleotide databases using a nucleotide query. The program "blastn" is specifically designed to efficiently find short alignments between very similar sequences and thus is the best tool to use to find the identical match to a query sequence. In this example, the query sequence was one of the tag sequences identified in step 1. Several different databases are available for search using BLAST, and the "nr" nucleotide database was used in this instance.

The goal of this screen was to identify sequences with minimal complementarity to sequences in the data base other than the desired target nucleic acid, thus minimizing the potential of unwanted cross reactivity with non-target nucleic acids that may be present in the assay reaction mixture. Particular care was taken to screen sequences that may be problematic in a given assay. For example, if a viral assay is being developed, the sequences corresponding to other non-target viruses as well as the non-target regions of the targeted virus were carefully examined.

Figure 2:
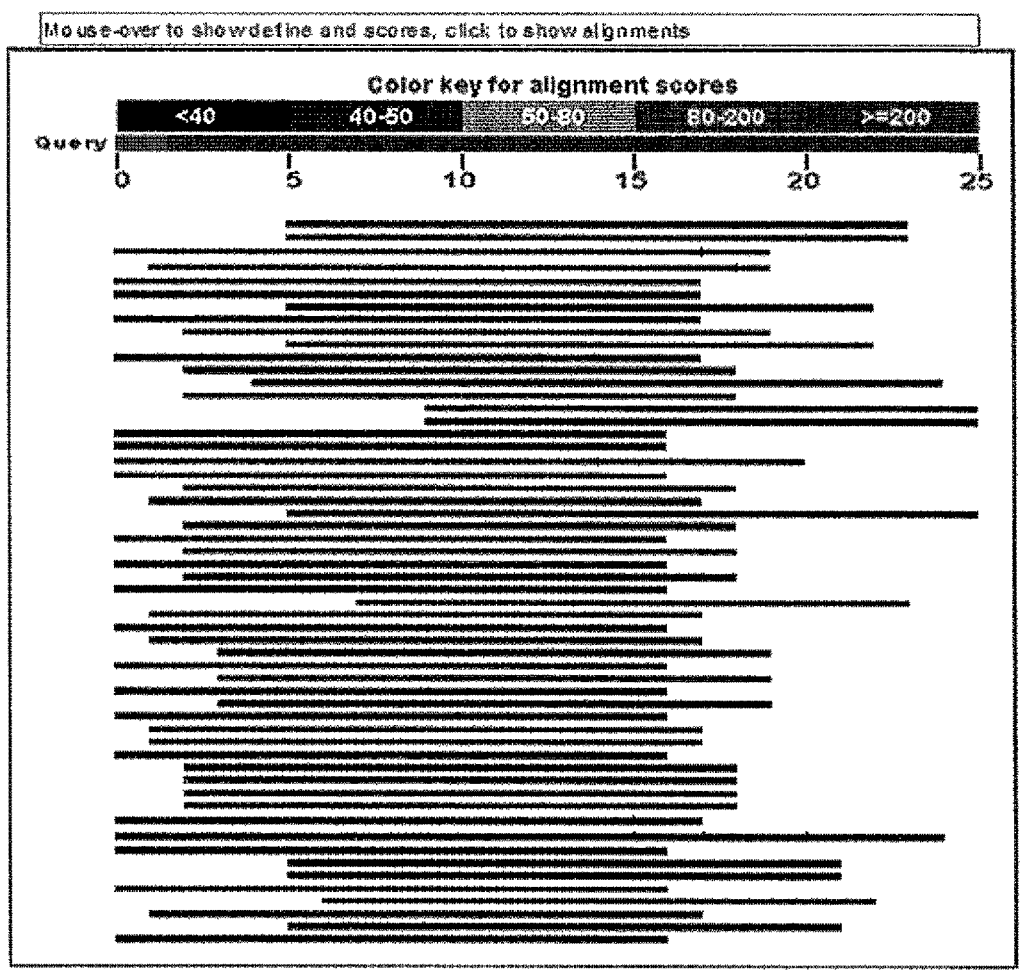
FIG. 2. In silico screen: Illustrative blast filtered screen of two exemplary random oligonucleotide sequences. in this illustration, the blast screen was designed to identify 3'-end dissimilarity, therefore, the sequences selected to advance to the next stage was the sequences that was most dissimilar at its 3'-end to sequences in the blast. The random oligo sequences are represented as the top line in each of the blast alignments.
Figure 2:
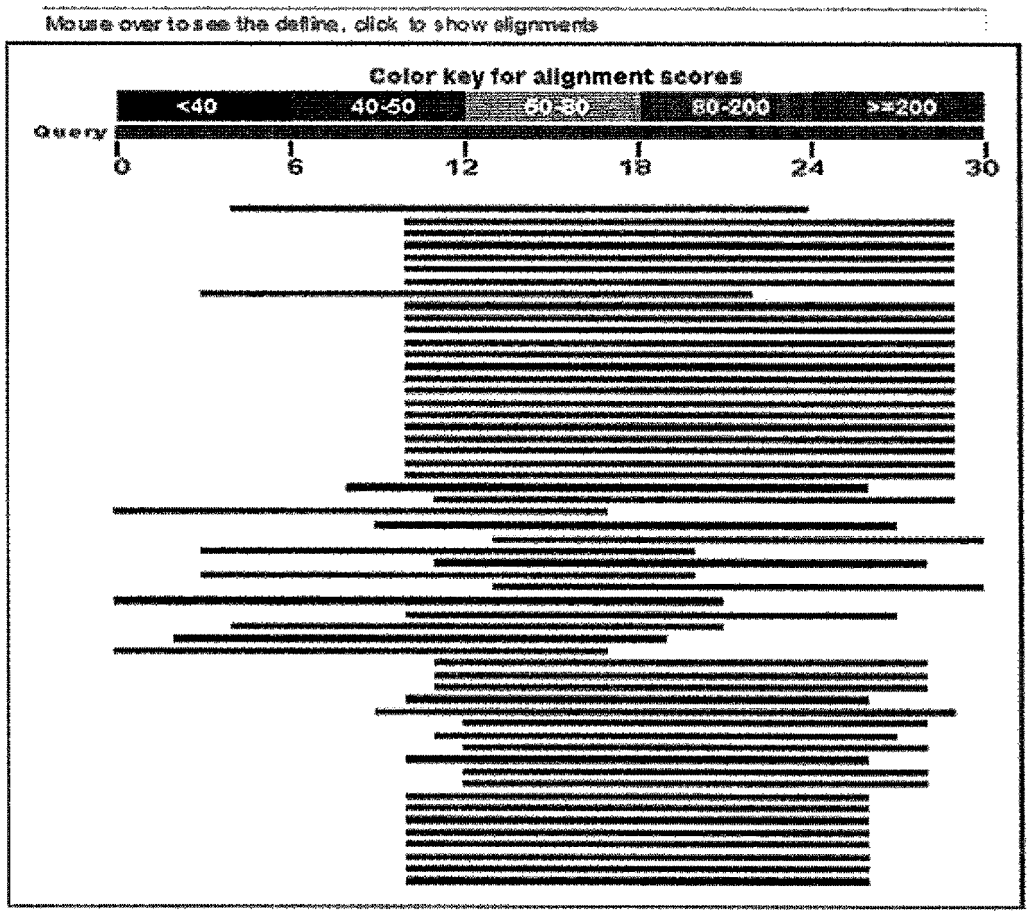

If a candidate tag sequence yielded greater than about 80% overall complementarity to any sequence in the data base, it was rejected. The value for percentage complementarity used as a cut-off will vary depending on the assay under developed as well as the specific requirements of that assay. The 80% value cited here is only an example of a cut-off. Additionally, candidate tag sequences that yielded greater than 6 to 8 contiguous bases of exact complementarity were also rejected in general. However, as discussed above, exact complementarity in the 3' portion of the molecule is undesirable if the tag is to function as a primer, for example. Therefore, more exact complementarity than listed above could be tolerated in the 5' portion of a tag primer candidate in this case, as long as 3' complementarity was low. FIG. 2 shows an example of such an analysis.

Other rejection criteria can also be set, depending on the particular specifications of the assay under development. Based on the chosen criteria, a fraction of the tag sequence candidates are rejected and the remainder taken on to the next screening step.

Step 3—Screen for Primer Parameters:

A pool of about 100 sequences (Table 1) was identified in steps 1 and 2 above out of an initial population of 1000 randomly generated sequences. These 100 sequences were then subjected to another screen wherein properties that could decrease a tag candidate's effectiveness in the desired application, such are hairpin or primer-dimer formation, were identified and those sequences were removed from the pool. For this second screen, the oligo analyzer software available from Integrated DNA technologies (www.idtdna.com/analyzer/Applications/OligoAnalyzer) was used.

Representative data from this second screen are shown in FIG. 3. Candidate tag sequences that were predicted to form hairpin structures with a stability of −4 kcal/mole or greater (i.e., a more negative value) were discarded. Candidate tag sequences that were predicted to form primer-dimer structures with a stability of −10 kcal/mole or greater (i.e., a more negative value) also were discarded. Candidate tag sequences with Tm values >72° C. were also discarded in this example.

Table 1 presents the results of the screens, wherein the asterisk symbol "*" following a value indicates that the corresponding sequence is discarded as a candidate tag sequence based on that result. Sequences which lack any asterisk are selected as tags.

TABLE 1

Results of Taq Parameter Screens

| Seq # | SEQ ID NO: | Sequence (5'-3') | Length | GC content | Tm (° C.) | Hairpin stabilization energy maximum (dG) in KCal/mol | self dimer stabilization energy maximum (dG) in KCal/mol |
|---|---|---|---|---|---|---|---|
| 1 | 2 | CCCCGTCAAACAAAAACGGGAGCGTGTACC | 30 | 56.7 | 65.9 | -4.81 | -11.00* |
| 4 | 3 | CCATAGGCCTTCTGCACTGCTCCATATACC | 30 | 53.3 | 63.2 | -1.18 | -12.47* |
| 6 | 4 | GTCCCCATCGGAGGGCATCTTATCGTGCCT | 30 | 60 | 67.5 | -3.36 | -8.16 |
| 8 | 5 | CCGCCCTCCTTCGCCCCCCGGTGAAATAAC | 30 | 66.7 | 70.1 | -1.67 | -9.75 |
| 12 | 6 | AATGCTCACCTCTATTCGGGACTTGAGTAC | 30 | 46.7 | 60.9 | -0.71 | -5.13 |
| 21 | 7 | CCCGCGCACCACCTCCATCACGCAGAAGAG | 30 | 66.7 | 70 | -2.19 | -10.36* |
| 25 | 8 | GTCGGAACGCCAGGTACAGTTAGCGCATCC | 30 | 60 | 66.7 | -2.08 | -9.89 |
| 26 | 9 | AAGTCACTGGCCAGCATAATGCGTGAAGGG | 30 | 53.3 | 65.4 | -0.76 | -16.38* |
| 27 | 10 | GTGATGCTTTATGAGATTCCGGTCTCCGAC | 30 | 50 | 61.7 | -2.15 | -9.75 |
| 28 | 11 | GACGGTGCATCACCCGCATTTGCTGTAGCG | 30 | 60 | 67.6 | -2.79 | -7.05 |
| 34 | 12 | AGAATTCTTGCAGGTAGAGGTCCCCTCATT | 30 | 46.7 | 62.2 | -2.22 | -11.71* |
| 35 | 13 | AAGCCAAAATTACAATCGATCCCTACCAAC | 30 | 40 | 59.1 | 1.41 | -9.71 |
| 37 | 14 | ATCTTGCACCTTCCCAGATGTAAACCCCCT | 30 | 50 | 64.3 | 0.4 | -7.05 |
| 42 | 15 | GAAGCGGCAGCTCAGCCGGTTCTCGGAGAG | 30 | 66.7 | 69.6 | -6.97* | -9.82 |
| 43 | 16 | GCACGCGGGCTCCTTGGGACACTATGATTG | 30 | 60 | 67.1 | -0.1 | -10.36* |
| 61 | 17 | CCCATCAGGACAGTCAGCTGCCCACGAATT | 30 | 56.7 | 66.5 | -1.35 | -10.24* |
| 78 | 18 | CTTTAGTGCGGTAGGACCGAGACTACCGTG | 30 | 56.7 | 64 | -5.07 | -10.58* |
| 79 | 19 | TTATGTGCCAGCTGGGCCTAAGGCTCCGGG | 30 | 63.3 | 69.6 | -2.6 | -16.38* |
| 80 | 20 | GACTCTCCTAGGGCGTTCGTCTGGGACTGC | 30 | 63.3 | 67.3 | -0.43 | -10.30* |
| 82 | 21 | CGGAGAATACCCTCGACTGTATCATATCGT | 30 | 46.7 | 60.1 | -0.83 | -6.76 |
| 84 | 22 | TTCATCGAGGTACATTGGTGCTATTCCATT | 30 | 40 | 59.6 | -0.18 | -6.76 |
| 86 | 23 | TACCACCTGGTTCAAGGTGTGCCGTACGCG | 30 | 60 | 67.9 | -3.73 | -10.87* |
| 87 | 24 | AGGAGAACCAGCCTGGAGCGTTTAAGCATC | 30 | 53.3 | 64.8 | -1.93 | -6.62 |

TABLE 1-continued

Results of Taq Parameter Screens

| Seq # | SEQ ID NO: | Sequence (5'-3') | Length | GC content | Tm (° C.) | Hairpin stabilization energy maximum (dG) in KCal/mol | self dimer stabilization energy maximum (dG) in KCal/mol |
|---|---|---|---|---|---|---|---|
| 88 | 25 | GATGTCCTAAAATGAGGCGTGGCAATAGAG | 30 | 46.7 | 60.6 | −0.28 | −4.67 |
| 89 | 26 | CAGAGTCATGTATACCCACTGTCGGTCGAA | 30 | 50 | 62.1 | −0.19 | −6.76 |
| 104 | 27 | GTCAGGCTAGGGGGTTATCCCAGCAACGGC | 30 | 63.3 | 68.2 | −2.62 | −6.14 |
| 106 | 28 | TGGGTTCTGCTAACCGGTGCCGTTCTTAAC | 30 | 53.3 | 65 | −2.02 | −12.43* |
| 116 | 29 | TTTTTGACAGTGATGAAGAGGGAGGTACGA | 30 | 43.3 | 60.7 | −1.61 | −3.65 |
| 133 | 30 | GAGAACTCGCGCTCCCTCACTCCGTTTAGA | 30 | 56.7 | 65.4 | 0.21 | −10.36* |
| 136 | 31 | CTATGGTTCGTTACTGAATCGAAAAGCCGC | 30 | 46.7 | 61 | −1.19 | −7.13 |
| 138 | 32 | TAGCTATCAAAACAGGCGTCATCGGTTAAG | 30 | 43.3 | 60 | −1.05 | −8.26 |
| 145 | 33 | AGGACGCTGACACCGTTGGGGTAAAGCGTG | 30 | 60 | 68.1 | −4.77* | −9.69 |
| 152 | 34 | CCTGCTTAGGGTCACTTAAACTACTGGCGC | 30 | 53.3 | 63.5 | −0.37 | −9.89 |
| 155 | 35 | GGTGATGGCCCATACCGATCACGCCCGCAG | 30 | 66.7 | 70.1 | −1.55 | −9.28 |
| 156 | 36 | CGGCAGGAGGGACTGCGATTTCCATAGAGC | 30 | 60 | 66.5 | −2.59 | −6.69 |
| 159 | 37 | TGGCCGGAGAGAGGATAGGAAGCGGGACTA | 30 | 60 | 67.5 | −1.62 | −9.75 |
| 161 | 38 | TAGCAGGTGTCTCGGTCCTCAACTGCAAAC | 30 | 53.3 | 64.6 | −4.25* | −7.05 |
| 163 | 39 | ACACATCCCAGGACTGCCGTGGCCTACGTA | 30 | 60 | 68.5 | −1.8 | −9.28 |
| 171 | 40 | GTGCTAGCCCGGGCCCTTCTTAACTCGGGA | 30 | 63.3 | 69 | −3.7 | −22.17* |
| 172 | 41 | CGGAATCTGAACATCTATCAGAGCCGCGCT | 30 | 53.3 | 64.5 | −3.69 | −10.36* |
| 174 | 42 | GACGAGCTTGTTCCAATTCCTCGAGCCGAG | 30 | 56.7 | 65 | −2.66 | −9.96 |
| 179 | 43 | GTTGGGGAGGGGCACTACGACTTAGGGCTA | 30 | 60 | 67 | −1.96 | −3.61 |
| 182 | 44 | AATGTGGACGGCCGCTCCGTACTTCTGACA | 30 | 56.7 | 67.3 | −3.59 | −16.50* |
| 183 | 45 | AGGGCCAGCAGCTGGTTCCTTCGCCAGTTA | 30 | 60 | 69.3 | −2.32 | −10.24* |
| 185 | 46 | GGCCGTCAATGTGTTTTGCACCCAACCGGA | 30 | 56.7 | 67.7 | −1.48 | −9.75 |
| 188 | 47 | CAGTGACTGGGCTAGTGAAGTGAGTCACAG | 30 | 53.3 | 62.9 | −4.43* | −7.81 |

TABLE 1-continued

Results of Taq Parameter Screens

| Seq # | SEQ ID NO: | Sequence (5'-3') | Length | GC content | Tm (° C.) | Hairpin stabilization energy maximum (dG) in KCal/mol | self dimer stabilization energy maximum (dG) in KCal/mol |
|---|---|---|---|---|---|---|---|
| 193 | 48 | TCCCACGTCCTTCGACGCACACTGTAACTT | 30 | 53.3 | 65.6 | -3.02 | -6.76 |
| >301 | 49 | TCATGTATCGCCCGTGGGTAAGCTC | 25 | 56 | 62.3 | -0.69 | -6.34 |
| >305 | 50 | ATGTTATGGAGAGTGGGTTAGGCAA | 25 | 44 | 57.9 | 0.75 | -3.14 |
| >307 | 51 | ATGAGGGAGTAAGGAGATTAGGTTC | 25 | 44 | 55.4 | 0.57 | -2.91 |
| >309 | 52 | CATGCTGCCCGCATACACTTGCGGG | 25 | 64 | 66.5 | -6.62* | -14.84* |
| >313 | 53 | GCCCAGCAGTTATACAATTCGTGGC | 25 | 52 | 60.3 | -0.2 | -6.21 |
| >314 | 54 | TTGGGCTCTCCAGTAGCCGAACAAA | 25 | 52 | 62.2 | -2.14 | -7.81 |
| >316 | 55 | TGACGTTAAACGCAATCCGCGTAAA | 25 | 44 | 59.4 | -3.94 | -10.36* |
| >325 | 56 | GTCGCCATTCAGGACACGCGAAACT | 25 | 56 | 63.4 | -1.92 | -10.36* |
| >327 | 57 | GTGGTTGCTACAGCCTAGCCTAGAT | 25 | 52 | 60 | -1.79 | -5.7 |
| >336 | 58 | CCACTTTTCATTCCGAGTCCACGCG | 25 | 56 | 62 | -0.08 | -10.36* |
| >339 | 59 | AGGAGGAACCGGAAGATCTAATCTG | 25 | 48 | 57.6 | -1.09 | -9.75 |
| >342 | 60 | CCAATGCTTTCAAATAACCCGTTCT | 25 | 40 | 56.2 | 0.57 | -3.89 |
| >343 | 61 | GCGACTGTGGCAACCCCATTTCGCA | 25 | 60 | 66 | -3.65 | -8.33 |
| >346 | 62 | AAAAAACGGAGGAGTCGAACCTTGG | 25 | 48 | 59.4 | -0.75 | -6.76 |
| >350 | 63 | AGTTGGATGGATATCTCGCTCGTGA | 25 | 48 | 59.4 | -0.32 | -7.06 |
| >356 | 64 | CGCTGTCCTCTCTGACACTAAAGGT | 25 | 52 | 60 | -1 | -4.87 |
| >357 | 65 | ATTTCAATAGTCAACCCGGTATCCA | 25 | 40 | 56.1 | 0.44 | -9.75 |
| >505 | 66 | TTCGCGCCAGCGACCCCACTTATGA | 25 | 60 | 66.3 | -3.52 | -10.36* |
| >510 | 67 | GGTTGGGGGCTCGGCTCATGTATC | 25 | 64 | 65.2 | 0.09 | -5.38 |
| >516 | 68 | ATGATGCTGAATCGCGATGGGGGGG | 25 | 60 | 65.1 | -0.13 | -16.46* |
| >517 | 69 | TAAGGAGACTAGGTTCCAATAGCTG | 25 | 44 | 55.5 | -0.84 | -6.34 |
| >523 | 70 | TTACACAAATCGTGGGTTGGCCTCT | 25 | 48 | 60.6 | -1.86 | -9.28 |

TABLE 1-continued

Results of Taq Parameter Screens

| Seq # | SEQ ID NO: | Sequence (5'-3') | Length | GC content | Tm (° C.) | Hairpin stabilization energy maximum (dG) in KCal/mol | self dimer stabilization energy maximum (dG) in KCal/mol |
|---|---|---|---|---|---|---|---|
| >534 | 71 | CGAAAGCGTTCCGCAGGAC CCCCTT | 25 | 64 | 67.1 | -2.4 | -6.75 |
| >538 | 72 | CACCCTTGGACACGTGGAA GTGGGC | 25 | 64 | 65.7 | -1.49 | -10.20* |
| >541 | 73 | AAAGTCTGAGAATGAGTGA TACCAT | 25 | 36 | 53.8 | 0.92 | -3.43 |
| >544 | 74 | ATATTGGTAGTTTTGTCCG CTGTAG | 25 | 40 | 54.9 | 0.67 | -3.91 |
| >549 | 75 | CGGAAGATCTAATCTGCAC GCAATT | 25 | 44 | 57.5 | -0.78 | -7.82 |
| >608 | 76 | GCGCCTCGTTGGGCAGAAG TTTGTGGAAAT | 30 | 53.3 | 66 | -2.36 | -9.89 |
| >610 | 77 | ATCTTCACCTACCGAGTTC TACGGGCCTAC | 30 | 53.3 | 63.4 | -2.39 | -9.28 |
| >613 | 78 | CCCACAACTTGCACCCGCT ATGCGACCCTG | 30 | 63.3 | 68.9 | -2.32 | -7.05 |
| >618 | 79 | GCCCAGGAGCTCTCCTGGG TAACAGTAGCG | 30 | 63.3 | 67.5 | -7.98* | -15.93 |
| >620 | 80 | CACGGCCCCCAGGCGGCGT ATCAGGGATGA | 30 | 70 | 72.5* | -3.3 | -9.28 |
| >623 | 81 | TCCCCGGCACGGACCGCAA GGGACCAAAGC | 30 | 70 | 73.2* | -5.63* | -9.75 |
| >629 | 82 | GATTAGTGGCCCAACGGGA ACAAACTTCCT | 30 | 50 | 63.6 | -2.04 | -9.28 |
| >701 | 83 | CGCCCGTCCCAGACCCTTA CTCACTATGGA | 30 | 60 | 66.8 | -0.61 | -5.02 |
| >703 | 84 | GCTACACGCCAGAGGCGCC GCTACAGCGAT | 30 | 66.7 | 71 | -7.27* | -16.03* |
| >706 | 85 | GAGATTGTACCCTACAGTC CGATTACCGAT | 30 | 46.7 | 60.4 | -1.58 | -4.26 |
| >715 | 86 | CGCAGTAAAAGGGCACAGG TAATTACCTTA | 30 | 43.3 | 60.1 | -2.05 | -19.3 |
| >718 | 87 | AGGGTGTCTTGAACTACTG GCGCAGCCCAT | 30 | 56.7 | 67.6 | -3.43 | -9.89 |
| >721 | 88 | CCGCAATCCGGTGACGGCC GGACCGGCAGG | 30 | 76.7 | 74.8* | -5.90* | -16.50* |
| >723 | 89 | TCGGCGGCGGGTAGTCAGT TCGCTACCTGG | 30 | 66.7 | 70.3 | -3.26 | -6.97 |
| >729 | 90 | CCAGGACTGCCGTGGCCCA CGCACTCACGA | 30 | 70 | 72.7* | -2.93 | -9.98 |
| >740 | 91 | TTGACGCAGGCCCCCGGGG CGACTTCATAC | 30 | 66.7 | 71.2 | -2.92 | -22.03* |
| >743 | 92 | CGAAAGGAGTTCGAGTGTA TCCGGAAGGCG | 30 | 56.7 | 64.7 | -3.81 | -12.90* |
| >745 | 93 | AGGCGCACTGCGACTTAGG GCTAGCCCCCC | 30 | 70 | 72.5 | -4.68* | -22.71* |

TABLE 1-continued

Results of Tag Parameter Screens

| Seq # | SEQ ID NO: | Sequence (5'-3') | Length | GC content | Tm (° C.) | Hairpin stabilization energy maximum (dG) in KCal/mol | self dimer stabilization energy maximum (dG) in KCal/mol |
|---|---|---|---|---|---|---|---|
| >751 | 94 | GATGTGATCTGGACCCTACGGGAGGGGACA | 30 | 60 | 66.7 | -3.51 | -7.74 |
| >754 | 95 | TGGGCTGGGGGAGTGAGTCGCTCCCGCAGC | 30 | 73.3 | 74.1* | -10.51* | -9.31 |
| >757 | 96 | AGTCCCAGATATGAGAGAAGCGAAGCATAA | 30 | 43.3 | 60.4 | -3.75 | -4.39 |
| >805 | 97 | CGTTTCAGCATCGATGTCCTAAAAT | 25 | 40 | 55.7 | -0.04 | -13.62* |
| >815 | 98 | ACTATTACACCACGTACCGTAGGTC | 25 | 48 | 57.5 | -2.43 | -6.3 |
| >816 | 99 | GGGCAACACCGCGAGCTAATTATCC | 25 | 56 | 61.9 | -0.21 | -10.60* |
| >818 | 100 | GCGCGCGGCCGAGAATCGTTGGAGG | 25 | 72 | 69.7 | -1.77 | -17.11* |
| >826 | 101 | CGCGTCGGGCTTTCGTCTACCCTGG | 25 | 68 | 67 | -1.3 | -10.60* |
| >829 | 102 | GGGCGGCCACCGGGGGACCCTGCCC | 25 | 88 | 77.7 | -3.41 | -9.75 |
| U20 tag (Std) | 1 | GTCATATGCGACGATCTCAG | 20 | 50 | 52.8 | 0.38 | -7.82 |

Step 4—Synthesis and In Vitro TMA Assay:

Based on the screen for primer parameters, about 55-60 candidate sequences were identified as good candidate tag sequences (Table 2).

TABLE 2

Synthesized Universal non-T7 primer tags for in vitro experimentation

| Tag Name | Sequence # | SEQ ID NO: | Sequence (5' to 3') |
|---|---|---|---|
| N1 | 6 | 4 | GTCCCCATCGGAGGGCATCTTATCGTGCCT |
| N2 | 8 | 5 | CCGCCCTCCTTCGCCCCCGGTGAAATAAC |
| N3 | 12 | 6 | AATGCTCACCTCTATTCGGGACTTGAGTAC |
| N4 | 25 | 8 | GTCGGAACGCCAGGTACAGTTAGCGCATCC |
| N5 | 27 | 10 | GTGATGCTTTATGAGATTCCGGTCTCCGAC |
| N6 | 28 | 11 | GACGGTGCATCACCCGCATTTGCTGTAGCG |
| N7 | 35 | 13 | AAGCCAAAATTACAATCGATCCCTACCAAC |
| N8 | 37 | 14 | ATCTTGCACCTTCCCAGATGTAAACCCCCT |
| N9 | 82 | 21 | CGGAGAATACCCTCGACTGTATCATATCGT |
| N10 | 84 | 22 | TTCATCGAGGTACATTGGTGCTATTCCATT |
| N11 | 87 | 24 | AGGAGAACCAGCCTGGAGCGTTTAAGCATC |
| N12 | 88 | 25 | GATGTCCTAAAATGAGGCGTGGCAATAGAG |
| N13 | 89 | 26 | CAGAGTCATGTATACCCACTGTCGGTCGAA |
| N14 | 104 | 27 | GTCAGGCTAGGGGGTTATCCCAGCAACGGC |
| N15 | 116 | 29 | TTTTTGACAGTGATGAAGAGGGAGGTACGA |
| N16 | 136 | 31 | CTATGGTTCGTTACTGAATCGAAAAGCCGC |
| N17 | 138 | 32 | TAGCTATCAAAACAGGCGTCATCGGTTAAG |
| N18 | 152 | 34 | CCTGCTTAGGGTCACTTAAACTACTGGCGC |
| N19 | 155 | 35 | GGTGATGGCCCATACCGATCACGCCCGCAG |
| N20 | 156 | 36 | CGGCAGGAGGGACTGCGATTTCCATAGAGC |
| N21 | 159 | 37 | TGGCCGGAGAGAGGATAGGAAGCGGGACTA |
| N22 | 163 | 39 | ACACATCCCAGGACTGCCGTGGCCTACGTA |
| N23 | 174 | 42 | GACGAGCTTGTTCCAATTCCTCGAGCCGAG |
| N24 | 179 | 43 | GTTGGGGAGGGGCACTACGACTTAGGGCTA |

TABLE 2-continued

Synthesized Universal non-T7 primer tags for in vitro experimentation

| Tag Name | Sequence # | SEQ ID NO: | Sequence (5' to 3') |
|---|---|---|---|
| N25 | 185 | 46 | GGCCGTCAATGTGTTTTGCACCCAACCGGA |
| N26 | 193 | 48 | TCCCACGTCCTTCGACGCACACTGTAACTT |
| N27 | >301 | 49 | TCATGTATCGCCCGTGGGTAAGCTC |
| N28 | >305 | 50 | ATGTTATGGAGAGTGGGTTAGGCAA |
| N29 | >307 | 51 | ATGAGGGAGTAAGGAGATTAGGTTC |
| N30 | >313 | 53 | GCCCAGCAGTTATACAATTCGTGGC |
| N31 | >314 | 54 | TTGGGCTCTCCAGTAGCCGAACAAA |
| N32 | >327 | 57 | GTGGTTGCTACAGCCTAGCCTAGAT |
| N33 | >339 | 59 | AGGAGGAACCGGAAGATCTAATCTG |
| N34 | >343 | 61 | GCGACTGTGGCAACCCATTTCGCA |
| N35 | >350 | 63 | AGTTGGATGGATATCTCGCTCGTGA |
| N36 | >356 | 64 | CGCTGTCCTCTCTGACACTAAAGGT |
| N37 | >357 | 65 | ATTTCAATAGTCAACCCGGTATCCA |
| N38 | >510 | 67 | GGTTGGGGGCTCGGCTCATGTATC |
| N39 | >517 | 69 | TAAGGAGACTAGGTTCCAATAGCTG |
| N40 | >523 | 70 | TTACACAAATCGTGGGTTGGCCTCT |
| N41 | >534 | 71 | CGAAAGCGTTCCGCAGGACCCCCTT |
| N42 | >541 | 73 | AAAGTCTGAGAATGAGTGATACCAT |
| N43 | >544 | 74 | ATATTGGTAGTTTTGTCCGCTGTAG |
| N44 | >549 | 75 | CGGAAGATCTAATCTGCACGCAATT |
| N45 | >608 | 76 | GCGCCTCGTTGGGCAGAAGTTTGTGGAAAT |
| N46 | >610 | 77 | ATCTTCACCTACCGAGTTCTACGGGCCTAC |
| N47 | >613 | 78 | CCCACAACTTGCACCCGCTATGCGACCCTG |
| N48 | >629 | 82 | GATTAGTGGCCCAACGGGAACAAACTTCCT |
| N49 | >701 | 83 | CGCCCGTCCCAGACCCTTACTCACTATGGA |
| N50 | >706 | 85 | GAGATTGTACCCTACAGTCCGATTACCGAT |
| N51 | >715 | 86 | CGCAGTAAAAGGGCACAGGTAATTACCTTA |
| N52 | >718 | 87 | AGGGTGTCTTGAACTACTGGCGCAGCCCAT |
| N53 | >723 | 89 | TCGGCGGCGGGTAGTCAGTTCGCTACCTGG |
| N54 | >751 | 94 | GATGTGATCTGGACCCTACGGGAGGGGACA |
| N55 | >757 | 96 | AGTCCCAGATATGAGAGAAGCGAAGCATAA |
| N56 | >815 | 98 | ACTATTACACCACGTACCGTAGGTC |

The above sequences were synthesized either as the tag alone (as shown in Table 2 above) or as an oligonucleotide containing both a target-specific sequence and a tag sequence (TS-tag) and were tested as described in the following paragraphs:

Prostate cancer markers PCA3, PSA, T2:ERGa and CAP were used as target nucleic acids in these examples. However, the target nucleic acids that can be used in the presently claimed methods are not hereby limited.

A TMA nucleic acid assay with PCA3 as a target nucleic acid was used to evaluate the candidate tag sequences. Testing was performed with 4 replicates of 2 different PCA3 concentration levels. Results were compared with those obtained using a tag which has been characterized in other amplification assays, the NT7 tag, also referred to as "U20." All assays used the same T7 provider.

Figure 4:
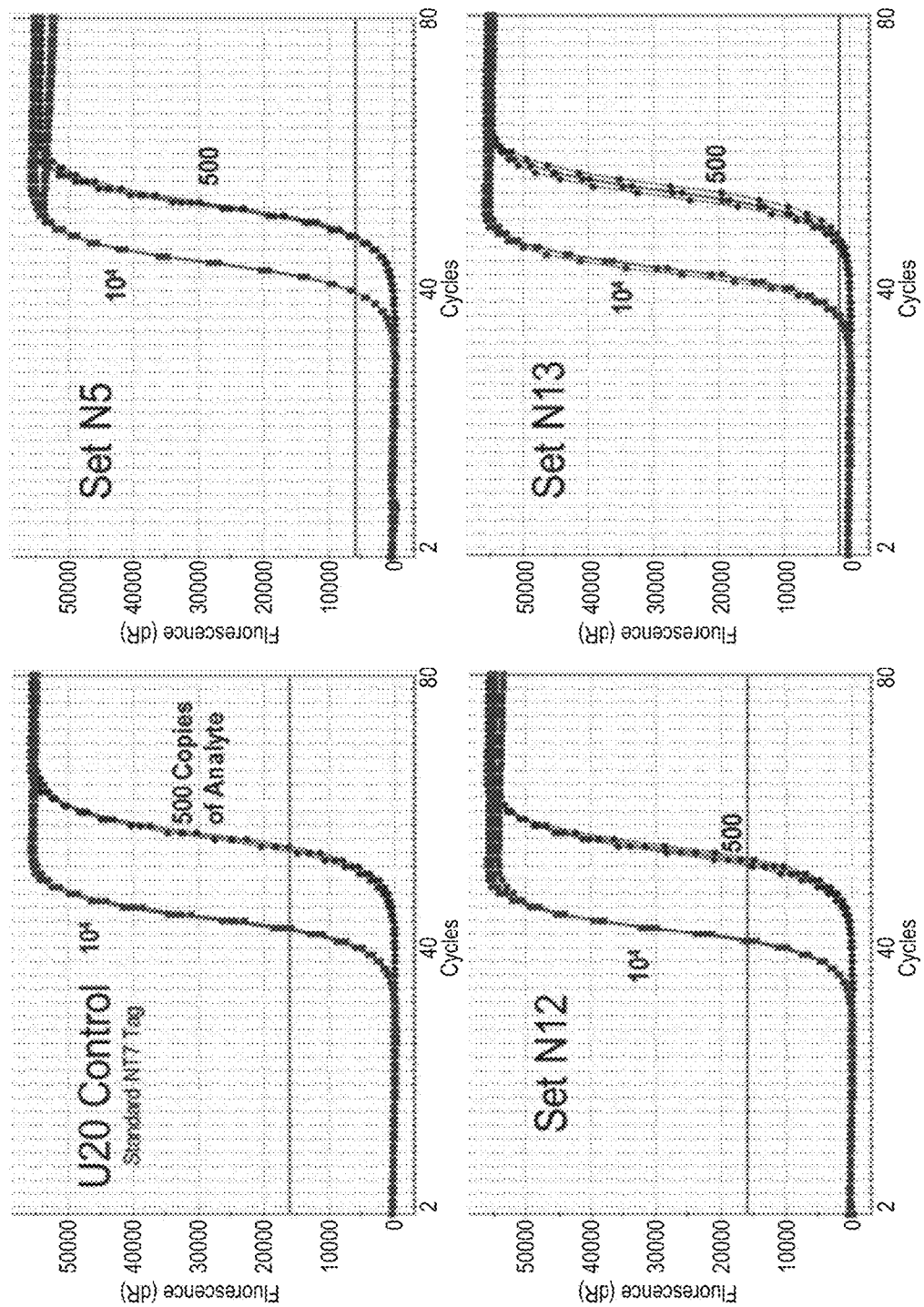
FIGS. 4-10. Each illustrates a uniplex in vitro nucleic acid amplification screen of random oligonucleotide sequences used as tags in a non-T7 amplification oligomer (FIGS. 4-6) or as tags in a T7 amplification oligomer (FIGS. 7-9). The target analyte in each of these assays was PCA3, except
Figure 5:
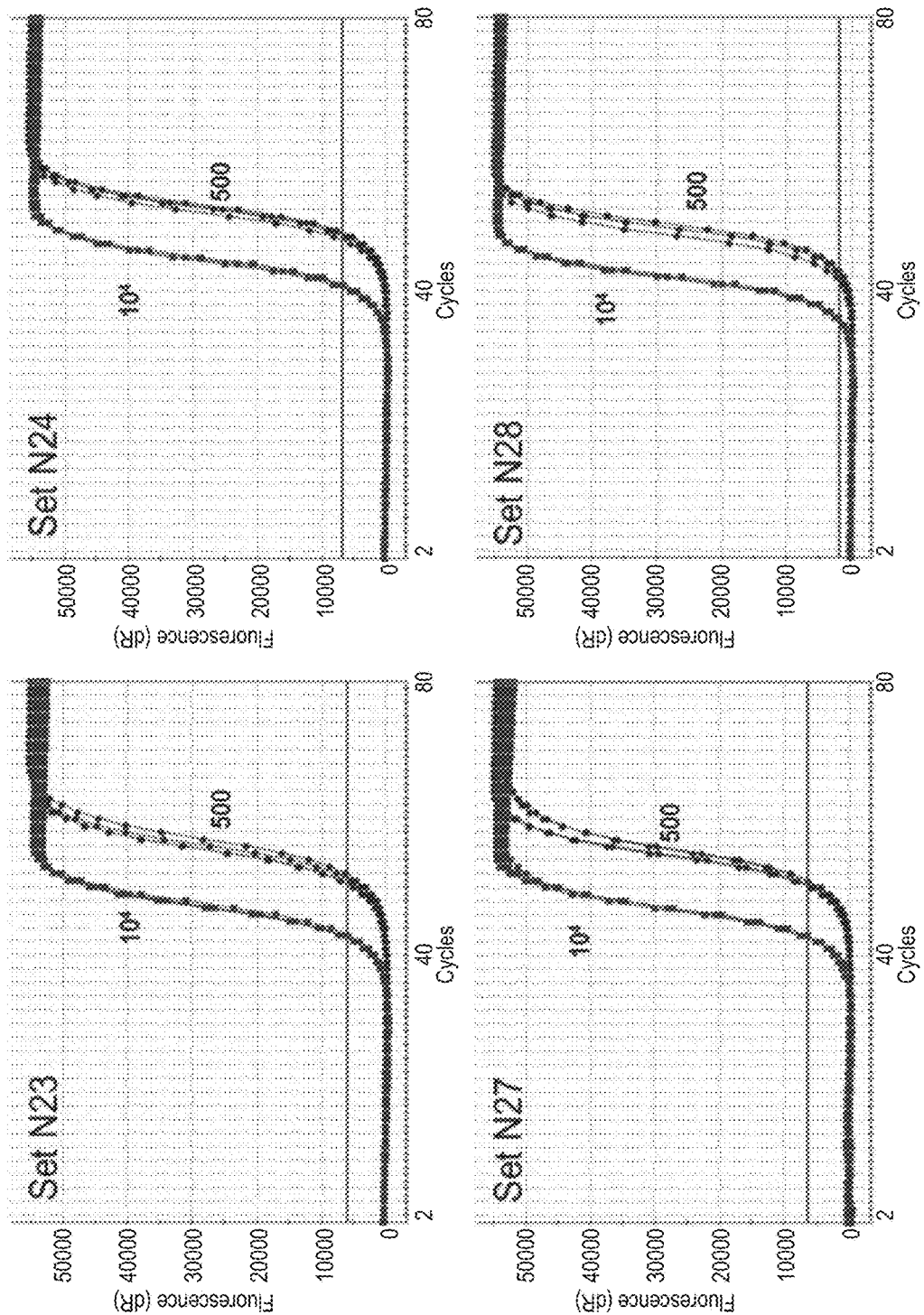
Figure 6A:
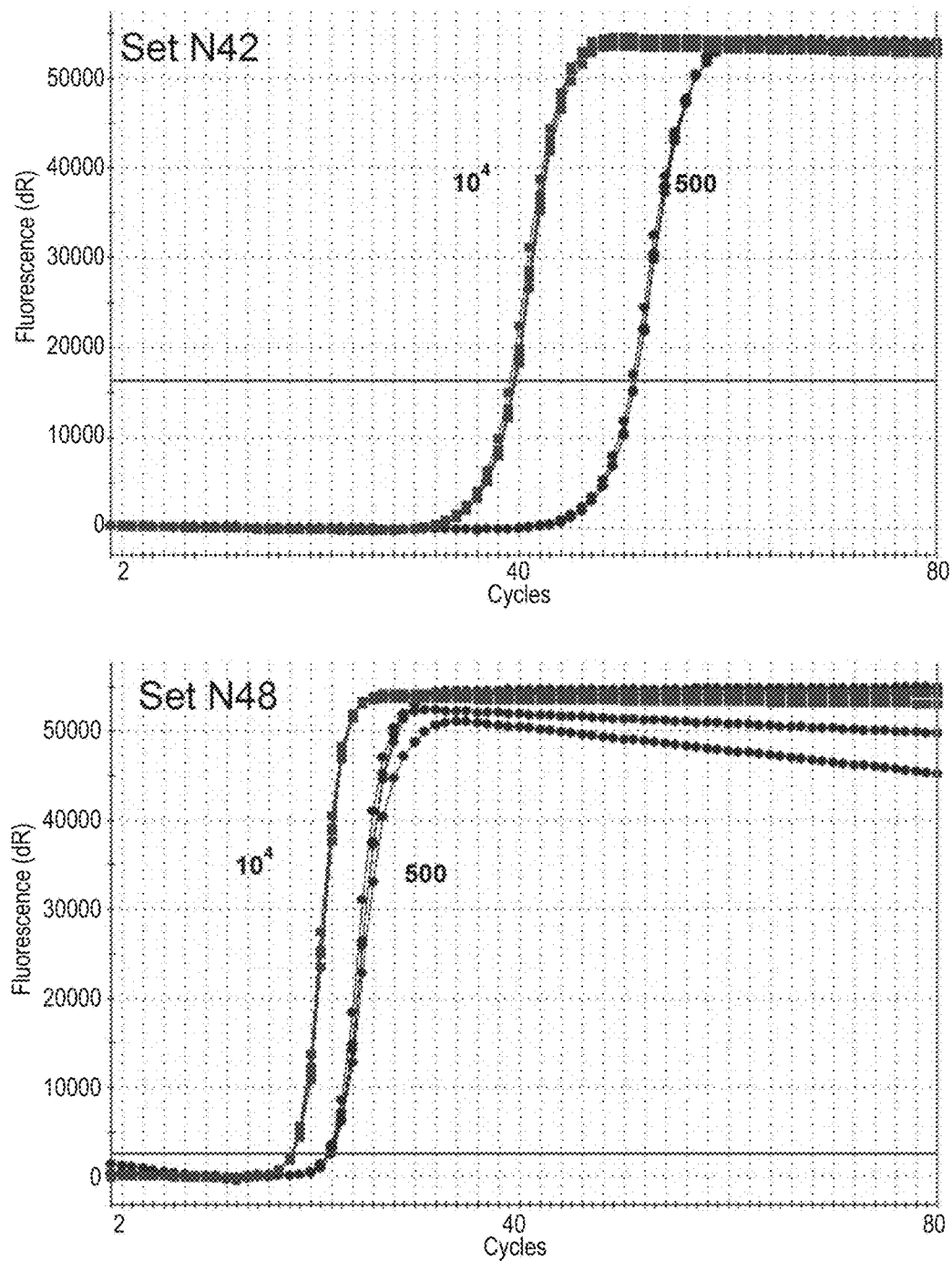
Figure 6B:
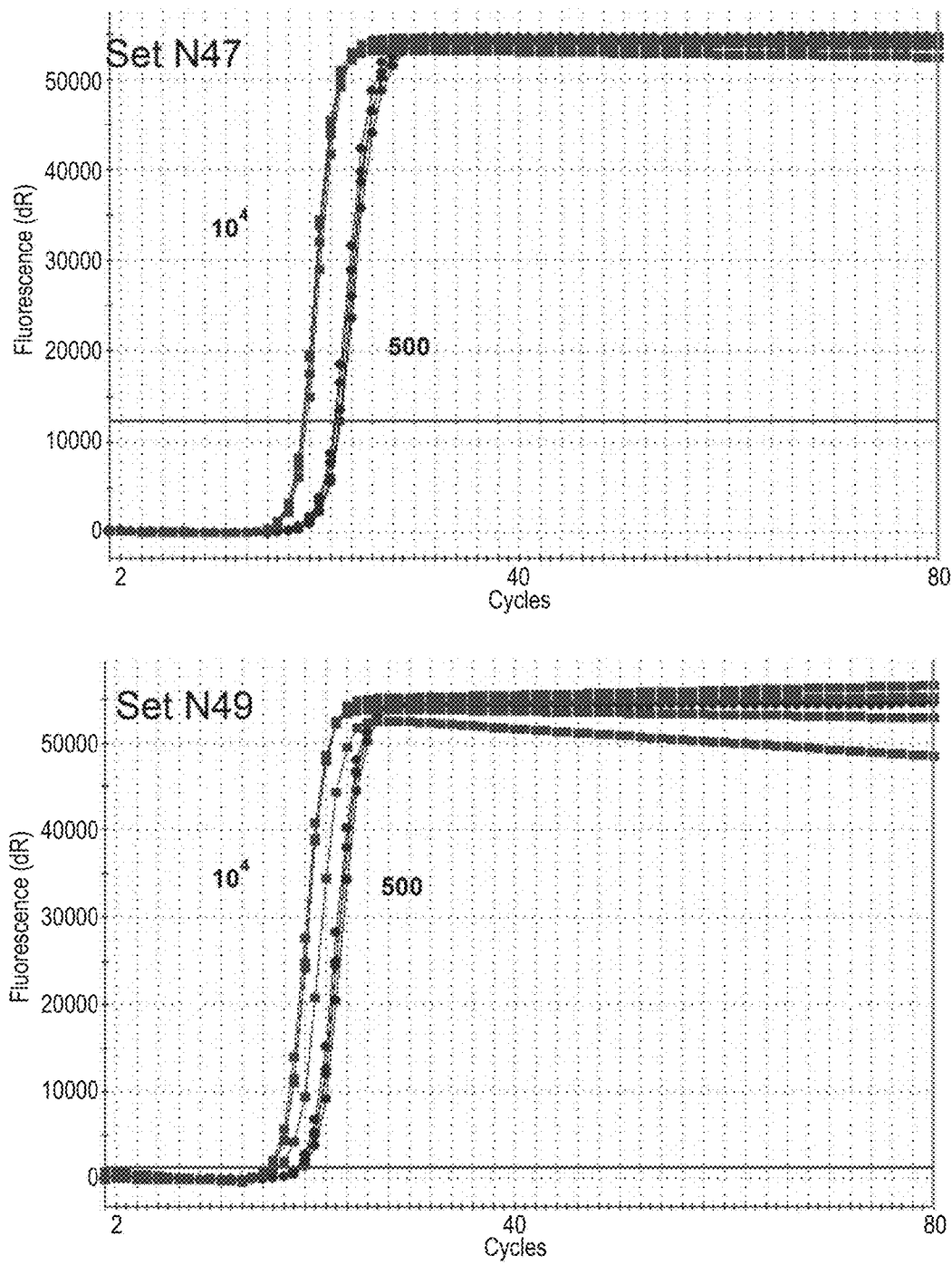

Some representative real time curves from the NT7 tag evaluation are shown in FIGS. 4-6. Performance of the different tags varied in this assay. Some performed approximately the same as U20, some performed much more poorly and some performed better. The best performing previously uncharacterized tags are N47, N48 and N49, which yielded dramatic decreases in emergence times. These results demonstrate the power of this technique in identifying tags with preferable characteristics.

Example 2: Screen for T7 Tag Sequences

A similar strategy to Example 1 was performed for screening tags for use with the T7 provider. A total of 22 sequences were identified for experimental testing and shown in Table 3.

TABLE 3

Sequences Selected for Screening of T7 Tags

| Sequence # | Tag Name | SEQ ID NO: | Sequence (5' to 3') |
|---|---|---|---|
| >1003 | T1 | 103 | 5' TGGCTAATCCCG |
| >1005 | T2 | 105 | 5' CTGTGCTAGAGG |
| >1006 | T3 | 106 | 5' CATGTACCAACG |
| >1007 | T4 | 108 | 5' TCGGTCGGACTA |
| >1011 | T5 | 109 | 5' CCTCCCCAAGC |
| >1012 | T6 | 110 | 5' GGGTTTGCTACG |
| >1014 | T7 | 111 | 5' ATGTGCGCACAA |
| >1022 | T8 | 112 | 5' CGGGACTAGAGA |
| >1026 | T9 | 113 | 5' AATCTCCGAGCG |
| >1034 | T10 | 114 | 5' AAGTGCAGGTTC |
| >1042 | T11 | 115 | 5' TCCAGTTTAACC |
| >1043 | T12 | 116 | 5' TAGCCGCACAGG |
| >1003b | T13 | 104 | 5' GCGTTGGCTAAT CCCG |
| >1006b | T14 | 107 | 5' TCACCATGTACC AACG |
| >1054 | T15 | 117 | 5' TATGAATGCGAC CCGGAA |
| >1063 | T16 | 118 | 5' AACAATGGTCAC TGCATC |
| >1066 | T17 | 119 | 5' GGGCCGTTTCCC GGACATAA |
| >1067 | T18 | 120 | 5' AGGTTGAGTCCG CATCTGAA |

TABLE 3-continued

Sequences Selected for Screening of T7 Tags

| Sequence # | Tag Name | SEQ ID NO: | Sequence (5' to 3') |
|---|---|---|---|
| >1070 | T19 | 121 | 5' TCGACCAAGAGCCGCTAGATGC |
| >1076 | T20 | 122 | 5' AGCTCGTGTCAAGCCGTCGCCT |
| >1083 | T21 | 123 | 5' TGAAAGAGTTGTCAGTTTGCTGGT |
| >1084 | T22 | 124 | 5' TCAGGTAAAGGTTCCTCACGCTACC |

The sequences of Table 3 were synthesized either as the tag alone (as shown in the table) plus a T7 promoter sequence [5'-aatttaatacgactcactatagggaga-3] or as an oligonucleotide containing both a target-specific sequence and a tag sequence plus the T7 promoter sequence (i.e., construct of TS-tag=T7) and tested as described in the following paragraphs:

The-TMA assay (which in this case used a directly hybridized amplification oligomer complex with the "cPRO" configuration (US Published Application 2008-0305482)) with PCA3 as a target was used in the initial evaluation of the candidate tag sequences. That is, evaluated in a uniplex amplification reaction. Testing was performed with 4 replicates of 2 different PCA3 target levels. Results were compared with a previously characterized tag incorporated into a T7 promoter-based amplification oligomer, referred to as "12 in [5'-CCACAACGGTTT-3]" All assays in this initial evaluation used the same NT7 primer comprising a previously characterized tag (U20).

Figure 7A:
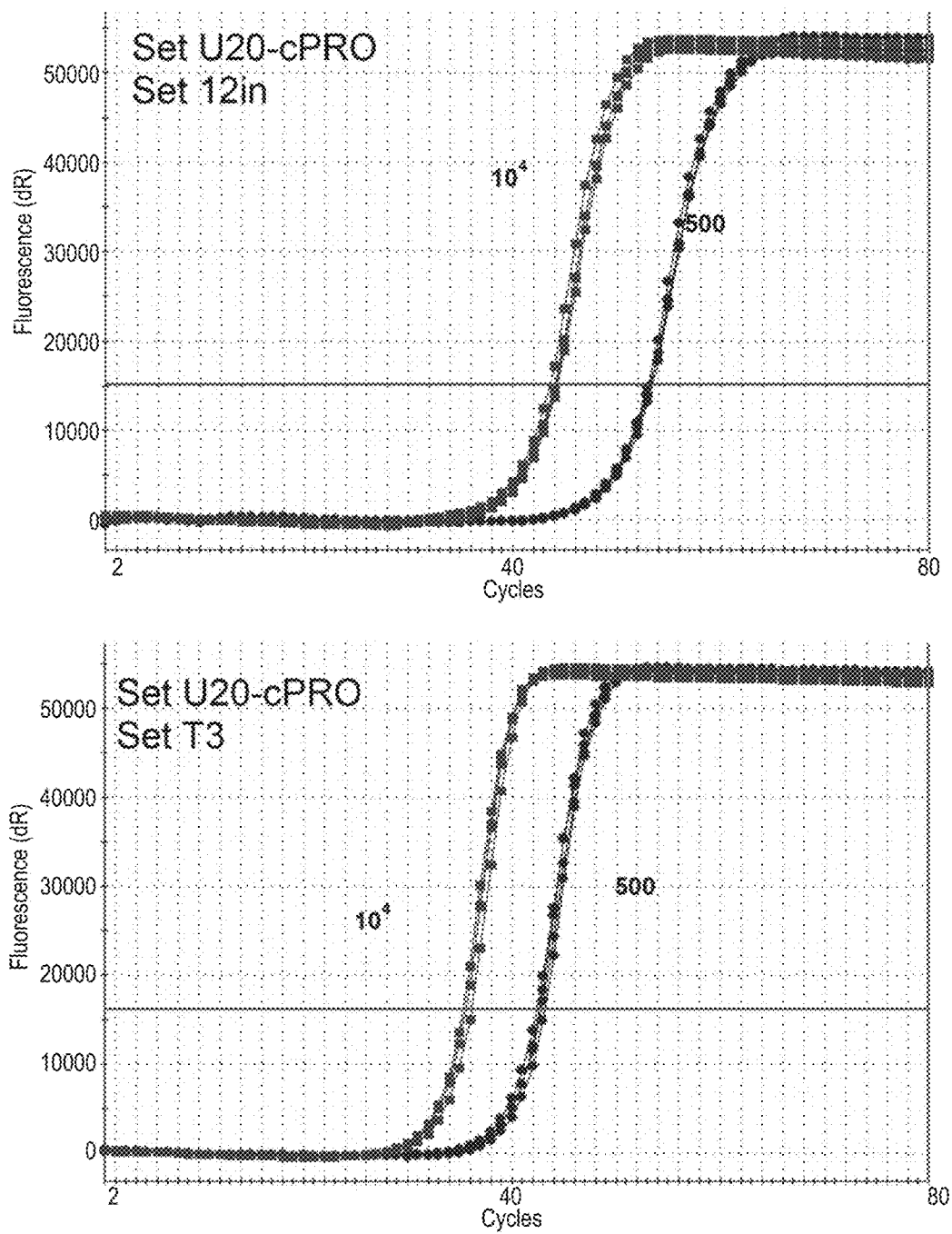
Figure 7B:
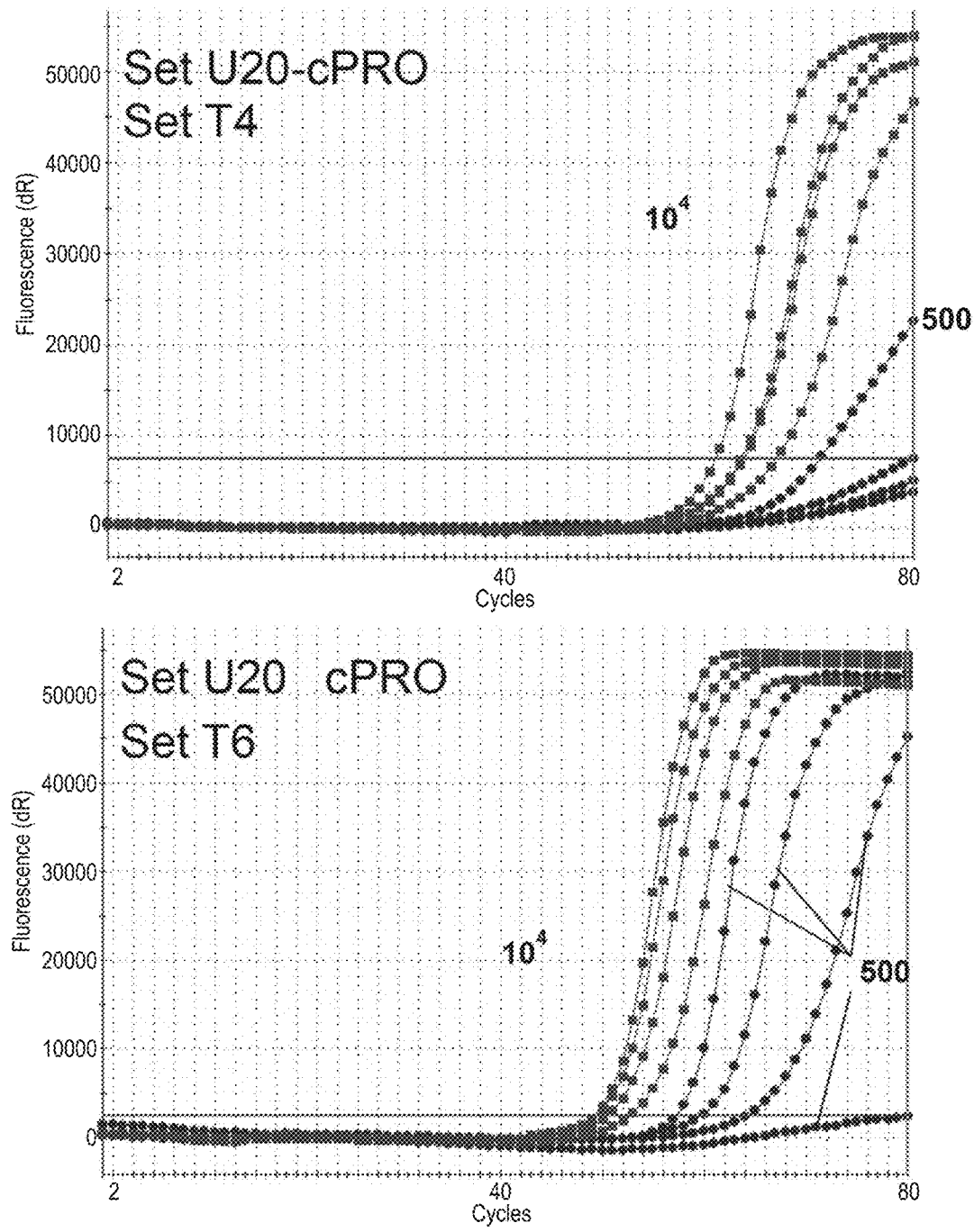
Figure 8:
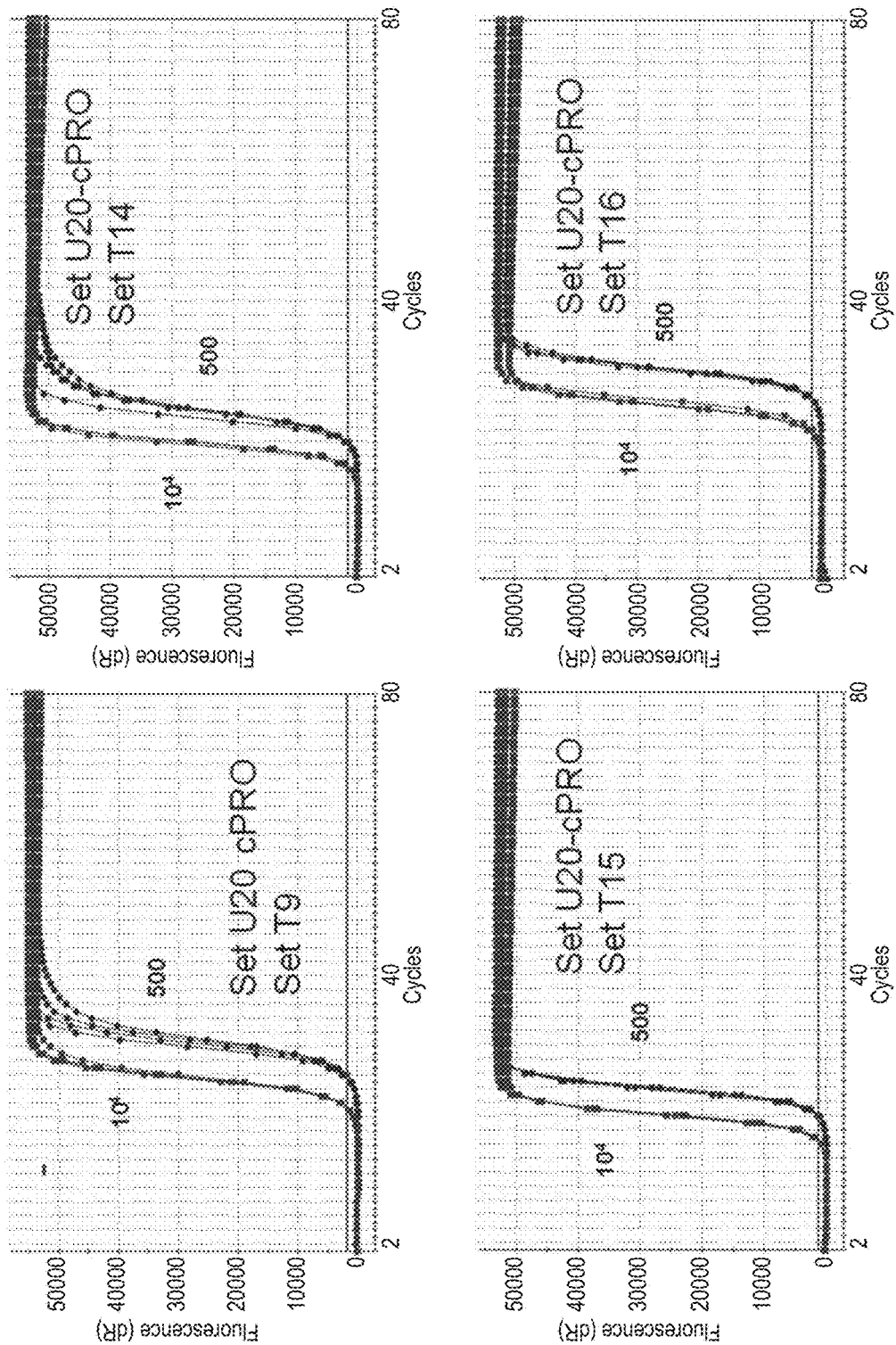
Figure 9:
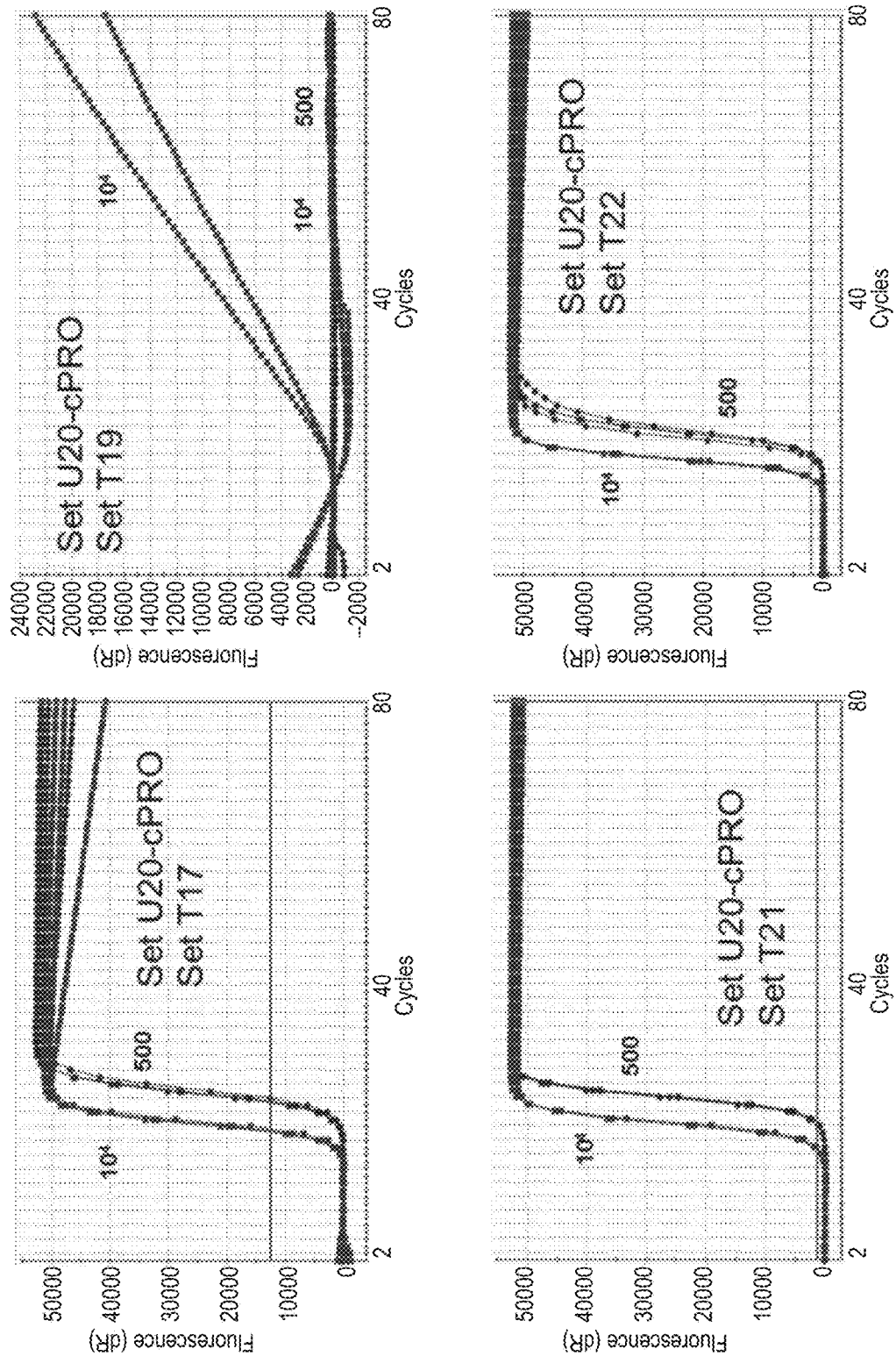
Figure 10A:
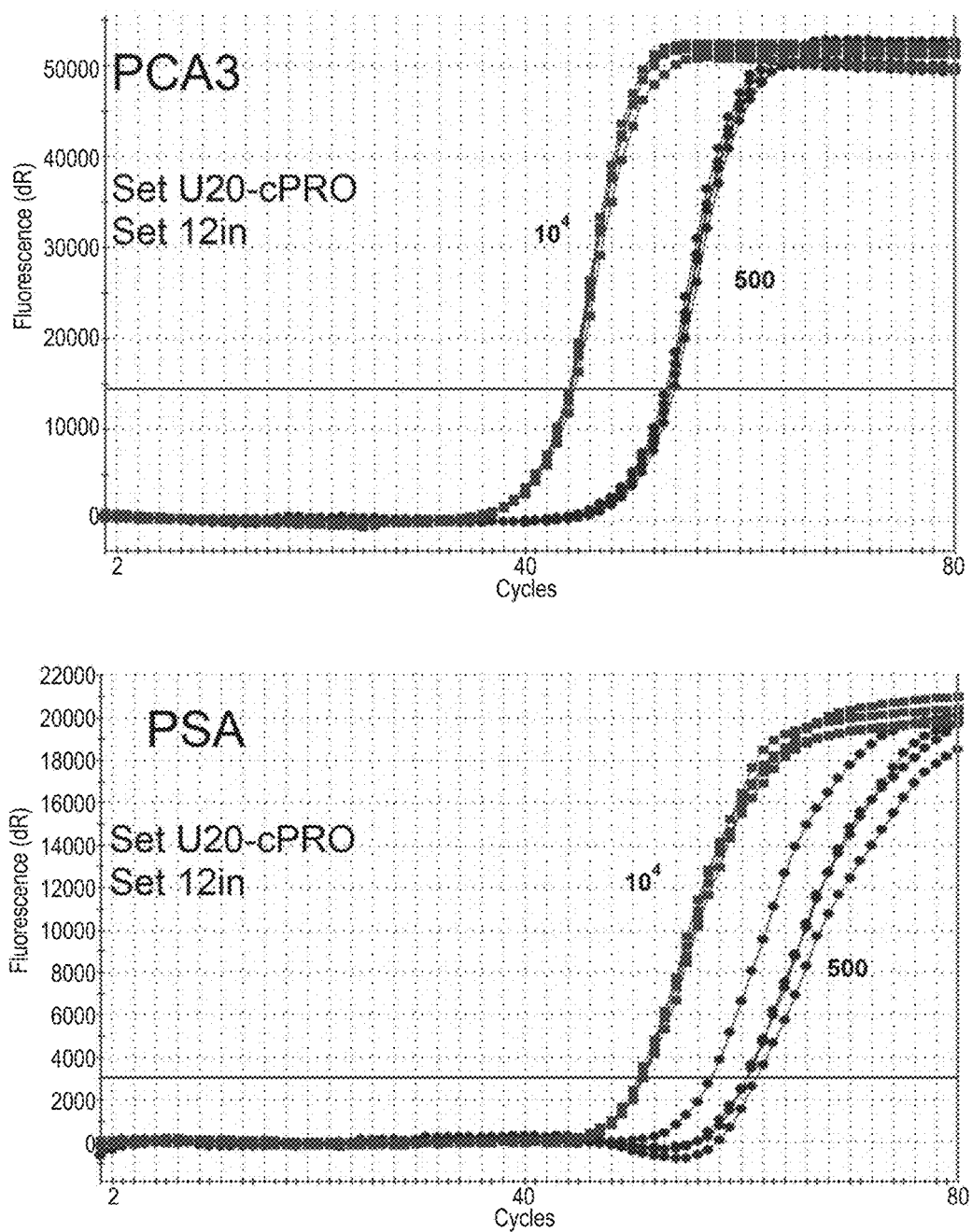
Figure 10B:
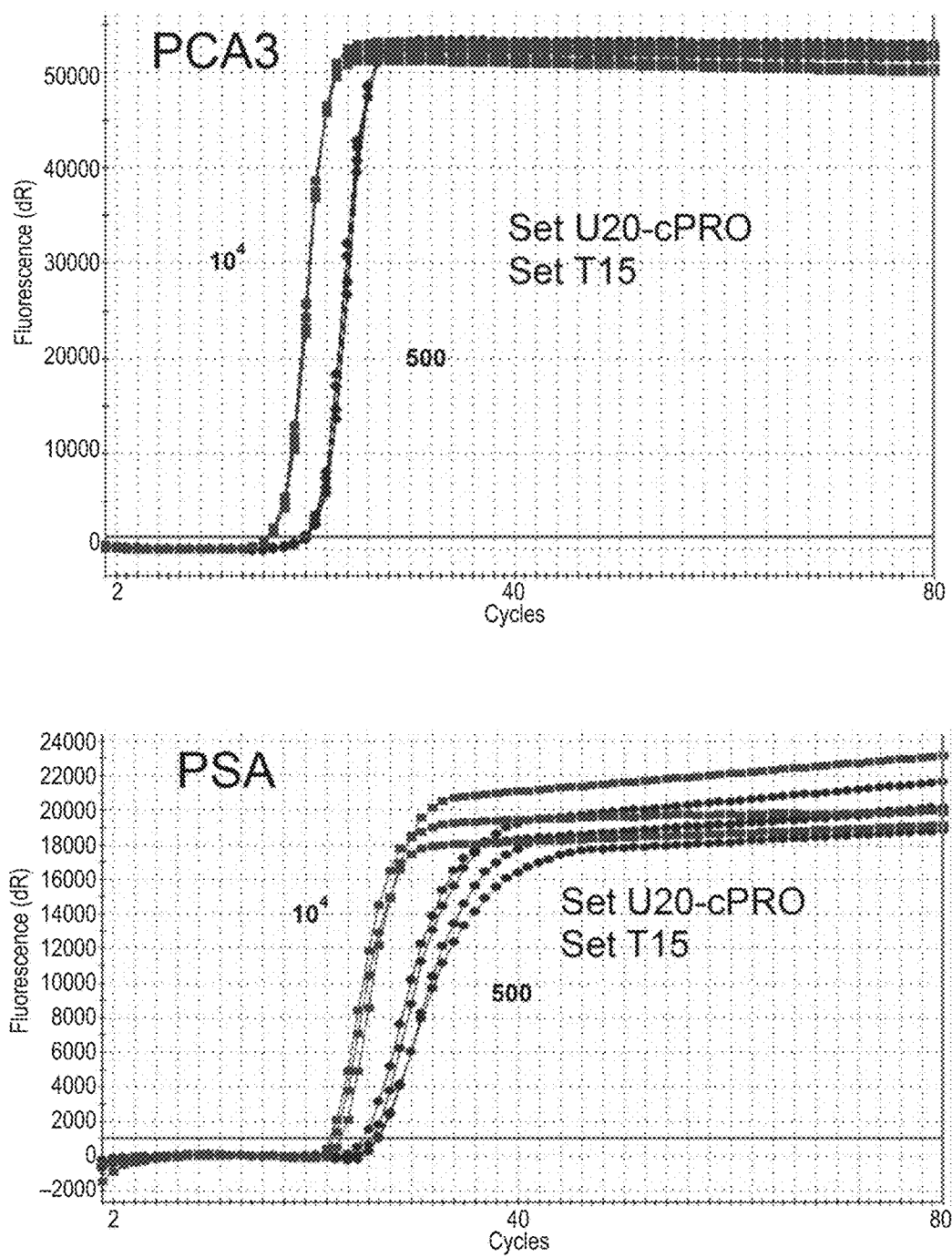
Figure 11:
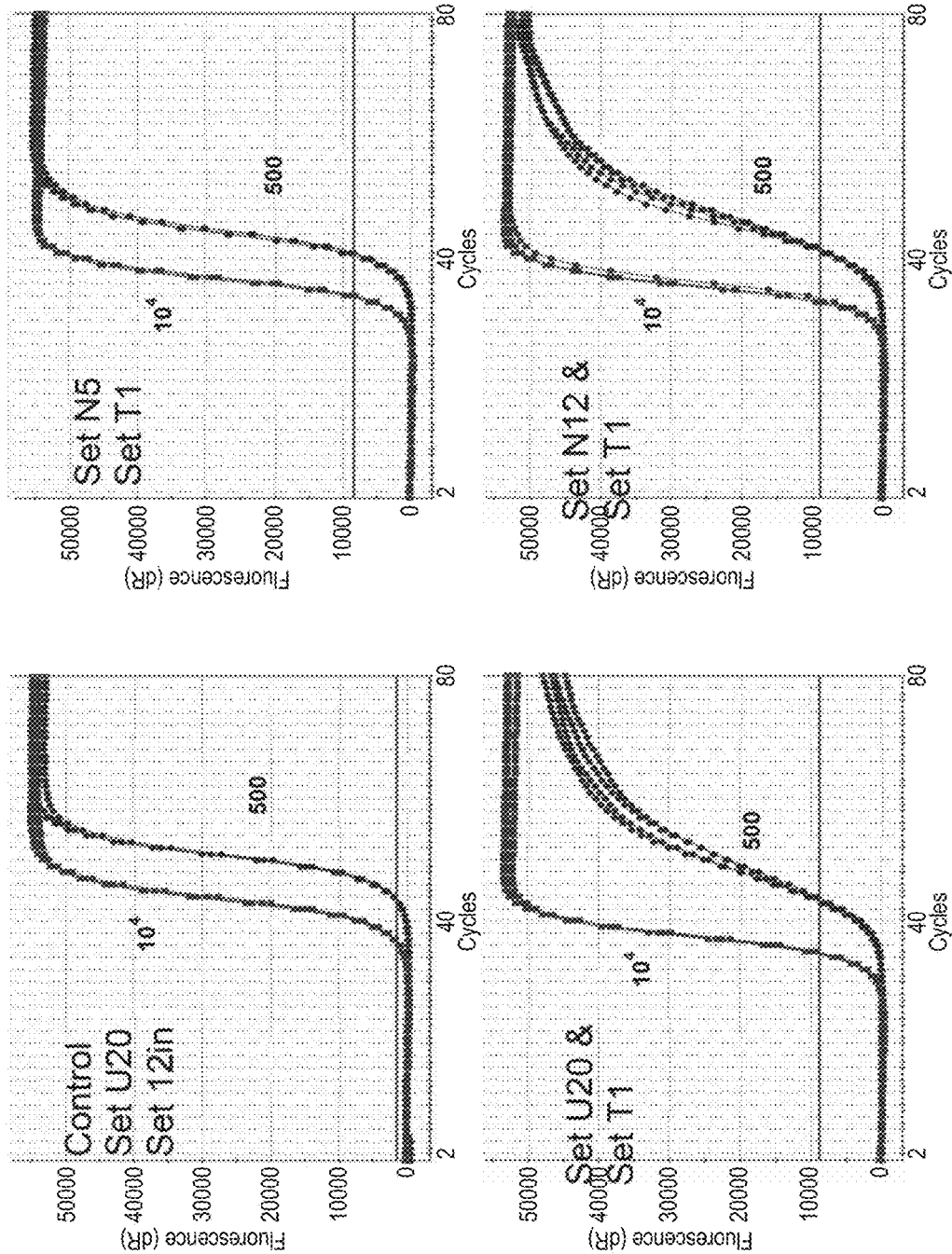
FIGS. 11-17. Each figure illustrates a uniplex in vitro nucleic acid amplification screen using random oligonucleotide sequences as tags in non-T7 and T7 amplification oligomers. Both amplification oligomer species (non-T7 and T7) contain a tag sequence. The target analyte was PCA3. The in vitro nucleic acid assays are TMA reaction in the RUt (FIGS. 11-15) or RUf formats (FIGS. 16-17), with RUf format using a direct hybridization amplification oligomer complex (cPRO).
Figure 12:
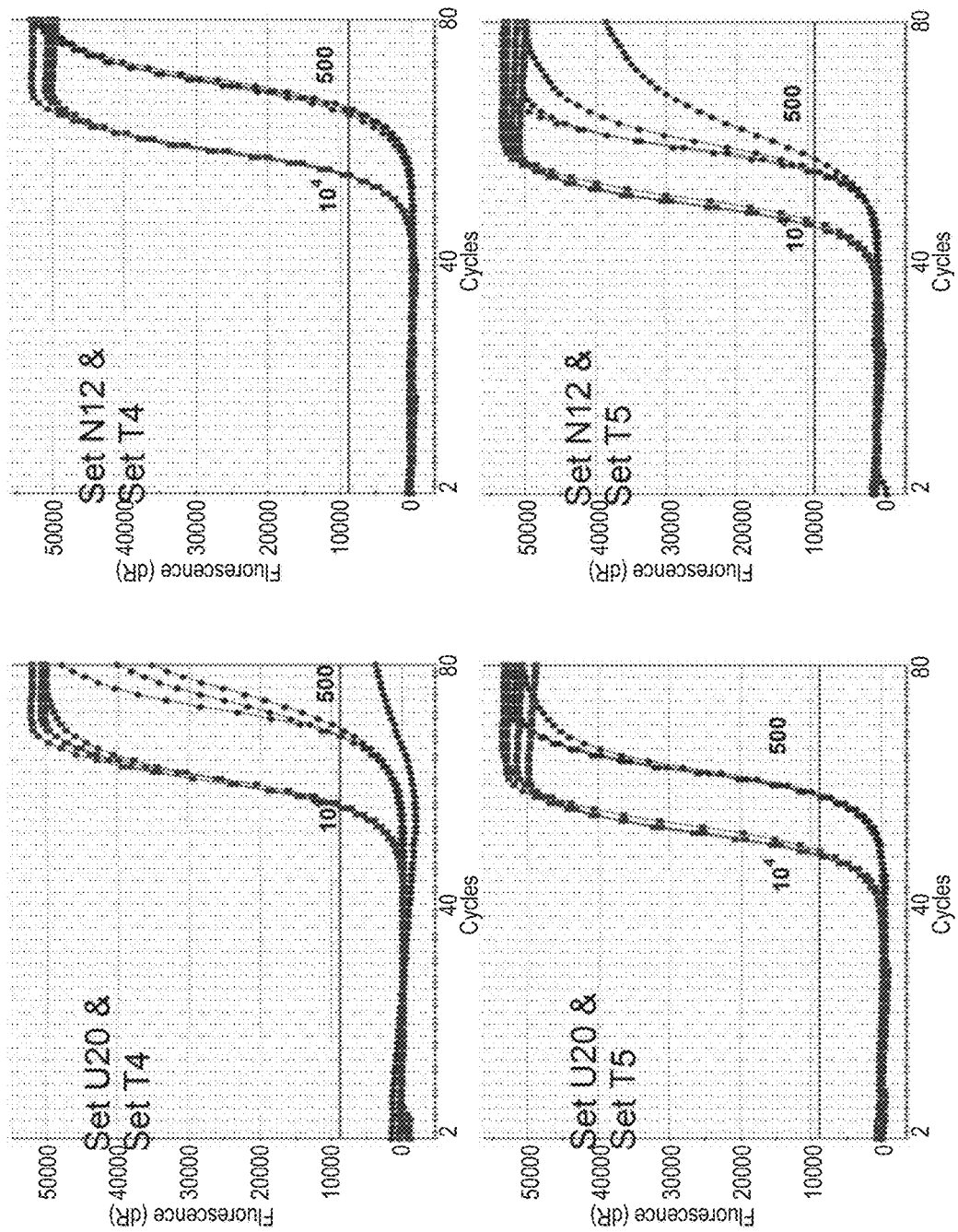
Figure 13:
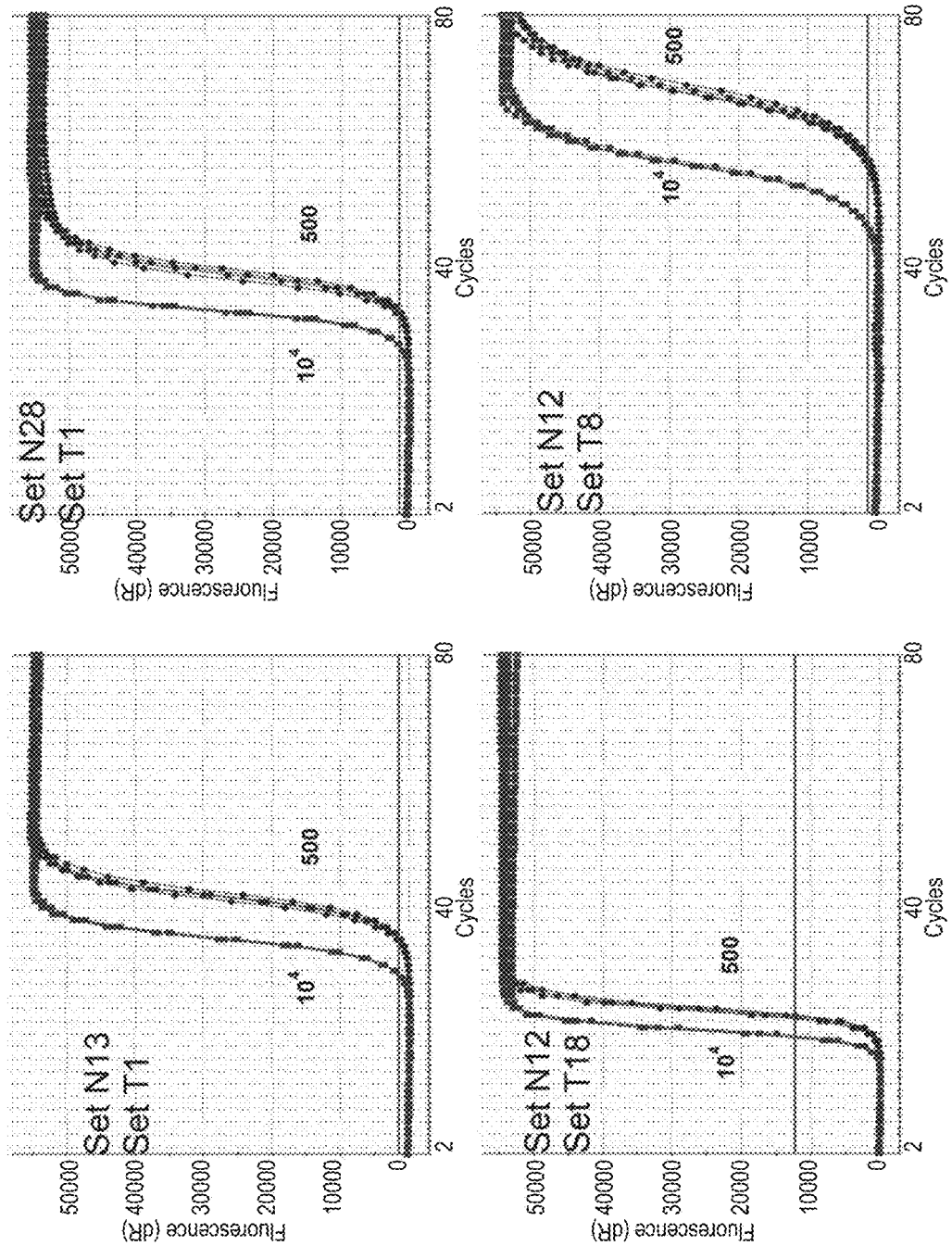
Figure 14:
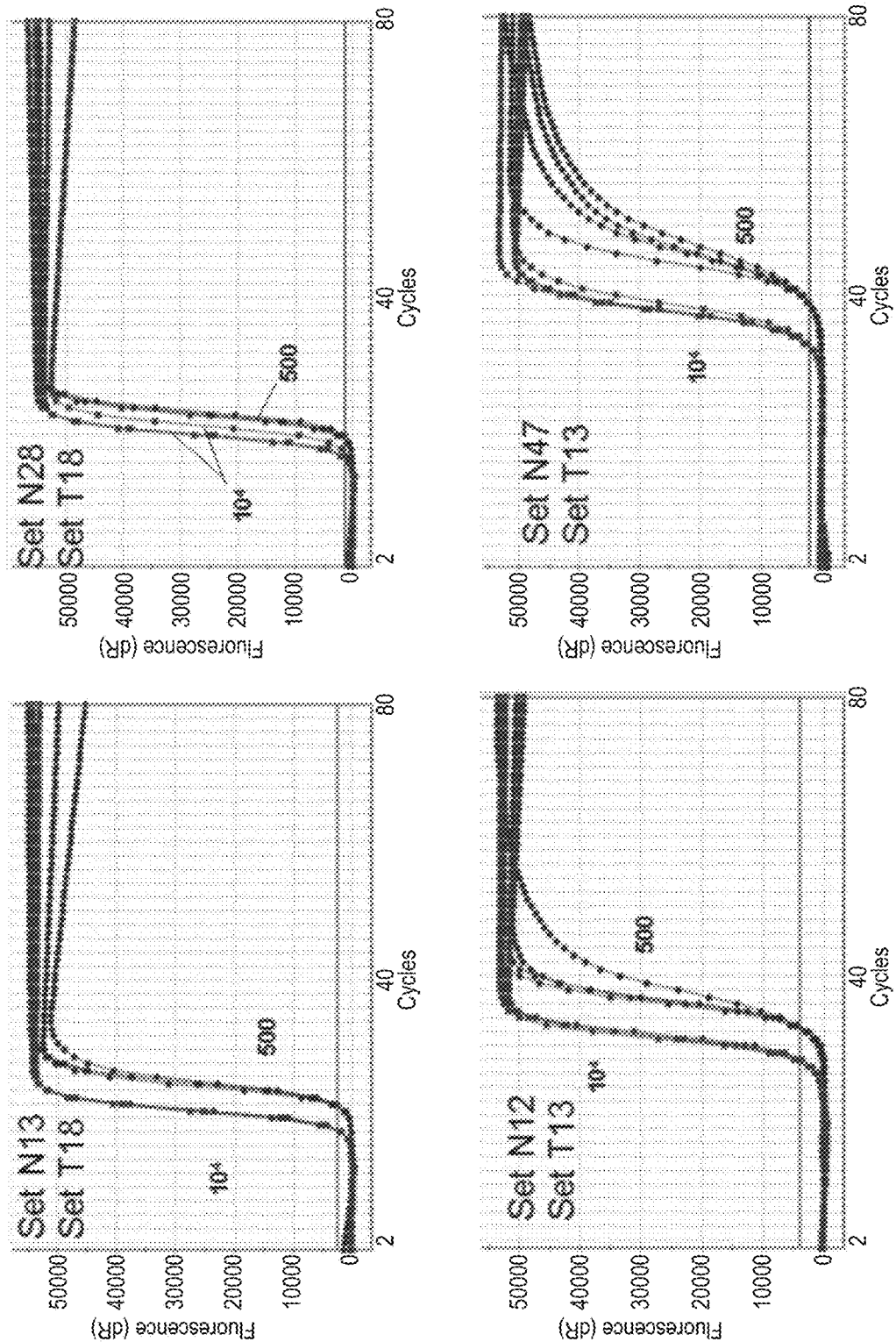
Figure 15:
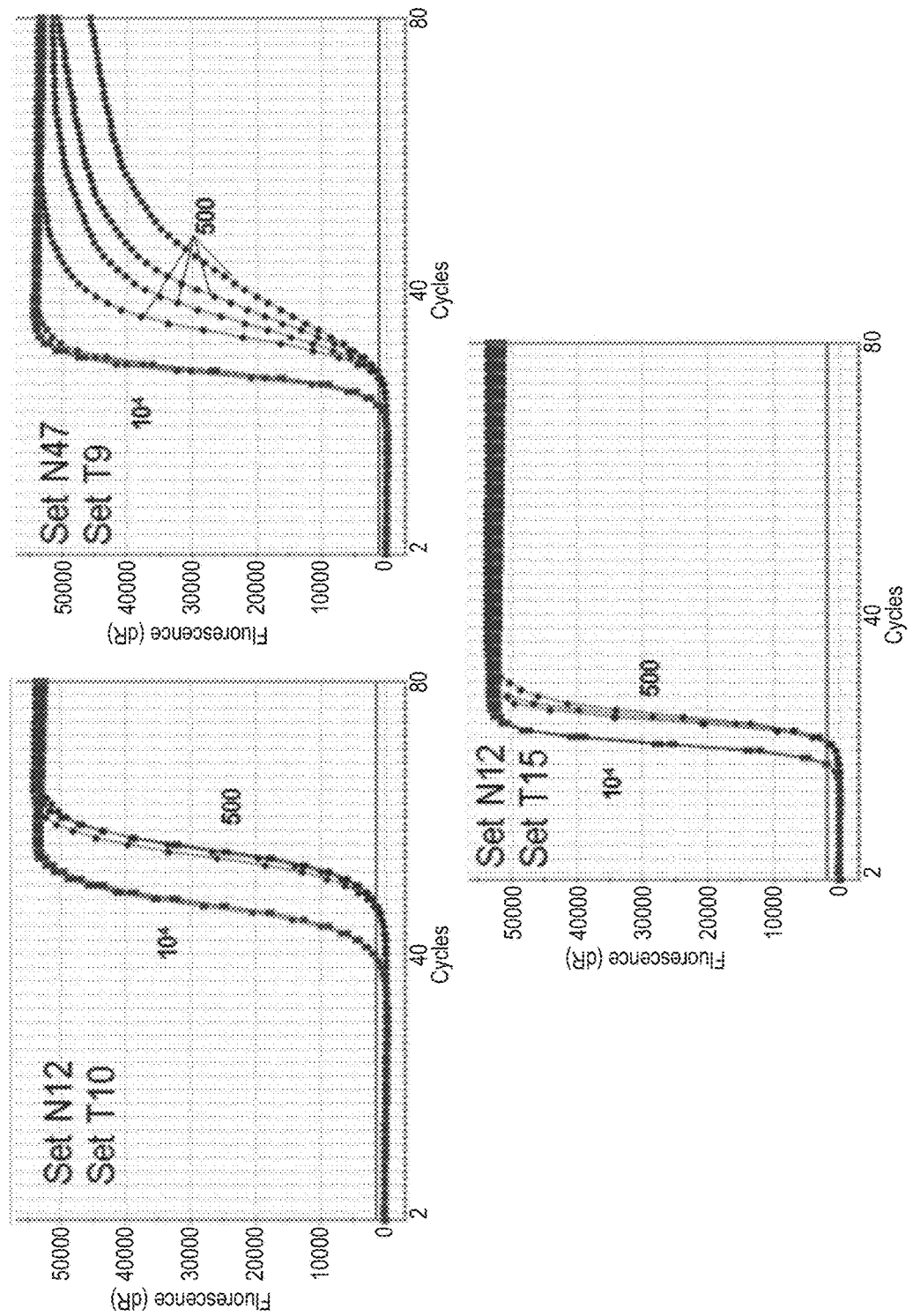
Figure 16:
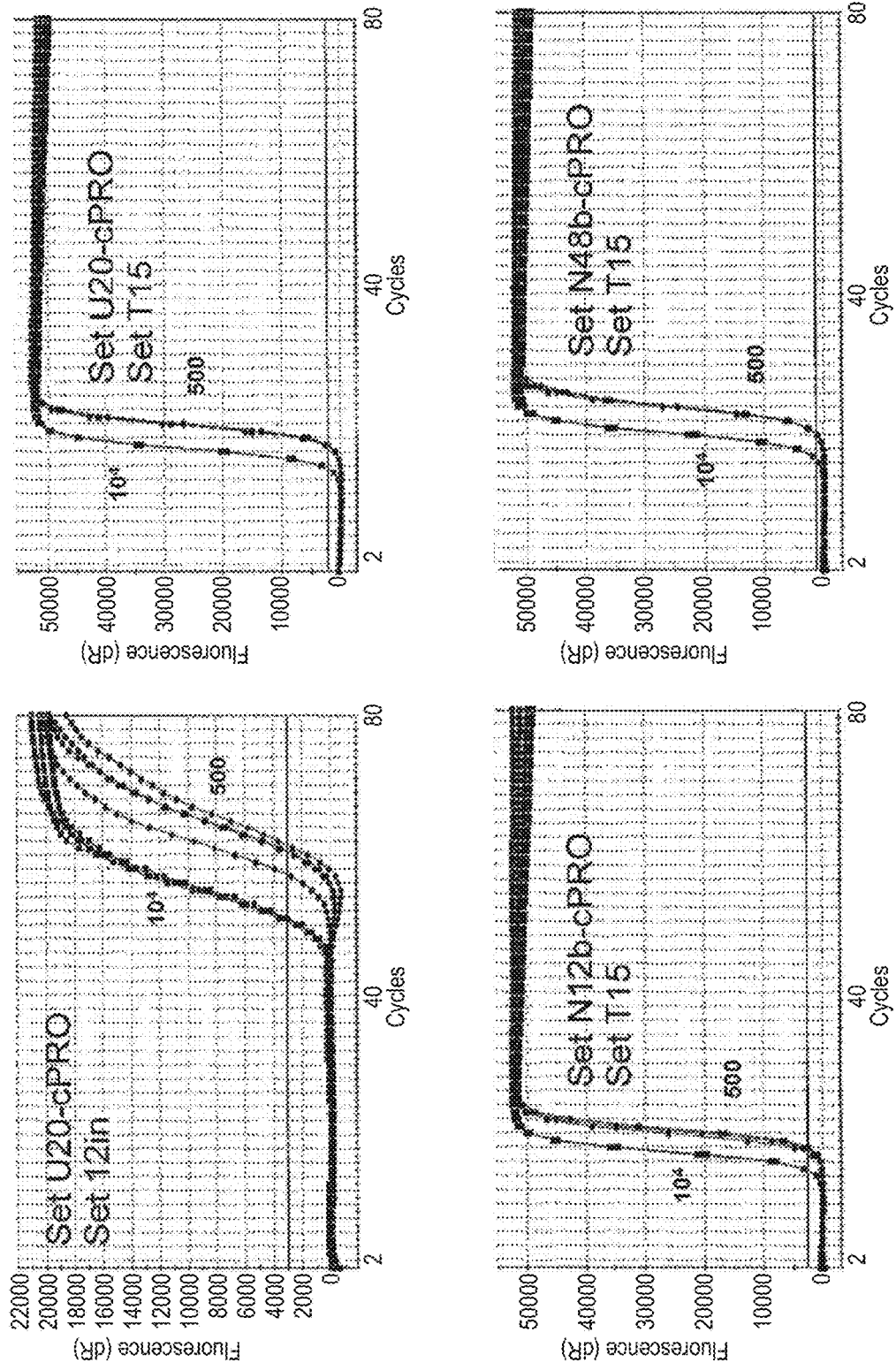
Figure 17:
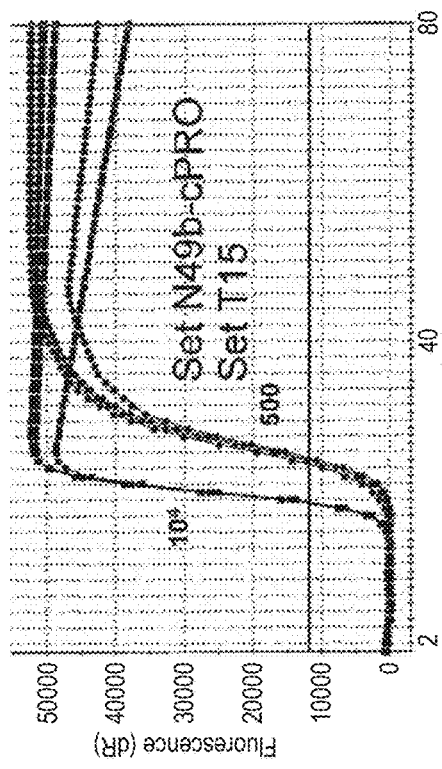

Some representative real time curves from the T7 tag evaluation are shown in FIGS. 7-9. Performance of the different tags varied in this assay. Some performed approximately the same as the standard 12 in, some performed much more poorly and some performed better. The best performing previously uncharacterized tags in this system were T9, T14, T15, T16, T17, T20, T21 and T22, which yielded dramatic decreases in emergence times. One of the best performing tags—T15—was further tested using PSA as a target nucleic acid, the results of which are shown in FIG. 10. Again, performance was dramatically improved using tag sequences identified by the current methods. These results demonstrate the power of this technique in identifying tags with preferable characteristics.

Example 3: Testing Combinations of NT7 and T7 Tags

Combinations of NT7 and T7 tags are also tested using different TMA formats (see FIGS. 11-17). Combinations are identified whose performance is superior to that of the standard U20/12 in pair, again demonstrating the power of this technique in identifying tags with preferable characteristics.

Example 4: Further Refining Tag Sequences

Figure 18A:
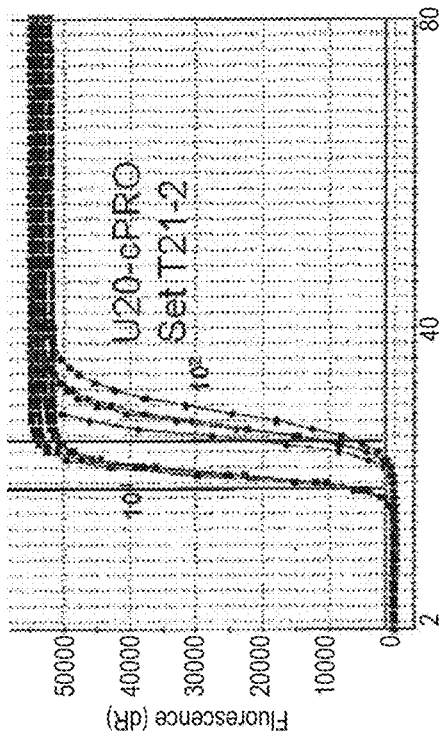
Figure 18B:
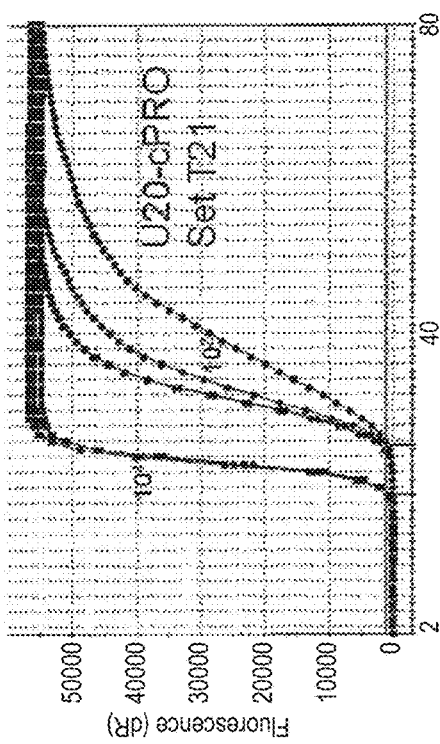

As mentioned above, once good tag sequences have been identified, performance can be further optimized by the process of incremental changes and subsequent screening. An example of this is depicted in FIGS. 18-19, wherein the T7 tag T21 is systematically shortened and then tested in a TMA amplification assay. The T21 tag sequence was shortened by removing residues from the 3' end of the tag sequence. Shortening the T21 tag sequence by 2 nucleotides ("T21-2") slightly improved performance. Shortening the T21 tag sequence by a total of 6 or 8 nucleotides dramatically decreased its performance in this assay. Unexpectedly, shortening the T21 tag sequence even further by removing a total of 10 or 12 nucleotides restored some (although not all) of the original activity (especially 10 nucleotides shorter). This demonstrates the ability of the method to identify sequences possessing unexpected activities, such as the example here wherein a very short tag yielded good performance. Further refining the tag sequence, as illustrated here, is useful for "tuning" the tagged oligonucleotide to perform at a certain level. In some instances, a better performing tagged oligonucleotide is useful; while in other instances decreasing its performance is useful.

It should be noted that the differences in performance identified by this method are useful in a wide variety of ways. For example, the differences in amplification kinetics identified are useful in balancing multiple amplification reactions in a multiplex reaction in order that no one (or more) reactions is so much faster than the others that it (or they) unduly compete for essential shared components in the multiplex amplification mixture. Thus, the method of invention provides a means for evaluating and selecting useful tags by analyzing a variety of performance parameters, by which methods preferred sequence modifications can be identified that would not have been a priori predictable.

Example 5: Screen for NT7 Tag Sequences with Minimal Interference in the PCA3-PSA Duplex Template System Using the Reverse TMA with a Portion of the Amplification Oligomers Containing Tag Sequences The example described below illustrates the use of the method to select the best tag sequences with minimal interference for use in a universal reverse TMA assay format using the PCA3-PSA target sequence combination. This example is intended only to demonstrate the use of this screening method and does not limit the scope of application to only this assay.

Step 5—Screening in Uniplex:

The 56 NT7 tags that were identified after step 3, and were then synthesized (Table 2) were screened for amplification of a PCA3 target nucleic acid in a uniplex format.

Figure 20:
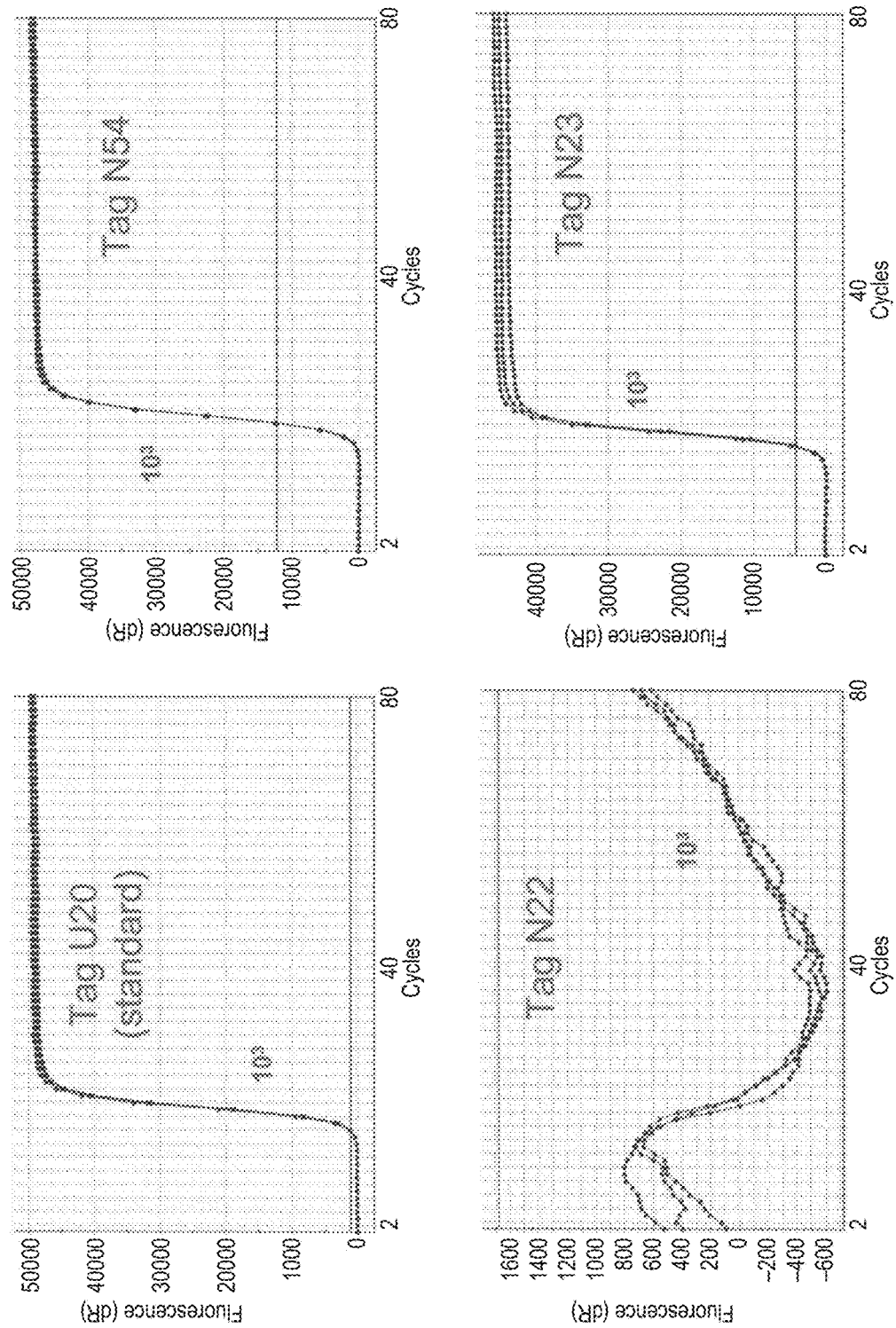
FIGS. 20-21 illustrate uniplex RUh TMA assays wherein the Non-T7 amplification oligomers include a tag sequence indicated in each panel. Target nucleic acids are PCA3 (FIG. 20) or PSA (FIG. 21).
Figure 21:
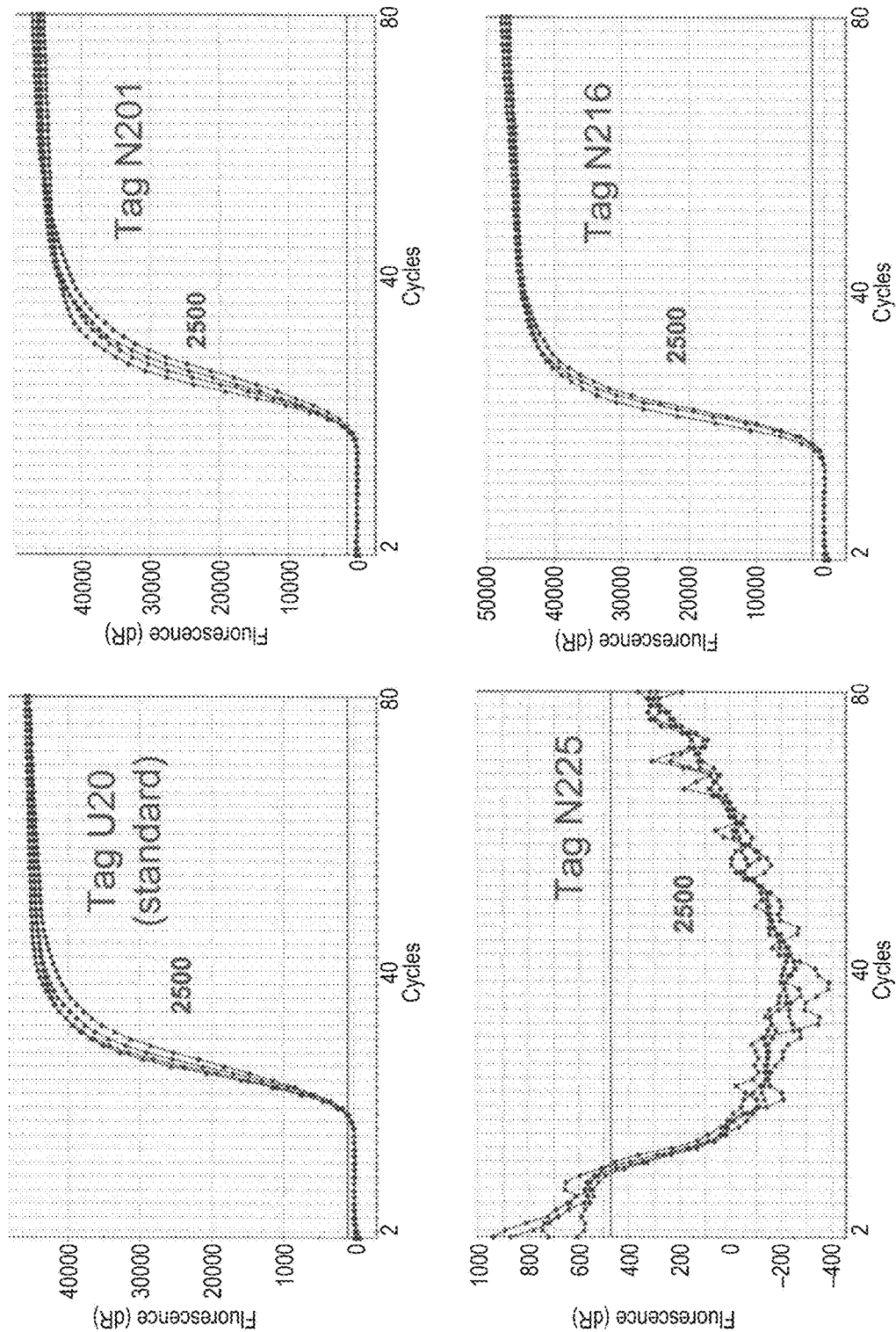

Each tag was screened in a uniplex RUh (reverse half universal TMA, where the universal sequence is on the primer member (NT7) of an amplification oligomer pair comprising a primer and a promoter-based amplification oligomer) reaction for amplifying PCA3 target nucleic acid. Amplification results were evaluated qualitatively. Out of 56 NT7 tags screened, 41 tag sequences optimally amplified PCA3 in this system (see FIG. 20 for representative examples). Separately, 38 NT7 tag sequences were designed and screened for amplification of a PSA target nucleic acid. After qualitative evaluation, 16 of these tags sufficiently amplified PSA (see FIG. 21 for representative examples).

Figure 22:
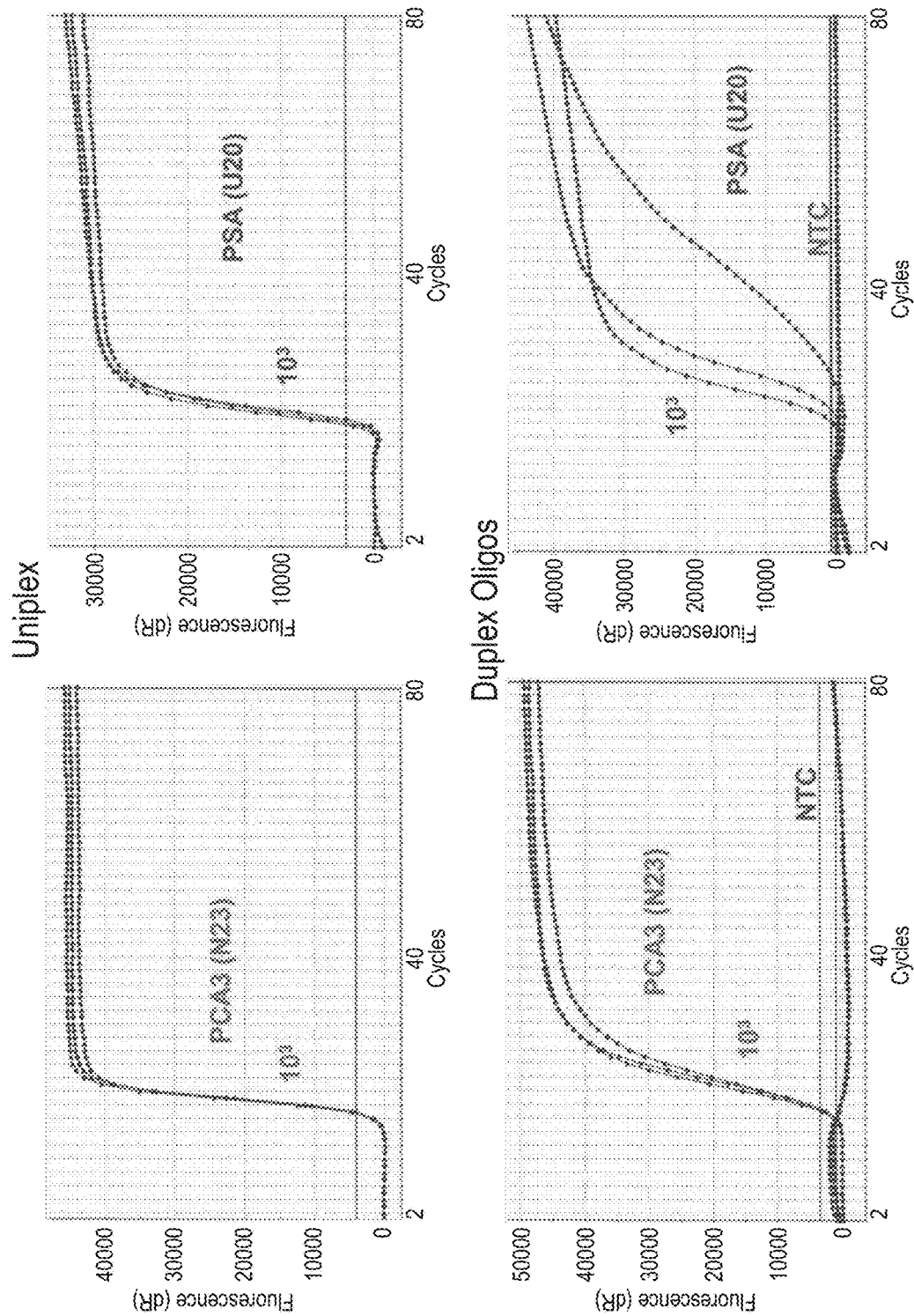
FIGS. 22-23 illustrate TMA amplification reactions wherein a reaction is performed in the presence or absence of a potentially interfering nucleic acid containing a tag sequence. In both of FIGS. 22 and 23, the top two panels show amplification of PCA3 or PSA using an amplification oligomer tagged as indicated. No potentially interfering tagged nucleic acid was present. In both of FIGS. 22 and 23, the bottom two panels show a similar amplification as the corresponding top panels, except that amplification was performed in the presence of a potentially interfering tagged nucleic acid. The potentially interfering tagged nucleic acid used in a duplex oligo reaction was the tagged amplification oligomers disclosed in the figure, but not directed to the target (e.g., FIG. 22 bottom left panel=PSA(U20)
Figure 23:
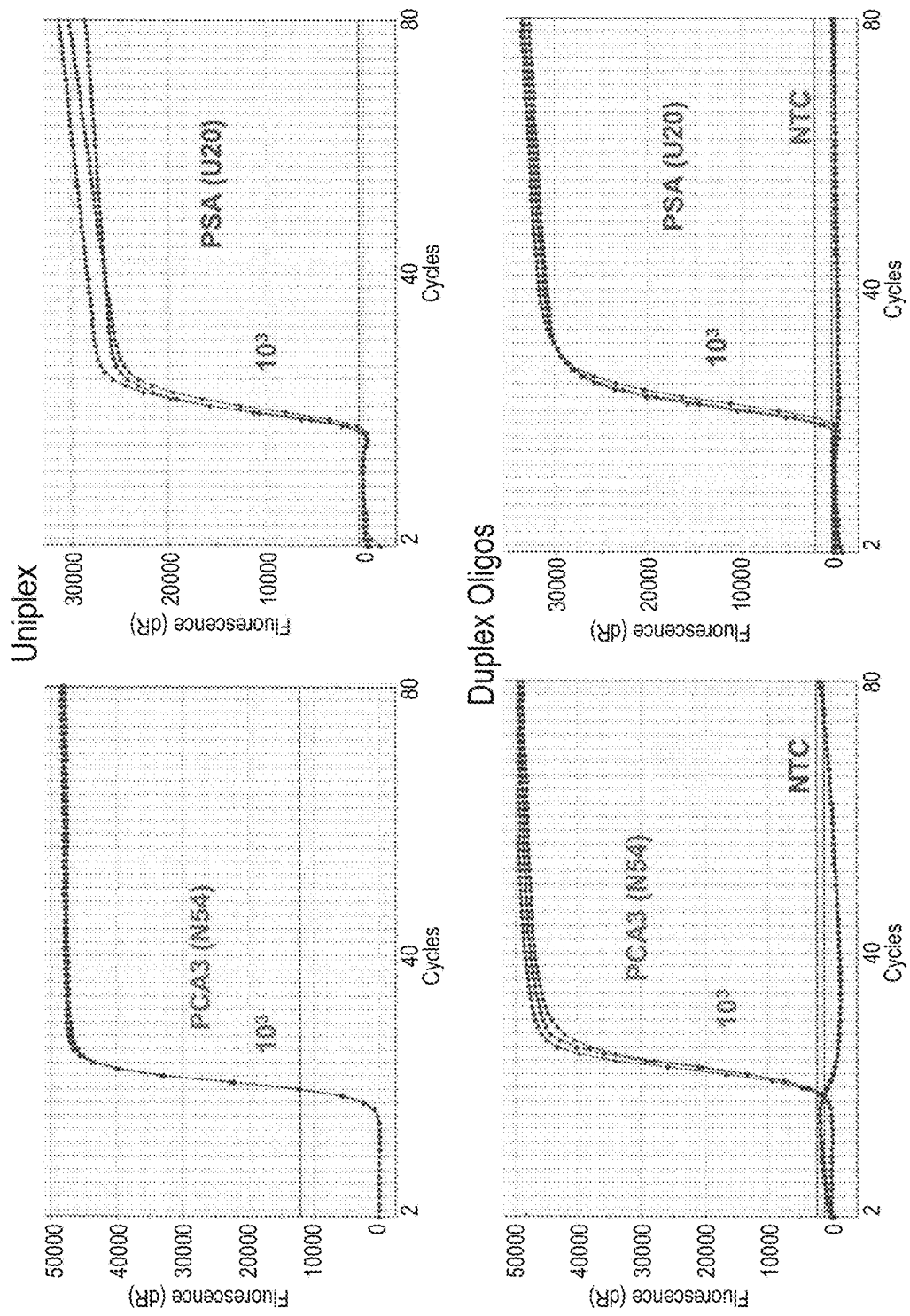

Step 6—Screening Using Duplex Amplification Oligos:

Each of the 41 PCA3 tags passing qualitative criteria in uniplex were then screened in duplex oligo format. PCA3 amplification driven by each tag was observed in presence of PSA oligos containing the U20 standard tag sequence. Similarly, PSA amplification driven by the previously characterized U20 tag was evaluated in the presence of PCA3 amplification oligos with each of 41 tags (see FIGS. 22 and 23 for representative examples). These duplex oligo screens were evaluated qualitatively, and 12 PCA3 tags were confirmed to work well in the presence of PSA oligos comprising standard tag U20.

Each of 16 tag sequences that passed qualitative criteria for PSA amplification in uniplex were then screened against several good tags for PCA3. 27 of these unique tag combinations successfully amplified PCA3 and PSA under duplex oligos conditions.

Figure 24:
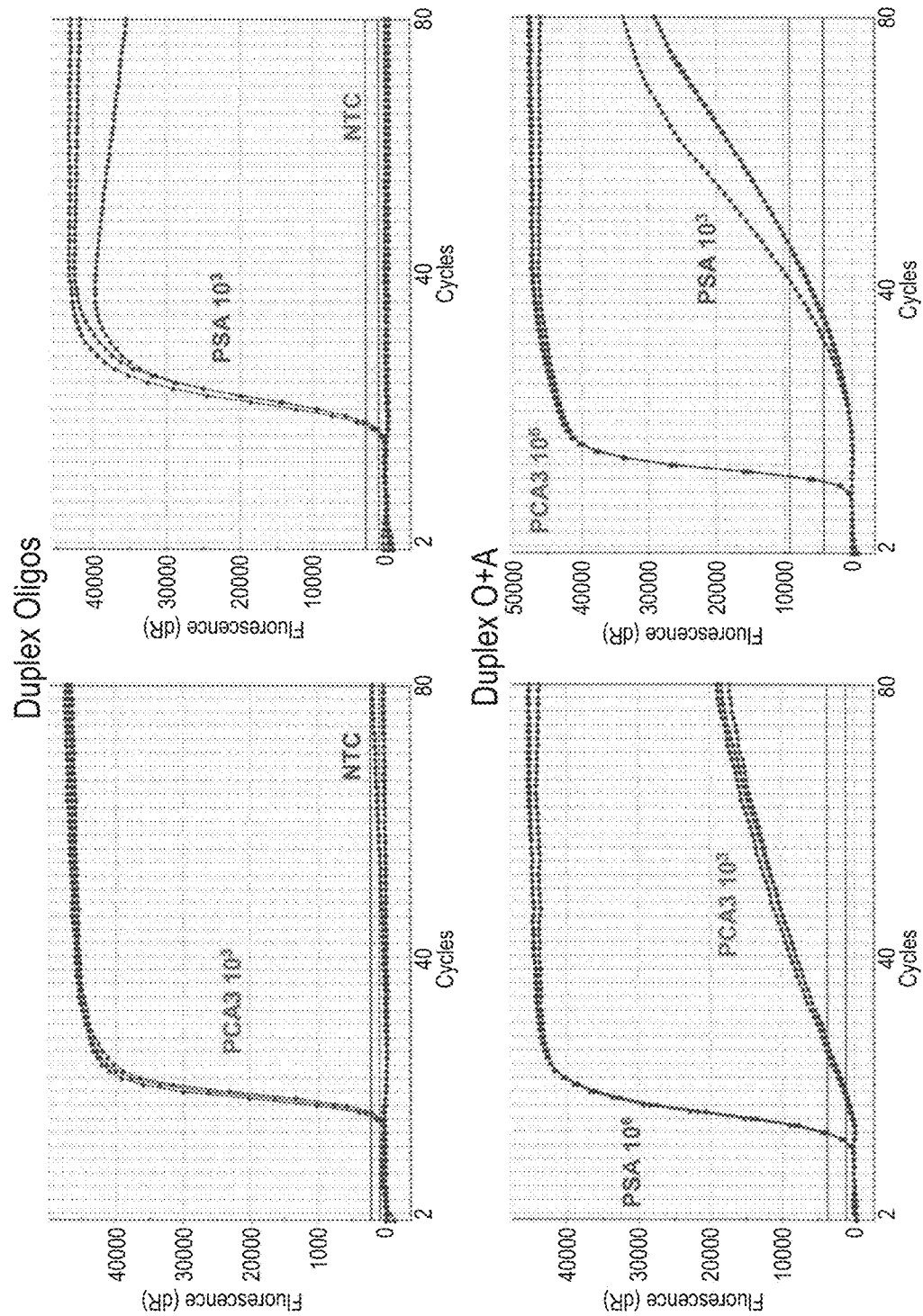
FIG. 24 illustrates in the top two panels a TMA amplification reaction performed in the presence of a potentially interfering tagged nucleic acid (e.g., left top panel is a PCA3 amplification reaction using a U20-tagged non-T7 amplification oligomer in the presence of a U20 tagged non-T7 targeting PSA; and the top right panel is a PSA amplification reaction using a U20-tagged non-T7 amplification oligomer in the presence of a U20 tagged non-T7 targeting PCA3). The bottom two panels illustrate duplex TMA reactions wherein two amplification oligomer sets are provided in each reaction; one directed to PCA3 and one to PSA, and wherein each target analyte is present in the reaction. In these duplex reactions, the amplification oligomer sets each had tagged non-T7 amplification oligomers and each used the U20 tag sequence. The concentration of target was $10^6$ PSA and $10^3$ PCA3 for the bottom left panel, and $10^3$ PSA and $10^6$ PCA3 for the bottom right panel.

Step 7—Screening Using Duplex Amplification Oligos and Target Nucleic Acids:

All tag combinations passing qualitative criteria under duplex oligos conditions were subsequently screened in duplex oligos and target sequences format. Amplification of $10^3$ copies of PCA3 was evaluated in the presence of $10^6$ copies of PSA, and $10^3$ copies PSA was evaluated in the presence of $10^6$ copies of PCA3. This target input window was chosen based on the interference observed in the standard tag sequence (U20) universal system; specifically, 1000 copies of either PSA or PCA3 target nucleic acid amplified only weakly in the presence of 3-log greater copies of the other target nucleic acid when using a U20 tag (FIG. 24). The levels of template interference with each new tag combination were qualitatively determined relative to the amplification with the U20 standard tag.

Step 8—Interference Analysis:

The interference analysis method was then used to quantitate the magnitude of target sequence interference (I-values) for each tag combination screened in duplex oligos+ templates condition. See FIGS. 25 and 26. The tested combinations are shown in FIG. 27 together with the results of the screening test. The lowest I-value of 19.97 for an Analyte Interference Score was seen for the tag sequence combination, Tag N54 (PCA3) and standard tag U20 (PSA). The top 10 tag combinations displaying minimal I-value, are listed in Table 5. A summary of results from all the screens performed for this example is given in FIG. 27.

| PCA3 Tag | PSA Tag | Delta PCA3 | Delta PSA | Score |
|---|---|---|---|---|
| U20 | U20 | 27 | 24 | 51 |
| N54 | U20 | 12 | 7 | 19 |
| N54 | N209 | 16 | 4 | 20 |
| N34 | N201 | 9 | 12 | 21 |
| N14 | U20 | 8 | 13 | 21 |
| N54 | N226 | 19 | 3 | 22 |
| N54 | N216 | 15 | 8 | 23 |
| N14 | N216 | 12 | 12 | 24 |
| N34 | N216 | 6 | 20 | 25 |
| N14 | N207 | 6 | 22 | 28 |
| N14 | N201 | 9 | 24 | 33 |

Figure 28A:
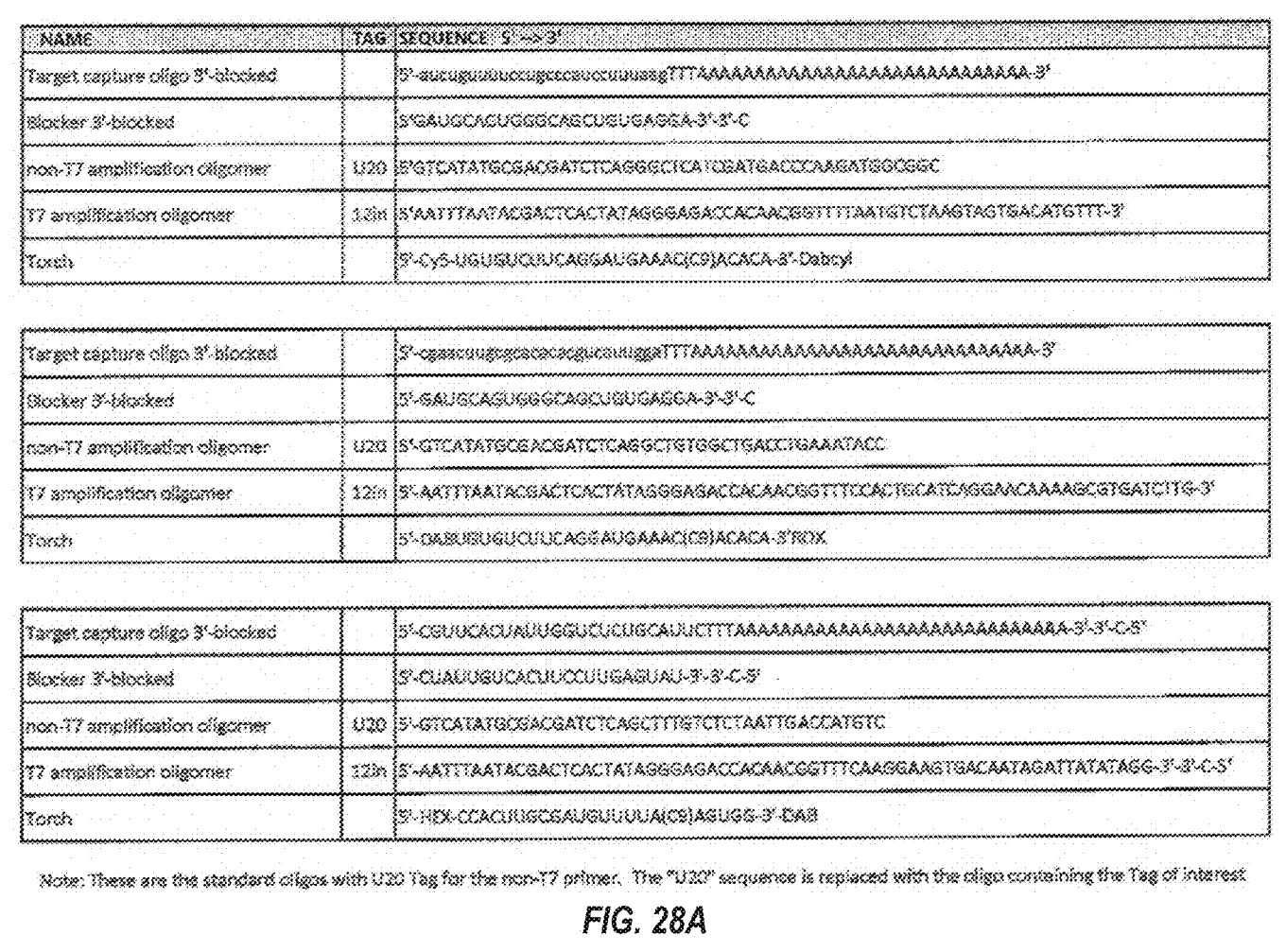
Figure 29:
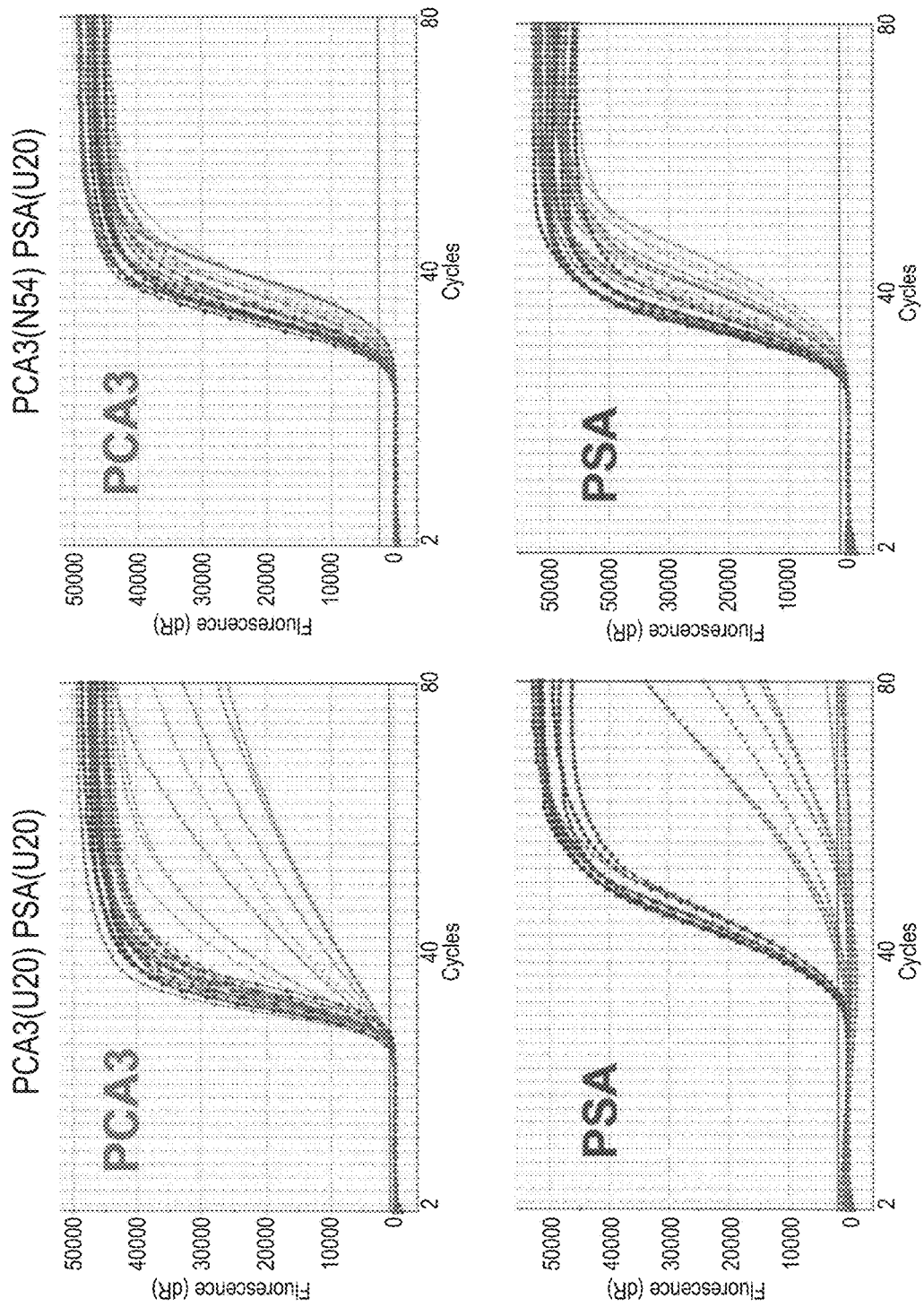
FIGS. 29 and 31 illustrates reaction curves for amplification reactions using amplification oligomers having one of the tag sequences selected according to the reactions illustrated in FIGS. 28 and 30.
Figure 31:
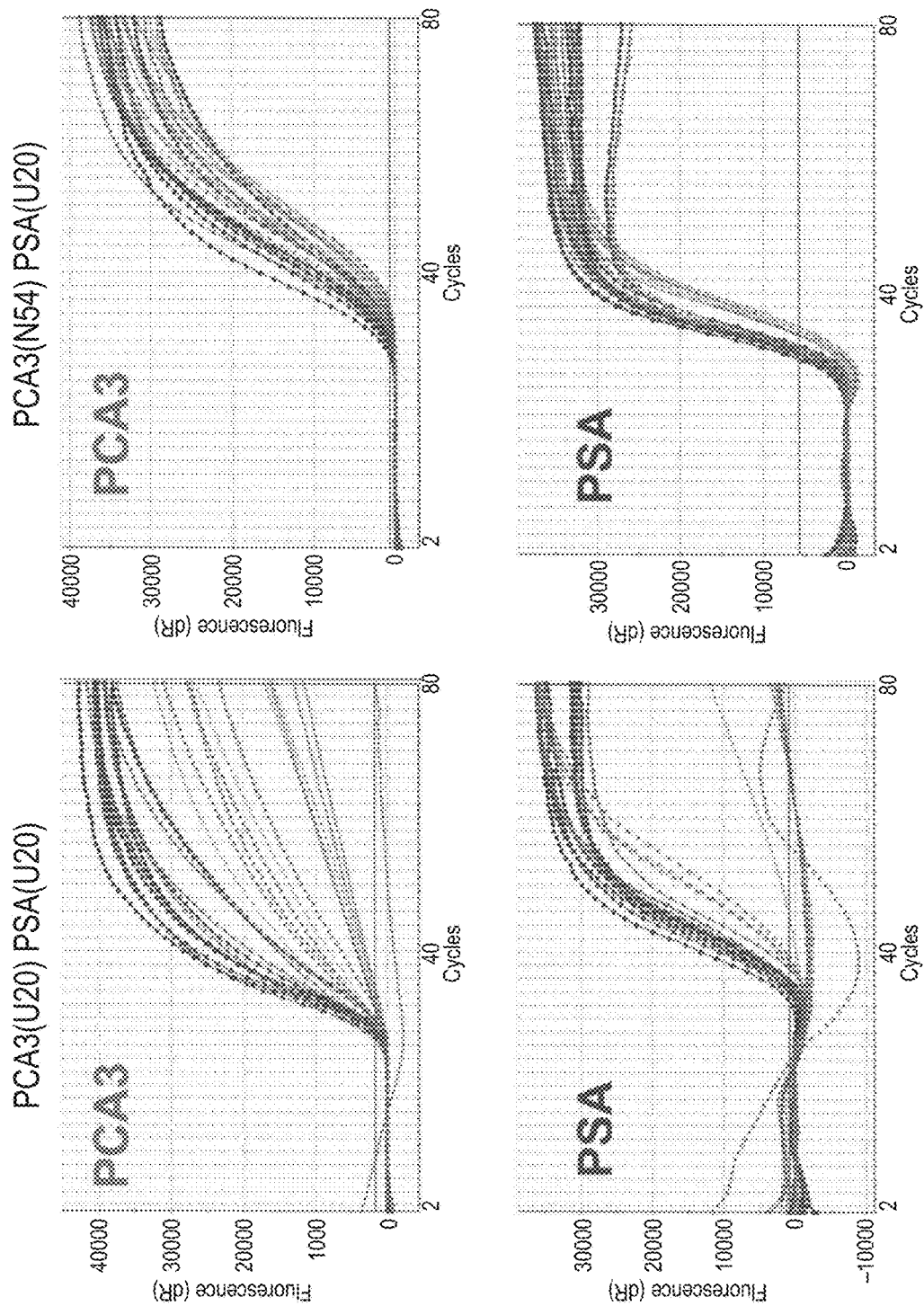

The best tag combination obtained from this screen was N54/U20. Finally, using the combinations of tags that were selected from the screens, tag N54 (PCA3) and tag U20 (PSA), it was demonstrated that the interference observed was minimal in a Triplex system (PCA3/PSA/IC) compared to the standard system (FIGS. 28 to 31). Reactions conditions in this triplex system were generally set up as follows. For a first set of triplex reactions the non-T7 amplification oligomers for each target nucleic acid (PCA3, PSA and Internal Control) were tagged with the U20 tag sequence (see FIG. 28). Each target capture reaction contained 5 pmol of each target capture oligomer, 5 pmol of each blocker and varied copy numbers of the target nucleic acids according to the chart in FIG. 28 along with internal control. Target capture reactions were performed resulting in capture of the target nucleic acid hybridized with a non-T7 amplification oligomer and a blocker. The captured nucleic acids were then placed into an amplification reaction containing 2.8 pmol, 1.3 pmol and 0.6 pmol of PCA3 T7 amp oligos, PSA T7 amp oligos and internal control T7 amp oligos, respectively; 20 pmol each of PCA3 torch and PSA torch; 10 pmol of internal control torch; and 10 pmol of a non-T7 amplification oligomer targeting the complement of the U20 tag sequence. A real time TMA reaction was performed and the results are shown in FIG. 29. Two nearly identical assays were also performed, the differences being that the non-T7 amplification oligomer targeting PCA3 was tagged with N54 rather than U20. Each of these additional assays contained the same oligomers and target nucleic acids. However, to off-set the impact of a more robust amplification of one of the targets within the multiplex, the T7 concentrations were adjusted. In these additional two reactions, the PCA3 reaction included 3.0-3.8 pmol T7 and 15-20 pmol of torch; the PSA reaction included 15-20 pmol torch and the internal control included 15-20 pmol torch. Other differences compared to the full U20 reaction included using 7.5 or 15 pmol of non-T7 targeting the complement of U20 or N54, respectively. Target copy numbers for these three reactions are shown in FIGS. 28 and 30. Results are shown in FIGS. 29 and 31.

The system using the N54 tag was able to amplify 102 copies of PCA3 and 2491 copies PSA in presence of the highest calibrator level of the competing analyte, whereas the U20 universal "standard" system would not under a balanced set of condition (see FIG. 29). An 'unbalanced' system was tested with several different low copy levels in presence of high copy levels of analyte, and the N54/U20/U20 system demonstrated very little interference compared to the U20 standard triplex system (see FIG. 31). Therefore one the advantage of using the tag identification system disclosed herein is that the unbalanced system achieved the same level of quantitation across the dynamic range without interference as did a balanced system.

Thus, the screening method described herein successfully identified tag sequences with minimal multiplex interference in a model system. In general, improved sequence tags provide selective advantage to any under-performing amplification system, and can be selected for a variety of desired properties like speed of amplification, performance, etc, along with minimal interference. In addition, screens can be modified and adapted for identifying improved tags, for alternate TMA formats, other isothermal and non-isothermal amplification formats, including PCR, and in higher plex amplifications. The methods described herein for tag selection can be readily automated to provide a high throughput combinatorial method that quickly screens for tag sequences for several types of assays.

Example 7: Identification and Selection of Tags that are Used in Conjunction with T2:ERGa Target Sequence in T2:ERGa/PSA/IC Triplex TMA Assay System T2:ERGa is a particularly challenging target nucleic acid for amplification using TMA due, in part, to its Guanine-rich sequence. The standard tag (U20) interferes with T2:ERGa amplification and is not able to amplify and detect the analyte in a universal TMA format. The tags described herein which were identified using the disclosed invention method are able to detect and quantitate T2:ERGa and PSA with sufficient sensitivity, accuracy and precision in the reverse TMA reaction wherein a portion of the amplification oligomers used contain tag sequences.

Figure 32:
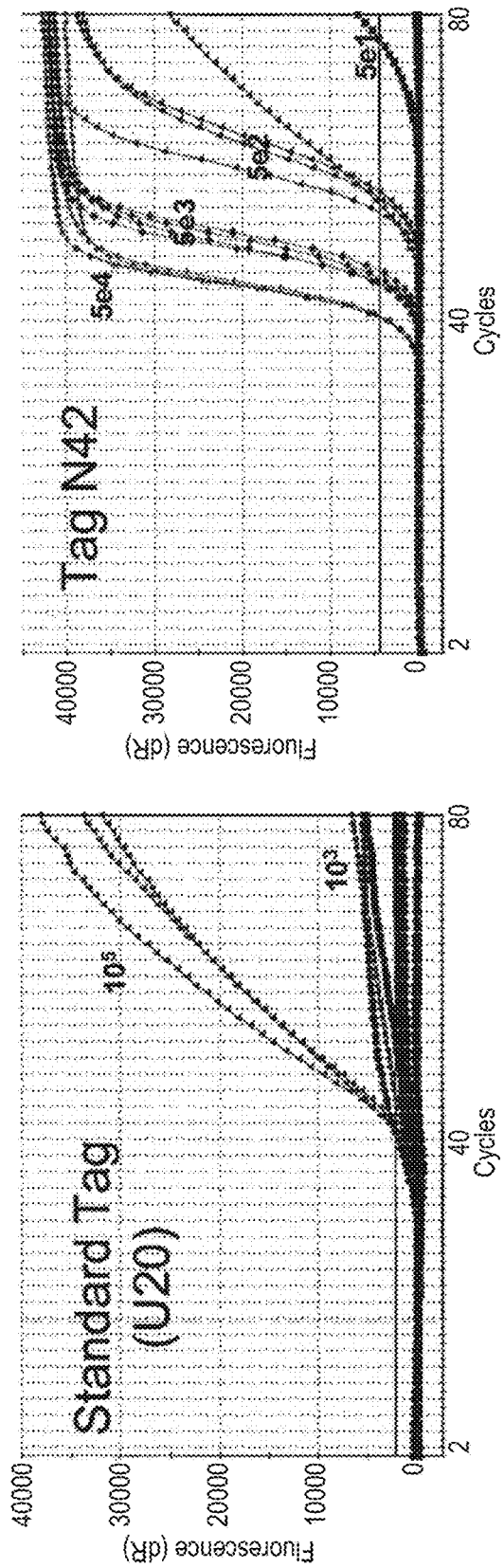
FIG. 32. T2 ERGa: Comparison of standard u20 with N42 Tag (RUh TMA)

Previously known tags were not able to amplify T2:ERGa with desired sensitivity and precision. A comparison of the assay performance with the standard tag (U20) and tag N42 is shown in FIG. 32.

Figure 33A:
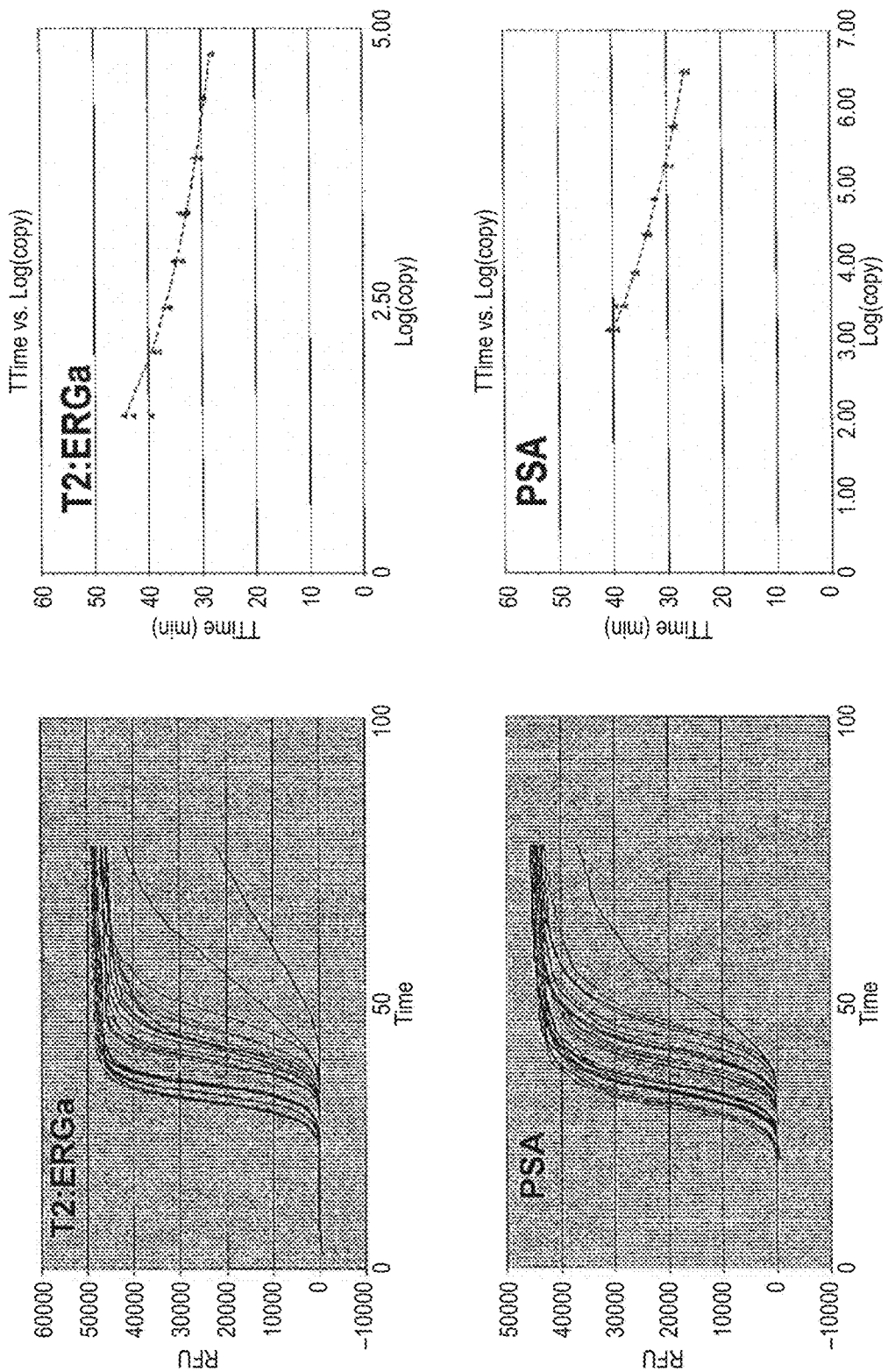
FIG. 33. Triplex RUh TMA reaction containing T2 ERGa/PSA/Internal Control, wherein the all non-T7 amplification oligomers contain a N42 Tag.
Figures 33B, 34A:
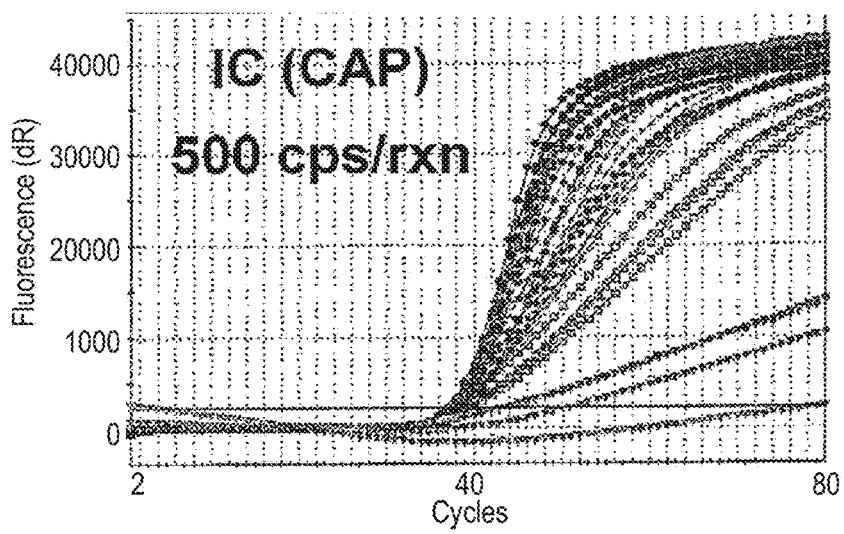
FIG. 34 illustrates quantitation data from the T2 ERGa/PSA/IC triplex RUh TMA reaction using N42 tagged non-T7 amplification oligomers from FIG. 33. "Cal" means calibrator and "CON" means control sample.
Figures 34B, 35B:
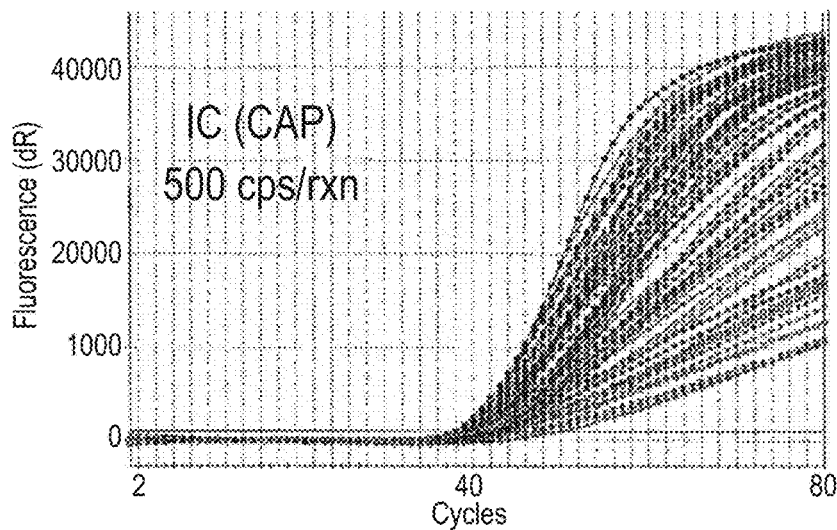
FIG. 35. Triplex RUh TMA reaction containing T2 ERGa/PSA/Internal Control, wherein the non-T7 amplification oligomers contain N42/N6/N42, respectively.
Figure 35A:
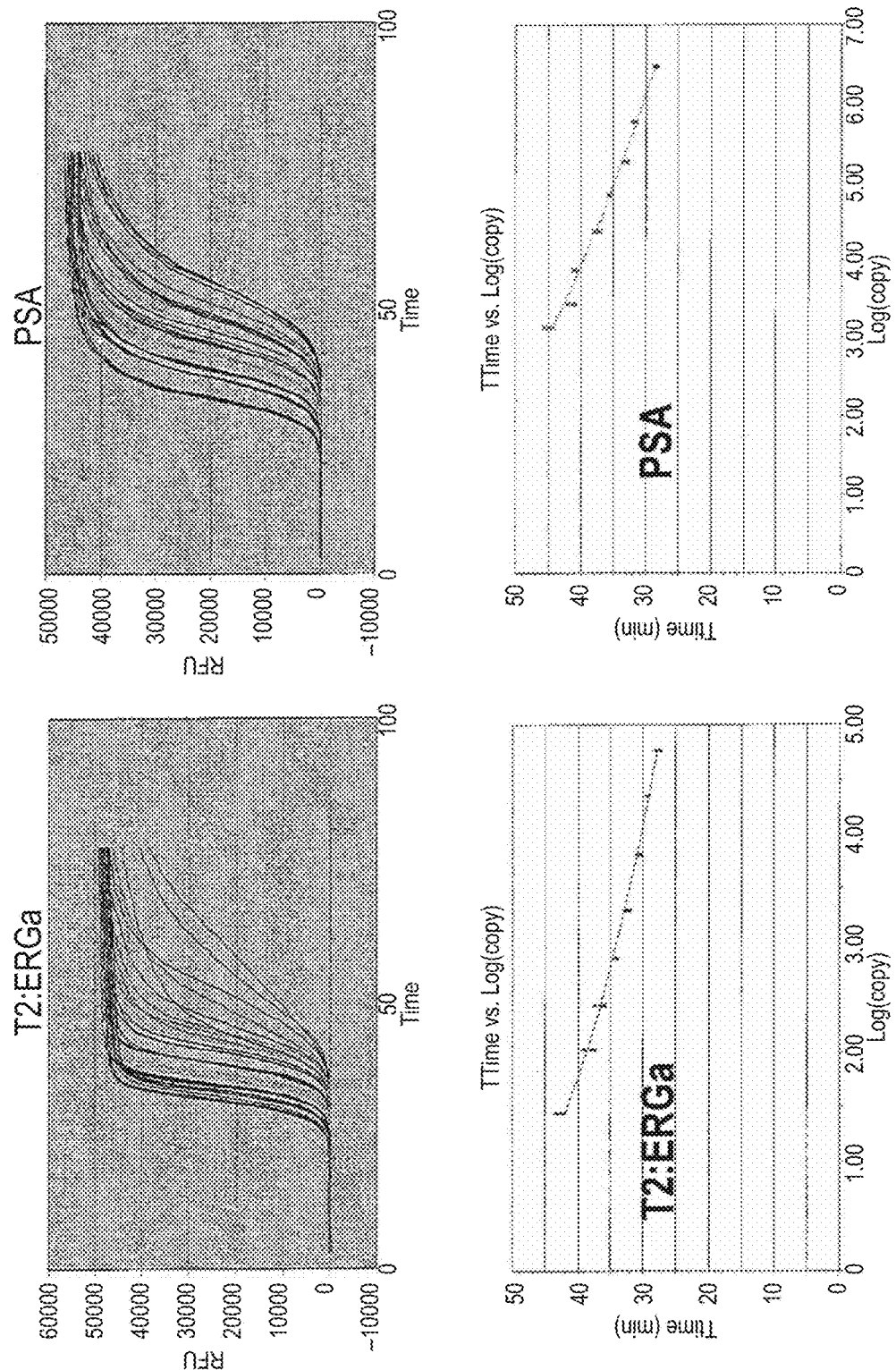
Figure 37:
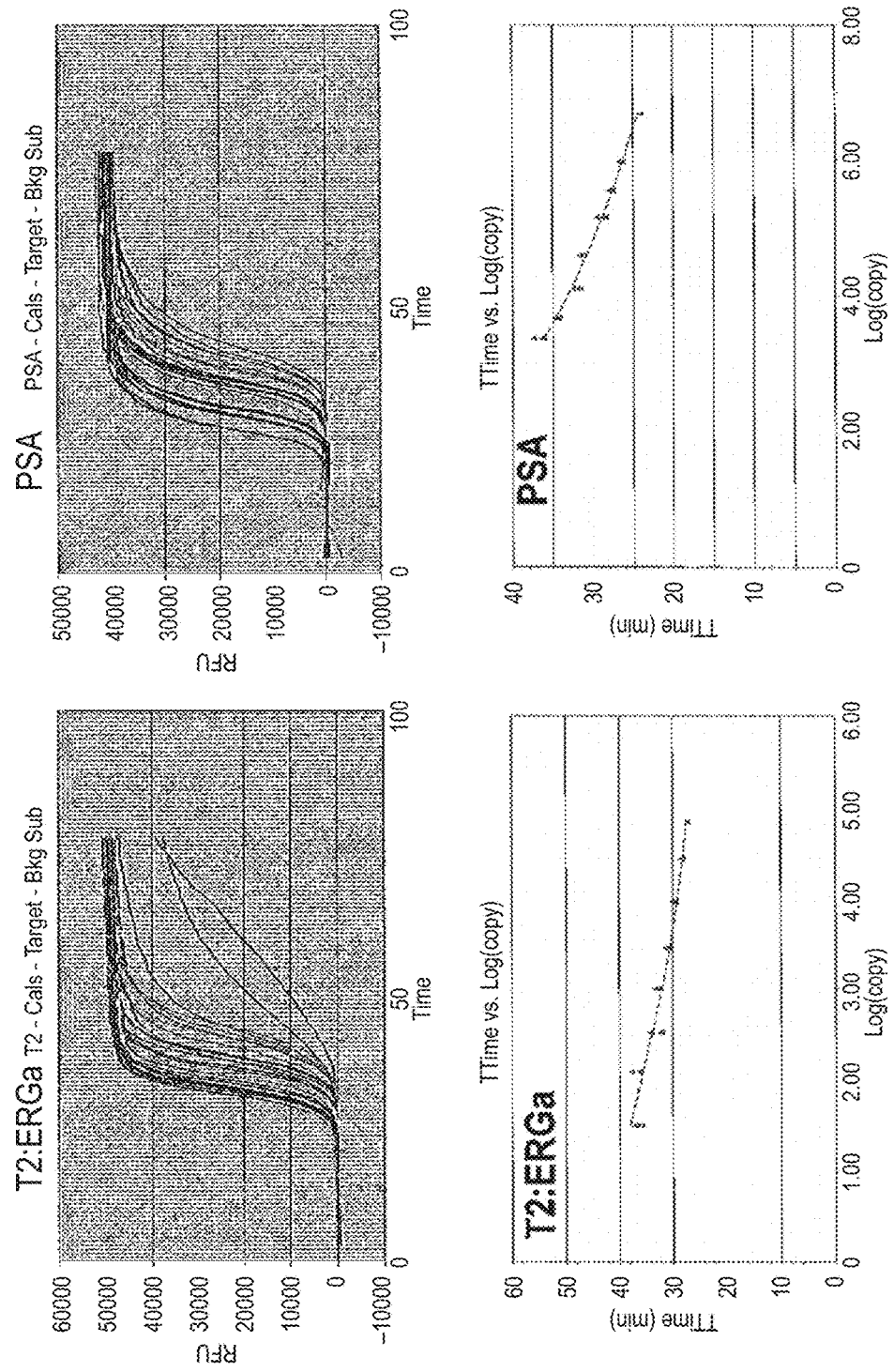
FIG. 37. Triplex RUh TMA reaction containing T2 ERGa/PSA/Internal Control, wherein the non-T7 amplification oligomers contain N42/N15/N42, respectively.

The N42 tag, for example, was capable of amplifying T2:ERGa in uniplex as well as in a triplex assay that comprised PSA target sequence and an internal control sequence along with T2:ERGa target nucleic acid. The triplex assay performed by using the N42 tag to amplify all the three target sequences in a one tube multiplex format yielded the desired performance characteristics (see FIGS. 33 and 34).

The N42 tag was also found to be compatible with several other unique tag sequence combinations which are useful in conjunction with T2:ERGa. A couple of examples of assays performed with compatible unique tag sequences in the T2:ERGa/PSA/IC system are shown in FIGS. 35 to 38.

All the tag sequences and combinations disclosed in FIGS. 32-38 are useful for amplification and quantitative detection of T2:ERGa and PSA templates in the T2:ERGa/PSA/IC triplex assay in pure system (using IVT) as well as in clinical urine samples.

TABLE 4

Summary and cross-identification of the sequences described herein and in the Sequence Listing.

| Oligo Name | SEQ ID NO: | Sequence 5' → 3' | Function |
| --- | --- | --- | --- |
| U20 tag (Std) | 1 | GTCATATGCGACGATCTCAG | tag |
| 1 | 2 | CCCCGTCAAACAAAAACGGGAGCGTGTACC | tag |
| 4 | 3 | CCATAGGCCTTCTGCACTGCTCCATATACC | tag |
| 6/N1 | 4 | GTCCCCATCGGAGGGCATCTTATCGTGCCT | tag |
| 8/N2 | 5 | CCGCCCTCCTTCGCCCCCCGGTGAAATAAC | tag |
| 12/N3 | 6 | AATGCTCACCTCTATTCGGGACTTGAGTAC | tag |
| 21 | 7 | CCCGCGCACCACCTCCATCACGCAGAAGAG | tag |
| 25/N4 | 8 | GTCGGAACGCCAGGTACAGTTAGCGCATCC | tag |
| 26 | 9 | AAGTCACTGGCCAGCATAATGCGTGAAGGG | tag |
| 27/N5 | 10 | GTGATGCTTTATGAGATTCCGGTCTCCGAC | tag |
| 28/N6 | 11 | GACGGTGCATCACCCGCATTTGCTGTAGCG | tag |
| 34 | 12 | AGAATTCTTGCAGGTAGAGGTCCCCTCATT | tag |
| 35/N7 | 13 | AAGCCAAAATTACAATCGATCCCTACCAAC | tag |
| 37/N8 | 14 | ATCTTGCACCTTCCCAGATGTAAACCCCCT | tag |
| 42 | 15 | GAAGCGGCAGCTCAGCCGGTTCTCGGAGAG | tag |
| 43 | 16 | GCACGCGGGCTCCTTGGGACACTATGATTG | tag |
| 61 | 17 | CCCATCAGGACAGTCAGCTGCCCACGAATT | tag |
| 78 | 18 | CTTTAGTGCGGTAGGACCGAGACTACCGTG | tag |
| 79 | 19 | TTATGTGCCAGCTGGGCCTAAGGCTCCGGG | tag |
| 80 | 20 | GACTCTCCTAGGGCGTTCGTCTGGGACTGC | tag |
| 82/N9 | 21 | CGGAGAATACCCTCGACTGTATCATATCGT | tag |
| 84/N10 | 22 | TTCATCGAGGTACATTGGTGCTATTCCATT | tag |
| 86 | 23 | TACCACCTGGTTCAAGGTGTGCCGTACGCG | tag |
| 87/N11 | 24 | AGGAGAACCAGCCTGGAGCGTTTAAGCATC | tag |
| 88/N12 | 25 | GATGTCCTAAAATGAGGCGTGGCAATAGAG | tag |
| 89/N13 | 26 | CAGAGTCATGTATACCCACTGTCGGTCGAA | tag |
| 104/N14 | 27 | GTCAGGCTAGGGGGTTATCCCAGCAACGGC | tag |
| 106 | 28 | TGGGTTCTGCTAACCGGTGCCGTTCTTAAC | tag |

TABLE 4-continued

Summary and cross-identification of the sequences described herein and in the Sequence Listing.

| Oligo Name | SEQ ID NO: | Sequence 5' → 3' | Function |
|---|---|---|---|
| 116/N15 | 29 | TTTTTGACAGTGATGAAGAGGGAGGTACGA | tag |
| 133 | 30 | GAGAACTCGCGCTCCCTCACTCCGTTTAGA | tag |
| 136/N16 | 31 | CTATGGTTCGTTACTGAATCGAAAAGCCGC | tag |
| 138/N17 | 32 | TAGCTATCAAAACAGGCGTCATCGGTTAAG | tag |
| 145 | 33 | AGGACGCTGACACCGTTGGGGTAAAGCGTG | tag |
| 152/N18 | 34 | CCTGCTTAGGGTCACTTAAACTACTGGCGC | tag |
| 155/N19 | 35 | GGTGATGGCCCATACCGATCACGCCCGCAG | tag |
| 156/N20 | 36 | CGGCAGGAGGGACTGCGATTTCCATAGAGC | tag |
| 159/N21 | 37 | TGGCCGGAGAGAGGATAGGAAGCGGGACTA | tag |
| 161 | 38 | TAGCAGGTGTCTCGGTCCTCAACTGCAAAC | tag |
| 163/N22 | 39 | ACACATCCCAGGACTGCCGTGGCCTACGTA | tag |
| 171 | 40 | GTGCTAGCCCGGGCCCTTCTTAACTCGGGA | tag |
| 172 | 41 | CGGAATCTGAACATCTATCAGAGCCGCGCT | tag |
| 174/N23 | 42 | GACGAGCTTGTTCCAATTCCTCGAGCCGAG | tag |
| 179/N24 | 43 | GTTGGGGAGGGGCACTACGACTTAGGGCTA | tag |
| 182 | 44 | AATGTGGACGGCCGCTCCGTACTTCTGACA | tag |
| 183 | 45 | AGGGCCAGCAGCTGGTTCCTTCGCCAGTTA | tag |
| 185/N25 | 46 | GGCCGTCAATGTGTTTTGCACCCAACCGGA | tag |
| 188 | 47 | CAGTGACTGGGCTAGTGAAGTGAGTCACAG | tag |
| 193/N26 | 48 | TCCCACGTCCTTCGACGCACACTGTAACTT | tag |
| 301/N27 | 49 | TCATGTATCGCCCGTGGGTAAGCTC | tag |
| 305/N28 | 50 | ATGTTATGGAGAGTGGGTTAGGCAA | tag |
| 307/N29 | 51 | ATGAGGGAGTAAGGAGATTAGGTTC | tag |
| 309 | 52 | CATGCTGCCCGCATACACTTGCGGG | tag |
| 313/N30 | 53 | GCCCAGCAGTTATACAATTCGTGGC | tag |
| 314/N31 | 54 | TTGGGCTCTCCAGTAGCCGAACAAA | tag |
| 316 | 55 | TGACGTTAAACGCAATCCGCGTAAA | tag |
| 325 | 56 | GTCGCCATTCAGGACACGCGAAACT | tag |
| 327/N32 | 57 | GTGGTTGCTACAGCCTAGCCTAGAT | tag |
| 336 | 58 | CCACTTTTCATTCCGAGTCCACGCG | tag |
| 339/N33 | 59 | AGGAGGAACCGGAAGATCTAATCTG | tag |
| 342 | 60 | CCAATGCTTTCAAATAACCCGTTCT | tag |
| 343/N34 | 61 | GCGACTGTGGCAACCCCATTTCGCA | tag |
| 346 | 62 | AAAAAACGGAGGAGTCGAACCTTGG | tag |
| 350/N35 | 63 | AGTTGGATGGATATCTCGCTCGTGA | tag |
| 356/N36 | 64 | CGCTGTCCTCTCTGACACTAAAGGT | tag |
| 357/N37 | 65 | ATTTCAATAGTCAACCCGGTATCCA | tag |

TABLE 4-continued

Summary and cross-identification of the sequences described herein and in the Sequence Listing.

| Oligo Name | SEQ ID NO: | Sequence 5' → 3' | Function |
|---|---|---|---|
| 505 | 66 | TTCGCGCCAGCGACCCCACTTATGA | tag |
| 510/N38 | 67 | GGTTGGGGGGCTCGGCTCATGTATC | tag |
| 516 | 68 | ATGATGCTGAATCGCGATGGGGGGG | tag |
| 517/N39 | 69 | TAAGGAGACTAGGTTCCAATAGCTG | tag |
| 523/N40 | 70 | TTACACAAATCGTGGGTTGGCCTCT | tag |
| 534/N41 | 71 | CGAAAGCGTTCCGCAGGACCCCCTT | tag |
| 538 | 72 | CACCCTTGGACACGTGGAAGTGGGC | tag |
| 541/N42 | 73 | AAAGTCTGAGAATGAGTGATACCAT | tag |
| 544/N43 | 74 | ATATTGGTAGTTTTGTCCGCTGTAG | tag |
| 549/N44 | 75 | CGGAAGATCTAATCTGCACGCAATT | tag |
| 608/N45 | 76 | GCGCCTCGTTGGGCAGAAGTTTGTGGAAAT | tag |
| 610/N46 | 77 | ATCTTCACCTACCGAGTTCTACGGGCCTAC | tag |
| 613/N47 | 78 | CCCACAACTTGCACCCGCTATGCGACCCTG | tag |
| 618 | 79 | GCCCAGGAGCTCTCCTGGGTAACAGTAGCG | tag |
| 620 | 80 | CACGGCCCCCAGGCGGCGTATCAGGGATGA | tag |
| 623 | 81 | TCCCCGGCACGGACCGCAAGGGACCAAAGC | tag |
| 629/N48 | 82 | GATTAGTGGCCCAACGGGAACAAACTTCCT | tag |
| 701/N49 | 83 | CGCCCGTCCCAGACCCTTACTCACTATGGA | tag |
| 703 | 84 | GCTACACGCCAGAGGCGCCGCTACAGCGAT | tag |
| 706/N50 | 85 | GAGATTGTACCCTACAGTCCGATTACCGAT | tag |
| 715/N51 | 86 | CGCAGTAAAAGGGCACAGGTAATTACCTTA | tag |
| 718/N52 | 87 | AGGGTGTCTTGAACTACTGGCGCAGCCCAT | tag |
| 721 | 88 | CCGCAATCCGGTGACGGCCGGACCGGCAGG | tag |
| 723/N53 | 89 | TCGGCGGCGGGTAGTCAGTTCGCTACCTGG | tag |
| 729 | 90 | CCAGGACTGCCGTGGCCCACGCACTCACGA | tag |
| 740 | 91 | TTGACGCAGGCCCCCGGGGCGACTTCATAC | tag |
| 743 | 92 | CGAAAGGAGTTCGAGTGTATCCGGAAGGCG | tag |
| 745 | 93 | AGGCGCACTGCGACTTAGGGCTAGCCCCCC | tag |
| 751/N54 | 94 | GATGTGATCTGGACCCTACGGGAGGGGACA | tag |
| 754 | 95 | TGGGCTGGGGAGTGAGTCGCTCCCGCAGC | tag |
| 757/N55 | 96 | AGTCCCAGATATGAGAGAAGCGAAGCATAA | tag |
| 805 | 97 | CGTTTCAGCATCGATGTCCTAAAAT | tag |
| 815/N56 | 98 | ACTATTACACCACGTACCGTAGGTC | tag |
| 816 | 99 | GGGCAACACCGCGAGCTAATTATCC | tag |
| 818 | 100 | GCGCGCGGCCGAGAATCGTTGGAGG | tag |
| 826 | 101 | CGCGTCGGGCTTTCGTCTACCCTGG | tag |
| 829 | 102 | GGGCGGCCACCGGGGGACCCTGCCC | tag |

TABLE 4-continued

Summary and cross-identification of the sequences described herein and in the Sequence Listing.

| Oligo Name | SEQ ID NO: | Sequence 5' → 3' | Function |
|---|---|---|---|
| 1003/T1 | 103 | TGGCTAATCCCG | tag |
| 1003b/T13 | 104 | GCGTTGGCTAATCCCG | tag |
| 1005/T2 | 105 | CTGTGCTAGAGG | tag |
| 1006/T3 | 106 | CATGTACCAACG | tag |
| 1006b/T14 | 107 | TCACCATGTACCAACG | tag |
| 1007/T4 | 108 | TCGGTCGGACTA | tag |
| 1011/T5 | 109 | CCTCCCCCAAGC | tag |
| 1012/T6 | 110 | GGGTTTGCTACG | tag |
| 1014/T7 | 111 | ATGTGCGCACAA | tag |
| 1022/T8 | 112 | CGGGACTAGAGA | tag |
| 1026/T9 | 113 | AATCTCCGAGCG | tag |
| 1034/T10 | 114 | AAGTGCAGGTTC | tag |
| 1042/T11 | 115 | TCCAGTTTAACC | tag |
| 1043/T12 | 116 | TAGCCGCACAGG | tag |
| 1054/T15 | 117 | TATGAATGCGACCCGGAA | tag |
| 1063/T16 | 118 | AACAATGGTCACTGCATC | tag |
| 1066/T17 | 119 | GGGCCGTTTCCCGGACATAA | tag |
| 1067/T18 | 120 | AGGTTGAGTCCGCATCTGAA | tag |
| 1070/T19 | 121 | TCGACCAAGAGCCGCTAGATGC | tag |
| 1076/T20 | 122 | AGCTCGTGTCAAGCCGTCGCCT | tag |
| 1083/T21 | 123 | TGAAAGAGTTGTCAGTTTGCTGGT | tag |
| 1084/T22 | 124 | TCAGGTAAAGGTTCCTCACGCTACC | tag |
| N200 | 125 | CCCATAACTTGGTGCGAATACGGGT | tag |
| N201 | 126 | CGTAGCAATGTTCGTCTGACTATGA | tag |
| N202 | 127 | CAACTACGGGGATTCTTGGAGAGCC | tag |
| N203 | 128 | GTGTAGTATTAGCAAACGATAAGTC | tag |
| N204 | 129 | CGGGGGCTGGGAATCTGTGACATGA | tag |
| N205 | 130 | TGCCTGTCGATCCATAGGACTCGTG | tag |
| N206 | 131 | GAAATGTCCGGGGCCAAAGACAACC | tag |
| N207 | 132 | CTGACATAGTATAGCATAGATATTG | tag |
| N208 | 133 | GAATTTATAGATACTGCCAATCTAG | tag |
| N209 | 134 | ATCAGTTGGACAGAGGGCTGTGTTA | tag |
| N210 | 135 | CTTCTAGAGAAGAAGAGTACTGACT | tag |
| N211 | 136 | GGTTCAGTTGTAACCATATACTTAC | tag |
| N212 | 137 | AATGACGTAGCTATGTATTTTGCAC | tag |
| N213 | 138 | AGGTAGCCAACGGGTTTCACATTTC | tag |
| N214 | 139 | GCGTAAACTACGATGGCACCTACTC | tag |

TABLE 4-continued

Summary and cross-identification of the sequences
described herein and in the Sequence Listing.

| Oligo Name | SEQ ID NO: | Sequence 5' → 3' | Function |
|---|---|---|---|
| N215 | 140 | CTCATAACTTGGTGCGAATACGGGT | tag |
| N216 | 141 | TGTAGCAATGTTCGTCTGACTATGA | tag |
| N217 | 142 | TAAAATAGTACAGCTACTGGTGATC | tag |
| N218 | 143 | CAACTACGAGGATTTTTAGAGAGCC | tag |
| N219 | 144 | ATGTAGTATTAGCAAACAATAAGTC | tag |
| N220 | 145 | AATTGAATGGAGTCTGATCAATCTT | tag |
| N221 | 146 | GAAGTTGGAGGATTAACGTGGGAAT | tag |
| N222 | 147 | GGTTTACTATTGTCTCTAATGGGAG | tag |
| N223 | 148 | TTGACATAGTATAGCATAGATATTG | tag |
| N224 | 149 | CAGATAACTTACCTACATTGAAAGT | tag |
| N225 | 150 | TATAGACGACTATTCCGACTAGCAA | tag |
| N226 | 151 | GAATTTATAGATACTACCAATCTAG | tag |
| N227 | 152 | ATTAATTGGACAGAGGGCTGTGTTA | tag |
| N228 | 153 | CTGTTGCCACTCTTTAGAAAGATTA | tag |
| N301 | 154 | ACTACAATAATACCAACTATTTGCC | tag |
| N302 | 155 | GATACTAAATAACAACTTAGTTTTT | tag |
| N303 | 156 | TAGATTTCATTCCGAGTCCACATGT | tag |
| N304 | 157 | AACTCTAATATAAGATATCAAGTTA | tag |
| N305 | 158 | ATTGTTAAAGTAGACTAATTATCTA | tag |
| N306 | 159 | GAAGGAACTGGAAGATTTAATTTGC | tag |
| N307 | 160 | ACGCAATTAATATACATATTTATAC | tag |
| N308 | 161 | CAATTATGCGAATTCCATTTCACAT | tag |
| N309 | 162 | CTTATGAGATGTTAGATATAGTATT | tag |
| N310 | 163 | CTTTTACAATATCAGACTTTAGCAA | tag |
| N311 | 164 | GATGTAGACGGATTCCATAGAATTT | tag |
| N312 | 165 | AATGATTGTGTGGAGTACAAACCAA | tag |
| N313 | 166 | TTTTTTTGGCGTAAAGTCTAGAGTT | tag |
| N314 | 167 | ATCACGTAAGACCACTGTTAGTATA | tag |
| N315 | 168 | CTTTAATAGTCAAACCGATATCCAT | tag |
| N316 | 169 | CAGTCAAGTGATGGACTCTAACACA | tag |
| N317 | 170 | TCATTAGCGGAAAAAACTGACCTTC | tag |
| N318 | 171 | CTCCTATCCTTCGCCACAACTTTAG | tag |
| N319 | 172 | TTGCTTTGAGATTGAAATATAAAAG | tag |
| N320 | 173 | ATCATATACAGTGCCAGGGAACAAC | tag |
| N321 | 174 | ACTTGTAGAAATACCTTATAAAGTT | tag |
| N322 | 175 | ATTCTTGATGTATGTAGAGTCCTAA | tag |
| N323 | 176 | TGATATCGAATACATAAGTACTCGA | tag |

TABLE 4-continued

Summary and cross-identification of the sequences described herein and in the Sequence Listing.

| Oligo Name | SEQ ID NO: | Sequence 5' → 3' | Function |
|---|---|---|---|
| N324 | 177 | ATGACTGAATTGCTTACACATTTAA | tag |
| N325 | 178 | AAAAACAATTAGTATATAACTATTA | tag |
| N326 | 179 | TAATAGTGTCATCGGCTCCACTTAT | tag |
| N327 | 180 | TACAATCAAAACGTGAAGTTATTGA | tag |
| N328 | 181 | GTTTAGTTATTGACTTGTAGATAGT | tag |
| N329 | 182 | CTCGACACCGAGTGCTAGATCAACG | tag |
| N330 | 183 | ACCCGGACATATTGGCTATTCAAAC | tag |
| N331 | 184 | AATATTTAAAAGCCTGGTTTATGTA | tag |
| N332 | 185 | CTTTAGTGCCGATTTACGGCCTTGG | tag |
| N333 | 186 | GGTAAGATAACGAAGTTTTAATAGC | tag |
| N334 | 187 | TGCTTTGACACTGTTCATTATACCG | tag |
| N335 | 188 | TTTTCTTTTACCCACTGGTGAAATA | tag |
| N336 | 189 | TCAAGATTGTCCTTGATTGTTGAAT | tag |
| N337 | 190 | AAAGATCTGATTAACTTATAACAGA | tag |
| N338 | 191 | ATGAATAAATCTTGTAAAGTGTGGC | tag |
| N339 | 192 | AGCTACACTAAACCTAGAATGATCT | tag |
| N340 | 193 | CTTCAATTTGAGACTTGAAATCTAA | tag |
| N341 | 194 | GTTTCACTCAGTGTAGACATCATCC | tag |
| N342 | 195 | TGGTATCTGAATTACTGCTTTGTCA | tag |
| N343 | 196 | AAGTGTCTATTATCCTTAAACGCAT | tag |
| N344 | 197 | ATCTCGCATAATAACTCCTCAATAT | tag |
| N345 | 198 | GAGTTAGTCTTGTGCTCACGGAATT | tag |
| N346 | 199 | AATGTTAGTTAGCTCGTTCAAGTA | tag |
| N347 | 200 | AAAGTTCTTCACACTACGTCAAAAT | tag |
| N348 | 201 | AAAAAAATGGTTGTAACAAAAAAAA | tag |
|  | 202 | GGCTCATCGATGACCCAAGATGGCGGC | Promoter |
|  | 203 | TCTCCCTATAGTGAGTCGTATTAAATT | Reverse Complement Promoter |
|  | 204 | GTCTAAGTAGTGACATGTTT | PCA3 target specific portion for promoter primer |
|  | 205 | TGGCTAATCCCGTCTAAGTAGTGACATGTTT | T1/PCA3 |
| T1 | 206 | GGCTCATCGATGACCCAAGATGGCGGCTGGCTAATCCCG | Prom/T1 |
| T1b | 207 | GGCTCATCGATGACCCAAGATGGCGGCTGGCTAATCCCGGTCTAAGTAGTGACATGTTT | Prom/T1/PCA3 |
|  | 208 | CTGTGCTAGAGGGTCTAAGTAGTGACATGTTT | T2/PCA3 |
| T2 | 209 | GGCTCATCGATGACCCAAGATGGCGGCCTGTGCTAGAGG | Prom/T2 |

TABLE 4-continued

Summary and cross-identification of the sequences
described herein and in the Sequence Listing.

| Oligo Name | SEQ ID NO: | Sequence 5' → 3' | Function |
|---|---|---|---|
| T2b | 210 | GGCTCATCGATGACCCAAGATGGCGGCCTGTGCTAGAGGGTCTAAGTAGTGACATGTTT | Prom/T2/PCA3 |
|  | 211 | CATGTACCAACGGTCTAAGTAGTGACATGTTT | T3/PCA3 |
| T3 | 212 | GGCTCATCGATGACCCAAGATGGCGGCCATGTACCAACG | Prom/T3 |
| T3b | 213 | GGCTCATCGATGACCCAAGATGGCGGCCATGTACCAACGGTCTAAGTAGTGACATGTTT | Prom/T3/PCA3 |
|  | 214 | TCGGTCGGACTAGTCTAAGTAGTGACATGTTT | T4/PCA3 |
| T4 | 215 | GGCTCATCGATGACCCAAGATGGCGGCTCGGTCGGACTA | Prom/T4 |
| T4b | 216 | GGCTCATCGATGACCCAAGATGGCGGCTCGGTCGGACTAGTCTAAGTAGTGACATGTTT | Prom/T4/PCA3 |
|  | 217 | CCTCCCCCAAGCGTCTAAGTAGTGACATGTTT | T5/PCA3 |
| T5 | 218 | GGCTCATCGATGACCCAAGATGGCGGCCCTCCCCCAAGC | Prom/T5 |
| T5b | 219 | GGCTCATCGATGACCCAAGATGGCGGCCCTCCCCCAAGCGTCTAAGTAGTGACATGTTT | Prom/T5/PCA3 |
|  | 220 | GGGTTTGCTACGGTCTAAGTAGTGACATGTTT | T6/PCA3 |
| T6 | 221 | GGCTCATCGATGACCCAAGATGGCGGCGGGTTTGCTACG | Prom/T6 |
| T6b | 222 | GGCTCATCGATGACCCAAGATGGCGGCGGGTTTGCTACGGTCTAAGTAGTGACATGTTT | Prom/T6/PCA3 |
|  | 223 | ATGTGCGCACAAGTCTAAGTAGTGACATGTTT | T7/PCA3 |
| T7 | 224 | GGCTCATCGATGACCCAAGATGGCGGCATGTGCGCACAA | Prom/T7 |
| T7b | 225 | GGCTCATCGATGACCCAAGATGGCGGCATGTGCGCACAAGTCTAAGTAGTGACATGTTT | Prom/T7/PCA3 |
|  | 226 | CGGGACTAGAGAGTCTAAGTAGTGACATGTTT | T8/PCA3 |
| T8 | 227 | GGCTCATCGATGACCCAAGATGGCGGCCGGGACTAGAGA | Prom/T8 |
| T8b | 228 | GGCTCATCGATGACCCAAGATGGCGGCCGGGACTAGAGAGTCTAAGTAGTGACATGTTT | Prom/T8/PCA3 |
|  | 229 | AATCTCCGAGCGGTCTAAGTAGTGACATGTTT | T9/PCA3 |
| T9 | 230 | GGCTCATCGATGACCCAAGATGGCGGCAATCTCCGAGCG | Prom/T9 |
| T9b | 231 | GGCTCATCGATGACCCAAGATGGCGGCAATCTCCGAGCGGTCTAAGTAGTGACATGTTT | Prom/T9/PCA3 |
|  | 232 | AAGTGCAGGTTCGTCTAAGTAGTGACATGTTT | T10/PCA3 |
| T10 | 233 | GGCTCATCGATGACCCAAGATGGCGGCAAGTGCAGGTTC | Prom/T10 |
| T10b | 234 | GGCTCATCGATGACCCAAGATGGCGGCAAGTGCAGGTTCGTCTAAGTAGTGACATGTTT | Prom/T10/PCA3 |
|  | 235 | TCCAGTTTAACCGTCTAAGTAGTGACATGTTT | T11/PCA3 |
| T11 | 236 | GGCTCATCGATGACCCAAGATGGCGGCTCCAGTTTAACC | Prom/T11 |
| T11b | 237 | GGCTCATCGATGACCCAAGATGGCGGCTCCAGTTTAACCGTCTAAGTAGTGACATGTTT | Prom/T11/PCA3 |
|  | 238 | TAGCCGCACAGGGTCTAAGTAGTGACATGTTT | T12/PCA3 |
| T12 | 239 | GGCTCATCGATGACCCAAGATGGCGGCTAGCCGCACAGG | Prom/T12 |

TABLE 4-continued

Summary and cross-identification of the sequences described herein and in the Sequence Listing.

| Oligo Name | SEQ ID NO: | Sequence 5' → 3' | Function |
|---|---|---|---|
| T12b | 240 | GGCTCATCGATGACCCAAGATGGCGGCTAGCCGCACAGGGTCTAAGTAGTGACATGTTT | Prom/T12/PCA3 |
|  | 241 | GCGTTGGCTAATCCCGGTCTAAGTAGTGACATGTTT | T13/PCA3 |
| T13 | 242 | GGCTCATCGATGACCCAAGATGGCGGCGCGTTGGCTAATCCCG | Prom/T13 |
| T13b | 243 | GGCTCATCGATGACCCAAGATGGCGGCGCGTTGGCTAATCCCGGTCTAAGTAGTGACATGTTT | Prom/T13/PCA3 |
|  | 244 | TCACCATGTACCAACGGTCTAAGTAGTGACATGTTT | T14/PCA3 |
| T14 | 245 | GGCTCATCGATGACCCAAGATGGCGGCTCACCATGTACCAACG | Prom/T14 |
| T14b | 246 | GGCTCATCGATGACCCAAGATGGCGGCTCACCATGTACCAACGGTCTAAGTAGTGACATGTTT | Prom/T14/PCA3 |
|  | 247 | TATGAATGCGACCCGGAAGTCTAAGTAGTGACATGTTT | T15/PCA3 |
| T15 | 248 | GGCTCATCGATGACCCAAGATGGCGGCTATGAATGCGACCCGGAA | Prom/T15 |
| T15b | 249 | GGCTCATCGATGACCCAAGATGGCGGCTATGAATGCGACCCGGAAGTCTAAGTAGTGACATGTTT | Prom/T15/PCA3 |
|  | 250 | AACAATGGTCACTGCATCGTCTAAGTAGTGACATGTTT | T16/PCA3 |
| T16 | 251 | GGCTCATCGATGACCCAAGATGGCGGCAACAATGGTCACTGCATC | Prom/T16 |
| T16b | 252 | GGCTCATCGATGACCCAAGATGGCGGCAACAATGGTCACTGCATCGTCTAAGTAGTGACATGTTT | Prom/T16/PCA3 |
|  | 253 | GGGCCGTTTCCCGGACATAAGTCTAAGTAGTGACATGTTT | T17/PCA3 |
| T17 | 254 | GGCTCATCGATGACCCAAGATGGCGGCGGGCCGTTTCCCGGACATAA | Prom/T17 |
| T17b | 255 | GGCTCATCGATGACCCAAGATGGCGGCGGGCCGTTTCCCGGACATAAGTCTAAGTAGTGACATGTTT | Prom/T17/PCA3 |
|  | 256 | AGGTTGAGTCCGCATCTGAAGTCTAAGTAGTGACATGTTT | T18/PCA3 |
| T18 | 257 | GGCTCATCGATGACCCAAGATGGCGGCAGGTTGAGTCCGCATCTGAA | Prom/T18 |
| T18b | 258 | GGCTCATCGATGACCCAAGATGGCGGCAGGTTGAGTCCGCATCTGAAGTCTAAGTAGTGACATGTTT | Prom/T18/PCA3 |
|  | 259 | TCGACCAAGAGCCGCTAGATGCGTCTAAGTAGTGACATGTTT | T19/PCA3 |
| T19 | 260 | GGCTCATCGATGACCCAAGATGGCGGCTCGACCAAGAGCCGCTAGATGC | Prom/T19 |
| T19b | 261 | GGCTCATCGATGACCCAAGATGGCGGCTCGACCAAGAGCCGCTAGATGCGTCTAAGTAGTGACATGTTT | Prom/T19/PCA3 |
|  | 262 | AGCTCGTGTCAAGCCGTCGCCTGTCTAAGTAGTGACATGTTT | T20/PCA3 |
| T20 | 263 | GGCTCATCGATGACCCAAGATGGCGGCAGCTCGTGTCAAGCCGTCGCCT | Prom/T20 |
| T20b | 264 | GGCTCATCGATGACCCAAGATGGCGGCAGCTCGTGTCAAGCCGTCGCCTGTCTAAGTAGTGACATGTTT | Prom/T20/PCA3 |
|  | 265 | TGAAAGAGTTGTCAGTTTGCTGGTGTCTAAGTAGTGACATGTTT | T21/PCA3 |

TABLE 4-continued

Summary and cross-identification of the sequences
described herein and in the Sequence Listing.

| Oligo Name | SEQ ID NO: | Sequence 5' → 3' | Function |
| --- | --- | --- | --- |
| T21 | 266 | <u>GGCTCATCGATGACCCAAGATGGCGGC</u>TGAAAGAGTTGTCA GTTTGCTGGT | Prom/T21 |
| T21b | 267 | <u>GGCTCATCGATGACCCAAGATGGCGGC</u>TGAAAGAGTTGTCA GTTTGCTGGTGTCTAAGTAGTGACATGTTT | Prom/T21/PCA3 |
|  | 268 | TCAGGTAAAGGTTCCTCACGCTACCGTCTAAGTAGTGACAT GTTT | T22/PCA3 |
| T22 | 269 | <u>GGCTCATCGATGACCCAAGATGGCGGC</u>TCAGGTAAAGGTTC CTCACGCTACC | Prom/T22 |
| T22b | 270 | <u>GGCTCATCGATGACCCAAGATGGCGGC</u>TCAGGTAAAGGTTC CTCACGCTACCGTCTAAGTAGTGACATGTTT | Prom/T22/PCA3 |
|  | 271 | GGCTCATCGATGACCCAAGATGGCGGC | PCA3 target specific sequence for non-promoter primer |
| RPCA3 21 U20 | 272 | GTCATATGCGACGATCTCAGGGCTCATCGATGACCCAAGAT GGCGGC | U20/PCA3 |
| N1b | 273 | GTCCCCATCGGAGGGCATCTTATCGTGCCTGGCTCATCGAT GACCCAAGATGGCGGC | N1/PCA3 non-prom |
| N2b | 274 | CCGCCCTCCTTCGCCCCCCGGTGAAATAACGGCTCATCGAT GACCCAAGATGGCGGC | N2/PCA3 non-prom |
| N3b | 275 | AATGCTCACCTCTATTCGGGACTTGAGTACGGCTCATCGAT GACCCAAGATGGCGGC | N3/PCA3 non-prom |
| N4b | 276 | GTCGGAACGCCAGGTACAGTTAGCGCATCCGGCTCATCGAT GACCCAAGATGGCGGC | N4/PCA3 non-prom |
| N5b | 277 | GTGATGCTTTATGAGATTCCGGTCTCCGACGGCTCATCGAT GACCCAAGATGGCGGC | N5/PCA3 non-prom |
| N6b | 278 | GACGGTGCATCACCCGCATTTGCTGTAGCGGGCTCATCGAT GACCCAAGATGGCGGC | N6/PCA3 non-prom |
| N7b | 279 | AAGCCAAAATTACAATCGATCCCTACCAACGGCTCATCGAT GACCCAAGATGGCGGC | N7/PCA3 non-prom |
| N8b | 280 | ATCTTGCACCTTCCCAGATGTAAACCCCTGGCTCATCGAT GACCCAAGATGGCGGC | N8/PCA3 non-prom |
| N9b | 281 | CGGAGAATACCCTCGACTGTATCATATCGTGGCTCATCGAT GACCCAAGATGGCGGC | N9/PCA3 non-prom |
| N10b | 282 | TTCATCGAGGTACATTGGTGCTATTCCATTGGCTCATCGAT GACCCAAGATGGCGGC | N10/PCA3 non-prom |
| N11b | 283 | AGGAGAACCAGCCTGGAGCGTTTAAGCATCGGCTCATCGAT GACCCAAGATGGCGGC | N11/PCA3 non-prom |
| N12b | 284 | GATGTCCTAAAATGAGGCGTGGCAATAGAGGGCTCATCGAT GACCCAAGATGGCGGC | N12/PCA3 non-prom |
| N13b | 285 | CAGAGTCATGTATACCCACTGTCGGTCGAAGGCTCATCGAT GACCCAAGATGGCGGC | N13/PCA3 non-prom |
| N14b | 286 | GTCAGGCTAGGGGGTTATCCCAGCAACGGCGGCTCATCGAT GACCCAAGATGGCGGC | N14/PCA3 non-prom |
| N15b | 287 | TTTTTGACAGTGATGAAGAGGGAGGTACGAGGCTCATCGAT GACCCAAGATGGCGGC | N15/PCA3 non-prom |
| N16b | 288 | CTATGGTTCGTTACTGAATCGAAAAGCCGCGGCTCATCGAT GACCCAAGATGGCGGC | N16/PCA3 non-prom |

TABLE 4-continued

Summary and cross-identification of the sequences described herein and in the Sequence Listing.

| Oligo Name | SEQ ID NO: | Sequence 5' → 3' | Function |
|---|---|---|---|
| N17b | 289 | TAGCTATCAAAACAGGCGTCATCGGTTAAGGGCTCATCGAT GACCCAAGATGGCGGC | N17/PCA3 non-prom |
| N18b | 290 | CCTGCTTAGGGTCACTTAAACTACTGGCGCGGCTCATCGAT GACCCAAGATGGCGGC | N18/PCA3 non-prom |
| N19b | 291 | GGTGATGGCCCATACCGATCACGCCCGCAGGGCTCATCGAT GACCCAAGATGGCGGC | N19/PCA3 non-prom |
| N20b | 292 | CGGCAGGAGGGACTGCGATTTCCATAGAGCGGCTCATCGAT GACCCAAGATGGCGGC | N20/PCA3 non-prom |
| N21b | 293 | TGGCCGGAGAGAGGATAGGAAGCGGGACTAGGCTCATCGAT GACCCAAGATGGCGGC | N21/PCA3 non-prom |
| N22b | 294 | ACACATCCCAGGACTGCCGTGGCCTACGTAGGCTCATCGAT GACCCAAGATGGCGGC | N22/PCA3 non-prom |
| N23b | 295 | GACGAGCTTGTTCCAATTCCTCGAGCCGAGGGCTCATCGAT GACCCAAGATGGCGGC | N23/PCA3 non-prom |
| N24b | 296 | GTTGGGGAGGGCACTACGACTTAGGGCTAGGCTCATCGAT GACCCAAGATGGCGGC | N24/PCA3 non-prom |
| N25b | 297 | GGCCGTCAATGTGTTTTGCACCCAACCGGAGGCTCATCGAT GACCCAAGATGGCGGC | N25/PCA3 non-prom |
| N26b | 298 | TCCCACGTCCTTCGACGCACACTGTAACTTGGCTCATCGAT GACCCAAGATGGCGGC | N26/PCA3 non-prom |
| N27b | 299 | TCATGTATCGCCCGTGGGTAAGCTCGGCTCATCGATGACCC AAGATGGCGGC | N27/PCA3 non-prom |
| N28b | 300 | ATGTTATGGAGAGTGGGTTAGGCAAGGCTCATCGATGACCC AAGATGGCGGC | N28/PCA3 non-prom |
| N29b | 301 | ATGAGGGAGTAAGGAGATTAGGTTCGGCTCATCGATGACCC AAGATGGCGGC | N29/PCA3 non-prom |
| N30b | 302 | GCCCAGCAGTTATACAATTCGTGGCGGCTCATCGATGACCC AAGATGGCGGC | N30/PCA3 non-prom |
| N31b | 303 | TTGGGCTCTCCAGTAGCCGAACAAAGGCTCATCGATGACCC AAGATGGCGGC | N31/PCA3 non-prom |
| N32b | 304 | GTGGTTGCTACAGCCTAGCCTAGATGGCTCATCGATGACCC AAGATGGCGGC | N32/PCA3 non-prom |
| N33b | 305 | AGGAGGAACCGGAAGATCTAATCTGGGCTCATCGATGACCC AAGATGGCGGC | N33/PCA3 non-prom |
| N34b | 306 | GCGACTGTGGCAACCCCATTTCGCAGGCTCATCGATGACCC AAGATGGCGGC | N34/PCA3 non-prom |
| N35b | 307 | AGTTGGATGGATATCTCGCTCGTGAGGCTCATCGATGACCC AAGATGGCGGC | N35/PCA3 non-prom |
| N36b | 308 | CGCTGTCCTCTCTGACACTAAAGGTGGCTCATCGATGACCC AAGATGGCGGC | N36/PCA3 non-prom |
| N37b | 309 | ATTTCAATAGTCAACCCGGTATCCAGGCTCATCGATGACCC AAGATGGCGGC | N37/PCA3 non-prom |
| N38b | 310 | GGTTGGGGGGCTCGGCTCATGTATCGGCTCATCGATGACCC AAGATGGCGGC | N38/PCA3 non-prom |
| N39b | 311 | TAAGGAGACTAGGTTCCAATAGCTGGGCTCATCGATGACCC AAGATGGCGGC | N39/PCA3 non-prom |
| N40b | 312 | TTACACAAATCGTGGGTTGGCCTCTGGCTCATCGATGACCC AAGATGGCGGC | N40/PCA3 non-prom |

TABLE 4-continued

Summary and cross-identification of the sequences described herein and in the Sequence Listing.

| Oligo Name | SEQ ID NO: | Sequence 5' → 3' | Function |
|---|---|---|---|
| N41b | 313 | CGAAAGCGTTCCGCAGGACCCCCTTGGCTCATCGATGACCC AAGATGGCGGC | N41/PCA3 non-prom |
| N42b | 314 | AAAGTCTGAGAATGAGTGATACCATGGCTCATCGATGACCC AAGATGGCGGC | N42/PCA3 non-prom |
| N43b | 315 | ATATTGGTAGTTTTGTCCGCTGTAGGGCTCATCGATGACCC AAGATGGCGGC | N43/PCA3 non-prom |
| N44b | 316 | CGGAAGATCTAATCTGCACGCAATTGGCTCATCGATGACCC AAGATGGCGGC | N44/PCA3 non-prom |
| N45b | 317 | GCGCCTCGTTGGGCAGAAGTTTGTGGAAATGGCTCATCGAT GACCCAAGATGGCGGC | N45/PCA3 non-prom |
| N46b | 318 | ATCTTCACCTACCGAGTTCTACGGGCCTACGGCTCATCGAT GACCCAAGATGGCGGC | N45/PCA3 non-prom |
| N47b | 319 | CCCACAACTTGCACCCGCTATGCGACCCTGGGCTCATCGAT GACCCAAGATGGCGGC | N47/PCA3 non-prom |
| N48b | 320 | GATTAGTGGCCCAACGGGAACAAACTTCCTGGCTCATCGAT GACCCAAGATGGCGGC | N48/PCA3 non-prom |
| N49b | 321 | CGCCCGTCCCAGACCCTTACTCACTATGGAGGCTCATCGAT GACCCAAGATGGCGGC | N49/PCA3 non-prom |
| N50b | 322 | GAGATTGTACCCTACAGTCCGATTACCGATGGCTCATCGAT GACCCAAGATGGCGGC | N50/PCA3 non-prom |
| N51b | 323 | CGCAGTAAAAGGGCACAGGTAATTACCTTAGGCTCATCGAT GACCCAAGATGGCGGC | N51/PCA3 non-prom |
| N52b | 324 | AGGGTGTCTTGAACTACTGGCGCAGCCCATGGCTCATCGAT GACCCAAGATGGCGGC | N52/PCA3 non-prom |
| N53b | 325 | TCGGCGGCGGGTAGTCAGTTCGCTACCTGGGGCTCATCGAT GACCCAAGATGGCGGC | N53/PCA3 non-prom |
| N54b | 326 | GATGTGATCTGGACCCTACGGGAGGGGACAGGCTCATCGAT GACCCAAGATGGCGGC | N54/PCA3 non-prom |
| N55b | 327 | AGTCCCAGATATGAGAGAAGCGAAGCATAAGGCTCATCGAT GACCCAAGATGGCGGC | N55/PCA3 non-prom |
| N56b | 328 | ACTATTACACCACGTACCGTAGGTCGGCTCATCGATGACCC AAGATGGCGGC | N56/PCA3 non-prom |
| | 329 | GTCATATGCGACGATCTCAGGGCTCATCGATGACCCAAGAT GGCGGC | U20/PCA3 |
| | 330 | <u>TCTCCCTATAGTGAGTCGTATTAAATTGTCATATGCGACGA TCTCAG</u> | RC PROM/U20 |
| PCA3 U20-cPRO | 331 | <u>TCTCCCTATAGTGAGTCGTATTAAATTGTCATATGCGACGA TCTCAG</u>GGCTCATCGATGACCCAAGATGGCGGC | RC Prom/U20/PCA3 (NOTE: PCA3 sequence same as non-promoter primer) |
| | 332 | GTGATGCTTTATGAGATTCCGGTCTCCGACGGCTCATCGAT GACCCAAGATGGCGGC | N5/PCA3 |
| | 333 | <u>TCTCCCTATAGTGAGTCGTATTAAATTGTGATGCTTTATGA GATTCCGGTCTCCGAC</u> | RC PROM/N5 |
| N5b_cPRO | 334 | <u>TCTCCCTATAGTGAGTCGTATTAAATTGTGATGCTTTATGA GATTCCGGTCTCCGAC</u>GGCTCATCGATGACCCAAGATGGCG GC | RC Prom/N5/PCA3 |

TABLE 4-continued

Summary and cross-identification of the sequences described herein and in the Sequence Listing.

| Oligo Name | SEQ ID NO: | Sequence 5' → 3' | Function |
|---|---|---|---|
|  | 335 | TTCATCGAGGTACATTGGTGCTATTCCATTGGCTCATCGAT GACCCAAGATGGCGGC | N10/PCA3 |
|  | 336 | <u>TCTCCCTATAGTGAGTCGTATTAAATT</u>TTCATCGAGGTACA TTGGTGCTATTCCATT | RC PROM/PCA3 |
| N10_cPRO | 337 | <u>TCTCCCTATAGTGAGTCGTATTAAATT</u>TTCATCGAGGTACA TTGGTGCTATTCCATTGGCTCATCGATGACCCAAGATGGCG GC | RC Prom/N10/PCA3 |
|  | 338 | GATGTCCTAAAATGAGGCGTGGCAATAGAGGGCTCATCGAT GACCCAAGATGGCGGC | N12/PCA3 |
|  | 339 | <u>TCTCCCTATAGTGAGTCGTATT</u>AAATTGATGTCCTAAAATG AGGCGTGGCAATAGAG | RC PROM/N12 |
| N12_cPRO | 340 | <u>TCTCCCTATAGTGAGTCGTATT</u>AAATTGATGTCCTAAAATG AGGCGTGGCAATAGAGGGCTCATCGATGACCCAAGATGGCG GC | RC Prom/N12/PCA3 |
|  | 341 | CAGAGTCATGTATACCCACTGTCGGTCGAAGGCTCATCGAT GACCCAAGATGGCGGC | N13/PROM |
|  | 342 | <u>TCTCCCTATAGTGAGTCGTATT</u>AAATTCAGAGTCATGTATA CCCACTGTCGGTCGAA | RC PROM/N13 |
| N13b_cPRO | 343 | <u>TCTCCCTATAGTGAGTCGTATT</u>AAATTCAGAGTCATGTATA CCCACTGTCGGTCGAAGGCTCATCGATGACCCAAGATGGCG GC | Prom/N13/PCA3 |
|  | 344 | ATGTTATGGAGAGTGGGTTAGGCAAGGCTCATCGATGACCC AAGATGGCGGC | N28/PCA3 |
|  | 345 | <u>TCTCCCTATAGTGAGTCGTATT</u>AAATTATGTTATGGAGAGT GGGTTAGGCAA | RC PROM PCA3 |
| N28b_cPRO | 346 | <u>TCTCCCTATAGTGAGTCGTATT</u>AAATTATGTTATGGAGAGT GGGTTAGGCAAGGCTCATCGATGACCCAAGATGGCGGC | RC Prom/N28/PCA3 |
|  | 347 | AAAGTCTGAGAATGAGTGATACCATGGCTCATCGATGACCC AAGATGGCGGC | N42/PCA3 |
|  | 348 | <u>TCTCCCTATAGTGAGTCGTATT</u>AAATTAAAGTCTGAGAATG AGTGATACCAT | RC RPOM/N42 |
| N42b_cPRO | 349 | <u>TCTCCCTATAGTGAGTCGTATT</u>AAATTAAAGTCTGAGAATG AGTGATACCATGGCTCATCGATGACCCAAGATGGCGGC | RC Prom/N42/PCA3 |
|  | 350 | CCCACAACTTGCACCCGCTATGCGACCCTGGGCTCATCGAT GACCCAAGATGGCGGC | N47/PCA3 |
|  | 351 | <u>TCTCCCTATAGTGAGTCGTATT</u>AAATTCCCACAACTTGCAC CCGCTATGCGACCCTG | RC PROM/N47 |
| N47b_cPRO | 352 | <u>TCTCCCTATAGTGAGTCGTATT</u>AAATTCCCACAACTTGCAC CCGCTATGCGACCCTGGGCTCATCGATGACCCAAGATGGCG GC | RC Prom/N47/PCA3 |
|  | 353 | GATTAGTGGCCCAACGGGAACAAACTTCCTGGCTCATCGAT GACCCAAGATGGCGGC | N48/PCA3 |
|  | 354 | <u>TCTCCCTATAGTGAGTCGTATTAAATT</u>GATTAGTGGCCCAA CGGGAACAAACTTCCT | RC PROM/N48 |
| N48b_cPRO | 355 | <u>TCTCCCTATAGTGAGTCGTATTAAATT</u>GATTAGTGGCCCAA CGGGAACAAACTTCCTGGCTCATCGATGACCCAAGATGGCG GC | RC Prom/N48/PCA3 |
|  | 356 | CGCCCGTCCCAGACCCTTACTCACTATGGAGGCTCATCGAT GACCCAAGATGGCGGC | N49/PCA3 |
|  | 357 | <u>TCTCCCTATAGTGAGTCGTATTAAATT</u>CGCCCGTCCCAGAC CCTTACTCACTATGGA | RC PROM/N49 |

TABLE 4-continued

Summary and cross-identification of the sequences
described herein and in the Sequence Listing.

| Oligo Name | SEQ ID NO: | Sequence 5' → 3' | Function |
|---|---|---|---|
| N49b_cPRO | 358 | TCTCCCTATAGTGAGTCGTATTAAATTCGCCCGTCCCAGACCCTTACTCACTATGGAGGCTCATCGATGACCCAAGATGGCGGC | RC Prom/N49/PCA3 |
| BOmePCA3 3e3(-) 112-3'blk | 359 | GAUGCAGUGGGCAGCUGUGAGGAC | PCA3 BLOCKER |
| RPCA3e3(-) 147-166_C9 (21/22) | 360 | UGUGUCUUCAGGAUGAAACACACA | PCA3 PROBE |
|  | 361 | AUCUGUUUUCCUGCCCAUCCUUUAAG | PCA3 TARGET CAPTURE |
| PCA3e4(-) 109dT3A30 3'-blocked | 362 | AUCUGUUUUCCUGCCCAUCCUUUAAGTTTAAAAAAAAAAAAAAAAAAAAAAAAA | PCA3 TARGET CAPTURE |
|  | 363 | CCACTGCATCAGGAACAAAAGCGTGATCTTG | PSA target specific sequence for promoter primer |
|  | 364 | TGGCTAATCCCGCCACTGCATCAGGAACAAAAGCGTGATCTTG | T1/PSA |
| T1 | 365 | GGCTCATCGATGACCCAAGATGGCGGCTGGCTAATCCCG | Prom/T1 |
| PSA T1b | 366 | GGCTCATCGATGACCCAAGATGGCGGCTGGCTAATCCCGCCACTGCATCAGGAACAAAAGCGTGATCTTG | Prom/T1/PSA |
|  | 367 | AGGTTGAGTCCGCATCTGAACCACTGCATCAGGAACAAAAGCGTGATCTTG | T18/PSA |
| T18 | 368 | GGCTCATCGATGACCCAAGATGGCGGCAGGTTGAGTCCGCATCTGAA | Prom/T18 |
| PSA T18b | 369 | GGCTCATCGATGACCCAAGATGGCGGCAGGTTGAGTCCGCATCTGAACCACTGCATCAGGAACAAAAGCGTGATCTTG | Prom/T18/PSA |
|  | 370 | ATGTGCGCACAACCACTGCATCAGGAACAAAAGCGTGATCTTG | T7/PSA |
| T7 | 371 | GGCTCATCGATGACCCAAGATGGCGGCATGTGCGCACAA | Prom/T7 |
| PSA T7b | 372 | GGCTCATCGATGACCCAAGATGGCGGCATGTGCGCACAACCACTGCATCAGGAACAAAAGCGTGATCTTG | Prom/T7/PSA |
|  | 373 | TATGAATGCGACCCGGAACCACTGCATCAGGAACAAAAGCGTGATCTTG | T15/PSA |
| T15 | 374 | GGCTCATCGATGACCCAAGATGGCGGCTATGAATGCGACCCGGAA | Prom/T15 |
| PSA T15b | 375 | GGCTCATCGATGACCCAAGATGGCGGCTATGAATGCGACCCGGAACCACTGCATCAGGAACAAAAGCGTGATCTTG | Prom/T15/PSA |
|  | 376 | CATGTACCAACGCCACTGCATCAGGAACAAAAGCGTGATCTTG | T3/PSA |
| T3 | 377 | GGCTCATCGATGACCCAAGATGGCGGCCATGTACCAACG | Prom/T3 |
| PSA T3b | 378 | GGCTCATCGATGACCCAAGATGGCGGCCATGTACCAACGCCACTGCATCAGGAACAAAAGCGTGATCTTG | Prom/T3/PSA |
|  | 379 | AATCTCCGAGCGCCACTGCATCAGGAACAAAAGCGTGATCTTG | T9/PSA |

TABLE 4-continued

Summary and cross-identification of the sequences described herein and in the Sequence Listing.

| Oligo Name | SEQ ID NO: | Sequence 5' → 3' | Function |
|---|---|---|---|
| T9 | 380 | GGCTCATCGATGACCCAAGATGGCGGCAATCTCCGAGCG | Prom/T9 |
| PSA T9b | 381 | GGCTCATCGATGACCCAAGATGGCGGCAATCTCCGAGCGCCACTGCATCAGGAACAAAAGCGTGATCTTG | Prom/T9/PSA |
|  | 382 | TCACCATGTACCAACGCCACTGCATCAGGAACAAAAGCGTGATCTTG | T14/PSA |
| T14 | 383 | GGCTCATCGATGACCCAAGATGGCGGCTCACCATGTACCAACG | Prom/T14 |
| PSA T14b | 384 | GGCTCATCGATGACCCAAGATGGCGGCTCACCATGTACCAACGCCACTGCATCAGGAACAAAAGCGTGATCTTG | Prom/T14/PSA |
|  | 385 | AACAATGGTCACTGCATCCCACTGCATCAGGAACAAAAGCGTGATCTTG | T16/PSA |
| T16 | 386 | GGCTCATCGATGACCCAAGATGGCGGCAACAATGGTCACTGCATC | Prom/T16 |
| PSA T16b | 387 | GGCTCATCGATGACCCAAGATGGCGGCAACAATGGTCACTGCATCCCACTGCATCAGGAACAAAAGCGTGATCTTG | Prom/T16/PSA |
|  | 388 | GGGCCGTTTCCCGGACATAACCACTGCATCAGGAACAAAAGCGTGATCTTG | T17/PSA |
| T17 | 389 | GGCTCATCGATGACCCAAGATGGCGGCGGGCCGTTTCCCGGACATAA | Prom/T17 |
| PSA T17b | 390 | GGCTCATCGATGACCCAAGATGGCGGCGGGCCGTTTCCCGGACATAACCACTGCATCAGGAACAAAAGCGTGATCTTG | Prom/T17/PSA |
|  | 391 | TGAAAGAGTTGTCAGTTTGCTGGTCCACTGCATCAGGAACAAAAGCGTGATCTTG | T21/PSA |
| T21 | 392 | GGCTCATCGATGACCCAAGATGGCGGCTGAAAGAGTTGTCAGTTTGCTGGT | Prom/T21 |
| PSA T21b | 393 | GGCTCATCGATGACCCAAGATGGCGGCTGAAAGAGTTGTCAGTTTGCTGGTCCACTGCATCAGGAACAAAAGCGTGATCTTG | Prom/T21/PSA |
|  | 394 | TCAGGTAAAGGTTCCTCACGCTACCCCACTGCATCAGGAACAAAAGCGTGATCTTG | T22/PSA |
| T22 | 395 | GGCTCATCGATGACCCAAGATGGCGGCTCAGGTAAAGGTTCCTCACGCTACC | Prom/T22 |
| PSA T22b | 396 | GGCTCATCGATGACCCAAGATGGCGGCTCAGGTAAAGGTTCCTCACGCTACCCCACTGCATCAGGAACAAAAGCGTGATCTTG | Prom/T22/PSA |
|  | 397 | GCTGTGGCTGACCTGAAATACC | PSA target specific sequence for non-promoter primer |
| PSA N5b | 398 | GTGATGCTTTATGAGATTCCGGTCTCCGACGCTGTGGCTGACCTGAAATACC | N5/ PSA non-prom |
| PSA N12b | 399 | GATGTCCTAAAATGAGGCGTGGCAATAGAGGCTGTGGCTGACCTGAAATACC | N12/PSA non-prom |
| PSA N13b | 400 | CAGAGTCATGTATACCCACTGTCGGTCGAAGCTGTGGCTGACCTGAAATACC | N13/PSA non-prom |
| PSA N28b | 401 | ATGTTATGGAGAGTGGGTTAGGCAGCTGTGGCTGACCTGAATACC | N28/PSA non-prom |
| PSA N42b | 402 | AAAGTCTGAGAATAGAGTGATACCATGCTGTGGCTGACCTGAATACC | N42/PSA non-prom |

TABLE 4-continued

Summary and cross-identification of the sequences
described herein and in the Sequence Listing.

| Oligo Name | SEQ ID NO: | Sequence 5' → 3' | Function |
|---|---|---|---|
| PSA N47b | 403 | CCCACAACTTGCACCCGCTATGCGACCCTG<u><u>GCTGTGGCTGA CCTGAAATACC</u></u> | N47/PSA non-prom |
| PSA N48b | 404 | GATTAGTGGCCCAACGGGAACAAACTTCCT<u><u>GCTGTGGCTGA CCTGAAATACC</u></u> | N48/PSA non-prom |
| PSA N49b | 405 | CGCCCGTCCCAGACCCTTACTCACTATGGA<u><u>GCTGTGGCTGA CCTGAAATACC</u></u> | N49/PSA non-prom |
| RPSAe2e3 (-)222-244_BKD | 406 | <u><u>GAUGCAGUGGGCAGCUGUGAGGAC</u></u> | PSA BLOCKER |
| RPSAe3(-) 32-51_C9 (19,20) | 407 | <u><u>UGUGUCUUCAGGAUGAAACACACA</u></u> | PSA PROBE |
|  | 408 | <u><u>CGAACUUGCGCACACACGUCAUUGGA</u></u> | PSA TARGET CAPTURE |
| PSA(-) 581dT3A30 | 409 | <u><u>CGAACUUGCGCACACACGUCAUUGGA</u></u>*TTTAAAAAAAAAAAA AAAAAAAAAAAAAAAAA* | PSA TARGET CAPTURE |

Key to identity of sequences:
Normal- tag sequences
Bold- pca3 target specific sequences
<u>Double Underline</u>- PSA target specific sequences
<u>Underline</u>- promoter sequence
*Italics*- dT(3)A(30) tail The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

---

The invention claimed is:

1. An oligonucleotide comprising a T7 promoter and a tag having the sequence of SEQ ID NO: 113, 107, 117, 118, 119, 122, 123 or 124.

2. The oligonucleotide of claim 1, wherein the tag has the sequence of SEQ ID NO:117.

3. A method of improving performance of a tag in a transcription mediated amplification assay, comprising modifying the tag sequence of an oligonucleotide of claim 1 to produce a modified oligonucleotide; and determining performance of the oligonucleotide in a transcription mediated amplification assay.

4. The method of claim 3, wherein modifying the tag sequence comprising deleting one or more nucleotides from the sequence.

* * * * *